United States Patent
Park et al.

(10) Patent No.: US 12,037,338 B2
(45) Date of Patent: Jul. 16, 2024

(54) IMIDAZOPYRIMIDINE AND IMIDAZOTRIAZINE DERIVATIVE, AND PHARMACEUTICAL COMPOSITION COMPRISING THE SAME

(71) Applicant: SK BIOPHARMACEUTICALS CO., LTD., Gyeonggi-do (KR)

(72) Inventors: Chun Eung Park, Daejeon (KR); Young Koo Jang, Daejeon (KR); Yong Je Shin, Daejeon (KR); Ji Yeon Kim, Daejeon (KR); Seung Mo Ham, Daejeon (KR); Yong Gil Kim, Daejeon (KR); Hye Kyung Min, Daejeon (KR); Soo Bong Cha, Daejeon (KR); Hyo Jun Jung, Daejeon (KR); Ju Young Lee, Daejeon (KR); Seung Nam Han, Daejeon (KR); Jin Yong Chung, Daejeon (KR); Eun Ju Choi, Daejeon (KR); Chan Mi Joung, Daejeon (KR); Jong Sil Park, Daejeon (KR); Ji Won Lee, Daejeon (KR); Nahm Ryune Cho, Daejeon (KR); Eun Ju Ryu, Daejeon (KR); Cheol Young Maeng, Daejeon (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 642 days.

(21) Appl. No.: 17/335,196

(22) Filed: Jun. 1, 2021

(65) Prior Publication Data

US 2021/0300933 A1 Sep. 30, 2021

Related U.S. Application Data

(60) Continuation of application No. 16/851,493, filed on Apr. 17, 2020, now Pat. No. 11,046,702, which is a continuation of application No. 16/146,644, filed on Sep. 28, 2018, now abandoned, which is a continuation of application No. 15/664,633, filed on Jul. 31, 2017, now Pat. No. 10,100,057, which is a division of application No. 15/053,569, filed on Feb. 25, 2016, now Pat. No. 9,745,310.

(30) Foreign Application Priority Data

Feb. 26, 2015 (KR) ........................ 10-2015-0027395

(51) Int. Cl.
C07D 487/04 (2006.01)
(52) U.S. Cl.
CPC ................................ *C07D 487/04* (2013.01)
(58) Field of Classification Search
CPC .................................................. C07D 487/04
See application file for complete search history.

(56) References Cited

U.S. PATENT DOCUMENTS 9,745,310 B2 8/2017 Park et al.
10,100,057 B2 10/2018 Park et al.

FOREIGN PATENT DOCUMENTS

| WO | WO-2008/151184 A1 | 12/2008 |
| WO | WO-2010/124055 A1 | 10/2010 |
| WO | WO-2011/035324 A1 | 3/2011 |
| WO | WO-2011/082010 A1 | 7/2011 |
| WO | WO-2012/078817 A1 | 6/2012 |
| WO | WO-2012/083224 A1 | 6/2012 |

OTHER PUBLICATIONS

Matosin, et al. (2013) "Metabotropic glutamate receptor 5 binding and protein expression in schizophrenia and following antipsychotic drug treatment." *Schizophrenia Research*, 146:170-176.
Nakanishi, et al. (1998) "Glutamate receptors: brain function and signal transduction." *Brain Research Reviews*, 26:230-235.
Gasparini et al, mGluR5 antagonists: discovery, characterization, and drug development, 2008, Curr Opin Drug Discov Devel., 11(5), pp. 655-665.
Grados et al, A selective review of glutamate pharmacological therapy in obsessive-compulsive and related disorders, 2015, Psychology Research and Behavior Management, 8, pp. 115-131.
Office Action (Non-Final) from corresponding U.S. Appl. No. 16/146,644, dated Jan. 14, 2019.

(Continued)

*Primary Examiner* — Kamal A Saeed
*Assistant Examiner* — Karen Cheng
(74) *Attorney, Agent, or Firm* — Harness, Dickey & Pierce, P.L.C.

(57) ABSTRACT

The present disclosure provides a compound of Chemical Formula (1) or a pharmaceutically acceptable salt thereof, and a pharmaceutical composition comprising the same:

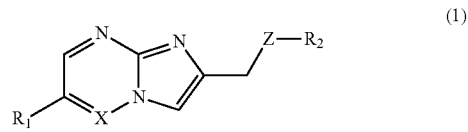

(1)

wherein X, Z, $R_1$ and $R_2$ are as defined in the specification.

The compound of Chemical Formula (1) or pharmaceutically acceptable salt thereof acts as a positive allosteric modulator of metabotropic glutamate receptor subtype 5 (mGluR5), thereby being useful in the prevention or treatment of disorder mediated by glutamate dysfunction and mGluR5.

18 Claims, No Drawings

(56) References Cited

OTHER PUBLICATIONS

Office Action (Final) from corresponding U.S. Appl. No. 16/146,644, dated Oct. 22, 2019.
Office Action (Non-Final) from corresponding U.S. Appl. No. 15/664,633, dated Oct. 12, 2017.
Office Action (Non-Final) from corresponding U.S. Appl. No. 15/053,569, dated Nov. 23, 2016.
Office Action (Non-Final) from corresponding U.S. Appl. No. 16/851,493, dated Jun. 15, 2020.

IMIDAZOPYRIMIDINE AND IMIDAZOTRIAZINE DERIVATIVE, AND PHARMACEUTICAL COMPOSITION COMPRISING THE SAME

CROSS-REFERENCE TO RELATED APPLICATIONS

This application is a continuation of U.S. application Ser. No. 16/851,493, filed on 17 Apr. 2020, which is a continuation of U.S. application Ser. No. 16/146,644, filed on 28 Sep. 2018, which is a continuation of U.S. application Ser. No. 15/664,633, filed on 31 Jul. 2017, now U.S. Pat. No. 10,100,057, issued on 16 Oct. 2018, which is a divisional application of U.S. application Ser. No. 15/053,569, filed on 25 Feb. 2016, now U.S. Pat. No. 9,745,310, issued on 29 Aug. 2017, claiming priority to Korean Patent Application 10-2015-0027395, filed on 26 Feb. 2015. The entire disclosures of the applications identified in this paragraph are incorporated herein by reference.

FIELD

The present disclosure generally relates to a compound modulating receptor activity, pharmaceutical compositions comprising the compound, and methods useful for treating diseases. The present disclosure relates to a compound useful as a positive allosteric modulator (PAM) of metabotropic glutamate receptor subtype 5 (mGluR5) or a pharmaceutically acceptable salt thereof, and a pharmaceutical composition for the prevention and/or treatment of disorders mediated by glutamate dysfunction and mGluR5 comprising a therapeutically effective amount of the same.

BACKGROUND

Glutamate is the most prevalent excitatory neurotransmitter in the central nervous system (CNS) of mammals. Glutamate plays an important role in numerous physiological functions such as cardiovascular regulation, perception and recognition, and synaptogenesis as well as learning and memory. As such, in the occurrence of imbalance in glutamate neurotransmission, various nervous and mental diseases such as schizophrenia may be caused, and thus glutamate plays an important role in physiology.

Glutamate mediates synaptic neurotransmission via ionotropic glutamate receptors (iGluR)—i.e., the activation of NMDA receptors, AMPA receptors and kainate receptors involved in rapid excitatory transmission (Nakanishi S. et al., Brain Res. Rev., (1998) 26: 230-235). In addition, glutamate plays a role in subtly regulating excitatory synaptic neurotransmission via the activation of metabotropic glutamate receptor (mGluR).

Metabotropic glutamate receptors (mGluR) consist of eight (8) subtypes and are sub-divided into three groups (Groups I, II and III) according to arrangement, homology and pharmacological property. mGluR5 belongs to Group I, and it is known that mGluR5 interacts with NMDA receptors via various proteins and neurotransmission pathways. Therefore, because the balance of deficiency or hyperactivity of physiological function by NMDA receptors can be regulated via the modulation of mGluR5, to modulate mGluR5 is very important.

Since a variety of pathophysiological processes and disease states affecting the CNS are thought to be related to abnormal glutamate neurotransmission and NMDA receptor malfunction, modulators of mGluR5 receptors could be therapeutically beneficial in the treatment of various CNS diseases. Moreover, because mGluR5 receptor modulators which act through allosteric binding site have some advantages such as subtype selectivity, brain penetration and safety potential, many studies have reported that the mGluR5 positive allosteric modulators were useful for the treatment of schizophrenia and CNS diseases.

International Publication Nos. WO 2008/151184 and WO 2011/035324 disclose benzamide and O-benzyl nicotinamide derivatives as an mGluR5 positive allosteric modulator, respectively. International Publication No. WO 2010/124055 discloses 2-alkyl piperidine derivatives as an mGluR5 positive allosteric modulator, and International Publication No. WO 2011/082010 discloses tetrahydrotriazolopyridine derivative compounds. International Publication Nos. WO 2012/078817 and WO 2012/083224 disclose bicyclic pyrazole and bicyclic triazole compounds as an mGluR5 positive allosteric modulator, respectively.

SUMMARY

In an embodiment, there is provided imidazopyrimidine and imidazotriazine derivative compound as a positive allosteric modulator of metabotropic glutamate receptor subtype 5 (mGluR5) or a pharmaceutically acceptable salt thereof.

In another embodiment, there is provided a pharmaceutical composition comprising the above imidazopyrimidine and imidazotriazine derivative compound or a pharmaceutically acceptable salt thereof as an active ingredient.

The present inventors have synthesized imidazopyrimidine and imidazotriazine derivative compounds of Chemical Formula (1) and confirmed that said compounds show effective and selective effects as a positive allosteric modulator of metabotropic glutamate receptor subtype 5 (mGluR5), thereby being useful in the treatment of disorders mediated by glutamate dysfunction and mGluR5 such as schizophrenia.

DETAILED DESCRIPTION

The following description is merely exemplary in nature and is not intended to limit the present disclosure, application, or uses.

The present disclosure provides a compound of Chemical Formula (1) and a pharmaceutically acceptable salt thereof:

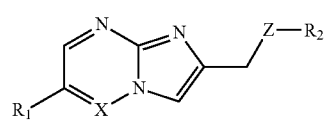

(1)

wherein
  X represents CH or N;
  Z represents O or S;
  $R_1$ represents aryl which is unsubstituted or substituted with one or more substituents selected from halo, hydroxy, alkyl, alkoxy, alkylthio, amino, dialkylamino, cyano, formyl, haloalkyl, hydroxyalkyl, alkoxyalkyl, carbamoyloxy alkyl, alkyl-C(O)O-alkyl, dialkylaminoalkyl and 5- or 6-membered heterocycloalkylalkyl in which the heterocycloalkyl has 1-3 heteroatoms selected from N, O and S; or 5- to 12-membered, unsaturated heterocyclyl having 1-5 heteroatoms selected from N, O and S, which is unsubstituted or substituted with one or more substituents selected from halo, hydroxy, alkyl, alkoxy and haloalkyl; and $R_2$ represents aryl which is unsubstituted or substituted with one or more substituents selected from halo, deuterium, hydroxy and alkyl; or 5- to 12-membered, unsaturated heterocyclyl having 1-3 heteroatoms selected from N, O and S, which is unsubstituted or substituted with one or more substituents selected from halo and alkyl.

In a particular embodiment, $R_1$ represents aryl which is unsubstituted or substituted with one or more substituents selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl, $C_1$-$C_5$ alkyl-C(O)O—$C_1$-$C_5$ alkyl, di($C_1$-$C_5$ alkyl)amino-$C_1$-$C_5$ alkyl and 5- or 6-membered heterocycloalkyl-$C_1$-$C_5$ alkyl wherein the heterocycloalkyl has 1-3 heteroatoms selected from N, O and S; or 5- to 12-membered, unsaturated heterocyclyl having 1-5 heteroatoms selected from N, O and S, which is unsubstituted or substituted with one or more substituents selected from halo, hydroxy, $C_1$-$C_5$ alkyl, $C_1$-$C_5$ alkoxy and halo-$C_1$-$C_5$ alkyl; and $R_2$ represents aryl which is unsubstituted or substituted with one or more substituents selected from halo, deuterium, hydroxy and $C_1$-$C_5$ alkyl; or 5- to 12-membered, unsaturated heterocyclyl having 1-3 heteroatoms selected from N, O and S, which is unsubstituted or substituted with one or more substituents selected from halo and $C_1$-$C_5$ alkyl.

Unless stated otherwise, herein the term "alkyl," either alone or in combination with further terms (for example, haloalkyl), means a radical of saturated aliphatic hydrocarbyl group having 1 to 5 carbon atoms, which may be linear or branched. Examples of representative alkyl group include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl and 1,2-dimethylpropyl.

Unless stated otherwise, herein the term "halo," either alone or in combination with further terms (for example, haloalkyl), means a radical of F, Cl, Br or I.

Unless stated otherwise, herein the term "heterocycloalkyl" means a 5- or 6-membered, saturated monocyclic ring having 1 to 3 heteroatoms selected from N, O and S, and preferably a 5- or 6-membered, saturated monocyclic ring having 1 or 2 heteroatoms selected from N and O. Concrete examples of heterocycloalkyl include, but are not limited to, pyrrolidinyl, piperidinyl, tetrahydrofuranyl, tetrahydropyranyl and morpholinyl.

Unless stated otherwise, herein the term "aryl" means an aromatic radical having 6 to 12 carbon atoms. Concrete examples of aryl include, but are not limited to, phenyl and naphthyl.

Unless stated otherwise, herein the term "unsaturated heterocyclyl" means a 5- or 12-membered, unsaturated monocyclic or bicyclic ring having 1 to 5 heteroatoms selected from N, O and S. Concrete examples of unsaturated heterocyclyl include, but are not limited to, 1,3-benzodioxolyl, or heteroaryl such as pyridyl, pyrimidinyl, thienyl, pyrazinyl, quinolinyl and isoquinolinyl.

According to one aspect of the present disclosure, $R_1$ is selected from the group consisting of:

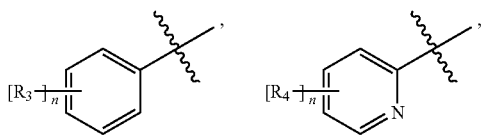

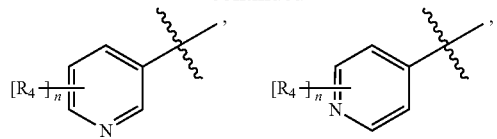

wherein n is 0, 1, 2, 3 or 4; each $R_3$ is selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl, $C_1$-$C_5$ alkyl-C(O)O—$C_1$-$C_5$ alkyl, di($C_1$-$C_5$ alkyl)amino-$C_1$-$C_5$ alkyl and 5- or 6-membered heterocycloalkyl-$C_1$-$C_5$ alkyl; and each $R_4$ is selected from halo, hydroxy, $C_1$-$C_5$ alkyl, $C_1$-$C_5$ alkoxy and halo-$C_1$-$C_5$ alkyl; and $R_2$ is selected from the group consisting of:

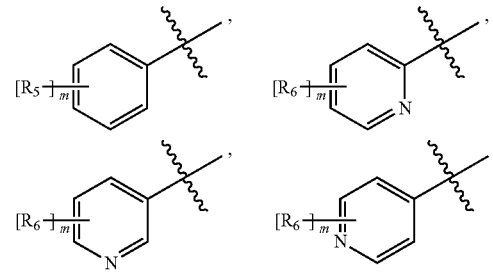

wherein m is 0, 1, 2, 3 or 4; $R_5$ is selected from halo, deuterium, hydroxy and $C_1$-$C_5$ alkyl; and $R_5$ is selected from halo and $C_1$-$C_5$ alkyl.

According to one aspect of the present disclosure, in Chemical Formula (1), $R_1$ represents phenyl which is unsubstituted or substituted with 1 to 3 substituents selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl and $C_1$-$C_5$ alkyl-C(O)O—$C_1$-$C_5$ alkyl; or 5- to 10-membered, unsaturated heterocyclyl having 1-3 heteroatoms selected from N, O and S, which is unsubstituted or substituted with 1 to 3 substituents selected from halo, hydroxy, $C_1$-$C_5$ alkyl, $C_1$-$C_5$ alkoxy and halo-$C_1$-$C_5$ alkyl.

According to another aspect of the present disclosure, in Chemical Formula (1), $R_2$ represents phenyl unsubstituted or substituted with 1 to 5 substituents selected from halo, deuterium, hydroxy and $C_1$-$C_5$ alkyl; or 5- or 6-membered heteroaryl having 1 to 3 heteroatoms selected from N, O and S, which is unsubstituted or substituted with 1 to 3 substituents selected from halo and $C_1$-$C_5$ alkyl.

According to still another aspect of the present disclosure, in Chemical Formula (1), X represents CH or N;

Z represents 0;

$R_1$ represents phenyl which is unsubstituted or substituted with 1 to 3 substituents selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl and $C_1$-$C_5$ alkyl-C(O)O—$C_1$-$C_5$ alkyl; or 5- to 9-membered, unsaturated heterocyclyl having 1 or 2 heteroatoms selected from N, O and S, which is unsubstituted or substituted with 1 or 2 substituents selected from halo, hydroxy, $C_1$-$C_5$ alkyl, $C_1$-$C_5$ alkoxy and halo-$C_1$-$C_5$ alkyl; and $R_2$ represents phenyl which is unsubstituted or substituted with 1 to 5 substituents selected from halo, deuterium, hydroxy and $C_1$-$C_5$ alkyl; or 6-membered heteroaryl having 1 or 2 nitrogen atoms, which is unsubstituted or substituted with 1 or 2 substituents selected from halo and $C_1$-$C_5$ alkyl.

According to still another aspect of the present disclosure, in Chemical Formula (1), $R_1$ represents phenyl which is unsubstituted or substituted with 1 to 3 substituents selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl and $C_1$-$C_5$ alkyl-C(O)O—$C_1$-$C_5$ alkyl; 1,3-benzodioxolyl which is unsubstituted or substituted with 1 or 2 halo; or pyridyl or pyrimidinyl which is unsubstituted or substituted with 1 or 2 substituents selected from halo, hydroxy, $C_1$-$C_5$ alkyl, $C_1$-$C_5$ alkoxy and halo-$C_1$-$C_5$ alkyl; and $R_2$ represents phenyl which is unsubstituted or substituted with 1 to 5 substituents selected from halo, deuterium, hydroxy and $C_1$-$C_5$ alkyl; or pyridyl which is unsubstituted or substituted with 1 or 2 substituents selected from halo and $C_1$-$C_5$ alkyl.

According to still another aspect of the present disclosure, in Chemical Formula (1), X represents CH;
Z represents O;
$R_1$ represents phenyl which is unsubstituted or substituted with 1 to 3 substituents selected from halo, hydroxy, $C_1$-$C_5$ alkyl, $C_1$-$C_5$ alkoxy, $C_1$-$C_5$ alkylthio, amino, halo-$C_1$-$C_5$ alkyl, hydroxy-$C_1$-$C_5$ alkyl and $C_1$-$C_5$ alkoxy-$C_1$-$C_5$ alkyl; and $R_2$ represents pyridyl which is unsubstituted or substituted with 1 or 2 substituents selected from halo and $C_1$-$C_5$ alkyl.

In an embodiment, there is provided a compound of Chemical Formula (2) or a pharmaceutically acceptable salt thereof:

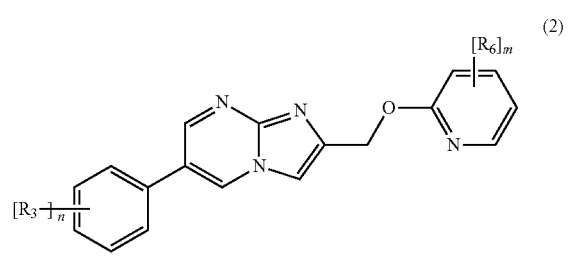

(2)

wherein n is 0, 1, 2 or 3;
each $R_3$ is independently selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl, $C_1$-$C_5$ alkyl-C(O)O—$C_1$-$C_5$ alkyl, di($C_1$-$C_5$ alkyl)amino-$C_1$-$C_5$ alkyl and 5- or 6-membered heterocycloalkyl-$C_1$-$C_5$ alkyl wherein the heterocycloalkyl has 1-3 heteroatoms selected from N, O and S;
m is 0, 1, 2 or 3; and
each $R_6$ is independently selected from halo and $C_1$-$C_5$ alkyl.

In various embodiments, n is 0, 1 or 2; each $R_3$ is selected from halo, halo-$C_1$-$C_5$ alkyl, $C_1$-$C_5$ alkyl, and hydroxy-$C_1$-$C_5$ alkyl; m is 0 or 1; and $R_6$ is halo. In a particular embodiment, n is 1 or 2; each $R_3$ is selected from fluoro, fluoromethyl, trifluoromethyl, methyl, and hydroxymethyl; m is 0 or 1; and $R_6$ is fluoro.

The compounds of Chemical Formula (1) according to the present disclosure include, but are not limited to, the following compounds:

6-(2-fluorophenyl)-2-phenoxymethylimidazo[1,2-a]pyrimidine;
2-phenoxymethyl-6-phenylimidazo[1,2-a]pyrimidine;
6-(2,4-difluorophenyl)-2-phenoxymethylimidazo[1,2-a]pyrimidine;
6-(2-methoxyphenyl)-2-phenoxymethylimidazo[1,2-a]pyrimidine;
6-(2-methylphenyl)-2-phenoxymethylimidazo[1,2-a]pyrimidine;
6-(4-fluoro-2-methylphenyl)-2-phenoxymethylimidazo[1,2-a]pyrimidine;
6-(2,3-difluorophenyl)-2-phenoxymethylimidazo[1,2-a]pyrimidine;
6-(4-fluorophenyl)-2-phenoxymethylimidazo[1,2-a]pyrimidine;
6-(3-aminophenyl)-2-phenoxymethylimidazo[1,2-a]pyrimidine;
6-(2-aminophenyl)-2-phenoxymethylimidazo[1,2-a]pyrimidine;
6-(3-amino-6-methylphenyl)-2-phenoxymethylimidazo[1,2-a]pyrimidine;
6-(3-amino-4-fluorophenyl)-2-phenoxymethylimidazo[1,2-a]pyrimidine;
6-(3-chloro-4-fluorophenyl)-2-phenoxymethylimidazo[1,2-a]pyrimidine;
6-(2-dimethylaminophenyl)-2-phenoxymethylimidazo[1,2-a]pyrimidine;
6-(2-chloro-4-fluorophenyl)-2-phenoxymethylimidazo[1,2-a]pyrimidine;
6-(2-hydroxyphenyl)-2-phenoxymethylimidazo[1,2-a]pyrimidine;
6-(3-hydroxyphenyl)-2-phenoxymethylimidazo[1,2-a]pyrimidine;
6-(4-fluoro-2-trifluoromethylphenyl)-2-phenoxymethylimidazo[1,2-a]pyrimidine;
6-(3,4-difluorophenyl)-2-phenoxymethylimidazo[1,2-a]pyrimidine;
6-(2-methoxy-4-fluorophenyl)-2-phenoxymethylimidazo[1,2-a]pyrimidine;
6-(4-fluoro-3-methoxyphenyl)-2-phenoxymethylimidazo[1,2-a]pyrimidine;
6-(4-chloro-2-methoxyphenyl)-2-phenoxymethylimidazo[1,2-a]pyrimidine;
6-(4-cyano-2-methoxyphenyl)-2-phenoxymethylimidazo[1,2-a]pyrimidine;
6-(7-fluorobenzo[1,3]dioxol-4-yl)-2-phenoxymethylimidazo[1,2-a]pyrimidine;
6-(4-fluoro-2-hydroxymethylphenyl)-2-phenoxymethylimidazo[1,2-a]pyrimidine;
6-(4-fluoro-2-methylthiophenyl)-2-phenoxymethylimidazo[1,2-a]pyrimidine;
6-(2-amino-4-fluorophenyl)-2-phenoxymethylimidazo[1,2-a]pyrimidine;
6-(2,4-difluoro-5-methoxyphenyl)-2-phenoxymethylimidazo[1,2-a]pyrimidine;
6-(2-fluoropyridin-3-yl)-2-phenoxymethylimidazo[1,2-a]pyrimidine;

6-(6-methoxypyridin-3-yl)-2-phenoxymethylimidazo[1,2-a]pyrimidine;
6-(6-fluoropyridin-3-yl)-2-phenoxymethylimidazo[1,2-a]pyrimidine;
6-(4-methylpyridin-3-yl)-2-phenoxymethylimidazo[1,2-a]pyrimidine;
6-(2,6-difluoropyridin-3-yl)-2-phenoxymethylimidazo[1,2-a]pyrimidine;
6-(6-chloropyridin-3-yl)-2-phenoxymethylimidazo[1,2-a]pyrimidine;
6-(2-fluoropyridin-4-yl)-2-phenoxymethylimidazo[1,2-a]pyrimidine;
6-(3-chloropyridin-4-yl)-2-phenoxymethylimidazo[1,2-a]pyrimidine;
6-(4-chlorophenyl)-2-phenoxymethylimidazo[1,2-a]pyrimidine;
6-(6-fluoro-4-methyl-3-pyridyl)-2-phenoxymethylimidazo[1,2-a]pyrimidine;
6-(6-fluoro-5-methyl-3-pyridyl)-2-phenoxymethylimidazo[1,2-a]pyrimidine;
6-(5-fluoro-2-pyridyl)-2-phenoxymethylimidazo[1,2-a]pyrimidine;
6-(2,4-difluorophenyl)-2-(3-fluorophenoxymethyl)imidazo[1,2-a]pyrimidine;
6-(4-fluoro-2-methoxyphenyl)-2-(3-fluorophenoxymethyl)imidazo[1,2-a]pyrimidine;
6-(4-fluoro-3-hydroxyphenyl)-2-(3-fluorophenoxymethyl)-imidazo[1,2-a]pyrimidine;
6-(2-aminophenyl)-2-(3-fluorophenoxymethyl)imidazo[1,2-a]pyrimidine;
6-(3-chloropyridin-4-yl)-2-(3-fluorophenoxymethyl)imidazo[1,2-a]pyrimidine;
6-(4-methylpyridin-3-yl)-2-(3-fluorophenoxymethyl)imidazo[1,2-a]pyrimidine;
6-(2,4-difluorophenyl)-2-(4-fluorophenoxymethyl)imidazo[1,2-a]pyrimidine;
6-(4-fluoro-2-methylphenyl)-2-(4-fluorophenoxymethyl)imidazo[1,2-a]pyrimidine;
6-(3-chloropyridin-4-yl)-2-(4-fluorophenoxymethyl)imidazo[1,2-a]pyrimidine;
6-(2,6-dimethylphenyl)-2-(4-fluorophenoxymethyl)imidazo[1,2-a]pyrimidine;
2-[(4-fluorophenoxy)methyl]-6-(6-fluoro-3-pyridyl)imidazo[1,2-a]pyrimidine;
4-[[6-(4-fluorophenyl)imidazo[1,2-a]pyrimidin-2-yl]methoxy]phenol;
2-[(4-fluorophenoxy)methyl]-6-(4-fluorophenyl)imidazo[1,2-a]pyrimidine;
2-[(3-fluorophenoxy)methyl]-6-(4-fluorophenyl)imidazo[1,2-a]pyrimidine;
2-fluoro-5-[2-[(4-fluorophenoxy)methyl]imidazo[1,2-a]pyrimidin-6-yl]phenol;
2-[(4-fluorophenoxy)methyl]-6-phenyl-imidazo[1,2-a]pyrimidine;
5-fluoro-2-[2-[(3-fluorophenoxy)methyl]imidazo[1,2-a]pyrimidin-6-yl]phenol;
5-fluoro-2-[2-[(4-fluorophenoxy)methyl]imidazo[1,2-a]pyrimidin-6-yl]phenol;
6-(4-fluorophenyl)-2-[(2,3,4,5,6-pentadeuteriophenoxy)methyl]imidazo[1,2-a]pyrimidine;
2-[(4-fluorophenoxy)methyl]6-(o-tolyl)imidazo[1,2-a]pyrimidine;
6-(5-fluoro-2-methyl-phenyl)-2-[(4-fluorophenoxy)methyl]imidazo[1,2-a]pyrimidine;
2-[(4-fluorophenoxy)methyl]-6-(2-fluoro-4-pyridyl)imidazo[1,2-a]pyrimidine;
2-[2-[(4-fluorophenoxy)methyl]imidazo[1,2-a]pyrimidin-6-yl]phenol;
6-(2-fluoro-4-methyl-phenyl)-2-[(4-fluorophenoxy)methyl]imidazo[1,2-a]pyrimidine;
2-[(4-fluorophenoxy)methyl]-6-[6-(trifluoromethyl)-3-pyridyl]imidazo[1,2-a]pyrimidine;
2-[2-[(4-fluorophenoxy)methyl]imidazo[1,2-a]pyrimidin-6-yl]aniline;
6-(2-chloro-4-fluoro-phenyl)-2-[(4-fluorophenoxy)methyl]imidazo[1,2-a]pyrimidine;
4-[2-[(4-fluorophenoxy)methyl]imidazo[1,2-a]pyrimidin-6-yl]-3-methoxy-benzonitrile;
6-(4-chloro-2-methoxy-phenyl)-2-[(4-fluorophenoxy)methyl]imidazo[1,2-a]pyrimidine;
2-fluoro-5-[2-[(4-fluorophenoxy)methyl]imidazo[1,2-a]pyrimidin-6-yl]aniline;
6-(2,6-difluoro-3-pyridyl)-2-[(3-fluorophenoxy)methyl]imidazo[1,2-a]pyrimidine;
5-[2-[(4-fluorophenoxy)methyl]imidazo[1,2-a]pyrimidin-6-yl]-2-methyl-aniline;
4,5-difluoro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-5-methyl-aniline;
5-chloro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-4-methyl-aniline;
5-fluoro-2-[2-[(4-fluorophenoxy)methyl]imidazo[1,2-a]pyrimidin-6-yl]aniline;
2-[(4-fluorophenoxy)methyl]-6-(4-methyl-3-pyridyl)imidazo[1,2-a]pyrimidine;
2-[(3-fluorophenoxy)methyl]-6-(2-fluoro-4-pyridyl)imidazo[1,2-a]pyrimidine;
2-[(3-fluorophenoxy)methyl]-6-[6-(trifluoromethyl)-3-pyridyl]imidazo[1,2-a]pyrimidine;
2-[(3-fluorophenoxy)methyl]-6-(6-fluoro-3-pyridyl)imidazo[1,2-a]pyrimidine;
2-[(3-fluorophenoxy)methyl]-6-(2-fluoro-3-pyridyl)imidazo[1,2-a]pyrimidine;
6-(5,6-difluoro-3-pyridyl)-2-[(4-fluorophenoxy)methyl]imidazo[1,2-a]pyrimidine;
5-[2-[(4-fluorophenoxy)methyl]imidazo[1,2-a]pyrimidin-6-yl]-2-methoxy-aniline;
2-[(4-fluorophenoxy)methyl]-6-(5-fluoro-2-pyridyl)imidazo[1,2-a]pyrimidine;
2-[(4-fluorophenoxy)methyl]-6-(5-methoxy-2-pyridyl)imidazo[1,2-a]pyrimidine;
6-(4-chloro-3-pyridyl)-2-[(4-fluorophenoxy)methyl]imidazo[1,2-a]pyrimidine;
6-(5-chloro-3-pyridyl)-2-[(4-fluorophenoxy)methyl]imidazo[1,2-a]pyrimidine;
2-[(4-fluorophenoxy)methyl]-6-(5-methoxy-3-pyridyl)imidazo[1,2-a]pyrimidine;
5-[2-[(4-fluorophenoxy)methyl]imidazo[1,2-a]pyrimidin-6-yl]pyridin-2-ol;
6-(6-fluoro-5-methyl-3-pyridyl)-2-[(4-fluorophenoxy)methyl]imidazo[1,2-a]pyrimidine;
2-[(4-fluorophenoxy)methyl]-6-(6-methyl-3-pyridyl)imidazo[1,2-a]pyrimidine;
2-[(3-fluorophenoxy)methyl]-6-(5-fluoro-2-pyridyl)imidazo[1,2-a]pyrimidine;
2-[(3-fluorophenoxy)methyl]-6-[4-fluoro-2-(trifluoromethyl)phenyl]imidazo[1,2-a]pyrimidine;
4-[2-[(3-fluorophenoxy)methyl]imidazo[1,2-a]pyrimidin-6-yl]-3-methoxy-benzonitrile;

[5-fluoro-2-[2-[(3-fluorophenoxy)methyl]imidazo[1,2-a]pyrimidin-6-yl]phenyl]methanol;
[5-fluoro-2-[2-[(4-fluorophenoxy)methyl]imidazo[1,2-a]pyrimidin-6-yl]phenyl]methanol;
6-(4-fluoro-2-methylsulfanyl-phenyl)-2-[(4-fluorophenoxy)methyl]imidazo[1,2-a]pyrimidine;
2-[(4-fluorophenoxy)methyl]-6-(2-methoxy-4-pyridyl)imidazo[1,2-a]pyrimidine;
2-[2-[(3-fluorophenoxy)methyl]imidazo[1,2-a]pyrimidin-6-yl]-4-methyl-aniline;
5-fluoro-2-[2-[(3-fluorophenoxy)methyl]imidazo[1,2-a]pyrimidin-6-yl]aniline;
6-(4-fluorophenyl)-2-(pyridin-2-yloxymethyl)imidazo[1,2-a]pyrimidine;
6-(2-methylphenyl)-2-(pyridin-2-yloxymethyl)imidazo[1,2-a]pyrimidine;
6-(4-fluoro-2-methoxyphenyl)-2-(pyridin-2-yloxymethyl)imidazo[1,2-a]pyrimidine;
6-(2,4-difluorophenyl)-2-(pyridin-2-yloxymethyl)imidazo[1,2-a]pyrimidine;
6-(4-fluoro-2-methylphenyl)-2-(pyridin-2-yloxymethyl)imidazo[1,2-a]pyrimidine;
6-(2,3-difluorophenyl)-2-(pyridin-2-yloxymethyl)imidazo[1,2-a]pyrimidine;
6-(5-fluoro-2-methylphenyl)-2-(pyridin-2-yloxymethyl)imidazo[1,2-a]pyrimidine;
6-(3-fluoro-2-methylphenyl)-2-(pyridin-2-yloxymethyl)imidazo[1,2-a]pyrimidine;
6-(7-fluoro-2H-benzo[1,3]dioxol-4-yl)-2-(pyridin-2-yloxymethyl)imidazo[1,2-a]pyrimidine;
6-(4-chloro-2-methoxyphenyl)-2-(pyridin-2-yloxymethyl)imidazo[1,2-a]pyrimidine;
6-(3-fluoro-2-methoxy-phenyl)-2-(2-pyridyloxymethyl)imidazo[1,2-a]pyrimidine;
6-[4-fluoro-2-(trifluoromethyl)phenyl]-2-(2-pyridyloxymethyl)imidazo[1,2-a]pyrimidine;
6-(4-fluoro-2-methyl-phenyl)-2-[(5-fluoro-2-pyridyl)oxymethyl]imidazo[1,2-a]pyrimidine;
6-(2-ethylphenyl)-2-(2-pyridyloxymethyl)imidazo[1,2-a]pyrimidine;
6-(4-fluoro-2-methyl-phenyl)-2-[(4-fluoro-2-pyridyl)oxymethyl]imidazo[1,2-a]pyrimidine;
6-(2-fluoro-4-methyl-phenyl)-2-(2-pyridyloxymethyl)imidazo[1,2-a]pyrimidine;
6-(4-fluoro-2-methoxy-phenyl)-2-[(4-fluoro-2-pyridyl)oxymethyl)imidazo[1,2-a]pyrimidine;
2-[(5-fluoro-2-pyridyl)oxymethyl]-6-[4-fluoro-2-(trifluoromethyl)phenyl]imidazo[1,2-a]pyrimidine;
6-(2,4-difluorophenyl)-2-[(4-fluoro-2-pyridyl)oxymethyl]imidazo[1,2-a]pyrimidine;
6-(3-fluoro-2-methoxy-phenyl)-2-[(4-fluoro-2-pyridyl)oxymethyl]imidazo[1,2-a]pyrimidine;
6-(2,3-difluorophenyl)-2-[(4-fluoro-2-pyridyl)oxymethyl]imidazo[1,2-a]pyrimidine;
6-(4-fluorophenyl)-2-[(4-fluoro-2-pyridyl)oxymethyl)imidazo[1,2-a]pyrimidine;
6-(3-fluoro-2-methyl-phenyl)-2-[(5-fluoro-2-pyridyl)oxymethyl]imidazo[1,2-a]pyrimidine;
2-[(4-fluoro-2-pyridyl)oxymethyl]-6-[4-fluoro-2-(trifluoromethyl)phenyl]imidazo[1,2-a]pyrimidine;
2-[(5-fluoro-2-pyridyl)oxymethyl]-6-(o-tolyl)imidazo[1,2-a]pyrimidine;
6-(4-chloro-2-methyl-phenyl)-2-[(5-fluoro-2-pyridyl)oxymethyl]imidazo[1,2-a]pyrimidine;
6-(2,4-dimethylphenyl)-2-[(5-fluoro-2-pyridyl)oxymethyl]imidazo[1,2-a]pyrimidine;
6-(4-fluorophenyl)-2-[(5-fluoro-2-pyridyl)oxymethyl)imidazo[1,2-a]pyrimidine;
2-(2-pyridyloxymethyl)-6-[6-(trifluoromethyl)-3-pyridyl]imidazo[1,2-a]pyrimidine;
2-[(5-fluoro-2-pyridyl)oxymethyl]-6-[6-(trifluoromethyl)-3-pyridyl]imidazo[1,2-a]pyrimidine;
6-(5-fluoro-2-pyridyl)-2-(2-pyridyloxymethyl)imidazo[1,2-a]pyrimidine;
2-fluoro-5-[2-[(5-fluoro-2-pyridyl)oxymethyl]imidazo[1,2-a]pyrimidin-6-yl]aniline;
2-fluoro-5-[2-(2-pyridyloxymethyl)imidazo[1,2-a]pyrimidin-6-yl]aniline;
[5-fluoro-2-[2-(2-pyridyloxymethyl)imidazo[1,2-a]pyrimidin-6-yl]phenyl]methanol;
3-methoxy-4-[2-(2-pyridyloxymethyl)imidazo[1,2-a]pyrimidin-6-yl]benzonitrile;
4-[2-[(5-fluoro-2-pyridyl)oxymethyl]imidazo[1,2-a]pyrimidin-6-yl]-3-methoxy-benzonitrile;
6-(4-fluoro-2-methylsulfanyl-phenyl)-2-(2-pyridyloxymethyl)imidazo[1,2-a]pyrimidine;
[5-fluoro-2-[2-[(5-fluoro-2-pyridyl)oxymethyl]imidazo[1,2-a]pyrimidin-6-yl]phenyl]methanol;
4-[2-(2-pyridyloxymethyl)imidazo[1,2-a]pyrimidin-6-yl]benzonitrile;
6-[4-fluoro-2-(methoxymethyl)phenyl]-2-(2-pyridyloxymethyl)imidazo[1,2-a]pyrimidine;
[2-[2-(2-pyridyloxymethyl)imidazo[1,2-a]pyrimidin-6-yl]-5-(trifluoromethyl)phenyl]methanol;
6-(2-isopropylphenyl)-2-(2-pyridyloxymethyl)imidazo[1,2-a]pyrimidine;
4-[2-(2-pyridyloxymethyl)imidazo[1,2-a]pyrimidin-6-yl]-3-(trifluoromethyl)benzaldehyde;
6-[4-chloro-2-(trifluoromethyl)phenyl]-2-(2-pyridyloxymethyl)imidazo[1,2-a]pyrimidine;
6-(4-fluorophenyl)-2-(pyridin-3-yloxymethyl)imidazo[1,2-a]pyrimidine;
6-(4-fluoro-2-methoxyphenyl)-2-(pyridin-3-yloxymethyl)imidazo[1,2-a]pyrimidine;
6-(2,4-difluorophenyl)-2-(pyridin-3-yloxymethyl)imidazo[1,2-a]pyrimidine;
6-(4-fluoro-2-methylphenyl)-2-(pyridin-3-yloxymethyl)imidazo[1,2-a]pyrimidine;
6-(4-fluoro-2-hydroxyphenyl)-2-(pyridin-3-yloxymethyl)imidazo[1,2-a]pyrimidine;
6-(4-fluoro-2-methoxyphenyl)-2-(pyridin-4-yloxymethyl)imidazo[1,2-a]pyrimidine;
6-(2,4-difluorophenyl)-2-(pyridin-4-yloxymethyl)imidazo[1,2-a]pyrimidine;
6-(2-methylphenyl)-2-(5-fluoro-pyridin-3-yloxymethyl)imidazo[1,2-a]pyrimidine;
6-(4-fluoro-2-methylphenyl)-2-(5-fluoro-pyridin-3-yloxymethyl)imidazo[1,2-a]pyrimidine;
6-(4-fluoro-2-methoxyphenyl)-2-(5-fluoropyridin-3-yloxymethyl)imidazo[1,2-a]pyrimidine;
6-(4-fluoro-2-hydroxyphenyl)-2-(5-fluoropyridin-3-yloxymethyl)imidazo[1,2-a]pyrimidine;
6-(2,4-difluorophenyl)-2-(6-fluoropyridin-3-yloxymethyl)imidazo[1,2-a]pyrimidine;
6-(4-fluoro-2-methylphenyl)-2-(6-fluoropyridin-3-yloxymethyl)imidazo[1,2-a]pyrimidine;
6-(4-fluoro-2-methylphenyl)-2-(2-fluoropyridin-3-yloxymethyl)imidazo[1,2-a]pyrimidine;
6-(4-fluoro-2-methylphenyl)-2-(5-chloropyridin-3-yloxymethyl)imidazo[1,2-a]pyrimidine;
6-(2,4-difluorophenyl)-2-(2-fluoropyridin-4-yloxymethyl)imidazo[1,2-a]pyrimidine;

6-(4-fluoro-2-methylphenyl)-2-(2-fluoropyridin-4-yloxymethyl)imidazo[1,2-a]pyrimidine;
6-(4-fluoro-2-methoxyphenyl)-2-(2-fluoropyridin-4-yloxymethyl)imidazo[1,2-a]pyrimidine;
6-(4-fluorophenyl)-2-(2-fluoropyridin-4-yloxymethyl)imidazo[1,2-a]pyrimidine;
6-(2,3-difluorophenyl)-2-(2-fluoropyridin-4-yloxymethyl)imidazo[1,2-a]pyrimidine;
6-(2-fluorophenyl)-2-(2-fluoropyridin-4-yloxymethyl)imidazo[1,2-a]pyrimidine;
6-(4-fluoro-2-hydroxyphenyl)-2-(2-fluoropyridin-4-yloxymethyl)imidazo[1,2-a]pyrimidine;
6-(2-methylphenyl)-2-(2-fluoropyridin-4-yloxymethyl)imidazo[1,2-a]pyrimidine;
6-(2-hydroxyphenyl)-2-(2-fluoropyridin-4-yloxymethyl)imidazo[1,2-a]pyrimidine;
6-(4-fluoro-2-hydroxymethylphenyl)-2-(2-fluoropyridin-4-yloxymethyl)imidazo[1,2-a]pyrimidine;
6-(4-fluorophenyl)-2-[(5-fluoro-3-pyridyl)oxymethyl)imidazo[1,2-a]pyrimidine;
2-[(2-chloro-4-pyridyl)oxymethyl]-6-(4-fluorophenyl)imidazo[1,2-a]pyrimidine;
2-[(5-fluoro-3-pyridyl)oxymethyl]-6-[4-fluoro-2-(trifluoromethyl)phenyl]imidazo[1,2-a]pyrimidine;
2-[(2-fluoro-4-pyridyl)oxymethyl]-6-[4-fluoro-2-(trifluoromethyl)phenyl]imidazo[1,2-a]pyrimidine;
5-fluoro-2-[2-[(5-fluoro-3-pyridyl)oxymethyl]imidazo[1,2-a]pyrimidin-6-yl]aniline;
5-fluoro-2-[2-[(2-fluoro-4-pyridyl)oxymethyl]imidazo[1,2-a]pyrimidin-6-yl]aniline;
[5-fluoro-2-[2-[(5-fluoro-3-pyridyl)oxymethyl]imidazo[1,2-a]pyrimidin-6-yl]phenyl]methanol;
2-(2,4-difluorophenyl)-6-(phenoxymethyl)imidazo[1,2-b][1,2,4]triazine;
2-(2,4-difluorophenyl)-6-((pyridin-4-yloxy)methyl)imidazo[1,2-b][1,2,4]triazine;
2-(2,4-difluorophenyl)-6-((pyridin-2-yloxy)methyl)imidazo[1,2-b][1,2,4]triazine;
2-(4-fluorophenyl)-6-((pyridin-4-yloxy)methyl)imidazo[1,2-b][1,2,4]triazine;
2-(2-methylphenyl)-6-((pyridin-4-yloxy)methyl)imidazo[1,2-b][1,2,4]triazine;
2-(2,4-difluorophenyl)-6-((2-fluoropyridin-4-yloxy)methyl)imidazo[1,2-b][1,2,4]triazine;
2-(4-fluoro-2-methylphenyl)-64(2-fluoropyridin-4-yloxy)methyl)imidazo[1,2-b][1,2,4]triazine;
2-(2-methylphenyl)-6-((2-fluoropyridin-4-yloxy)methyl)imidazo[1,2-b][1,2,4]triazine;
2-[4-fluoro-2-(trifluoromethyl)phenyl]-6-(2-pyridyloxymethyl)imidazo[1,2-b][1,2,4]triazine;
2-(3-fluoro-2-methyl-phenyl)-6-(2-pyridyloxymethyl)imidazo[1,2-b][1,2,4]triazine;
2-(4-fluoro-2-methyl-phenyl)-6-(2-pyridyloxymethyl)imidazo[1,2-b][1,2,4]triazine;
2-[4-chloro-2-(trifluoromethyl)phenyl]-6-(2-pyridyloxymethyl)imidazo[1,2-b][1,2,4]triazine;
2-(4-chloro-2-methyl-phenyl)-6-(2-pyridyloxymethyl)imidazo[1,2-b][1,2,4]triazine;
2-(4-fluoro-2-methyl-phenyl)-6-(2-pyridyloxymethyl)imidazo[1,2-b][1,2,4]triazine;
2-(4-fluoro-2-methyl-phenyl)-6-[(5-fluoro-2-pyridyl)oxymethyl]imidazo[1,2-b][1,2,4]triazine;
[5-fluoro-2-[2-[(4-fluorophenoxy)methyl]imidazo[1,2-a]pyrimidin-6-yl]phenyl]methyl carbamate;
[5-fluoro-2-[2-(phenoxymethyl)imidazo[1,2-a]pyrimidin-6-yl]phenyl]methyl carbamate;
[5-fluoro-2-[2-(2-pyridyloxymethyl)imidazo[1,2-a]pyrimidin-6-yl]phenyl]methyl carbamate;
[5-fluoro-2-[2-(2-pyridyloxymethyl)imidazo[1,2-a]pyrimidin-6-yl]phenyl]methyl acetate;
6[2-(chloromethyl)-4-fluoro-phenyl]-2-[(4-fluorophenoxy)methyl)imidazo[1,2-a]pyrimidine;
6-[4-fluoro-2-(fluoromethyl)phenyl]-2-(2-pyridyloxymethyl)imidazo[1,2-a]pyrimidine; and
6-[4-fluoro-2-(fluoromethyl)phenyl]-2-[(4-fluorophenoxy)methyl]imidazo[1,2-a]pyrimidine.

In various embodiments, $R_1$ and $R_2$ are optionally substituted phenyl and such compounds include, but are not limited to, the following compounds:
6-(2-fluorophenyl)-2-phenoxymethylimidazo[1,2-a]pyrimidine;
phenoxymethyl-6-phenylimidazo[1,2-a]pyrimidine;
6-(2,4-difluorophenyl)-2-phenoxymethylimidazo[1,2-a]pyrimidine;
6-(2-methoxyphenyl)-2-phenoxymethylimidazo[1,2-a]pyrimidine;
6-(2-methylphenyl)-2-phenoxymethylimidazo[1,2-a]pyrimidine;
6-(4-fluoro-2-methylphenyl)-2-phenoxymethylimidazo[1,2-a]pyrimidine;
6-(2,3-difluorophenyl)-2-phenoxymethylimidazo[1,2-a]pyrimidine;
6-(4-fluorophenyl)-2-phenoxymethylimidazo[1,2-a]pyrimidine;
6-(3-aminophenyl)-2-phenoxymethylimidazo[1,2-a]pyrimidine;
6-(2-aminophenyl)-2-phenoxymethylimidazo[1,2-a]pyrimidine;
6-(3-amino-6-methylphenyl)-2-phenoxymethylimidazo[1,2-a]pyrimidine;
6-(3-amino-4-fluorophenyl)-2-phenoxymethylimidazo[1,2-a]pyrimidine;
6-(3-chloro-4-fluorophenyl)-2-phenoxymethylimidazo[1,2-a]pyrimidine;
6-(2-dimethylaminophenyl)-2-phenoxymethylimidazo[1,2-a]pyrimidine;
6-(2-chloro-4-fluorophenyl)-2-phenoxymethylimidazo[1,2-a]pyrimidine;
6-(2-hydroxyphenyl)-2-phenoxymethylimidazo[1,2-a]pyrimidine;
6-(3-hydroxyphenyl)-2-phenoxymethylimidazo[1,2-a]pyrimidine;
6-(4-fluoro-2-trifluoromethylphenyl)-2-phenoxymethylimidazo[1,2-a]pyrimidine;
6-(3,4-difluorophenyl)-2-phenoxymethylimidazo[1,2-a]pyrimidine;
6-(2-methoxy-4-fluorophenyl)-2-phenoxymethylimidazo[1,2-a]pyrimidine;
6-(4-fluoro-3-methoxyphenyl)-2-phenoxymethylimidazo[1,2-a]pyrimidine;
6-(4-chloro-2-methoxyphenyl)-2-phenoxymethylimidazo[1,2-a]pyrimidine;
6-(4-cyano-2-methoxyphenyl)-2-phenoxymethylimidazo[1,2-a]pyrimidine;
6-(7-fluorobenzo[1,3]dioxol-4-yl)-2-phenoxymethylimidazo[1,2-a]pyrimidine;
6-(4-fluoro-2-hydroxymethylphenyl)-2-phenoxymethylimidazo[1,2-a]pyrimidine;
6-(4-fluoro-2-methylthiophenyl)-2-phenoxymethylimidazo[1,2-a]pyrimidine;
6-(2-amino-4-fluorophenyl)-2-phenoxymethylimidazo[1,2-a]pyrimidine;

6-(2,4-difluoro-5-methoxyphenyl)-2-phenoxymethylimidazo[1,2-a]pyrimidine;
6-(4-chlorophenyl)-2-phenoxymethylimidazo[1,2-a]pyrimidine;
6-(2,4-difluorophenyl)-2-(3-fluorophenoxymethyl)imidazo[1,2-a]pyrimidine;
6-(4-fluoro-2-methoxyphenyl)-2-(3-fluorophenoxymethyl)imidazo[1,2-a]pyrimidine;
6-(4-fluoro-3-hydroxyphenyl)-2-(3-fluorophenoxymethyl)imidazo[1,2-a]pyrimidine;
6-(2-aminophenyl)-2-(3-fluorophenoxymethyl)imidazo[1,2-a]pyrimidine;
6-(2,4-difluorophenyl)-2-(4-fluorophenoxymethyl)imidazo[1,2-a]pyrimidine;
6-(4-fluoro-2-methylphenyl)-2-(4-fluorophenoxymethyl)imidazo[1,2-a]pyrimidine;
6-(2,6-dimethylphenyl)-2-(4-fluorophenoxymethyl)imidazo[1,2-a]pyrimidine;
4-[[6-(4-fluorophenyl)imidazo[1,2-a]pyrimidin-2-yl]methoxy]phenol;
2-[(4-fluorophenoxy)methyl]-6-(4-fluorophenyl)imidazo[1,2-a]pyrimidine;
2-[(3-fluorophenoxy)methyl]-6-(4-fluorophenyl)imidazo[1,2-a]pyrimidine;
2-fluoro-5-[2-[(4-fluorophenoxy)methyl]imidazo[1,2-a]pyrimidin-6-yl]phenol;
2-[(4-fluorophenoxy)methyl]-6-phenyl-imidazo[1,2-a]pyrimidine;
5-fluoro-2-[2-[(3-fluorophenoxy)methyl]imidazo[1,2-a]pyrimidin-6-yl]phenol;
5-fluoro-2-[2-[(4-fluorophenoxy)methyl]imidazo[1,2-a]pyrimidin-6-yl]phenol;
6-(4-fluorophenyl)-2-[(2,3,4,5,6-pentadeuteriophenoxy)methyl]imidazo[1,2-a]pyrimidine;
2-[(4-fluorophenoxy)methyl]6-(o-tolyl)imidazo[1,2-a]pyrimidine;
6-(5-fluoro-2-methyl-phenyl)-2-[(4-fluorophenoxy)methyl]imidazo[1,2-a]pyrimidine;
2-[2-[(4-fluorophenoxy)methyl]imidazo[1,2-a]pyrimidin-6-yl]phenol;
6-(2-fluoro-4-methyl-phenyl)-2-[(4-fluorophenoxy)methyl]imidazo[1,2-a]pyrimidine;
2-[2-[(4-fluorophenoxy)methyl]imidazo[1,2-a]pyrimidin-6-yl]aniline;
6-(2-chloro-4-fluoro-phenyl)-2-[(4-fluorophenoxy)methyl]imidazo[1,2-a]pyrimidine; 4-[2-[(4-fluorophenoxy)methyl]imidazo[1,2-a]pyrimidin-6-yl]-3-methoxy-benzonitrile;
6-(4-chloro-2-methoxy-phenyl)-2-[(4-fluorophenoxy)methyl]imidazo[1,2-a]pyrimidine;
2-fluoro-5-[2-[(4-fluorophenoxy)methyl]imidazo[1,2-a]pyrimidin-6-yl]aniline;
5-[2-[(4-fluorophenoxy)methyl]imidazo[1,2-a]pyrimidin-6-yl]-2-methyl-aniline;
4,5-difluoro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-5-methyl-aniline;
5-chloro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-4-methyl-aniline;
5-fluoro-2-[2-[(4-fluorophenoxy)methyl]imidazo[1,2-a]pyrimidin-6-yl]aniline;
5-[2-[(4-fluorophenoxy)methyl]imidazo[1,2-a]pyrimidin-6-yl]-2-methoxy-aniline;
2-[(3-fluorophenoxy)methyl]-6-[4-fluoro-2-(trifluoromethyl)phenyl]imidazo[1,2-a]pyrimidine;
4-[2-[(3-fluorophenoxy)methyl]imidazo[1,2-a]pyrimidin-6-yl]-3-methoxy-benzonitrile;
[5-fluoro-2-[2-[(3-fluorophenoxy)methyl]imidazo[1,2-a]pyrimidin-6-yl]phenyl]methanol;
[5-fluoro-2-[2-[(4-fluorophenoxy)methyl]imidazo[1,2-a]pyrimidin-6-yl]phenyl]methanol;
6-(4-fluoro-2-methylsulfanyl-phenyl)-2-[(4-fluorophenoxy)methyl]imidazo[1,2-a]pyrimidine;
2-[2-[(3-fluorophenoxy)methyl]imidazo[1,2-a]pyrimidin-6-yl]-4-methyl-aniline;
5-fluoro-2-[2-[(3-fluorophenoxy)methyl]imidazo[1,2-a]pyrimidin-6-yl]aniline;
2-(2,4-difluorophenyl)-6-(phenoxymethyl)imidazo[1,2-b][1,2,4]triazine;
[5-fluoro-2-[2-[(4-fluorophenoxy)methyl]imidazo[1,2-a]pyrimidin-6-yl]phenyl]methyl carbamate;
[5-fluoro-2-[2-(phenoxymethyl)imidazo[1,2-a]pyrimidin-6-yl]phenyl]methyl carbamate
6-[2-(chloromethyl)-4-fluoro-phenyl]-2-[(4-fluorophenoxy)methyl)imidazo[1,2-a]pyrimidine; and
6-[4-fluoro-2-(fluoromethyl)phenyl]-2-[(4-fluorophenoxy)methyl]imidazo[1,2-a]pyrimidine.

In various embodiments, $R_1$ is optionally substituted pyridinyl and $R_2$ is optionally substituted phenyl, and such compounds include, but are not limited to, the following compounds:

6-(2-fluoropyridin-3-yl)-2-phenoxymethylimidazo[1,2-a]pyrimidine;
6-(6-methoxypyridin-3-yl)-2-phenoxymethylimidazo[1,2-a]pyrimidine;
6-(6-fluoropyridin-3-yl)-2-phenoxymethylimidazo[1,2-a]pyrimidine;
6-(4-methylpyridin-3-yl)-2-phenoxymethylimidazo[1,2-a]pyrimidine;
6-(2,6-difluoropyridin-3-yl)-2-phenoxymethylimidazo[1,2-a]pyrimidine;
6-(6-chloropyridin-3-yl)-2-phenoxymethylimidazo[1,2-a]pyrimidine;
6-(2-fluoropyridin-4-yl)-2-phenoxymethylimidazo[1,2-a]pyrimidine;
6-(3-chloropyridin-4-yl)-2-phenoxymethylimidazo[1,2-a]pyrimidine;
6-(6-fluoro-4-methyl-3-pyridyl)-2-phenoxymethylimidazo[1,2-a]pyrimidine;
6-(6-fluoro-5-methyl-3-pyridyl)-2-phenoxymethylimidazo[1,2-a]pyrimidine;
6-(5-fluoro-2-pyridyl)-2-phenoxymethylimidazo[1,2-a]pyrimidine;
6-(3-chloropyridin-4-yl)-2-(3-fluorophenoxymethyl)imidazo[1,2-a]pyrimidine;
6-(4-methylpyridin-3-yl)-2-(3-fluorophenoxymethyl)imidazo[1,2-a]pyrimidine;
6-(3-chloropyridin-4-yl)-2-(4-fluorophenoxymethyl)imidazo[1,2-a]pyrimidine;
2-[(4-fluorophenoxy)methyl]-6-(6-fluoro-3-pyridyl)imidazo[1,2-a]pyrimidine;
2-[(4-fluorophenoxy)methyl]-6-(2-fluoro-4-pyridyl)imidazo[1,2-a]pyrimidine;
2-[(4-fluorophenoxy)methyl]-6-[6-(trifluoromethyl)-3-pyridyl]imidazo[1,2-a]pyrimidine;
6-(2,6-difluoro-3-pyridyl)-2-[(3-fluorophenoxy)methyl]imidazo[1,2-a]pyrimidine;
2-[(4-fluorophenoxy)methyl]-6-(4-methyl-3-pyridyl)imidazo[1,2-a]pyrimidine;

2-[(3-fluorophenoxy)methyl]-6-(2-fluoro-4-pyridyl)imidazo[1,2-a]pyrimidine;
2-[(3-fluorophenoxy)methyl]-6-[6-(trifluoromethyl)-3-pyridyl]imidazo[1,2-a]pyrimidine;
2-[(3-fluorophenoxy)methyl]-6-(6-fluoro-3-pyridyl)imidazo[1,2-a]pyrimidine;
2-[(3-fluorophenoxy)methyl]-6-(2-fluoro-3-pyridyl)imidazo[1,2-a]pyrimidine;
6-(5,6-difluoro-3-pyridyl)-2-[(4-fluorophenoxy)methyl]imidazo[1,2-a]pyrimidine;
2-[(4-fluorophenoxy)methyl]-6-(5-fluoro-2-pyridyl)imidazo[1,2-a]pyrimidine;
2-[(4-fluorophenoxy)methyl]-6-(5-methoxy-2-pyridyl)imidazo[1,2-a]pyrimidine;
6-(4-chloro-3-pyridyl)-2-[(4-fluorophenoxy)methyl]imidazo[1,2-a]pyrimidine;
6-(5-chloro-3-pyridyl)-2-[(4-fluorophenoxy)methyl]imidazo[1,2-a]pyrimidine;
2-[(4-fluorophenoxy)methyl]-6-(5-methoxy-3-pyridyl)imidazo[1,2-a]pyrimidine;
5-[2-[(4-fluorophenoxy)methyl]imidazo[1,2-a]pyrimidin-6-yl]pyridin-2-ol;
6-(6-fluoro-5-methyl-3-pyridyl)-2-[(4-fluorophenoxy)methyl]imidazo[1,2-a]pyrimidine;
2-[(4-fluorophenoxy)methyl]-6-(6-methyl-3-pyridyl)imidazo[1,2-a]pyrimidine;
2-[(3-fluorophenoxy)methyl]-6-(5-fluoro-2-pyridyl)imidazo[1,2-a]pyrimidine; and
2-[(4-fluorophenoxy)methyl]-6-(2-methoxy-4-pyridyl)imidazo[1,2-a]pyrimidine.

In various embodiments, $R_1$ is optionally substituted phenyl and $R_2$ is optionally substituted pyridinyl, and such compounds include, but are not limited to, the following compounds:
6-(4-fluorophenyl)-2-(pyridin-2-yloxymethyl)imidazo[1,2-a]pyrimidine;
6-(2-methylphenyl)-2-(pyridin-2-yloxymethyl)imidazo[1,2-a]pyrimidine;
6-(4-fluoro-2-methoxyphenyl)-2-(pyridin-2-yloxymethyl)imidazo[1,2-a]pyrimidine;
6-(2,4-difluorophenyl)-2-(pyridin-2-yloxymethyl)imidazo[1,2-a]pyrimidine;
6-(4-fluoro-2-methylphenyl)-2-(pyridin-2-yloxymethyl)imidazo[1,2-a]pyrimidine;
6-(2,3-difluorophenyl)-2-(pyridin-2-yloxymethyl)imidazo[1,2-a]pyrimidine;
6-(5-fluoro-2-methylphenyl)-2-(pyridin-2-yloxymethyl)imidazo[1,2-a]pyrimidine;
6-(3-fluoro-2-methylphenyl)-2-(pyridin-2-yloxymethyl)imidazo[1,2-a]pyrimidine;
6-(7-fluoro-2H-benzo[1,3]dioxol-4-yl)-2-(pyridin-2-yloxymethyl)imidazo[1,2-a]pyrimidine;
6-(4-chloro-2-methoxyphenyl)-2-(pyridin-2-yloxymethyl)imidazo[1,2-a]pyrimidine;
6-(3-fluoro-2-methoxy-phenyl)-2-(2-pyridyloxymethyl)imidazo[1,2-a]pyrimidine;
6-[4-fluoro-2-(trifluoromethyl)phenyl]-2-(2-pyridyloxymethyl)imidazo[1,2-a]pyrimidine;
6-(4-fluoro-2-methyl-phenyl)-2-[(5-fluoro-2-pyridyl)oxymethyl]imidazo[1,2-a]pyrimidine;
6-(2-ethylphenyl)-2-(2-pyridyloxymethyl)imidazo[1,2-a]pyrimidine;
6-(4-fluoro-2-methyl-phenyl)-2-[(4-fluoro-2-pyridyl)oxymethyl]imidazo[1,2-a]pyrimidine;
6-(2-fluoro-4-methyl-phenyl)-2-(2-pyridyloxymethyl)imidazo[1,2-a]pyrimidine;
6-(4-fluoro-2-methoxy-phenyl)-2-[(4-fluoro-2-pyridyl)oxymethyl]imidazo[1,2-a]pyrimidine;
2-[(5-fluoro-2-pyridyl)oxymethyl]-6-[4-fluoro-2-(trifluoromethyl)phenyl]imidazo[1,2-a]pyrimidine;
6-(2,4-difluorophenyl)-2-[(4-fluoro-2-pyridyl)oxymethyl]imidazo[1,2-a]pyrimidine;
6-(3-fluoro-2-methoxy-phenyl)-2-[(4-fluoro-2-pyridyl)oxymethyl]imidazo[1,2-a]pyrimidine;
6-(2,3-difluorophenyl)-2-[(4-fluoro-2-pyridyl)oxymethyl]imidazo[1,2-a]pyrimidine;
6-(4-fluorophenyl)-2-[(4-fluoro-2-pyridyl)oxymethyl]imidazo[1,2-a]pyrimidine;
6-(3-fluoro-2-methyl-phenyl)-2-[(5-fluoro-2-pyridyl)oxymethyl]imidazo[1,2-a]pyrimidine;
2-[(4-fluoro-2-pyridyl)oxymethyl]-6-[4-fluoro-2-(trifluoromethyl)phenyl]imidazo[1,2-a]pyrimidine;
2-[(5-fluoro-2-pyridyl)oxymethyl]-6-(o-tolyl)imidazo[1,2-a]pyrimidine;
6-(4-chloro-2-methyl-phenyl)-2-[(5-fluoro-2-pyridyl)oxymethyl]imidazo[1,2-a]pyrimidine;
6-(2,4-dimethylphenyl)-2-[(5-fluoro-2-pyridyl)oxymethyl]imidazo[1,2-a]pyrimidine;
6-(4-fluorophenyl)-2-[(5-fluoro-2-pyridyl)oxymethyl]imidazo[1,2-a]pyrimidine;
2-fluoro-5-[2-[(5-fluoro-2-pyridyl)oxymethyl]imidazo[1,2-a]pyrimidin-6-yl]aniline;
2-fluoro-5-[2-(2-pyridyloxymethyl)imidazo[1,2-a]pyrimidin-6-yl]aniline;
[5-fluoro-2-[2-(2-pyridyloxymethyl)imidazo[1,2-a]pyrimidin-6-yl]phenyl]methanol;
3-methoxy-4-[2-(2-pyridyloxymethyl)imidazo[1,2-a]pyrimidin-6-yl]benzonitrile;
4-[2-[(5-fluoro-2-pyridyl)oxymethyl]imidazo[1,2-a]pyrimidin-6-yl]-3-methoxy-benzonitrile;
6-(4-fluoro-2-methylsulfanyl-phenyl)-2-(2-pyridyloxymethyl)imidazo[1,2-a]pyrimidine;
[5-fluoro-2-[2-[(5-fluoro-2-pyridyl)oxymethyl]imidazo[1,2-a]pyrimidin-6-yl]phenyl]methanol;
4-[2-(2-pyridyloxymethyl)imidazo[1,2-a]pyrimidin-6-yl]benzonitrile;
6-[4-fluoro-2-(methoxymethyl)phenyl]-2-(2-pyridyloxymethyl)imidazo[1,2-a]pyrimidine;
[2-[2-(2-pyridyloxymethyl)imidazo[1,2-a]pyrimidin-6-yl]-5-(trifluoromethyl)phenyl]methanol;
6-(2-isopropylphenyl)-2-(2-pyridyloxymethyl)imidazo[1,2-a]pyrimidine; 4-[2-(2-pyridyloxymethyl)imidazo[1,2-a]pyrimidin-6-yl]-3-(trifluoromethyl)benzaldehyde;
6-[4-chloro-2-(trifluoromethyl)phenyl]-2-(2-pyridyloxymethyl)imidazo[1,2-a]pyrimidine;
6-(4-fluorophenyl)-2-(pyridin-3-yloxymethyl)imidazo[1,2-a]pyrimidine;
6-(4-fluoro-2-methoxyphenyl)-2-(pyridin-3-yloxymethyl)imidazo[1,2-a]pyrimidine;
6-(2,4-difluorophenyl)-2-(pyridin-3-yloxymethyl)imidazo[1,2-a]pyrimidine;
6-(4-fluoro-2-methylphenyl)-2-(pyridin-3-yloxymethyl)imidazo[1,2-a]pyrimidine;
6-(4-fluoro-2-hydroxyphenyl)-2-(pyridin-3-yloxymethyl)imidazo[1,2-a]pyrimidine;
6-(4-fluoro-2-methoxyphenyl)-2-(pyridin-4-yloxymethyl)imidazo[1,2-a]pyrimidine;
6-(2,4-difluorophenyl)-2-(pyridin-4-yloxymethyl)imidazo[1,2-a]pyrimidine;
6-(2-methylphenyl)-2-(5-fluoro-pyridin-3-yloxymethyl)imidazo[1,2-a]pyrimidine;
6-(4-fluoro-2-methylphenyl)-2-(5-fluoro-pyridin-3-yloxymethyl)imidazo[1,2-a]pyrimidine;

6-(4-fluoro-2-methoxyphenyl)-2-(5-fluoropyridin-3-yloxymethyl)imidazo[1,2-a]pyrimidine;
6-(4-fluoro-2-hydroxyphenyl)-2-(5-fluoropyridin-3-yloxymethyl)imidazo[1,2-a]pyrimidine;
6-(2,4-difluorophenyl)-2-(6-fluoropyridin-3-yloxymethyl)imidazo[1,2-a]pyrimidine;
6-(4-fluoro-2-methylphenyl)-2-(6-fluoropyridin-3-yloxymethyl)imidazo[1,2-a]pyrimidine;
6-(4-fluoro-2-methylphenyl)-2-(2-fluoropyridin-3-yloxymethyl)imidazo[1,2-a]pyrimidine;
6-(4-fluoro-2-methylphenyl)-2-(5-chloropyridin-3-yloxymethyl)imidazo[1,2-a]pyrimidine;
6-(2,4-difluorophenyl)-2-(2-fluoropyridin-4-yloxymethyl)imidazo[1,2-a]pyrimidine;
6-(4-fluoro-2-methylphenyl)-2-(2-fluoropyridin-4-yloxymethyl)imidazo[1,2-a]pyrimidine;
6-(4-fluoro-2-methoxyphenyl)-2-(2-fluoropyridin-4-yloxymethyl)imidazo[1,2-a]pyrimidine;
6-(4-fluorophenyl)-2-(2-fluoropyridin-4-yloxymethyl)imidazo[1,2-a]pyrimidine;
6-(2,3-difluorophenyl)-2-(2-fluoropyridin-4-yloxymethyl)imidazo[1,2-a]pyrimidine;
6-(2-fluorophenyl)-2-(2-fluoropyridin-4-yloxymethyl)imidazo[1,2-a]pyrimidine;
6-(4-fluoro-2-hydroxyphenyl)-2-(2-fluoropyridin-4-yloxymethyl)imidazo[1,2-a]pyrimidine;
6-(2-methylphenyl)-2-(2-fluoropyridin-4-yloxymethyl)imidazo[1,2-a]pyrimidine;
6-(2-hydroxyphenyl)-2-(2-fluoropyridin-4-yloxymethyl)imidazo[1,2-a]pyrimidine;
6-(4-fluoro-2-hydroxymethylphenyl)-2-(2-fluoropyridin-4-yloxymethyl)imidazo[1,2-a]pyrimidine;
6-(4-fluorophenyl)-2-[(5-fluoro-3-pyridyl)oxymethyl)imidazo[1,2-a]pyrimidine;
2-[(2-chloro-4-pyridyl)oxymethyl]-6-(4-fluorophenyl)imidazo[1,2-a]pyrimidine;
2-[(5-fluoro-3-pyridyl)oxymethyl]-6-[4-fluoro-2-(trifluoromethyl)phenyl]imidazo[1,2-a]pyrimidine;
2-[(2-fluoro-4-pyridyl)oxymethyl]-6-[4-fluoro-2-(trifluoromethyl)phenyl]imidazo[1,2-a]pyrimidine;
5-fluoro-2-[2-[(5-fluoro-3-pyridyl)oxymethyl]imidazo[1,2-a]pyrimidin-6-yl]aniline;
5-fluoro-2-[2-[(2-fluoro-4-pyridyl)oxymethyl]imidazo[1,2-a]pyrimidin-6-yl]aniline;
[5-fluoro-2-[2-[(5-fluoro-3-pyridyl)oxymethyl]imidazo[1,2-a]pyrimidin-6-yl]phenyl]methanol;
2-(2,4-difluorophenyl)-6-((pyridin-4-yloxy)methyl)imidazo[1,2-b][1,2,4]triazine;
2-(2,4-difluorophenyl)-6-((pyridin-2-yloxy)methyl)imidazo[1,2-b][1,2,4]triazine;
2-(4-fluorophenyl)-6-((pyridin-4-yloxy)methyl)imidazo[1,2-b][1,2,4]triazine;
2-(2-methylphenyl)-6-((pyridin-4-yloxy)methyl)imidazo[1,2-b][1,2,4]triazine;
2-(2,4-difluorophenyl)-64(2-fluoropyridin-4-yloxy)methyl)imidazo[1,2-b][1,2,4]triazine;
2-(4-fluoro-2-methylphenyl)-6-((2-fluoropyridin-4-yloxy)methyl)imidazo[1,2-b][1,2,4]triazine;
2-(2-methylphenyl)-6-((2-fluoropyridin-4-yloxy)methyl)imidazo[1,2-b][1,2,4]triazine;
2-[4-fluoro-2-(trifluoromethyl)phenyl]-6-(2-pyridyloxymethyl)imidazo[1,2-b][1,2,4]triazine;
2-(3-fluoro-2-methyl-phenyl)-6-(2-pyridyloxymethyl)imidazo[1,2-b][1,2,4]triazine;
2-(4-fluoro-2-methyl-phenyl)-6-(2-pyridyloxymethyl)imidazo[1,2-b][1,2,4]triazine;
2-[4-chloro-2-(trifluoromethyl)phenyl]-6-(2-pyridyloxymethyl)imidazo[1,2-b][1,2,4]triazine;
2-(4-chloro-2-methyl-phenyl)-6-(2-pyridyloxymethyl)imidazo[1,2-b][1,2,4]triazine;
2-(4-fluoro-2-methyl-phenyl)-6-(2-pyridyloxymethyl)imidazo[1,2-b][1,2,4]triazine;
2-(4-fluoro-2-methyl-phenyl)-6-[(5-fluoro-2-pyridyl)oxymethyl]imidazo[1,2-b][1,2,4]triazine;
[5-fluoro-2-[2-(2-pyridyloxymethyl)imidazo[1,2-a]pyrimidin-6-yl]phenyl]methyl carbamate;
[5-fluoro-2-[2-(2-pyridyloxymethyl)imidazo[1,2-a]pyrimidin-6-yl]phenyl]methyl acetate; and
6-[4-fluoro-2-(fluoromethyl)phenyl]-2-(2-pyridyloxymethyl)imidazo[1,2-a]pyrimidine.

In various embodiments, both $R_1$ and $R_2$ are optionally substituted pyridinyl, and such compounds include, but are not limited to, the following compounds:
2-(2-pyridyloxymethyl)-6-[6-(trifluoromethyl)-3-pyridyl]imidazo[1,2-a]pyrimidine;
2-[(5-fluoro-2-pyridyl)oxymethyl]-6-[6-(trifluoromethyl)-3-pyridyl]imidazo[1,2-a]pyrimidine; and
6-(5-fluoro-2-pyridyl)-2-(2-pyridyloxymethyl)imidazo[1,2-a]pyrimidine.

As described herein, it is confirmed that the compounds of Chemical Formula (1) are effective as a positive allosteric modulator of metabotropic glutamate receptor subtype 5 (mGluR5 PAM). Also, they have selective activity as a positive allosteric modulator of mGluR5 PAM. Such medicinal effects of the compounds of Chemical Formula (1) can be maintained in the form of pharmaceutically acceptable salts.

Therefore, in still another aspect of the present disclosure, there is provided a pharmaceutical composition for the prevention or treatment of disorder mediated by glutamate dysfunction and metabotropic glutamate receptor subtype 5 (mGluR5) comprising a therapeutically effective amount of the compound of Chemical Formula (1) or a pharmaceutically acceptable salt thereof as an active ingredient, together with a pharmaceutically acceptable carrier or excipient. The pharmaceutical composition may further comprise one or more additives selected from the group consisting of a pharmaceutically acceptable carrier, diluent and adjuvant.

Specifically, the pharmaceutical composition may be a composition for a positive allosteric modulator of mGluR5.

In addition, the pharmaceutical composition may be a composition for the prevention and/or treatment of disorders mediated by glutamate dysfunction and mGluR5. The disorders mediated by glutamate dysfunction and mGluR5 may be, for example, schizophrenia, and include any disorders known as being related to glutamate dysfunction and mGluR5. In this regard, the article (N. Matosin et al., *Schizophrenia Research*, 2013, Vol. 146, pp. 170-176) reported the relation between a positive allosteric modulator of mGluR5 and the treatment of schizophrenia.

The pharmaceutically acceptable salt includes any acid or base addition salts, and any stereochemical isomer thereof. These salts are not specifically limited and may be any salt that is able to retain activity of a parent compound thereof in a target subject and does not cause any undesirable effect. Examples of these salts are both inorganic and organic salts, such as acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzenesulfonic acid, benzoic acid, stearic acid, cresylic acid, lactic acid, bicarbonic acid, bisulfuric acid, bitartaric acid, oxalic acid, butylic acid, calcium edatate, camsylic acid, carbonic acid, chlorobenzoic acid, citric acid, edetic acid, toluenesulfonic acid, edicylinic acid, ecylinic acid, fumaric acid, gluceptic acid, pamoic acid, gluconic acid, glycollarsanylic acid, methyl nitrate, polygalactronic acid, hexyllisorcynonic acid, malonic acid, hydrobamic acid, hydrochlorinic acid, hydroiodic acid, hydroxynaphtholic acid, isethionic acid, lactobionic acid, mandelic acid, estolinic acid, mucic acid, muconic acid, p-nitromethanesulfonic acid, hexamic acid, phantothenic acid, monohydrogen phosphoric acid, dihydrogen phosphoric acid, salicylic acid, sulfamine acid, sulfanilic acid, methanesulfonic acid and theoclic acid. In addition, examples of a basic salt are an ammonium salt, a salt of an alkali or alkali earth metal such as lithium, sodium, potassium, magnesium, or calcium, a salt containing an organic base such as benzathine, N-methyl-D-glucamine, or hydrabamine, and a salt containing an amino acid such as arginine or lysine. These salts may be converted into a free form by treatment with appropriate acid or base. The term "addition salt" may be taken to include solvates obtainable from any of the compounds of Chemical Formula (1) and salts thereof. Examples of these solvates are hydrates and alcoholates.

The pharmaceutical composition may be formulated into various types for oral or parenteral administration. For example, it may be formulated into any dosage form for oral administration such as tablets, pills, soft/hard capsules, solutions, suspensions, emulsions, syrups, granules and elixirs. Besides the effective ingredient, such a dosage form for oral administration may further include any pharmaceutically acceptable carriers depending on a typical construction of each formulation—for example, diluents such as lactose, dextrose, sucrose, mannitol, sorbitol, cellulose and/or glycine, or lubricants such as silica, talc, steric acid and its magnesium or calcium salt, and/or polyethylene glycol.

In addition, in case the formulation for oral administration is in a tablet form, it may also comprise binding agents such magnesium aluminum silicate, starch paste, gelatin, gum tragacanth, methyl cellulose, sodium carboxymethyl cellulose, and/or polyvinyl pyrrolidone, and if desired, it may also include disintegrating agents such as starch, agar, or alginic acid or its sodium salt, or a boiling mixture, and/or an absorbing agent, a colorant, a flavoring agent, or a sweetening agent.

The pharmaceutical composition may be formulated into a form of parenteral administration. In this case, it may be administered by means of parenteral administration methods such as a hypodermic injection, an intravenous injection, an intramuscular injection or an intrathoracic injection. In order for the pharmaceutical composition of the present disclosure to be formulated into a dosage form for parenteral administration, the effective ingredient (i.e., the compound of Chemical Formula (1) or a pharmaceutically acceptable salt thereof) may be mixed with a stabilizer or a buffering agent in water to prepare as a solution or a suspension, and this solution or suspension may then be produced as a unit dosage form such as an ampoule or a vial.

In addition, the pharmaceutical composition may be sterilized or may further comprise an adjuvant such as a preservative, a stabilizing agent, a hydrating agent, an emulsifying agent, or a salt for controlling osmotic pressure and/or a buffering agent, and it may further include other therapeutically beneficial substances and may be formulated in accordance with conventional methods of mixing, granulation or coating.

The pharmaceutical composition may comprise the effective ingredient—i.e., the compound of Chemical Formula (1) or a pharmaceutically acceptable salt thereof in an effective amount of 0.1 to 500 mg/kg (body weight), preferably 0.5 to 100 mg/kg (body weight) per day in case of mammals including a human, and such a pharmaceutical composition may be divided into one, or two or more doses per day and administered via an oral or parenteral route.

In still another aspect, the present disclosure also provides a role as a positive allosteric modulator of metabotropic glutamate receptor subtype 5 (mGluR5), comprising the step of administering a therapeutically effective amount of the compound of Chemical Formula (1) or a pharmaceutically acceptable salt thereof to a patient in need thereof. The modulation method may further comprise a step of identifying the patient who is in need of positive allosteric modulation of mGluR5 prior to the step of administration.

In addition, the present disclosure provides a method for the prevention and/or treatment of disorders mediated by glutamate dysfunction and mGluR5, comprising the step of administering a therapeutically effective amount of the compound of Chemical Formula (1) or a pharmaceutically acceptable salt thereof to a patient in need thereof. The method for the prevention and/or treatment may further comprise a step of identifying the patient who is in need of the prevention and/or treatment of disorders mediated by glutamate dysfunction and mGluR5 prior to the step of administration.

The disorders mediated by glutamate dysfunction and mGluR5 may be—for example, schizophrenia, and include any disorders known as being related to glutamate dysfunction and the modulation of mGluR5. The patient may be a mammal, preferably a human.

In addition, a person skilled in the art may easily select a specific administration method and a therapeutically effective amount of the compound of Chemical Formula (1) or a pharmaceutically acceptable salt thereof with no particular limitations, taking the type of the mammals to be administered and the disorder, and the specific type of the compound of Chemical Formula (1) and its activity on positive allosteric modulation of mGluR5.

According to still another aspect, the present disclosure provides a method of preparing the compound of Chemical Formula (1). The preparation of the compound of Chemical Formula (1) may be conducted by using a known compound or a compound easily prepared therefrom in the perspective of a person skilled in the art regarding a chemical synthesis. Therefore, the following explanations about the method of preparing the compound of Chemical Formula (1) merely present exemplary methods and if necessary, the order of the unit operation may be selectively altered and does not limit the scope of the disclosure.

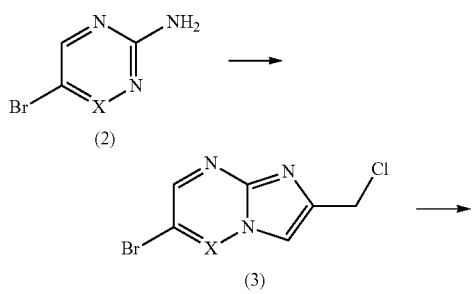

[Reaction Scheme 1]

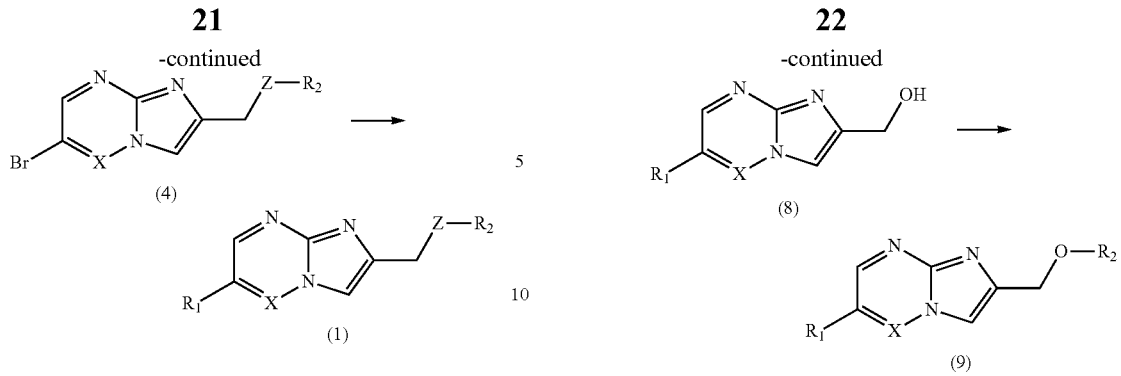

In a general synthesis method, from compound (2) as a starting material a heterocycle synthesis reaction is carried out with dichloroacetone to obtain imidazopyrimidine or imidazotriazine derivative (3). From this compound, a nucleophilic reaction is carried out to obtain compound (4), and then the final compound (1) can be obtained via Suzuki coupling reaction.

[Reaction Scheme 2]

In another synthesis method, from compound (2) as a starting material Suzuki coupling reaction is carried out to obtain compound (5) in which aryl or heteroaryl is substituted. Then, a heterocycle synthesis reaction is carried out with the obtained compound and dichloroacetone to obtain imidazopyrimidine or imidazotriazine derivative (6). From this compound, a nucleophilic reaction is carried out to obtain the final compound (1).

[Reaction Scheme 3]

A heterocycle synthesis reaction is carried out with compound (5) obtained in Reaction Scheme 2 and 1-acetoxy-3-chloroacetone to obtain compound (7), and the obtained compound is then hydrolyzed to obtain compound (8). An aromatic nucleophilic reaction of compound (8) is carried out to obtain the final compound (9).

According to the present disclosure, a novel imidazopyrimidine and imidazotriazine derivative, and a pharmaceutically acceptable salt thereof showing excellent effect on positive allosteric modulation of metabotropic glutamate receptor subtype 5 (mGluR5) are provided. Therefore, such imidazopyrimidine and imidazotriazine derivative, and a pharmaceutically acceptable salt thereof can be effectively used in the prevention or treatment of disorders mediated by glutamate dysfunction and mGluR5 such as schizophrenia.

In addition, according to the present disclosure, a method of preparing the novel imidazopyrimidine and imidazotriazine derivative, a pharmaceutical composition comprising the same and a method of positive allosteric modulation of mGluR5 by using the same, and a method for the treatment of disorders mediated by glutamate dysfunction and mGluR5 are provided.

EXAMPLES

Hereinafter, the present disclosure is explained in more detail with the following examples. However, it must be understood that the protection scope of the present disclosure is not limited to the examples.

Example 1: Synthesis of 6-(2-fluorophenyl)-2-phenoxymethylimidazo[1,2-a]pyrimidine

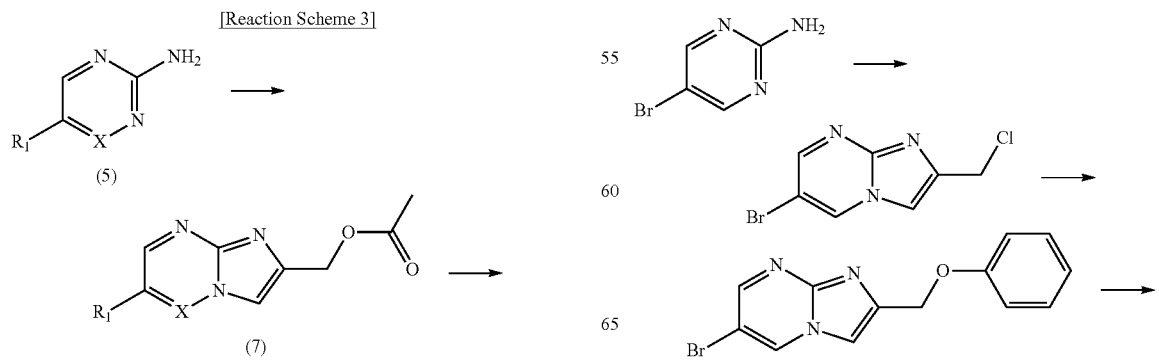

-continued

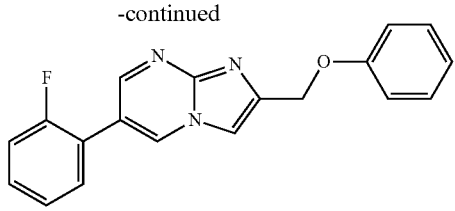

Example 1-1: Synthesis of 6-bromo-2-chloromethylimidazo[1,2-a]pyrimidine

5-Bromopyrimidin-2-amine (2 g, 11.5 mmol) and 1,3-dichloropropan-2-one (2.9 g, 23 mmol) were dissolved in DMF (20 ml), and then agitated at 110° C. for 2 hours. After confirmation of the reaction termination by liquid chromatography, the reaction solution was diluted with ethyl acetate and washed three times with water. Then, the solution was dried with magnesium sulfate and filtrated. This was under reduced pressure, and the resulting solids were washed with ethyl acetate to obtain the title compound (amount: 0.85 g, yield: 30%).

Example 1-2: Synthesis of 6-bromo-2-phenoxymethylimidazo[1,2-a]pyrimidine

6-Bromo-2-chloromethylimidazo[1,2-a]pyrimidine (2 g, 8.11 mmol) and phenol (1.5 g, 16.23 mmol) were dissolved in DMF (40 ml), and potassium carbonate (3.4 g, 24.34 mmol) was added thereto at room temperature. Then, the reaction solution was agitated at 60° C. for 15 hours. After confirmation of the reaction termination by liquid chromatography, the reaction solution was diluted with ethyl acetate and washed three times with water. Then, the solution was dried with magnesium sulfate and filtrated. This was under reduced pressure, and the resulting solids were washed with ethyl acetate to obtain the title compound (amount: 0.9 g, yield: 38%).

Example 1-3: Synthesis of 6-(2-fluorophenyl)-2-phenoxymethylimidazo[1,2-a]pyrimidine synthesis 6-Bromo-2-phenoxymethylimidazo[1,2-a]pyrimidine (0.3 g, 0.99 mmol) obtained in Example 1-2 and 2-fluorophenylboronic acid (0.2 g, 1.43 mmol) were dissolved in 1,2-dimethoxyethane (8 ml), and [1,1'-bis(diphenylphosphine)ferrocene]dichloropalladium(II) complex dichloromethane (0.2 g, 0.24 mmol) and 2N sodium carbonate aqueous solution (1.8 ml, 3.6 mmol) were then added thereto at room temperature. Then, the reaction solution was agitated under reflux at 90° C. for 6 hours. After confirmation of the reaction termination by liquid chromatography, the reaction solution was diluted with methylene chloride and filtrated by the use of Cellite™. The solution was washed twice with water, and then dried with magnesium sulfate and filtrated. This was under reduced pressure and purified by column chromatography (methylene chloride:methanol=50:1) to obtain the title compound (amount: 0.1 g, yield: 32%).

$^1$H-NMR (CDCl$_3$, 500 MHz) δ 8.74 (s, 1H), 8.59 (s, 1H), 7.64 (s, 1H), 7.50 (m, 1H), 7.45 (m, 1H), 7.32 (m, 3H), 7.23 (m, 1H), 7.03 (m, 2H), 6.98 (m, 1H), 5.39 (s, 2H)

Example 2: Synthesis of 2-phenoxymethyl-6-phenylimidazo[1,2-a]pyrimidine

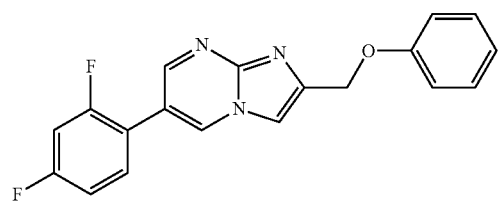

Phenylboronic acid as a starting material was used in the same manner as in Example 1-3 to obtain the title compound.

$^1$H-NMR (CDCl$_3$, 500 MHz) δ 8.80 (s, 1H), 8.51 (s, 1H), 7.64 (s, 1H), 7.52 (m, 3H), 7.45 (m, 2H), 7.31 (m, 2H), 7.04 (m, 2H), 6.97 (m, 1H), 5.38 (s, 2H)

Example 3: Synthesis of 6-(2,4-difluorophenyl)-2-phenoxymethylimidazo[1,2-a]pyrimidine

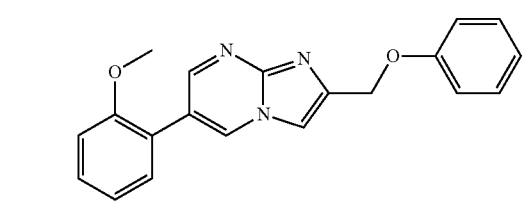 [SMILES: COc1ccccc1-c1cnc2nc(COc3ccccc3)cn2c1]

2,4-Difluoro phenylboronic acid as a starting material was used in the same manner as in Example 1-3 to obtain the title compound.

$^1$H-NMR (DMSO-d6, 500 MHz) δ 9.20 (s, 1H), 8.72 (s, 1H), 8.00 (s, 1H), 7.76 (m, 1H), 7.49 (m, 1H), 7.30 (m, 3H), 7.07 (d, 2H), 6.95 (t, 1H), 5.27 (s, 2H)

Example 4: Synthesis of 6-(2-methoxyphenyl)-2-phenoxymethylimidazo[1,2-a]pyrimidine 2-Methoxyphenylboronic acid as a starting material was used in the same manner as in Example 1-3 to obtain the title compound.

$^1$H-NMR (CDCl$_3$, 500 MHz) δ 8.74 (s, 1H), 8.55 (s, 1H), 7.61 (s, 1H), 7.42 (m, 2H), 7.37 (m, 1H), 7.29 (m, 1H), 7.13 (m, 1H), 7.05 (m, 3H), 6.95 (m, 1H), 5.40 (s, 2H), 3.87 (s, 3H)

Example 5: Synthesis of 6-(2-methylphenyl)-2-phenoxymethylimidazo[1,2-a]pyrimidine

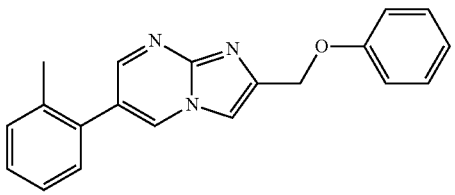 [SMILES: Cc1ccccc1-c1cnc2nc(COc3ccccc3)cn2c1]

2-Methylphenylboronic acid as a starting material was used in the same manner as in Example 1-3 to obtain the title compound.

$^1$H-NMR (CDCl$_3$, 500 MHz) δ 8.58 (s, 1H), 8.33 (s, 1H), 7.64 (s, 1H), 7.35 (m, 5H), 7.25 (m, 1H), 7.06 (d, 2H), 7.00 (m, 1H), 5.42 (s, 2H), 2.33 (s, 3H)

Example 6: Synthesis of 6-(4-fluoro-2-methylphenyl)-2-phenoxymethylimidazo[1,2-a]pyrimidine

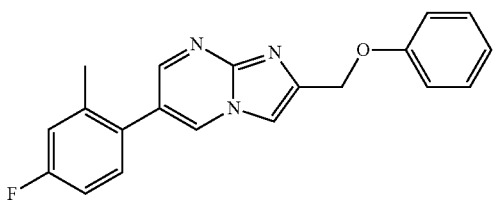 [SMILES: Cc1cc(F)ccc1-c1cnc2nc(COc3ccccc3)cn2c1]

4-Fluoro-2-methylphenylboronic acid as a starting material was used in the same manner as in Example 1-3 to obtain the title compound.

$^1$H-NMR (CDCl$_3$, 500 MHz) δ 8.52 (s, 1H), 8.29 (s, 1H), 7.63 (s, 1H), 7.33 (m, 2H), 7.21 (m, 1H), 7.06 (m, 3H), 6.99 (m, 2H), 5.41 (s, 2H), 2.31 (s, 3H)

Example 7: Synthesis of 6-(2,3-difluorophenyl)-2-phenoxymethylimidazo[1,2-a]pyrimidine

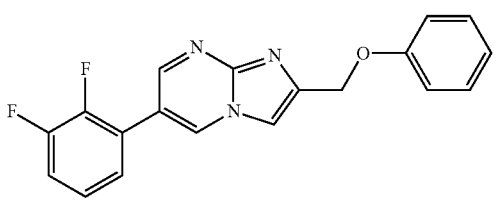 [SMILES: Fc1cccc(-c2cnc3nc(COc4ccccc4)cn3c2)c1F]

2,3-Difluorophenylboronic acid as a starting material was used in the same manner as in Example 1-3 to obtain the title compound.

$^1$H-NMR (CDCl$_3$, 500 MHz) δ 8.73 (s, 1H), 8.62 (s, 1H), 7.67 (s, 1H), 7.30 (m, 3H), 7.27 (m, 2H), 7.06 (m, 2H), 6.99 (m, 1H), 5.40 (s, 2H)

Example 8: Synthesis of 6-(4-fluorophenyl)-2-phenoxymethylimidazo[1,2-a]pyrimidine

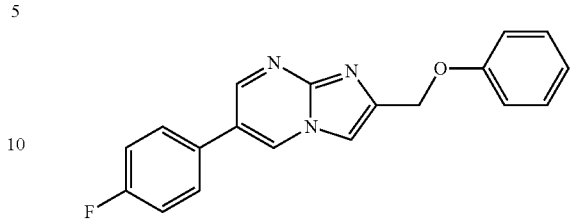

4-Fluorophenylboronic acid as a starting material was used in the same manner as in Example 1-3 to obtain the title compound.

$^1$H-NMR (CDCl$_3$, 500 MHz) δ 8.75 (s, 1H), 8.54 (s, 1H), 7.66 (d, 1H), 7.51 (m, 1H), 7.31 (m, 3H), 7.26 (m, 1H), 7.15 (m, 1H), 7.05 (m, 2H), 6.98 (m, 1H), 5.38 (s, 2H)

Example 9: Synthesis of 6-(3-aminophenyl)-2-phenoxymethylimidazo[1,2-a]pyrimidine

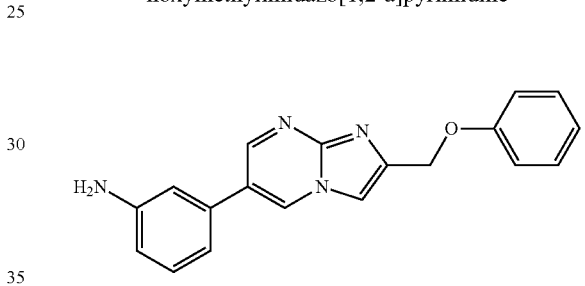

3-Aminophenylboronic acid as a starting material was used in the same manner as in Example 1-3 to obtain the title compound.

$^1$H-NMR (DMSO-d6, 500 MHz) δ 9.15 (s, 1H), 8.77 (s, 1H), 7.95 (s, 1H), 7.31 (t, 2H), 7.15 (t, 1H), 7.07 (d, 2H), 6.95 (t, 1H), 6.86 (s, 1H), 6.83 (d, 1H), 6.64 (d, 1H), 5.27 (s, 2H), 5.25 (s, 2H)

Example 10: Synthesis of 6-(2-aminophenyl)-2-phenoxymethylimidazo[1,2-a]pyrimidine

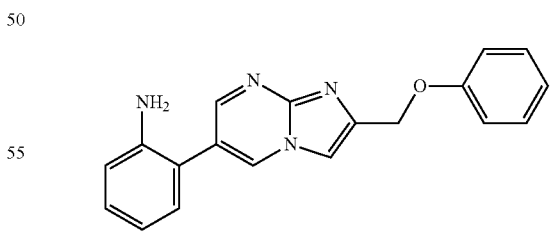

2-Aminophenylboronic acid as a starting material was used in the same manner as in Example 1-3 to obtain the title compound.

$^1$H-NMR (CDCl$_3$, 500 MHz) δ 8.67 (s, 1H), 8.48 (s, 1H), 7.62 (s, 1H), 7.33 (m, 2H), 7.20 (m, 1H), 7.13 (m, 1H), 7.05 (m, 2H), 6.99 (m, 1H), 6.90 (m, 1H), 6.83 (m, 1H), 5.40 (s, 2H)

Example 11: Synthesis of 6-(3-amino-6-methylphenyl)-2-phenoxymethylimidazo[1,2-a]pyrimidine

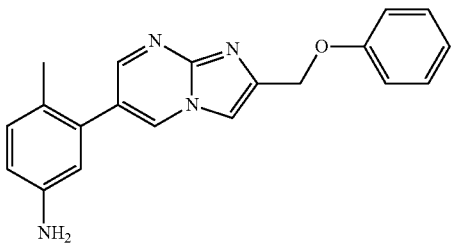 [SMILES: Cc1ccc(N)cc1-c1cnc2nc(COc3ccccc3)cn2c1]

3-Amino-6-methylphenylboronic acid as a starting material was used in the same manner as in Example 1-3 to obtain the title compound.

$^1$H-NMR (DMSO-d6, 500 MHz) δ 8.93 (s, 1H), 8.50 (s, 1H), 7.94 (s, 1H), 7.31 (t, 2H), 7.07 (d, 2H), 7.00 (m, 1H), 6.96 (m, 1H), 6.58 (d, 1H), 6.53 (s, 1H), 5.25 (s, 2H), 5.03 (s, 2H), 2.10 (s, 3H)

Example 12: Synthesis of 6-(3-amino-4-fluorophenyl)-2-phenoxymethylimidazo[1,2-a]pyrimidine

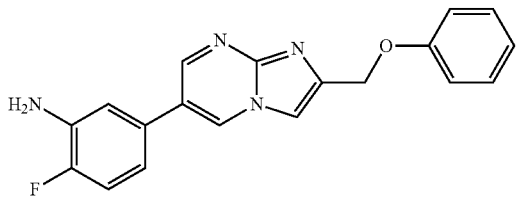 [SMILES: Nc1cc(-c2cnc3nc(COc4ccccc4)cn3c2)ccc1F]

3-Amino-4-fluorophenylboronic acid as a starting material was used in the same manner as in Example 1-3 to obtain the title compound.

$^1$H-NMR (DMSO-d6, 500 MHz) δ 9.14 (s, 1H), 8.75 (s, 1H), 7.95 (s, 1H), 7.54 (m, 2H), 7.30 (m, 2H), 7.15 (m, 1H), 7.11 (m, 2H), 6.95 (m, 1H), 5.35 (s, 2H), 5.24 (s, 2H)

Example 13: Synthesis of 6-(3-chloro-4-fluorophenyl)-2-phenoxymethylimidazo[1,2-a]pyrimidine

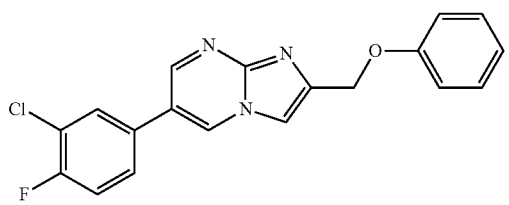 [SMILES: Fc1ccc(-c2cnc3nc(COc4ccccc4)cn3c2)cc1Cl]

3-Chloro-4-fluorophenylboronic acid as a starting material was used in the same manner as in Example 1-3 to obtain the title compound.

$^1$H-NMR (CDCl$_3$, 500 MHz) δ 8.73 (s, 1H), 8.50 (s, 1H), 7.66 (s, 1H), 7.61 (m, 1H), 7.44 (m, 1H), 7.32 (m, 3H), 7.05 (m, 2H), 7.00 (m, 1H), 5.40 (s, 2H)

Example 14: Synthesis of 6-(2-dimethylaminophenyl)-2-phenoxymethylimidazo[1,2-a]pyrimidine

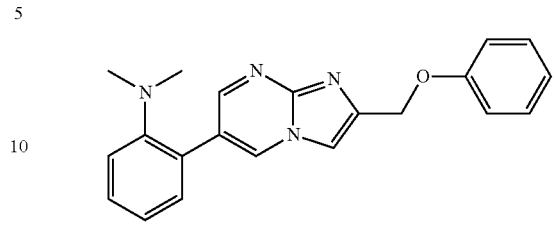

2-Dimethylaminophenylboronic acid as a starting material was used in the same manner as in Example 1-3 to obtain the title compound.

$^1$H-NMR (DMSO-d6, 500 MHz) δ 9.04 (s, 1H), 8.73 (s, 1H), 7.95 (s, 1H), 7.39 (m, 1H), 7.32 (m, 3H), 7.21 (m, 1H), 7.19 (m, 2H), 6.96 (m, 2H), 5.23 (s, 2H), 2.51 (s, 6H)

Example 15: Synthesis of 6-(2-chloro-4-fluorophenyl)-2-phenoxymethylimidazo[1,2-a]pyrimidine

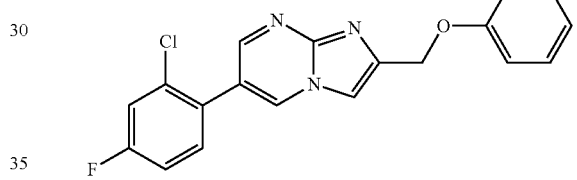

2-Chloro-4-fluorophenylboronic acid as a starting material was used in the same manner as in Example 1-3 to obtain the title compound.

$^1$H-NMR (DMSO-d6, 500 MHz) δ 9.08 (s, 1H), 8.59 (s, 1H), 7.98 (s, 1H), 7.65 (m, 2H), 7.40 (m, 1H), 7.31 (m, 2H), 7.06 (m, 2H), 6.95 (m, 1H), 5.25 (s, 2H)

Example 16: Synthesis of 6-(2-hydroxyphenyl)-2-phenoxymethylimidazo[1,2-a]pyrimidine

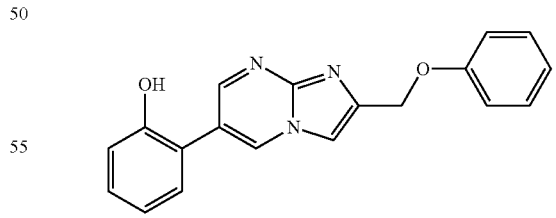

2-Hydroxyphenylboronic acid as a starting material was used in the same manner as in Example 1-3 to obtain the title compound.

$^1$H-NMR (CDCl$_3$, 500 MHz) δ 8.64 (s, 1H), 8.55 (s, 1H), 7.45 (s, 1H), 7.25 (m, 4H), 7.05 (m, 1H), 6.98 (m, 1H), 6.92 (m, 3H), 5.21 (s, 2H)

Example 17: Synthesis of 6-(3-hydroxyphenyl)-2-phenoxymethylimidazo[1,2-a]pyrimidine

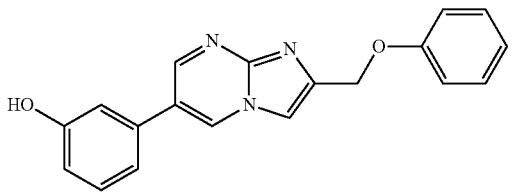 [SMILES: Oc1cccc(-c2cnc3nc(COc4ccccc4)cn3c2)c1]

3-Hydroxyphenylboronic acid as a starting material was used in the same manner as in Example 1-3 to obtain the title compound.

$^1$H-NMR (CDCl$_3$, 500 MHz) δ 8.77 (s, 1H), 8.46 (s, 1H), 7.59 (s, 1H), 7.35 (m, 1H), 7.26 (m, 2H), 7.07 (m, 2H), 6.99 (m, 2H), 6.90 (m, 2H), 5.35 (s, 2H)

Example 18: Synthesis of 6-(4-fluoro-2-trifluoromethylphenyl)-2-phenoxymethylimidazo[1,2-a]pyrimidine

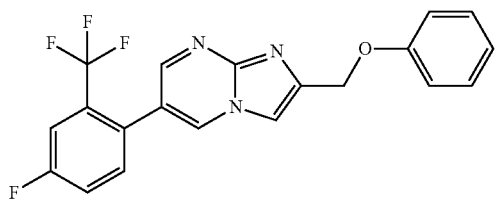 [SMILES: Fc1ccc(-c2cnc3nc(COc4ccccc4)cn3c2)c(C(F)(F)F)c1]

4-Fluoro-2-trifluoromethylphenylboronic acid as a starting material was used in the same manner as in Example 1-3 to obtain the title compound.

$^1$H-NMR (DMSO-d6, 500 MHz) δ 9.05 (s, 1H), 8.49 (s, 1H), 8.00 (s, 1H), 7.85 (m, 1H), 7.71 (m, 2H), 7.32 (m, 2H), 7.09 (m, 2H), 6.95 (m, 1H), 5.28 (s, 2H)

Example 19: Synthesis of 6-(3,4-difluorophenyl)-2-phenoxymethylimidazo[1,2-a]pyrimidine

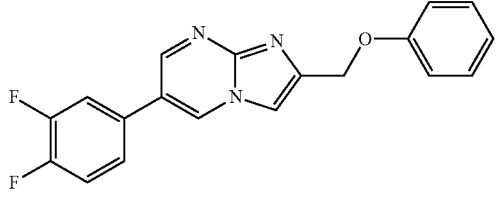 [SMILES: Fc1ccc(-c2cnc3nc(COc4ccccc4)cn3c2)cc1F]

3,4-Difluorophenylboronic acid as a starting material was used in the same manner as in Example 1-3 to obtain the title compound.

$^1$H-NMR (DMSO-d6, 500 MHz) δ 9.33 (s, 1H), 8.91 (s, 1H), 7.94 (m, 2H), 7.64 (m, 2H), 7.32 (m, 2H), 7.08 (m, 2H), 6.96 (m, 1H), 5.26 (s, 2H)

Example 20: Synthesis of 6-(2-methoxy-4-fluorophenyl)-2-phenoxymethylimidazo[1,2-a]pyrimidine

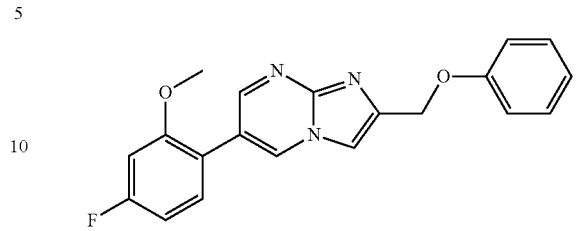

2-Methoxy-4-fluorophenylboronic acid as a starting material was used in the same manner as in Example 1-3 to obtain the title compound.

$^1$H-NMR (DMSO-d6, 500 MHz) δ 9.06 (s, 1H), 8.64 (s, 1H), 7.95 (s, 1H), 7.51 (t, 1H), 7.31 (t, 2H), 7.12 (m, 1H), 7.06 (d, 2H), 6.95 (m, 2H), 5.26 (s, 2H), 3.84 (s, 3H)

Example 21: Synthesis of 6-(4-fluoro-3-methoxyphenyl)-2-phenoxymethylimidazo[1,2-a]pyrimidine

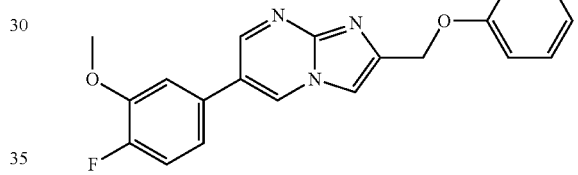

4-Fluoro-3-methoxyphenylboronic acid as a starting material was used in the same manner as in Example 1-3 to obtain the title compound.

$^1$H-NMR (DMSO-d6, 500 MHz) δ 9.30 (s, 1H), 8.93 (s, 1H), 7.94 (s, 1H), 7.56 (m, 1H), 7.35 (m, 4H), 7.08 (m, 2H), 6.95 (m, 1H), 5.26 (s, 2H), 3.94 (s, 3H)

Example 22: Synthesis of 6-(4-chloro-2-methoxyphenyl)-2-phenoxymethylimidazo[1,2-a]pyrimidine

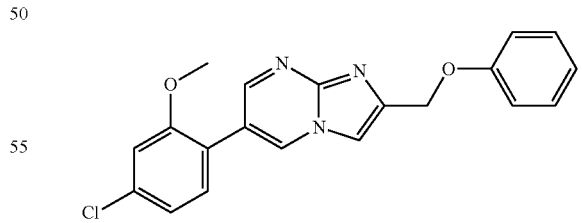

4-Chloro-2-methoxyphenylboronic acid as a starting material was used in the same manner as in Example 1-3 to obtain the title compound.

$^1$H-NMR (CDCl$_3$, 500 MHz) δ 8.66 (s, 1H), 8.54 (s, 1H), 7.62 (s, 1H), 7.29 (m, 3H), 7.05 (m, 5H), 5.37 (s, 2H), 3.86 (s, 3H)

Example 23: Synthesis of 6-(4-cyano-2-methoxyphenyl)-2-phenoxymethylimidazo[1,2-a]pyrimidine

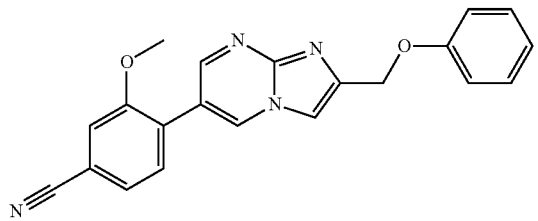 [SMILES: COc1cc(C#N)ccc1-c1cnc2nc(COc3ccccc3)cn2c1]

4-Cyano-2-methoxyphenylboronic acid as a starting material was used in the same manner as in Example 1-3 to obtain the title compound.

$^1$H-NMR (CDCl$_3$, 500 MHz) δ 8.70 (s, 1H), 8.63 (s, 1H), 7.66 (s, 1H), 7.49 (d, 2H), 7.32 (m, 3H), 7.06 (m, 2H), 7.01 (m, 1H), 5.40 (s, 2H), 3.93 (s, 3H)

Example 24: Synthesis of 6-(7-fluorobenzo[1,3]dioxol-4-yl)-2-phenoxymethylimidazo[1,2-a]pyrimidine

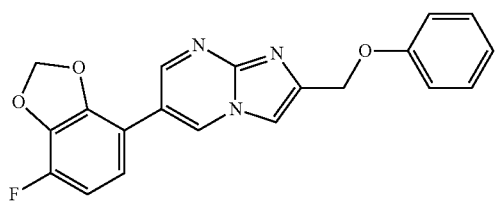 [SMILES: Fc1ccc(-c2cnc3nc(COc4ccccc4)cn3c2)c2c1OCO2]

7-Fluorobenzo[1,3]dioxol-4-ylboronic acid as a starting material was used in the same manner as in Example 1-3 to obtain the title compound.

$^1$H-NMR (DMSO-d6, 500 MHz) δ 9.29 (s, 1H), 8.89 (s, 1H), 8.02 (s, 1H), 7.30 (m, 3H), 7.06 (m, 3H), 6.95 (m, 1H), 6.26 (s, 2H), 5.25 (s, 2H)

Example 25: Synthesis of 6-(4-fluoro-2-hydroxymethylphenyl)-2-phenoxymethylimidazo[1,2-a]pyrimidine

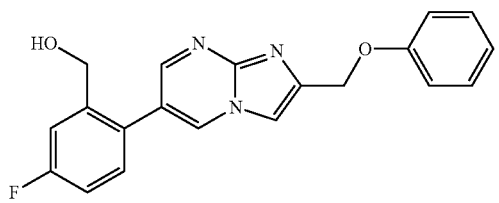 [SMILES: OCc1cc(F)ccc1-c1cnc2nc(COc3ccccc3)cn2c1]

4-Fluoro-2-hydroxymethylphenylboronic acid as a starting material was used in the same manner as in Example 1-3 to obtain the title compound.

$^1$H-NMR (DMSO-d6, 500 MHz) δ 8.99 (s, 1H), 8.56 (s, 1H), 7.95 (s, 1H), 7.43 (m, 2H), 7.32 (m, 2H), 7.27 (m, 1H), 7.06 (m, 2H), 6.95 (m, 1H), 5.44 (s, 1H), 5.27 (s, 2H), 4.47 (s, 2H)

Example 26: Synthesis of 6-(4-fluoro-2-methylthiophenyl)-2-phenoxymethylimidazo[1,2-a]pyrimidine

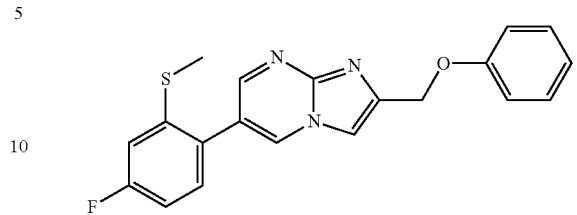

4-Fluoro-2-methylthiophenylboronic acid as a starting material was used in the same manner as in Example 1-3 to obtain the title compound.

$^1$H-NMR (DMSO-d6, 500 MHz) δ 9.01 (s, 1H), 8.51 (s, 1H), 7.96 (s, 1H), 7.42 (m, 1H), 7.35 (m, 3H), 7.15 (m, 1H), 7.06 (d, 2H), 6.95 (m, 1H), 5.27 (s, 2H), 2.47 (s, 3H)

Example 27: Synthesis of 6-(2-amino-4-fluorophenyl)-2-phenoxymethylimidazo[1,2-a]pyrimidine

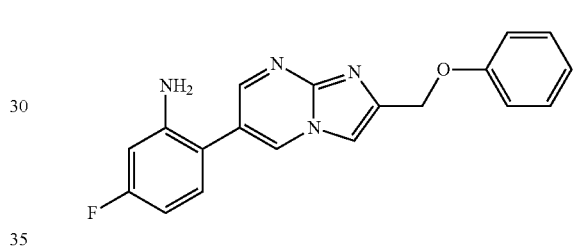

2-Amino-4-fluorophenylboronic acid as a starting material was used in the same manner as in Example 1-3 to obtain the title compound.

$^1$H-NMR (CDCl$_3$, 500 MHz) δ 8.59 (s, 1H), 8.39 (s, 1H), 7.58 (s, 1H), 7.29 (m, 2H), 7.05 (m, 4H), 6.55 (m, 2H), 5.39 (s, 2H), 3.89 (s, 2H)

Example 28: Synthesis of 6-(2,4-difluoro-5-methoxyphenyl)-2-phenoxymethylimidazo[1,2-a]pyrimidine

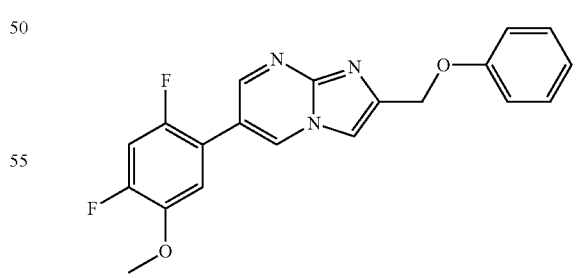

2,4-Difluoro-5-methoxyphenylboronic acid as a starting material was used in the same manner as in Example 1-3 to obtain the title compound.

$^1$H-NMR (DMSO-d6, 500 MHz) δ 9.14 (s, 1H), 8.69 (s, 1H), 7.95 (s, 1H), 7.43 (m, 1H), 7.32 (m, 3H), 7.06 (m, 2H), 6.96 (m, 1H), 5.26 (s, 2H), 3.81 (s, 3H)

Example 29: Synthesis of 6-(2-fluoropyridin-3-yl)-2-phenoxymethylimidazo[1,2-a]pyrimidine

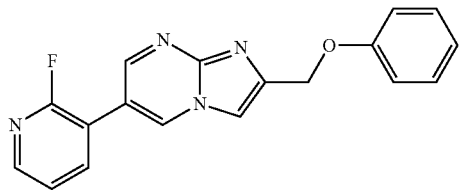 [SMILES: Fc1ncccc1-c1cnc2nc(COc3ccccc3)cn2c1]

(2-Fluoropyridin-3-yl)boronic acid as a starting material was used in the same manner as in Example 1-3 to obtain the title compound.

¹H-NMR (CDCl$_3$, 500 MHz) δ 8.75 (d, 1H), 8.70 (s, 1H), 8.33 (d, 1H), 7.99 (m, 1H), 7.69 (s, 1H), 7.41 (m, 1H), 7.32 (m, 2H), 7.05 (m, 2H), 6.95 (m, 1H), 5.41 (s, 2H)

Example 30: Synthesis of 6-(6-methoxypyridin-3-yl)-2-phenoxymethylimidazo[1,2-a]pyrimidine

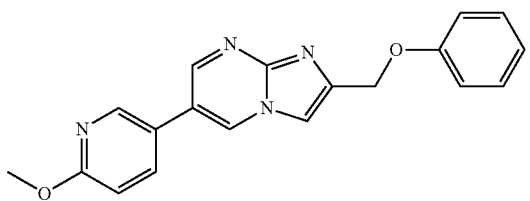 [SMILES: COc1ccc(-c2cnc3nc(COc4ccccc4)cn3c2)cn1]

6-Methoxypyridin-3-ylboronic acid as a starting material was used in the same manner as in Example 1-3 to obtain the title compound.

¹H-NMR (DMSO-d6, 500 MHz) δ 9.27 (s, 1H), 8.89 (s, 1H), 8.57 (s, 1H), 8.10 (m, 1H), 7.94 (s, 1H), 7.30 (m, 2H), 7.08 (m, 2H), 7.00 (m, 1H), 6.96 (t, 1H), 5.26 (s, 2H), 3.90 (s, 3H)

Example 31: Synthesis of 6-(6-fluoropyridin-3-yl)-2-phenoxymethylimidazo[1,2-a]pyrimidine

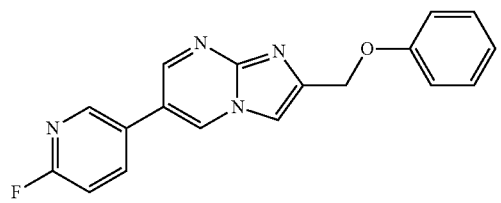 [SMILES: Fc1ccc(-c2cnc3nc(COc4ccccc4)cn3c2)cn1]

6-Fluoropyridin-3-ylboronic acid as a starting material was used in the same manner as in Example 1-3 to obtain the title compound.

¹H-NMR (DMSO-d6, 500 MHz) δ 9.36 (s, 1H), 8.93 (s, 1H), 8.65 (s, 1H), 8.41 (m, 1H), 7.97 (s, 1H), 7.40 (m, 1H), 7.31 (t, 2H), 7.08 (m, 2H), 6.95 (t, 1H), 5.27 (s, 2H)

Example 32: Synthesis of 6-(4-methylpyridin-3-yl)-2-phenoxymethylimidazo[1,2-a]pyrimidine

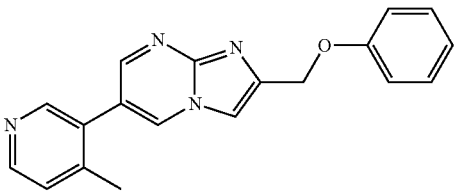 [SMILES: Cc1ccncc1-c1cnc2nc(COc3ccccc3)cn2c1]

4-Methylpyridin-3-ylboronic acid as a starting material was used in the same manner as in Example 1-3 to obtain the title compound.

¹H-NMR (CD3OD, 500 MHz) δ 9.47 (s, 1H), 9.15 (s, 1H), 8.95 (m, 1H), 8.88 (m, 1H), 8.39 (s, 1H), 8.15 (s, 1H), 7.35 (m, 2H), 7.12 (m, 2H), 7.04 (m, 1H), 5.48 (s, 2H), 2.69 (s, 3H)

Example 33: Synthesis of 6-(2,6-difluoropyridin-3-yl)-2-phenoxymethylimidazo[1,2-a]pyrimidine

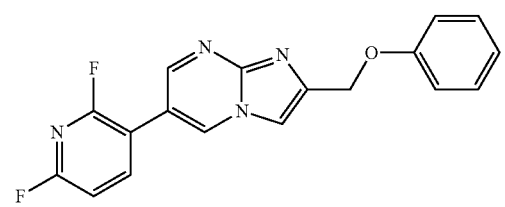 [SMILES: Fc1ccc(-c2cnc3nc(COc4ccccc4)cn3c2)c(F)n1]

2,6-Difluoropyridin-3-ylboronic acid as a starting material was used in the same manner as in Example 1-3 to obtain the title compound.

¹H-NMR (DMSO-d6, 500 MHz) δ 9.28 (s, 1H), 8.78 (s, 1H), 8.49 (q, 1H), 8.03 (s, 1H), 7.40 (d, 1H), 7.30 (t, 2H), 7.07 (d, 2H), 6.95 (t, 1H), 5.27 (s, 2H)

Example 34: Synthesis of 6-(6-chloropyridin-3-yl)-2-phenoxymethylimidazo[1,2-a]pyrimidine

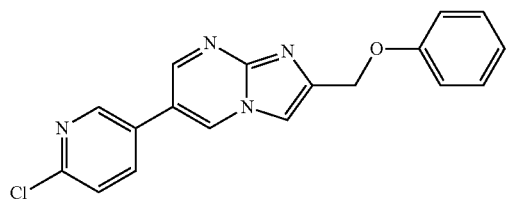 [SMILES: Clc1ccc(-c2cnc3nc(COc4ccccc4)cn3c2)cn1]

6-Chloropyridin-3-ylboronic acid as a starting material was used in the same manner as in Example 1-3 to obtain the title compound.

¹H-NMR (CD3OD, 500 MHz) δ 9.58 (s, 1H), 9.37 (s, 1H), 8.82 (s, 1H), 8.32 (s, 1H), 8.25 (d, 1H), 7.71 (m, 1H), 7.35 (m, 2H), 7.11 (m, 2H), 7.04 (m, 1H), 5.46 (s, 2H)

Example 35: Synthesis of 6-(2-fluoropyridin-4-yl)-2-phenoxymethylimidazo[1,2-a]pyrimidine

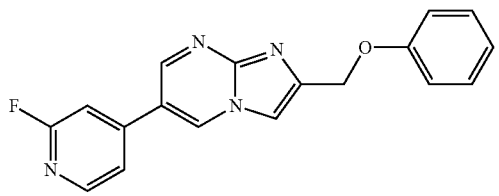 [SMILES: Fc1cc(-c2cnc3nc(COc4ccccc4)cn3c2)ccn1]

2-Fluoropyridin-4-ylboronic acid as a starting material was used in the same manner as in Example 1-3 to obtain the title compound.

$^1$H-NMR (DMSO-d6, 500 MHz) δ 9.57 (s, 1H), 9.06 (s, 1H), 8.38 (m, 1H), 7.99 (s, 1H), 7.82 (d, 1H), 7.69 (d, 1H), 7.31 (t, 2H), 7.08 (d, 2H), 6.95 (t, 1H), 5.28 (s, 2H)

Example 36: Synthesis of 6-(3-chloropyridin-4-yl)-2-phenoxymethylimidazo[1,2-a]pyrimidine

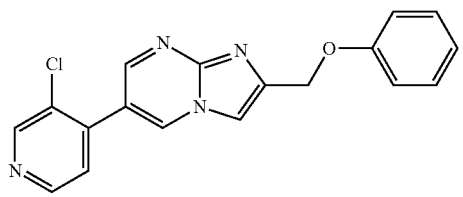 [SMILES: Clc1cnccc1-c1cnc2nc(COc3ccccc3)cn2c1]

3-Chloropyridin-4-ylboronic acid as a starting material was used in the same manner as in Example 1-3 to obtain the title compound.

$^1$H-NMR (DMSO-d6, 500 MHz) δ 9.42 (s, 1H), 8.91 (s, 1H), 8.85 (s, 1H), 8.71 (d, 1H), 8.18 (s, 1H), 7.70 (s, 1H), 7.32 (m, 2H), 7.09 (m, 2H), 6.97 (m, 1H), 5.35 (s, 2H)

Example 37: Synthesis of 6-(4-chlorophenyl)-2-phenoxymethylimidazo[1,2-a]pyrimidine

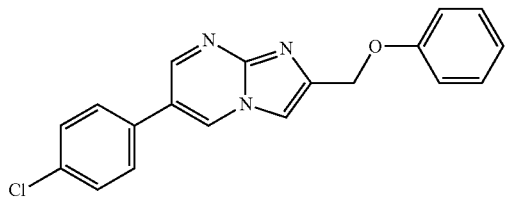 [SMILES: Clc1ccc(-c2cnc3nc(COc4ccccc4)cn3c2)cc1]

4-Chlorophenylboronic acid as a starting material was used in the same manner as in Example 1-3 to obtain the title compound.

$^1$H-NMR (DMSO-d6, 500 MHz) δ 9.33 (s, 1H), 8.91 (s, 1H), 7.96 (s, 1H), 7.81 (d, 2H), 7.60 (d, 2H), 7.31 (t, 2H), 7.09 (d, 2H), 6.95 (t, 1H), 5.27 (s, 2H)

Example 38: Synthesis of 6-(6-fluoro-4-methyl-3-pyridyl)-2-phenoxymethylimidazo[1,2-a]pyrimidine

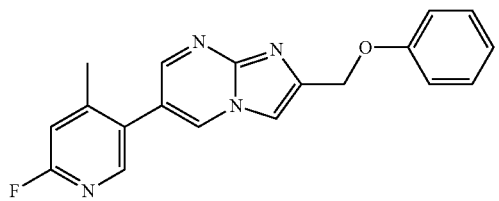 [SMILES: Cc1cc(F)ncc1-c1cnc2nc(COc3ccccc3)cn2c1]

6-Fluoro-4-methyl-3-pyridylboronic acid as a starting material was used in the same manner as in Example 1-3 to obtain the title compound.

$^1$H-NMR (CDCl$_3$, 500 MHz) δ 8.49 (s, 1H), 8.35 (s, 1H), 8.09 (s, 1H), 7.66 (s, 1H), 7.30 (m, 2H), 7.03 (m, 2H), 6.97 (m, 2H), 5.39 (s, 2H), 2.36 (s, 3H)

Example 39: Synthesis of 6-(6-fluoro-5-methyl-3-pyridyl)-2-phenoxymethylimidazo[1,2-a]pyrimidine

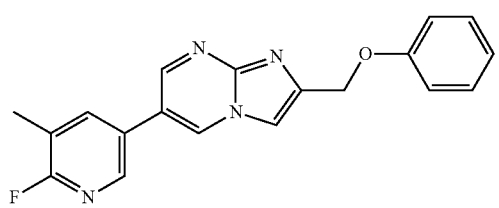 [SMILES: Cc1cc(-c2cnc3nc(COc4ccccc4)cn3c2)cnc1F]

6-Fluoro-5-methyl-3-pyridylboronic acid as a starting material was used in the same manner as in Example 1-3 to obtain the title compound.

$^1$H-NMR (DMSO-d6, 500 MHz) δ 9.35 (s, 1H), 8.89 (s, 1H), 8.42 (s, 1H), 8.22 (d, 1H), 7.94 (s, 1H), 7.29 (m, 2H), 7.05 (m, 2H), 6.94 (m, 1H), 5.27 (s, 2H), 2.35 (s, 3H)

Example 40: Synthesis of 6-(5-fluoro-2-pyridyl)-2-phenoxymethylimidazo[1,2-a]pyrimidine

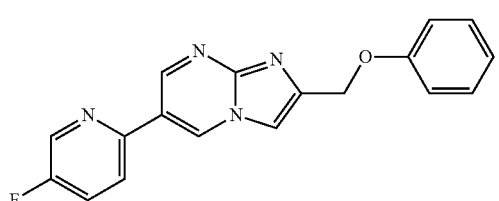

5-Fluoro-2-pyridylboronic acid as a starting material was used in the same manner as in Example 1-3 to obtain the title compound.

$^1$H-NMR (DMSO-d6, 500 MHz) δ 9.60 (s, 1H), 9.20 (s, 1H), 8.71 (s, 1H), 8.13 (d, 1H), 8.02 (s, 1H), 7.94 (t, 1H), 7.28 (t, 2H), 7.07 (d, 2H), 6.92 (t, 1H), 5.24 (s, 2H)

Example 41: Synthesis of 6-(2,4-difluorophenyl)-2-(3-fluorophenoxymethyl)imidazo[1,2-a]pyrimidine

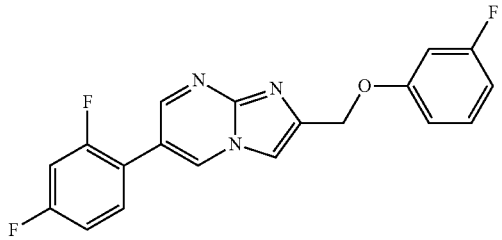

3-Fluorophenol as a starting material was used in the same manner as in Example 1-2 to obtain 6-bromo-2-(3-fluorophenoxymethylimidazo[1,2-a]pyrimidine. The obtained 6-bromo-2-(3-fluorophenoxymethylimidazo[1,2-a]pyrimidine and 2,4-difluorophenylboronic acid were used in the same manner as in Example 1-3 to obtain the title compound.

$^1$H-NMR (DMSO-d6, 500 MHz) δ 9.20 (s, 1H), 8.72 (s, 1H), 8.02 (s, 1H), 7.76 (m, 1H), 7.49 (m, 1H), 7.33 (m, 2H), 6.98 (m, 1H), 6.90 (m, 1H), 6.76 (m, 1H) 5.28 (s, 2H)

Example 42: Synthesis of 6-(4-fluoro-2-methoxyphenyl)-2-(3-fluorophenoxymethyl)imidazo[1,2-a]pyrimidine

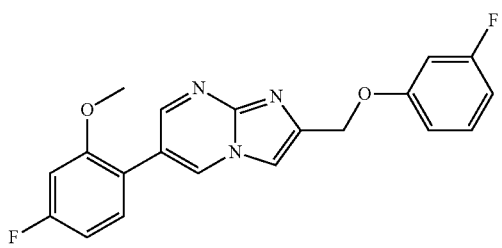 [SMILES: COc1cc(F)ccc1-c1cnc2nc(COc3cccc(F)c3)cn2c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and 4-fluoro-2-methoxyphenylboronic acid were used in the same manner as in Example 1-3 to obtain the title compound.

$^1$H-NMR (CDCl$_3$, 500 MHz) δ 8.68 (s, 1H), 8.52 (s, 1H), 7.61 (s, 1H), 7.30 (m, 1H), 7.23 (m, 1H), 6.82 (m, 2H), 6.76 (m, 2H), 6.68 (m, 1H), 5.35 (s, 2H), 3.85 (s, 3H)

Example 43: Synthesis of 6-(4-fluoro-3-hydroxyphenyl)-2-(3-fluorophenoxymethyl)-imidazo[1,2-a]pyrimidine

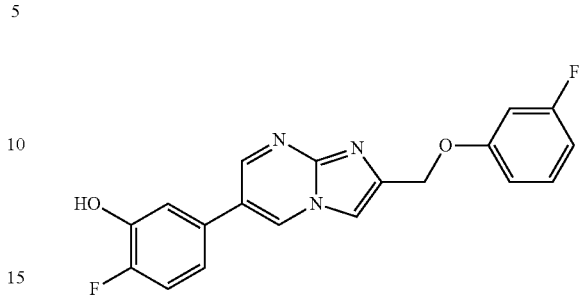

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and 4-fluoro-3-hydroxyphenylboronic acid were used in the same manner as in Example 1-3 to obtain the title compound.

$^1$H-NMR (DMSO-d6, 500 MHz) δ 9.20 (s, 1H), 8.81 (s, 1H), 7.98 (s, 1H), 7.33 (m, 3H), 7.18 (m, 1H), 6.99 (m, 1H), 6.93 (m, 1H), 6.78 (m, 1H), 5.28 (s, 2H)

Example 44: Synthesis of 6-(2-aminophenyl)-2-(3-fluorophenoxymethyl)imidazo[1,2-a]pyrimidine

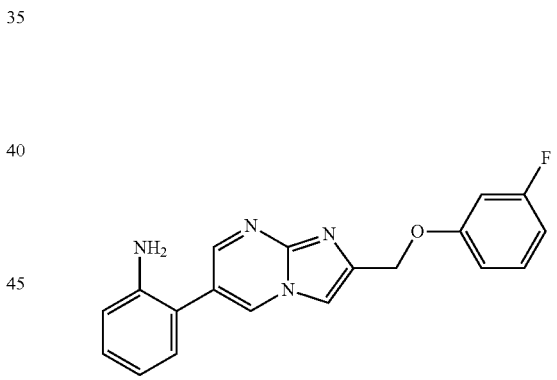

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and 2-aminophenylboronic acid were used in the same manner as in Example 1-3 to obtain the title compound.

$^1$H-NMR (DMSO-d6, 500 MHz) δ 8.93 (s, 1H), 8.54 (s, 1H), 7.95 (s, 1H), 7.31 (m, 1H), 7.10 (m, 2H), 6.98 (m, 1H), 6.92 (m, 1H), 6.79 (m, 2H), 6.63 (m, 1H), 5.27 (s, 2H), 5.14 (s, 2H)

Example 45: Synthesis of 6-(3-chloropyridin-4-yl)-2-(3-fluorophenoxymethyl)imidazo[1,2-a]pyrimidine

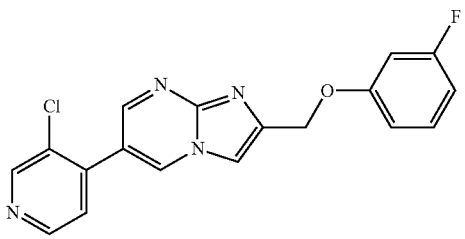 [SMILES: Fc1cccc(OCc2cn3cc(-c4ccncc4Cl)cnc3n2)c1]

3-Fluorophenol as a starting material was used in the same manner as in Example 1-2 to obtain 6-bromo-2-(3-fluorophenoxymethylimidazo[1,2-a]pyrimidine. The obtained 6-bromo-2-(3-fluorophenoxymethylimidazo[1,2-a]pyrimidine and 3-chloropyridin-4-ylboronic acid were used in the same manner as in Example 1-3 to obtain the title compound.

$^1$H-NMR (DMSO-d6, 500 MHz) δ 9.27 (s, 1H), 8.81 (s, 1H), 8.72 (s, 1H), 8.67 (s, 1H), 8.06 (s, 1H), 7.69 (m, 1H), 7.32 (m, 1H), 6.99 (m, 1H), 6.92 (m, 1H), 6.79 (m, 1H), 5.30 (s, 2H)

Example 46: Synthesis of 6-(4-methylpyridin-3-yl)-2-(3-fluorophenoxymethyl)imidazo[1,2-a]pyrimidine

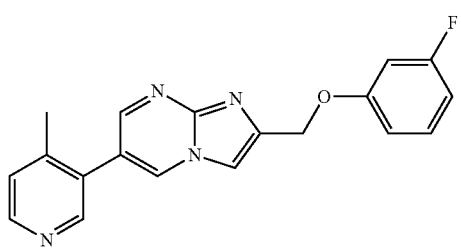 [SMILES: Cc1ccncc1-c1cnc2nc(COc3cccc(F)c3)cn2c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and 4-methylpyridin-3-ylboronic acid were used in the same manner as in Example 1-3 to obtain the title compound.

$^1$H-NMR (CDCl$_3$, 500 MHz) δ 9.34 (s, 1H), 9.00 (s, 2H), 8.78 (s, 1H), 8.62 (s, 1H), 7.73 (s, 1H), 7.32 (m, 2H), 7.06 (m, 2H), 7.01 (m, 1H), 5.42 (s, 2H)

Example 47: Synthesis of 6-(2,4-difluorophenyl)-2-(4-fluorophenoxymethyl)imidazo[1,2-a]pyrimidine

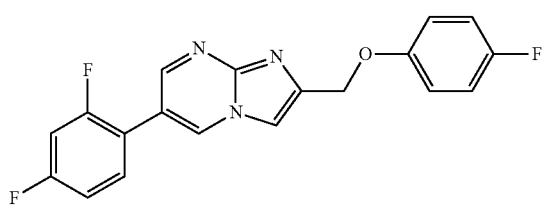 [SMILES: Fc1ccc(OCc2cn3cc(-c4ccc(F)cc4F)cnc3n2)cc1]

4-Fluorophenol as a starting material was used in the same manner as in Example 1-2 to obtain 6-bromo-2-(4-fluorophenoxymethylimidazo[1,2-a]pyrimidine. The obtained 6-bromo-2-(4-fluorophenoxymethylimidazo[1,2-a]pyrimidine and 2,4-difluorophenylboronic acid were used in the same manner as in Example 1-3 to obtain the title compound.

$^1$H-NMR (CDCl$_3$, 500 MHz) δ 8.70 (s, 1H), 8.57 (s, 1H), 7.64 (s, 1H), 7.47 (m, 1H), 6.99 (m, 6H), 5.35 (s, 2H)

Example 48: Synthesis of 6-(4-fluoro-2-methylphenyl)-2-(4-fluorophenoxymethyl)imidazo[1,2-a]pyrimidine

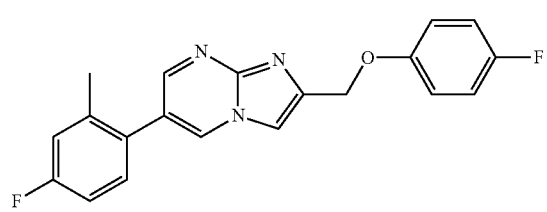 [SMILES: Cc1cc(F)ccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and 4-fluoro-2-methylphenylboronic acid were used in the same manner as in Example 1-3 to obtain the title compound.

$^1$H-NMR (CDCl$_3$, 500 MHz) δ 8.53 (s, 1H), 8.31 (s, 1H), 7.62 (s, 1H), 7.22 (m, 2H), 7.09 (m, 1H), 6.99 (m, 4H), 5.36 (s, 2H), 2.32 (s, 3H)

Example 49: Synthesis of 6-(3-chloropyridin-4-yl)-2-(4-fluorophenoxymethyl)imidazo[1,2-a]pyrimidine

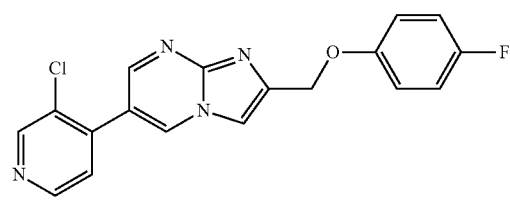 [SMILES: Fc1ccc(OCc2cn3cc(-c4ccncc4Cl)cnc3n2)cc1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and 3-chloropyridin-4-ylboronic acid were used in the same manner as in Example 1-3 to obtain the title compound.

$^1$H-NMR (CDCl$_3$, 500 MHz) δ 8.79 (s, 1H), 8.68 (m, 2H), 8.62 (m, 1H), 7.69 (s, 1H), 7.38 (m, 1H), 6.99 (m, 4H), 5.37 (s, 2H)

Example 50: Synthesis of 6-(2,6-dimethylphenyl)-2-(4-fluorophenoxymethyl)imidazo[1,2-a]pyrimidine

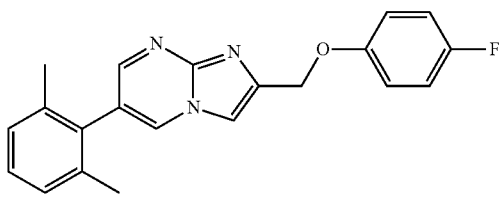 [SMILES: Cc1cccc(C)c1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and 2,6-dimethylphenylboronic acid were used in the same manner as in Example 1-3 to obtain the title compound.

$^1$H-NMR (DMSO-d6, 500 MHz) δ 8.88 (s, 1H), 8.38 (s, 1H), 7.92 (s, 1H), 7.26 (m, 1H), 7.20 (m, 2H), 7.10 (m, 4H), 5.25 (s, 2H), 2.07 (s, 6H)

Example 51: Synthesis of 2-[(4-fluorophenoxy)methyl]-6-(6-fluoro-3-pyridyl)imidazo[1,2-a]pyrimidine

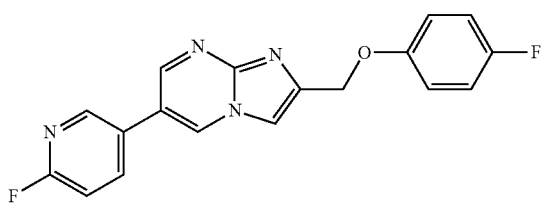 [SMILES: Fc1ccc(OCc2cn3cc(-c4ccc(F)nc4)cnc3n2)cc1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (6-fluoro-3-pyridyl)boronic acid were used in the same manner as in Example 1-3 to obtain the title compound.

$^1$H-NMR (CDCl$_3$, 500 MHz) δ 8.74 (s, 1H), 8.55 (s, 1H), 8.44 (s, 1H), 7.99 (m, 1H), 7.67 (s, 1H), 7.13 (m, 1H), 6.98 (m, 4H), 5.35 (s, 2H)

Example 52: Synthesis of 4-[[6-(4-fluorophenyl)imidazo[1,2-a]pyrimidin-2-yl]methoxy]phenol

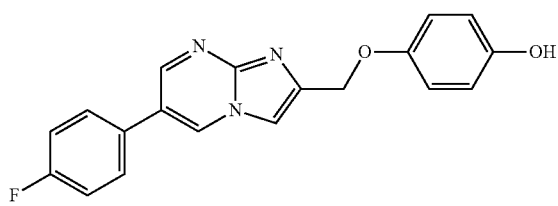 [SMILES: Oc1ccc(OCc2cn3cc(-c4ccc(F)cc4)cnc3n2)cc1]

Benzene-1,4-diol as a starting material was used in the same manner as in Example 1-2 to obtain 6-bromo-2-(4-hydroxyphenoxymethyl)imidazo[1,2-a]pyrimidine. The obtained 6-bromo-2-(4-hydroxyphenoxymethyl)imidazo[1,2-a]pyrimidine and 4-fluorophenylboronic acid were used in the same manner as in Example 1-3 to obtain the title compound.

$^1$H-NMR (DMSO-d6, 500 MHz) δ 9.27 (s, 1H), 8.95 (s, 1H), 8.88 (s, 1H), 7.90 (s, 1H), 7.82 (m, 2H), 7.38 (t, 2H), 6.89 (d, 2H), 6.68 (d, 2H), 5.14 (s, 2H)

Example 53: Synthesis of 2-[(4-fluorophenoxy)methyl]-6-(4-fluorophenyl)imidazo[1,2-a]pyrimidine

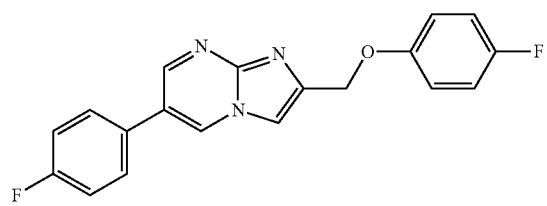

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and 4-fluorophenylboronic acid were used in the same manner as in Example 1-3 to obtain the title compound.

$^1$H-NMR (DMSO-d6, 500 MHz) δ 9.28 (s, 1H), 8.89 (s, 1H), 7.94 (s, 1H), 7.81 (s, 2H), 7.38 (s, 2H), 7.12 (m, 4H), 5.25 (s, 2H)

Example 54: Synthesis of 2-[(3-fluorophenoxy)methyl]-6-(4-fluorophenyl)imidazo[1,2-a]pyrimidine

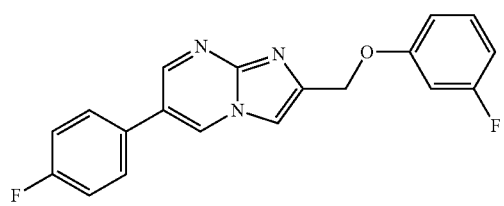 [SMILES: Fc1ccc(-c2cnc3nc(COc4cccc(F)c4)cn3c2)cc1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and 4-fluorophenylboronic acid were used in the same manner as in Example 1-3 to obtain the title compound.

$^1$H-NMR (CDCl$_3$, 500 MHz) δ 8.78 (s, 1H), 8.50 (s, 1H), 7.64 (s, 1H), 7.53 (m, 2H), 7.25 (m, 2H), 6.84 (m, 1H), 6.77 (m, 1H), 6.68 (m, 1H), 5.37 (s, 2H)

Example 55: Synthesis of 2-fluoro-5-[2-[(4-fluorophenoxy)methyl]imidazo[1,2-a]pyrimidin-6-yl]phenol

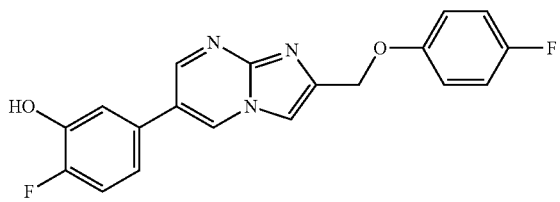 [SMILES: Oc1cc(-c2cnc3nc(COc4ccc(F)cc4)cn3c2)ccc1F]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (4-fluoro-3-hydroxy-phenyl)boronic acid were used in the same manner as in Example 1-3 to obtain the title compound.
$^1$H-NMR (DMSO-d6, 500 MHz) δ 10.21 (s, 1H), 9.21 (s, 1H), 8.80 (s, 1H), 7.95 (s, 1H), 7.28 (m, 2H), 7.11 (m, 5H), 5.24 (s, 2H)

Example 56: Synthesis of 2-[(4-fluorophenoxy)methyl]-6-phenyl-imidazo[1,2-a]pyrimidine

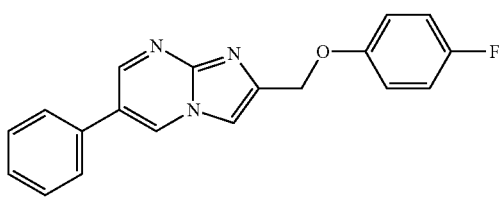 [SMILES: Fc1ccc(OCc2cn3cc(-c4ccccc4)cnc3n2)cc1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and phenylboronic acid were used in the same manner as in Example 1-3 to obtain the title compound.
$^1$H-NMR (DMSO-d6, 500 MHz) δ 9.30 (s, 1H), 8.91 (s, 1H), 7.95 (s, 1H), 7.78 (d, 2H), 7.55 (t, 2H), 7.46 (m, 1H), 7.12 (m, 4H), 5.25 (s, 2H)

Example 57: Synthesis of 5-fluoro-2-[2-[(3-fluorophenoxy)methyl]imidazo[1,2-a]pyrimidin-6-yl]phenol

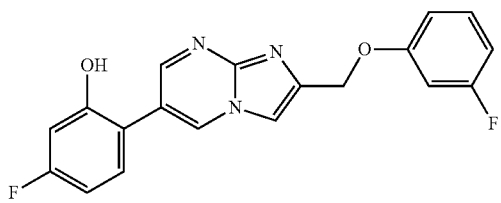

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and (4-fluoro-2-hydroxy-phenyl)boronic acid were used in the same manner as in Example 1-3 to obtain the title compound.
$^1$H-NMR (DMSO-d6, 500 MHz) δ 10.5 (s, 1H), 9.10 (s, 1H), 8.70 (s, 1H), 7.99 (s, 1H), 7.48 (m, 1H), 7.35 (m, 1H), 7.00 (m, 1H), 6.93 (m, 1H), 6.80 (m, 2H), 5.28 (s, 2H)

Example 58: Synthesis of 5-fluoro-2-[2-[(4-fluorophenoxy)methyl]imidazo[1,2-a]pyrimidin-6-yl]phenol

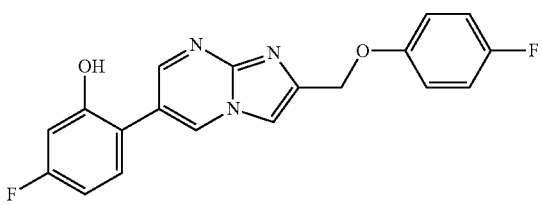

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (4-fluoro-2-hydroxy-phenyl)boronic acid were used in the same manner as in Example 1-3 to obtain the title compound.
$^1$H-NMR (DMSO-d6, 500 MHz) δ 10.5 (s, 1H), 9.07 (s, 1H), 8.68 (s, 1H), 7.94 (s, 1H), 7.45 (m, 1H), 7.08 (m, 4H), 6.78 (m, 2H), 5.22 (s, 2H)

Example 59: Synthesis of 6-(4-fluorophenyl)-2-[(2,3,4,5,6-pentadeuteriophenoxy)methyl]imidazo[1,2-a]pyrimidine

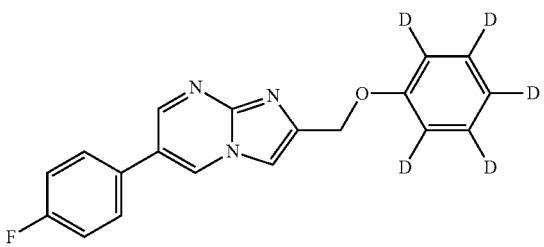 [SMILES: [2H]c1c([2H])c([2H])c(OCc2cn3cc(-c4ccc(F)cc4)cnc3n2)c([2H])c1[2H]]

2,3,4,5,6-Pentadeuteriophenol as a starting material was used in the same manner as in Example 1-2 to obtain 6-bromo-2-(2,3,4,5,6-pentadeuteriophenoxymethyl)imidazo[1,2-a]pyrimidine. The obtained 6-bromo-2-(2,3,4,5,6-pentadeuteriophenoxymethyl)imidazo[1,2-a]pyrimidine and (4-fluorophenyl)boronic acid were used in the same manner as in Example 1-3 to obtain the title compound.
$^1$H-NMR (DMSO-d6, 500 MHz) δ 9.29 (d, 1H), 8.89 (d, 1H), 7.95 (s, 1H), 7.82 (t, 2H), 7.39 (t, 2H), 5.27 (s, 2H)

Example 60: Synthesis of 2-[(4-fluorophenoxy)methyl]6-(o-tolyl)imidazo[1,2-a]pyrimidine

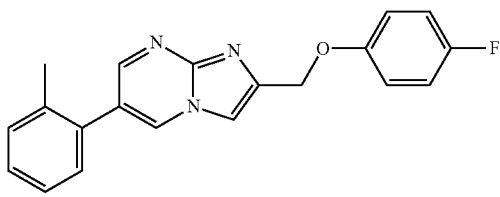 [SMILES: Cc1ccccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and o-tolylboronic acid were used in the same manner as in Example 1-3 to obtain the title compound.

$^1$H-NMR (DMSO-d6, 500 MHz) δ 9.00 (s, 1H), 8.58 (s, 1H), 7.93 (s, 1H), 7.35 (m, 4H), 7.12 (m, 4H), 5.25 (s, 2H), 2.30 (s, 3H)

Example 61: Synthesis of 6-(5-fluoro-2-methyl-phenyl)-2-[(4-fluorophenoxy)methyl]imidazo[1,2-a]pyrimidine

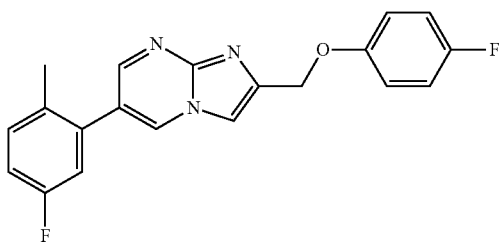 [SMILES: Cc1ccc(F)cc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (5-fluoro-2-methyl-phenyl)boronic acid were used in the same manner as in Example 1-3 to obtain the title compound.

$^1$H-NMR (DMSO-d6, 500 MHz) δ 9.04 (s, 1H), 8.59 (s, 1H), 7.94 (s, 1H), 7.40 (t, 1H), 7.28 (m, 1H), 7.22 (m, 1H), 7.12 (m, 4H), 5.25 (s, 2H), 2.27 (s, 3H)

Example 62: Synthesis of 2-[(4-fluorophenoxy)methyl]-6-(2-fluoro-4-pyridyl)imidazo[1,2-a]pyrimidine

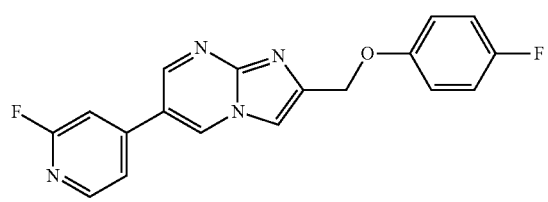 [SMILES: Fc1ccc(OCc2cn3cc(-c4ccnc(F)c4)cnc3n2)cc1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-fluoro-4-pyridyl)boronic acid were used in the same manner as in Example 1-3 to obtain the title compound.

$^1$H-NMR (DMSO-d6, 500 MHz) δ 9.57 (s, 1H), 9.05 (s, 1H), 8.38 (d, 1H), 7.98 (s, 1H), 7.82 (m, 1H), 7.70 (s, 1H), 7.12 (m, 4H), 5.25 (s, 2H)

Example 63: Synthesis of 2-[2-[(4-fluorophenoxy)methyl]imidazo[1,2-a]pyrimidin-6-yl]phenol

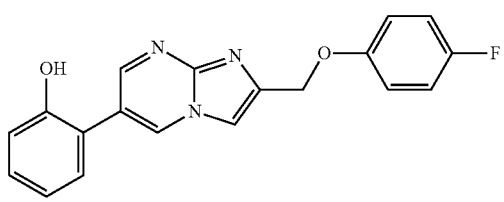 [SMILES: Oc1ccccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-hydroxyphenyl)boronic acid were used in the same manner as in Example 1-3 to obtain the title compound.

$^1$H-NMR (DMSO-d6, 500 MHz) δ 9.97 (s, 1H), 9.11 (s, 1H), 8.73 (s, 1H), 7.96 (s, 1H), 7.42 (d, 1H), 7.25 (m, 1H), 7.11 (m, 4H), 7.00 (m, 2H), 5.23 (s, 2H)

Example 64: Synthesis of 6-(2-fluoro-4-methyl-phenyl)-2-[(4-fluorophenoxy)methyl]imidazo[1,2-a]pyrimidine

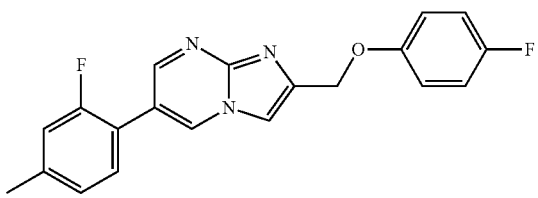

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-fluoro-4-methyl-phenyl)boronic acid were used in the same manner as in Example 1-3 to obtain the title compound.

$^1$H-NMR (DMSO-d6, 500 MHz) δ 9.27 (s, 1H), 8.88 (s, 1H), 7.93 (s, 1H), 7.63 (t, 1H), 7.15 (m, 6H), 5.24 (s, 2H), 2.32 (s, 3H)

Example 65: Synthesis of 2-[(4-fluorophenoxy) methyl]-6-[6-(trifluoromethyl)-3-pyridyl]imidazo[1,2-a]pyrimidine

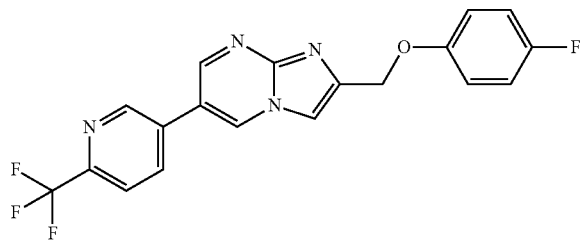 [SMILES: Fc1ccc(OCc2cn3cc(-c4ccc(C(F)(F)F)nc4)cnc3n2)cc1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and [6-(trifluoromethyl)-3-pyridyl]boronic acid were used in the same manner as in Example 1-3 to obtain the title compound.

$^1$H-NMR (DMSO-d6, 500 MHz) δ 9.48 (s, 1H), 9.17 (s, 1H), 9.00 (d, 1H), 8.48 (d, 1H), 8.07 (m, 1H), 7.98 (s, 1H), 7.10 (m, 4H), 5.25 (s, 2H)

Example 66: Synthesis of 2-[2-[(4-fluorophenoxy)methyl]imidazo[1,2-a]pyrimidin-6-yl]aniline

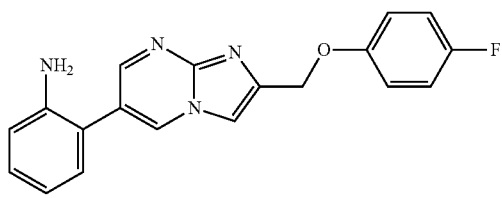 [SMILES: Nc1ccccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-aminophenyl)boronic acid were used in the same manner as in Example 1-3 to obtain the title compound.

$^1$H-NMR (DMSO-d6, 500 MHz) δ 8.92 (s, 1H), 8.48 (s, 1H), 7.90 (s, 1H), 7.08 (m, 6H), 6.76 (d, 1H), 6.65 (t, 1H), 5.22 (s, 2H), 5.13 (s, 1H), 3.15 (s, 1H)

Example 67: Synthesis of 6-(2-chloro-4-fluoro-phenyl)-2-[(4-fluorophenoxy)methyl]imidazo[1,2-a]pyrimidine

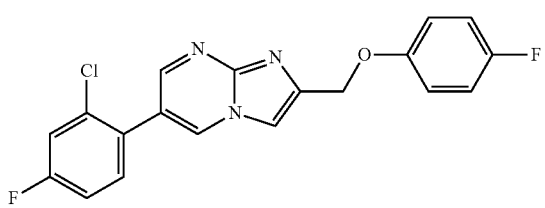

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-chloro-4-fluoro-phenyl)boronic acid were used in the same manner as in Example 1-3 to obtain the title compound.

$^1$H-NMR (DMSO-d6, 500 MHz) δ 9.09 (s, 1H), 8.59 (s, 1H), 7.96 (s, 1H), 7.67 (m, 2H), 7.40 (m, 1H), 7.12 (m, 4H), 5.24 (s, 2H)

Example 68: Synthesis of 4-[2-[(4-fluorophenoxy)methyl]imidazo[1,2-a]pyrimidin-6-yl]-3-methoxy-benzonitrile

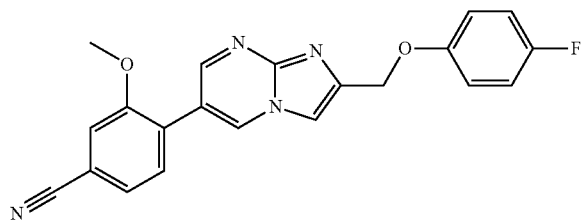 [SMILES: COc1cc(C#N)ccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (4-cyano-2-methoxy-phenyl)boronic acid were used in the same manner as in Example 1-3 to obtain the title compound.

$^1$H-NMR (DMSO-d6, 500 MHz) δ 9.18 (s, 1H), 8.71 (s, 1H), 7.97 (s, 1H), 7.70 (s, 2H), 7.58 (m, 1H), 7.10 (m, 4H), 5.25 (s, 2H)

Example 69: Synthesis of 6-(4-chloro-2-methoxy-phenyl)-2-[(4-fluorophenoxy)methyl]imidazo[1,2-a]pyrimidine

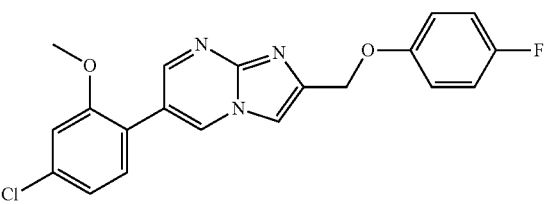 [SMILES: COc1cc(Cl)ccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (4-chloro-2-methoxy-phenyl)boronic acid were used in the same manner as in Example 1-3 to obtain the title compound.

$^1$H-NMR (DMSO-d6, 500 MHz) δ 9.08 (s, 1H), 8.64 (s, 1H), 7.94 (s, 1H), 7.48 (d, 1H), 7.26 (d, 1H), 7.14 (m, 5H), 5.23 (s, 2H), 3.83 (s, 3H)

Example 70: Synthesis of 2-fluoro-5-[2-[(4-fluorophenoxy)methyl]imidazo[1,2-a]pyrimidin-6-yl]aniline

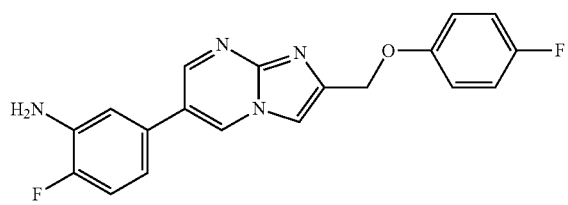

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (3-amino-4-fluoro-phenyl)boronic acid as a starting material were used in the same manner as in Example 1-3 to obtain the title compound.

$^1$H-NMR (DMSO-d6, 500 MHz) δ 9.15 (s, 1H), 8.75 (s, 1H), 7.94 (s, 1H), 7.09 (m, 6H), 6.85 (m, 1H), 5.36 (m, 2H), 5.23 (s, 2H)

Example 71: Synthesis of 6-(2,6-difluoro-3-pyridyl)-2-[(3-fluorophenoxy)methyl]imidazo[1,2-a]pyrimidine

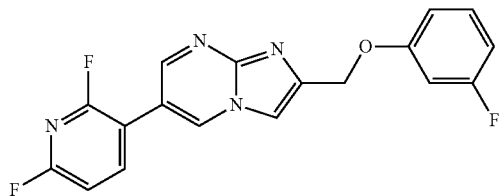

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and (2,6-difluoro-3-pyridyl)boronic acid were used in the same manner as in Example 1-3 to obtain the title compound.

$^1$H-NMR (CDCl$_3$, 500 MHz) δ 8.69 (m, 2H), 8.09 (m, 1H), 7.69 (s, 1H), 7.27 (m, 1H), 7.06 (m, 1H), 6.82 (s, 1H), 6.75 (m, 2H), 5.37 (s, 2H)

Example 72: Synthesis of 5-[2-[(4-fluorophenoxy)methyl]imidazo[1,2-a]pyrimidin-6-yl]-2-methyl-aniline

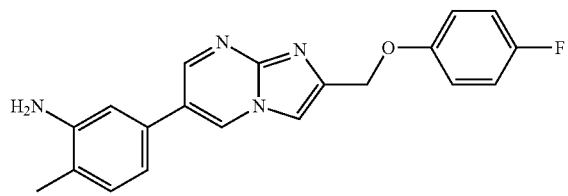 [SMILES: Cc1ccc(-c2cnc3nc(COc4ccc(F)cc4)cn3c2)cc1N]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (3-amino-4-methyl-phenyl)boronic acid were used in the same manner as in Example 1-3 to obtain the title compound.

$^1$H-NMR (DMSO-d6, 500 MHz) δ 9.12 (s, 1H), 8.74 (s, 1H), 7.93 (s, 1H), 7.08 (m, 5H), 6.90 (s, 1H), 6.80 (m, 1H), 5.22 (s, 2H), 5.03 (m, 2H), 2.08 (s, 3H)

Example 73: Synthesis of 4,5-difluoro-2-[2-[(4-fluorophenoxy)methyl]imidazo[1,2-a]pyrimidin-6-yl]aniline

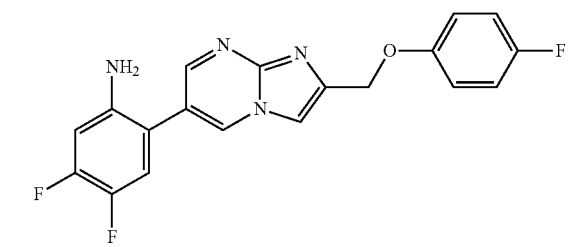 [SMILES: Nc1cc(F)c(F)cc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-amino-4,5-difluoro-phenyl)boronic acid were used in the same manner as in Example 1-3 to obtain the title compound.

$^1$H-NMR (DMSO-d6, 500 MHz) δ 8.96 (s, 1H), 8.48 (s, 1H), 7.94 (s, 1H), 7.27 (m, 1H), 7.15 (m, 4H), 6.74 (m, 1H), 5.35 (s, 2H), 5.24 (s, 2H)

Example 74: Synthesis of 2-[2-[(4-fluorophenoxy)methyl]imidazo[1,2-a]pyrimidin-6-yl]-5-methyl-aniline

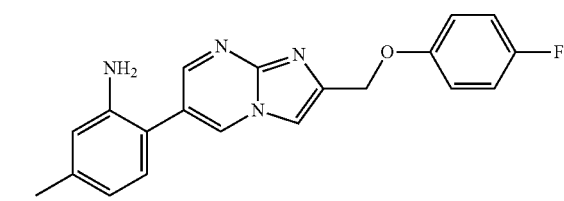 [SMILES: Cc1ccc(-c2cnc3nc(COc4ccc(F)cc4)cn3c2)c(N)c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-amino-4-methyl-phenyl)boronic acid were used in the same manner as in Example 1-3 to obtain the title compound.

$^1$H-NMR (DMSO-d6, 500 MHz) δ 8.88 (s, 1H), 8.46 (s, 1H), 7.90 (s, 1H), 7.10 (m, 4H), 6.95 (m, 1H), 6.57 (s, 1H), 6.47 (m, 1H), 5.22 (s, 2H), 5.06 (s, 2H), 2.19 (s, 3H)

Example 75: Synthesis of 5-chloro-2-[2-[(4-fluorophenoxy)methyl]imidazo[1,2-a]pyrimidin-6-yl]aniline

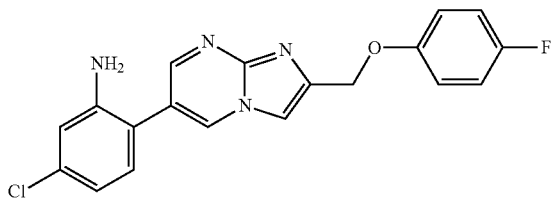 [SMILES: Nc1cc(Cl)ccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-amino-4-chloro-phenyl)boronic acid were used in the same manner as in Example 1-3 to obtain the title compound.

$^1$H-NMR (DMSO-d6, 500 MHz) δ 8.93 (s, 1H), 8.44 (s, 1H), 7.93 (s, 1H), 7.10 (m, 5H), 6.80 (s, 1H), 6.64 (d, 1H), 5.48 (s, 2H), 5.24 (s, 2H)

Example 76: Synthesis of 2-[2-[(4-fluorophenoxy)methyl]imidazo[1,2-a]pyrimidin-6-yl]-4-methylaniline

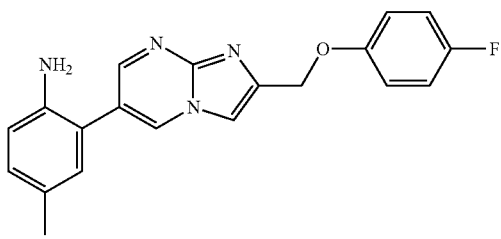 [SMILES: Cc1ccc(N)c(-c2cnc3nc(COc4ccc(F)cc4)cn3c2)c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-amino-5-methyl-phenyl)boronic acid were used in the same manner as in Example 1-3 to obtain the title compound.

$^1$H-NMR (DMSO-d6, 500 MHz) δ 8.92 (s, 1H), 8.50 (s, 1H), 7.91 (s, 1H), 7.11 (m, 4H), 6.92 (m, 2H), 6.67 (d, 1H), 5.24 (s, 2H), 4.93 (s, 2H), 2.17 (s, 3H)

Example 77: Synthesis of 5-fluoro-2-[2-[(4-fluorophenoxy)methyl]imidazo[1,2-a]pyrimidin-6-yl]aniline

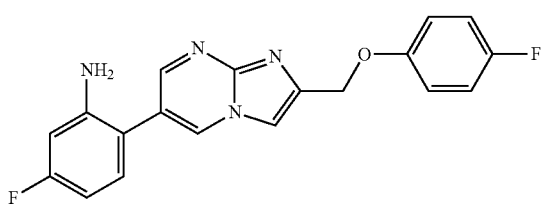 [SMILES: Nc1cc(F)ccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-amino-4-fluoro-phenyl)boronic acid were used in the same manner as in Example 1-3 to obtain the title compound.

$^1$H-NMR (DMSO-d6, 500 MHz) δ 8.90 (s, 1H), 8.43 (s, 1H), 7.93 (s, 1H), 7.10 (m, 5H), 6.53 (m, 1H), 6.42 (m, 1H), 5.46 (s, 2H), 5.23 (s, 2H)

Example 78: Synthesis of 2-[(4-fluorophenoxy)methyl]-6-(4-methyl-3-pyridyl)imidazo[1,2-a]pyrimidine

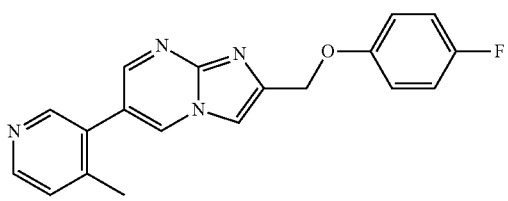 [SMILES: Cc1ccncc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (4-methyl-3-pyridyl)boronic acid as were used in the same manner as in Example 1-3 to obtain the title compound.

$^1$H-NMR (DMSO-d6, 500 MHz) δ 9.07 (s, 1H), 8.62 (s, 1H), 8.50 (t, 2H), 7.94 (s, 1H), 7.40 (m, 1H), 7.09 (m, 4H), 5.25 (s, 2H), 2.33 (s, 3H)

Example 79: Synthesis of 2-[(3-fluorophenoxy)methyl]-6-(2-fluoro-4-pyridyl)imidazo[1,2-a]pyrimidine

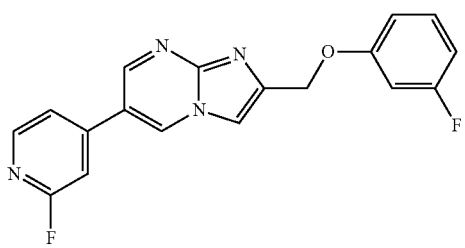 [SMILES: Fc1cccc(OCc2cn3cc(-c4ccnc(F)c4)cnc3n2)c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and (2-fluoro-4-pyridyl)boronic acid were used in the same manner as in Example 1-3 to obtain the title compound.

$^1$H-NMR (CDCl$_3$, 500 MHz) δ 8.84 (s, 1H), 8.70 (s, 1H), 8.41 (d, 1H), 7.73 (s, 1H), 7.44 (d, 1H), 7.26 (m, 1H), 7.18 (s, 1H), 6.85 (d, 1H), 6.76 (m, 2H), 5.39 (s, 2H)

Example 80: Synthesis of 2-[(3-fluorophenoxy)methyl]-6[6-(trifluoromethyl)-3-pyridyl)imidazo[1,2-a]pyrimidine

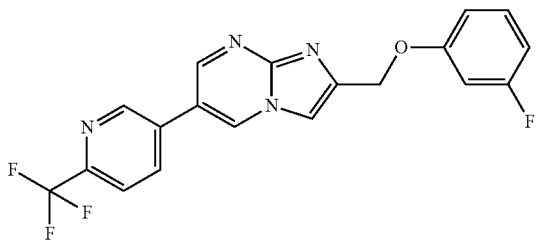 [SMILES: Fc1cccc(OCc2cn3cc(-c4ccc(C(F)(F)F)nc4)cnc3n2)c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and [6-(trifluoromethyl)-3-pyridyl)boronic acid were used in the same manner as in Example 1-3 to obtain the title compound.

$^1$H-NMR (CDCl$_3$, 500 MHz) δ 8.98 (s, 1H), 8.82 (s, 1H), 8.66 (s, 1H), 8.12 (d, 1H), 7.90 (m, 1H), 7.74 (s, 1H), 6.86 (m, 1H), 6.72 (m, 2H), 5.41 (s, 2H)

Example 81: Synthesis of 2-[(3-fluorophenoxy)methyl]-6-(6-fluoro-3-pyridyl)imidazo[1,2-a]pyrimidine

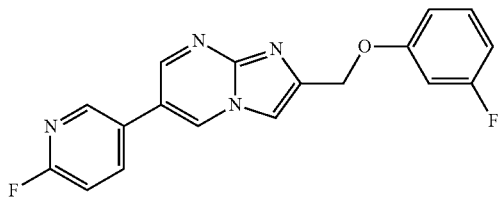 [SMILES: Fc1cccc(OCc2cn3cc(-c4ccc(F)nc4)cnc3n2)c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and (6-fluoro-3-pyridyl)boronic acid were used in the same manner as in Example 1-3 to obtain the title compound.

$^1$H-NMR (CDCl$_3$, 500 MHz) δ 8.74 (s, 1H), 8.54 (s, 1H), 8.44 (s, 1H), 8.00 (m, 1H), 7.67 (s, 1H), 7.13 (m, 1H), 6.83 (m, 1H), 6.76 (d, 1H), 6.71 (m, 1H), 5.37 (s, 2H)

Example 82: Synthesis of 2-[(3-fluorophenoxy)methyl]-6-(2-fluoro-3-pyridyl)imidazo[1,2-a]pyrimidine

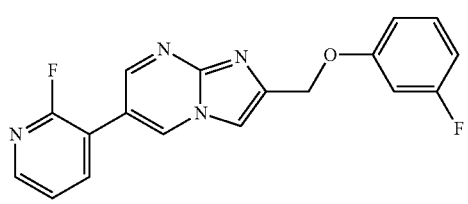 [SMILES: Fc1cccc(OCc2cn3cc(-c4cccnc4F)cnc3n2)c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and (2-fluoro-3-pyridyl)boronic acid were used in the same manner as in Example 1-3 to obtain the title compound.

$^1$H-NMR (CDCl$_3$, 500 MHz) δ 8.75 (s, 1H), 8.70 (s, 1H), 8.32 (d, 1H), 7.98 (t, 1H), 7.67 (s, 1H), 7.39 (t, 1H), 6.83 (m, 1H), 6.76 (d, 1H), 6.69 (m, 1H), 5.37 (s, 2H)

Example 83: Synthesis of 6-(5,6-difluoro-3-pyridyl)-2-[(4-fluorophenoxy)methyl]imidazo[1,2-a]pyrimidine

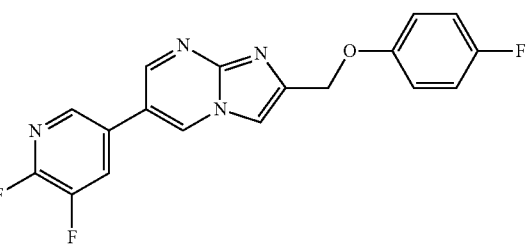

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (5,6-difluoro-3-pyridyl)boronic acid were used in the same manner as in Example 1-3 to obtain the title compound.

$^1$H-NMR (DMSO-d6, 500 MHz) δ 9.40 (s, 1H), 8.94 (s, 1H), 8.55 (m, 1H), 8.48 (s, 1H), 7.96 (s, 1H), 7.09 (m, 4H), 5.25 (s, 2H)

Example 84: Synthesis of 5-[2-[(4-fluorophenoxy)methyl]imidazo[1,2-a]pyrimidin-6-yl]-2-methoxyaniline

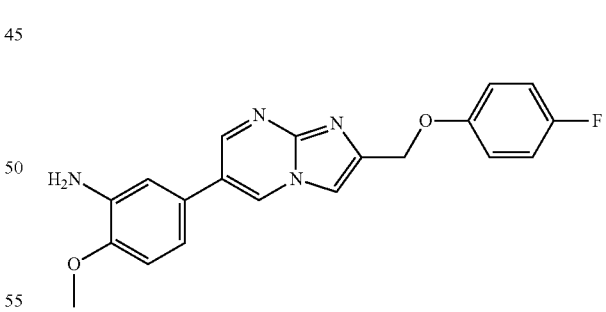

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (3-amino-4-methoxy-phenyl)boronic acid were used in the same manner as in Example 1-3 to obtain the title compound.

$^1$H-NMR (DMSO-d6, 500 MHz) δ 9.08 (s, 1H), 8.74 (s, 1H), 7.91 (s, 1H), 7.10 (m, 4H), 6.91 (m, 3H), 5.21 (s, 2H), 4.90 (s, 2H), 3.79 (s, 3H)

Example 85: Synthesis of 2-[(4-fluorophenoxy)methyl]-6-(5-fluoro-2-pyridyl)imidazo[1,2-a]pyrimidine

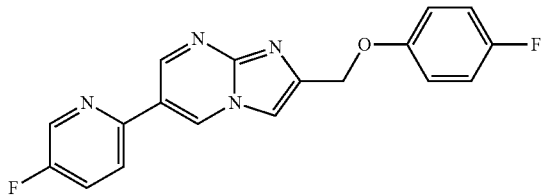 [SMILES: Fc1ccc(OCc2cn3cc(-c4ccc(F)cn4)cnc3n2)cc1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (5-fluoro-2-pyridyl)boronic acid were used in the same manner as in Example 1-3 to obtain the title compound.

$^1$H-NMR (CDCl$_3$, 500 MHz) δ 9.07 (m, 2H), 8.56 (s, 1H), 7.78 (s, 1H), 7.66 (s, 1H), 7.59 (m, 1H), 6.98 (m, 4H), 5.35 (s, 2H)

Example 86: Synthesis of 2-[(4-fluorophenoxy)methyl]-6-(5-methoxy-2-pyridyl)imidazo[1,2-a]pyrimidine

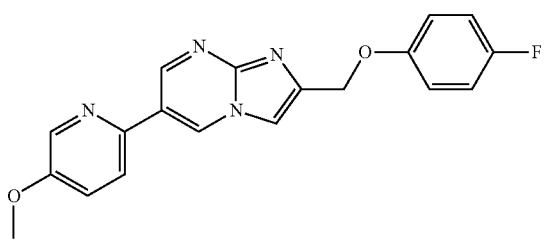 [SMILES: COc1ccc(-c2cnc3nc(COc4ccc(F)cc4)cn3c2)nc1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (5-methoxy-2-pyridyl)boronic acid were used in the same manner as in Example 1-3 to obtain the title compound.

$^1$H-NMR (DMSO-d6, 500 MHz) δ 9.54 (s, 1H), 9.17 (s, 1H), 8.40 (s, 1H), 8.00 (m, 2H), 7.56 (d, 1H), 7.10 (m, 4H), 5.22 (s, 2H), 3.88 (s, 3H)

Example 87: Synthesis of 6-(4-chloro-3-pyridyl)-2-[(4-fluorophenoxy)methyl]imidazo[1,2-a]pyrimidine

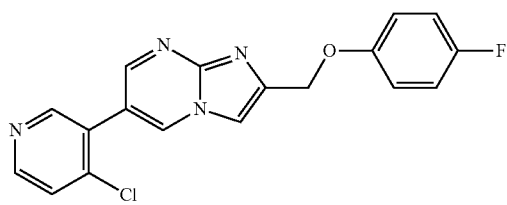 [SMILES: Fc1ccc(OCc2cn3cc(-c4cnccc4Cl)cnc3n2)cc1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (4-chloro-3-pyridyl)boronic acid were used in the same manner as in Example 1-3 to obtain the title compound.

$^1$H-NMR (DMSO-d6, 500 MHz) δ 9.22 (s, 1H), 8.77 (s, 1H), 8.71 (s, 1H), 8.64 (d, 1H), 8.02 (s, 1H), 7.77 (d, 1H), 7.12 (m, 4H), 5.28 (s, 2H)

Example 88: Synthesis of 6-(5-chloro-3-pyridyl)-2-[(4-fluorophenoxy)methyl]imidazo[1,2-a]pyrimidine

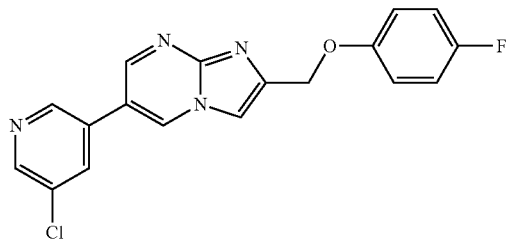 [SMILES: Fc1ccc(OCc2cn3cc(-c4cncc(Cl)c4)cnc3n2)cc1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (5-chloro-3-pyridyl)boronic acid were used in the same manner as in Example 1-3 to obtain the title compound.

$^1$H-NMR (DMSO-d6, 500 MHz) δ 9.46 (s, 1H), 8.99 (d, 2H), 8.70 (s, 1H), 8.42 (s, 1H), 7.97 (s, 1H), 7.11 (m, 4H), 5.26 (s, 2H)

Example 89: Synthesis of 2-[(4-fluorophenoxy)methyl]-6-(5-methoxy-3-pyridyl)imidazo[1,2-a]pyrimidine

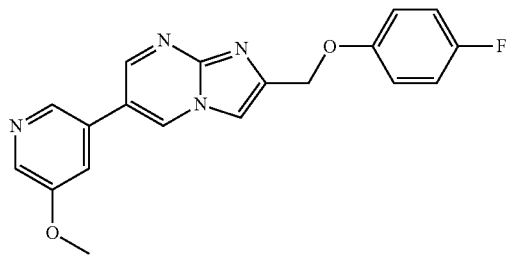 [SMILES: COc1cncc(-c2cnc3nc(COc4ccc(F)cc4)cn3c2)c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (5-methoxy-3-pyridyl)boronic acid were used in the same manner as in Example 1-3 to obtain the title compound.

$^1$H-NMR (DMSO-d6, 500 MHz) δ 9.38 (s, 1H), 8.96 (s, 1H), 8.55 (s, 1H), 8.34 (s, 1H), 7.94 (s, 1H), 7.78 (s, 1H), 7.09 (m, 4H), 5.24 (s, 2H), 3.90 (s, 3H)

Example 90: Synthesis of 5-[2-[(4-fluorophenoxy) methyl]imidazo[1,2-a]pyrimidin-6-yl]pyridin-2-ol

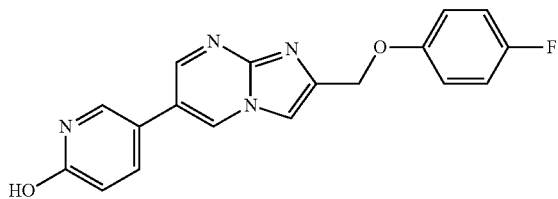 [SMILES: Oc1ccc(-c2cnc3nc(COc4ccc(F)cc4)cn3c2)cn1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (6-hydroxy-3-pyridyl)boronic acid were used in the same manner as in Example 1-3 to obtain the title compound.

$^1$H-NMR (DMSO-d6, 500 MHz) δ 9.35 (s, 1H), 8.91 (s, 1H), 8.62 (s, 1H), 8.39 (m, 1H), 7.95 (s, 1H), 7.38 (d, 1H), 7.11 (m, 4H), 5.22 (s, 2H)

Example 91: Synthesis of 6-(6-fluoro-5-methyl-3-pyridyl)-2-[(4-fluorophenoxy)methyl]imidazo[1,2-a]pyrimidine

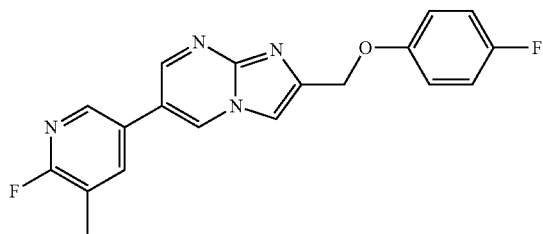 [SMILES: Cc1cc(-c2cnc3nc(COc4ccc(F)cc4)cn3c2)cnc1F]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (6-fluoro-5-methyl-3-pyridyl)boronic acid were used in the same manner as in Example 1-3 to obtain the title compound.

$^1$H-NMR (DMSO-d6, 500 MHz) δ 9.34 (s, 1H), 8.92 (s, 1H), 8.44 (s, 1H), 8.25 (d, 1H), 7.95 (s, 1H), 7.10 (m, 4H), 5.25 (s, 2H), 2.32 (s, 3H)

Example 92: Synthesis of 2-[(4-fluorophenoxy)methyl]-6-(6-methyl-3-pyridyl)imidazo[1,2-a]pyrimidine

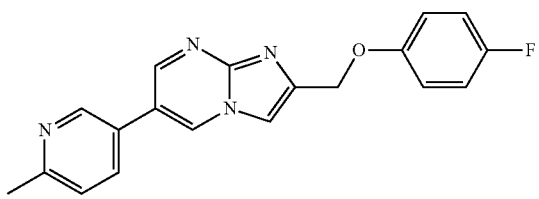 [SMILES: Cc1ccc(-c2cnc3nc(COc4ccc(F)cc4)cn3c2)cn1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (6-methyl-3-pyridyl)boronic acid were used in the same manner as in Example 1-3 to obtain the title compound.

$^1$H-NMR (DMSO-d6, 500 MHz) δ 9.34 (s, 1H), 8.92 (s, 1H), 8.84 (s, 1H), 8.06 (d, 1H), 7.95 (s, 1H), 7.41 (d, 1H), 7.10 (m, 4H), 5.25 (s, 2H), 2.32 (s, 3H)

Example 93: Synthesis of 2-[(3-fluorophenoxy)methyl]-6-(5-fluoro-2-pyridyl)imidazo[1,2-a]pyrimidine

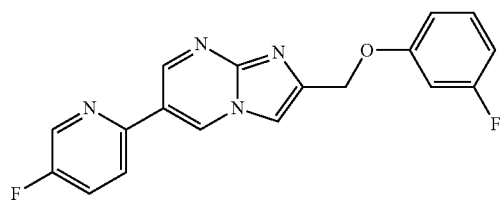 [SMILES: Fc1ccc(-c2cnc3nc(COc4cccc(F)c4)cn3c2)nc1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and (5-fluoro-2-pyridyl)boronic acid were used in the same manner as in Example 1-3 to obtain the title compound.

$^1$H-NMR (DMSO-d6, 500 MHz) δ 9.61 (s, 1H), 9.18 (s, 1H), 8.69 (s, 1H), 8.12 (t, 1H), 8.03 (s, 1H), 7.92 (t, 1H), 7.30 (m, 1H), 6.95 (d, 1H), 6.88 (d, 1H), 6.75 (t, 1H), 5.24 (s, 2H)

Example 94: Synthesis of 2-[(3-fluorophenoxy)methyl]-6-[4-fluoro-2-(trifluoromethyl)phenyl]imidazo[1,2-a]pyrimidine

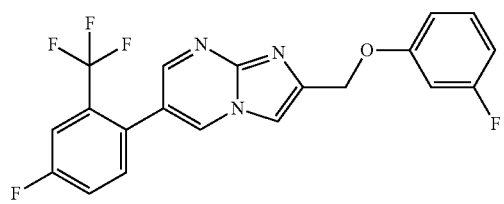 [SMILES: Fc1cccc(OCc2cn3cc(-c4ccc(F)cc4C(F)(F)F)cnc3n2)c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and [4-fluoro-2-(trifluoromethyl)phenyl]boronic acid were used in the same manner as in Example 1-3 to obtain the title compound.

$^1$H-NMR (DMSO-d6, 500 MHz) δ 9.27 (s, 1H), 8.77 (s, 1H), 8.23 (s, 1H), 7.89 (t, 1H), 7.76 (t, 1H), 7.68 (t, 1H), 7.35 (m, 1H), 7.01 (d, 1H), 6.93 (d, 1H), 6.81 (t, 1H), 5.38 (s, 2H)

Example 95: Synthesis of 4-[2-[(3-fluorophenoxy)methyl]imidazo[1,2-a]pyrimidin-6-yl]-3-methoxybenzonitrile

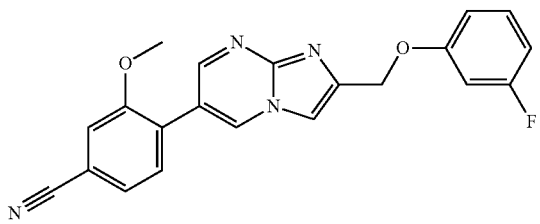 [SMILES: COc1cc(C#N)ccc1-c1cnc2nc(COc3cccc(F)c3)cn2c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and (4-cyano-2-methoxy-phenyl)boronic acid were used in the same manner as in Example 1-3 to obtain the title compound.

$^1$H-NMR (DMSO-d6, 500 MHz) δ 9.18 (s, 1H), 8.70 (s, 1H), 7.99 (s, 1H), 7.67 (m, 2H), 7.58 (m, 1H), 7.32 (m, 1H), 6.98 (m, 1H), 6.91 (m, 1H), 6.78 (m, 1H), 5.28 (s, 2H), 3.88 (s, 3H)

Example 96: Synthesis of [5-fluoro-2-[2-[(3-fluorophenoxy)methyl]imidazo[1,2-a]pyrimidin-6-yl]phenyl]methanol

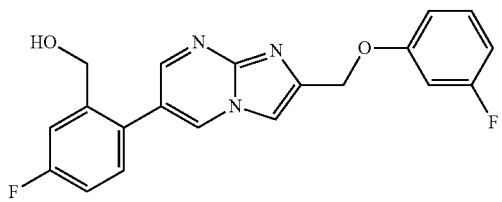 [SMILES: OCc1cc(F)ccc1-c1cnc2nc(COc3cccc(F)c3)cn2c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and [4-fluoro-2-(hydroxymethyl)phenyl]boronic acid were used in the same manner as in Example 1-3 to obtain the title compound.

$^1$H-NMR (DMSO-d6, 500 MHz) δ 8.98 (s, 1H), 8.55 (s, 1H), 7.95 (s, 1H), 7.42 (m, 2H), 7.33 (m, 1H), 7.24 (m, 1H), 6.97 (d, 1H), 6.91 (d, 1H), 6.76 (t, 1H), 5.41 (s, 1H), 5.28 (s, 2H) 4.45 (d, 2H)

Example 97: Synthesis of [5-fluoro-2-[2-[(4-fluorophenoxy)methyl]imidazo[1,2-a]pyrimidin-6-yl]phenyl]methanol

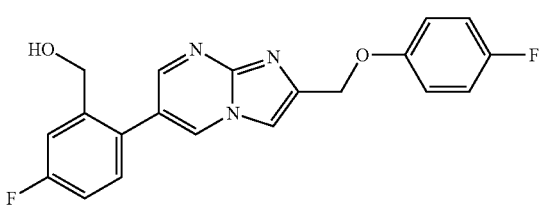 [SMILES: OCc1cc(F)ccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and [4-fluoro-2-(hydroxymethyl)phenyl]boronic acid were used in the same manner as in Example 1-3 to obtain the title compound.

$^1$H-NMR (DMSO-d6, 500 MHz) δ 8.97 (s, 1H), 8.54 (s, 1H), 7.93 (s, 1H), 7.41 (m, 2H), 7.24 (m, 1H), 7.10 (m, 4H), 5.74 (s, 1H), 5.23 (s, 2H) 4.45 (d, 2H)

Example 98: Synthesis of 6-(4-fluoro-2-methylsulfanyl-phenyl)-2-[(4-fluorophenoxy)methyl]imidazo[1,2-a]pyrimidine

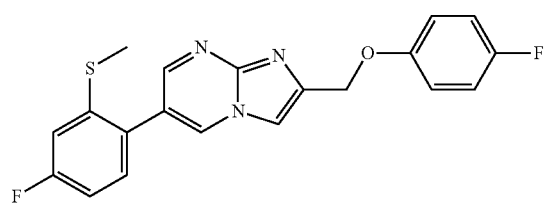 [SMILES: CSc1cc(F)ccc1-c1cnc2nc(COc3ccc(F)cc3)cn2c1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (4-fluoro-2-methylsulfanyl-phenyl)boronic acid were used in the same manner as in Example 1-3 to obtain the title compound.

$^1$H-NMR (DMSO-d6, 500 MHz) δ 9.01 (s, 1H), 8.51 (s, 1H), 7.98 (s, 1H), 7.43 (t, 1H), 7.28 (d, 1H), 7.12 (m, 5H), 5.26 (s, 2H), 2.48 (s, 3H)

Example 99: Synthesis of 2-[(4-fluorophenoxy)methyl]-6-(2-methoxy-4-pyridyl)imidazo[1,2-a]pyrimidine

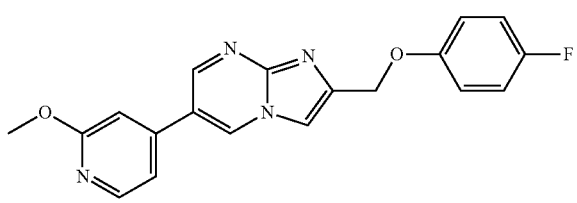 [SMILES: COc1cc(-c2cnc3nc(COc4ccc(F)cc4)cn3c2)ccn1]

4-Fluorophenol as a starting material was used in the same manner as in Example 1-2 to obtain 6-bromo-2-(4-fluorophenoxymethyl)imidazo[1,2-a]pyrimidine. The obtained 6-bromo-2-(4-fluorophenoxymethyl)imidazo[1,2-a]pyrimidine and (2-methoxy-4-pyridyl)boronic acid were used in the same manner as in Example 1-3 to obtain the title compound.

$^1$H-NMR (CDCl$_3$, 500 MHz) δ 8.80 (s, 1H), 8.60 (s, 1H), 8.30 (s, 1H), 7.66 (s, 1H), 6.98 (m, 6H), 5.34 (s, 2H), 4.01 (s, 3H)

Example 100: Synthesis of 2-[2-[(3-fluorophenoxy)methyl]imidazo[1,2-a]pyrimidin-6-yl]-4-methyl-aniline

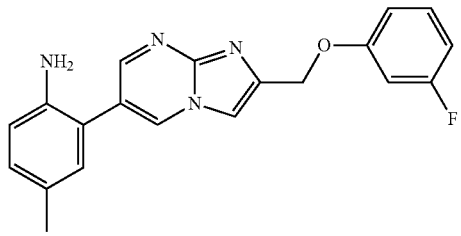 [SMILES: Cc1ccc(N)c(-c2cnc3nc(COc4cccc(F)c4)cn3c2)c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and (2-amino-5-methyl-phenyl)boronic acid were used in the same manner as in Example 1-3 to obtain the title compound.

$^1$H-NMR (DMSO-d6, 500 MHz) δ 8.95 (s, 1H), 8.51 (s, 1H), 7.94 (s, 1H), 7.33 (m, 1H), 6.98 (m, 1H), 6.93 (m, 3H), 6.79 (t, 1H), 6.68 (d, 1H), 5.41 (s, 2H), 4.95 (s, 2H), 2.21 (s, 3H)

Example 101: Synthesis of 5-fluoro-2-[2-[(3-fluorophenoxy)methyl]imidazo[1,2-a]pyrimidin-6-yl]aniline

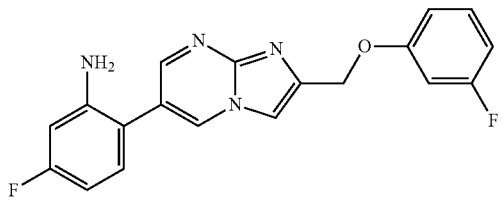 [SMILES: Nc1cc(F)ccc1-c1cnc2nc(COc3cccc(F)c3)cn2c1]

3-Fluorophenol as a starting material was used in the same manner as in Example 1-2 to obtain 6-bromo-2-(3-fluorophenoxymethyl)imidazo[1,2-a]pyrimidine. The obtained 6-bromo-2-(3-fluorophenoxymethyl)imidazo[1,2-a]pyrimidine and (2-amino-4-fluoro-phenyl)boronic acid were used in the same manner as in Example 1-3 to obtain the title compound.

$^1$H-NMR (DMSO-d6, 500 MHz) δ 8.91 (s, 1H), 8.44 (s, 1H), 7.93 (s, 1H), 7.31 (m, 1H), 7.08 (t, 1H), 6.97 (d, 1H), 6.90 (d, 1H), 6.77 (t, 1H), 6.52 (t, 1H), 5.48 (s, 2H), 5.27 (s, 2H)

Example 102: Synthesis of 6-(4-fluorophenyl)-2-(pyridin-2-yloxymethyl)imidazo[1,2-a]pyrimidine

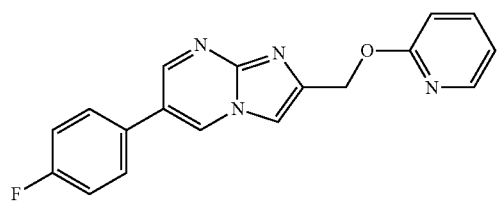 [SMILES: Fc1ccc(-c2cnc3nc(COc4ccccn4)cn3c2)cc1]

2-Hydroxypyridine and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 4-fluorophenylboronic acid were used in the same manner as in Example 1-3 to obtain the title compound.

$^1$H-NMR (CDCl$_3$, 500 MHz) δ 8.77 (s, 1H), 8.51 (s, 1H), 8.22 (s, 1H), 7.63 (m, 4H), 7.25 (m, 2H), 6.83 (m, 2H), 5.67 (s, 2H)

Example 103: Synthesis of 6-(2-methylphenyl)-2-(pyridin-2-yloxymethyl)imidazo[1,2-a]pyrimidine

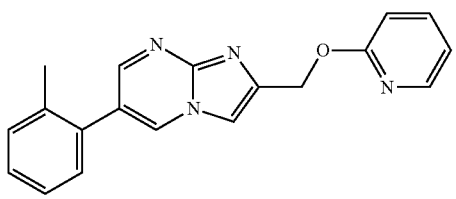 [SMILES: Cc1ccccc1-c1cnc2nc(COc3ccccn3)cn2c1]

2-Hydroxypyridine and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 2-methylphenylboronic acid were used in the same manner as in Example 1-3 to obtain the title compound.

$^1$H-NMR (CDCl$_3$, 500 MHz) δ 8.58 (s, 1H), 8.33 (s, 1H), 8.23 (s, 1H), 7.65 (m, 2H), 7.37 (m, 3H), 7.11 (m, 1H), 6.93 (m, 2H), 5.68 (s, 2H), 2.34 (s, 3H)

Example 104: Synthesis of 6-(4-fluoro-2-methoxyphenyl)-2-(pyridin-2-yloxymethyl)imidazo[1,2-a]pyrimidine

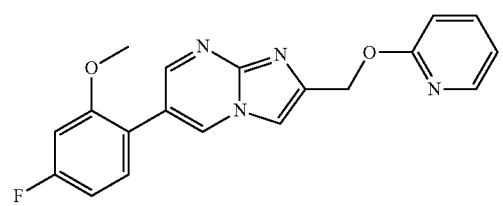 [SMILES: COc1cc(F)ccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 4-fluoro-2-methoxyphenylboronic acid were used in the same manner as in Example 1-3 to obtain the title compound.

$^1$H-NMR (CDCl$_3$, 500 MHz) δ 8.65 (s, 1H), 8.52 (s, 1H), 8.20 (s, 1H), 7.61 (s, 1H), 7.58 (t, 1H), 7.31 (t, 1H), 6.91 (t, 1H), 6.85 (d, 1H), 6.77 (m, 2H), 5.63 (s, 2H), 3.84 (s, 3H)

Example 105: Synthesis of 6-(2,4-difluorophenyl)-2-(pyridin-2-yloxymethyl)imidazo[1,2-a]pyrimidine

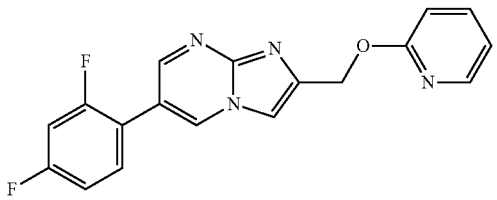 [SMILES: Fc1ccc(-c2cnc3nc(COc4ccccn4)cn3c2)c(F)c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 2,4-difluorophenylboronic acid were used in the same manner as in Example 1-3 to obtain the title compound.

$^1$H-NMR (DMSO-d6, 500 MHz) δ 9.59 (s, 1H), 9.19 (s, 1H), 8.35 (s, 1H), 8.23 (s, 1H), 7.82 (m, 2H), 7.59 (m, 1H), 7.39 (m, 1H), 7.09 (t, 1H), 6.98 (d, 1H), 5.65 (s, 2H)

Example 106: Synthesis of 6-(4-fluoro-2-methylphenyl)-2-(pyridin-2-yloxymethyl)imidazo[1,2-a]pyrimidine

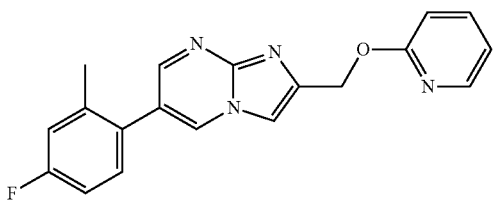 [SMILES: Cc1cc(F)ccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 4-fluoro-2-methylphenylboronic acid were used in the same manner as in Example 1-3 to obtain the title compound.

$^1$H-NMR (CDCl$_3$, 500 MHz) δ 8.53 (s, 1H), 8.31 (s, 1H), 8.22 (s, 1H), 7.66 (m, 2H), 7.24 (m, 1H), 7.05 (m, 2H), 6.90 (m, 2H), 5.68 (s, 2H), 2.32 (s, 3H)

Example 107: Synthesis of 6-(2,3-difluorophenyl)-2-(pyridin-2-yloxymethyl)imidazo[1,2-a]pyrimidine

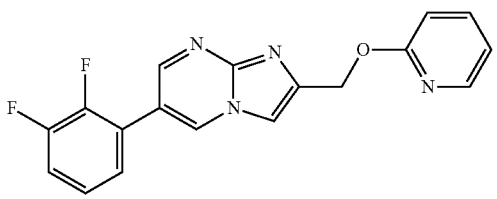 [SMILES: Fc1cccc(-c2cnc3nc(COc4ccccn4)cn3c2)c1F]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 2,3-difluorophenylboronic acid were used in the same manner as in Example 1-3 to obtain the title compound.

$^1$H-NMR (CDCl$_3$, 500 MHz) δ 8.69 (d, 2H), 8.19 (s, 1H), 7.70 (s, 1H), 7.61 (s, 1H), 7.28 (m, 3H), 6.90 (m, 2H), 5.65 (s, 2H)

Example 108: Synthesis of 6-(5-fluoro-2-methylphenyl)-2-(pyridin-2-yloxymethyl)imidazo[1,2-a]pyrimidine

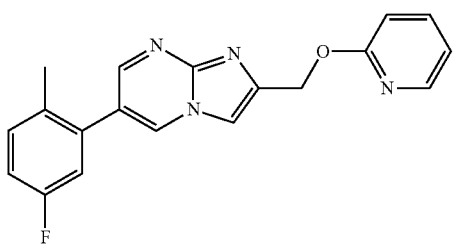 [SMILES: Cc1ccc(F)cc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 5-fluoro-2-methylphenylboronic acid were used in the same manner as in Example 1-3 to obtain the title compound.

$^1$H-NMR (CDCl$_3$, 500 MHz) δ 8.55 (s, 1H), 8.35 (s, 1H), 8.22 (s, 1H), 7.69 (s, 1H), 7.62 (m, 1H), 7.30 (m, 1H), 7.10 (m, 1H), 6.99 (d, 1H), 6.92 (t, 1H), 6.87 (m, 1H), 5.68 (s, 2H), 2.29 (s, 3H)

Example 109: Synthesis of 6-(3-fluoro-2-methylphenyl)-2-(pyridin-2-yloxymethyl)imidazo[1,2-a]pyrimidine

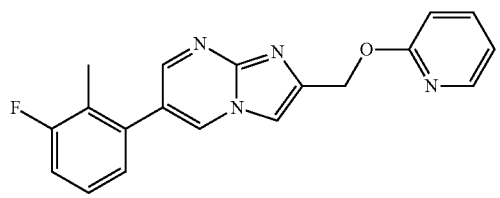 [SMILES: Cc1c(F)cccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 3-fluoro-2-methylphenylboronic acid were used in the same manner as in Example 1-3 to obtain the title compound.

$^1$H-NMR (CDCl$_3$, 500 MHz) δ 8.53 (s, 1H), 8.36 (s, 1H), 8.21 (s, 1H), 7.68 (s, 1H), 7.61 (m, 1H), 7.28 (m, 1H), 7.15 (t, 1H), 7.08 (t, 1H), 6.91 (t, 1H), 6.85 (d, 1H), 5.67 (s, 2H), 2.23 (s, 3H)

Example 110: Synthesis of 6-(7-fluoro-2H-benzo[1,3]dioxol-4-yl)-2-(pyridin-2-yloxymethyl)imidazo[1,2-a]pyrimidine

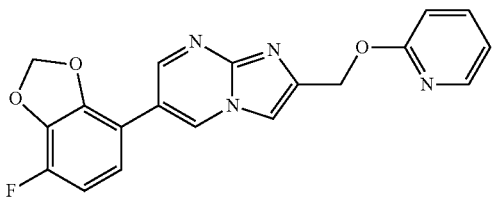 [SMILES: Fc1ccc(-c2cnc3nc(COc4ccccn4)cn3c2)c2c1OCO2]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 2-(7-fluoro-2H-1,3-benzodioxol-4-yl)-4,4,5,5-tetramethyl-1,3,2-dioxaborolane were used in the same manner as in Example 1-3 to obtain the title compound.

$^1$H-NMR (CDCl$_3$, 500 MHz) δ 8.84 (s, 1H), 8.75 (s, 1H), 8.21 (d, 1H), 7.62 (m, 2H), 7.06 (m, 1H), 6.93 (m, 1H), 6.85 (m, 2H), 6.16 (s, 2H), 5.65 (s, 2H)

Example 111: Synthesis of 6-(4-chloro-2-methoxyphenyl)-2-(pyridin-2-yloxymethyl)imidazo[1,2-a]pyrimidine

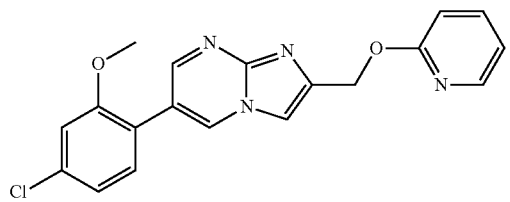 [SMILES: COc1cc(Cl)ccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 4-chloro-2-methoxyphenylboronic acid were used in the same manner as in Example 1-3 to obtain the title compound.

$^1$H-NMR (CDCl$_3$, 500 MHz) δ 8.64 (s, 1H), 8.54 (s, 1H), 8.18 (d, 1H), 7.59 (m, 2H), 7.28 (m, 1H), 7.07 (m, 2H), 6.88 (m, 2H), 5.62 (s, 2H), 3.84 (s, 3H)

Example 112: Synthesis of 6-(3-fluoro-2-methoxyphenyl)-2-(2-pyridyloxymethyl)imidazo[1,2-a]pyrimidine

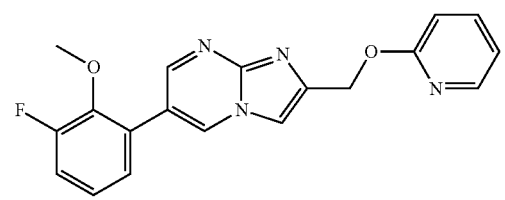 [SMILES: COc1c(F)cccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and (3-fluoro-2-methoxyphenyl)boronic acid were used in the same manner as in Example 1-3 to obtain the title compound.

$^1$H-NMR (CDCl$_3$, 500 MHz) δ 8.73 (d, 1H), 8.62 (d, 1H), 8.22 (t, 1H), 7.67 (s, 1H), 7.64 (m, 1H), 7.19 (m, 3H), 6.94 (t, 1H), 6.88 (m, 1H), 5.85 (s, 2H), 3.85 (s, 3H)

Example 113: Synthesis of 6-[4-fluoro-2-(trifluoromethyl)phenyl]-2-(2-pyridyloxymethyl)imidazo[1,2-a]pyrimidine

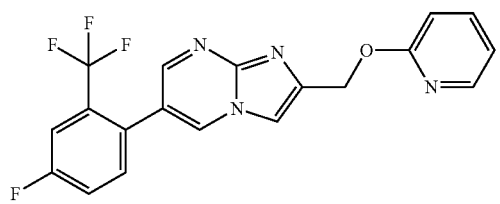 [SMILES: Fc1ccc(-c2cnc3nc(COc4ccccn4)cn3c2)c(C(F)(F)F)c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and [4-fluoro-2-(trifluoromethyl)phenyl]boronic acid were used in the same manner as in Example 1-3 to obtain the title compound.

$^1$H-NMR (CDCl$_3$, 500 MHz) δ 8.47 (s, 1H), 8.38 (s, 1H), 8.22 (d, 1H), 7.67 (s, 1H), 7.64 (m, 1H), 7.57 (m, 1H), 7.43 (m, 2H), 6.93 (m, 1H), 6.87 (m, 1H), 5.67 (s, 2H)

Example 114: Synthesis of 6-(4-fluoro-2-methylphenyl)-2-[(5-fluoro-2-pyridyl)oxymethyl)imidazo[1,2-a]pyrimidine

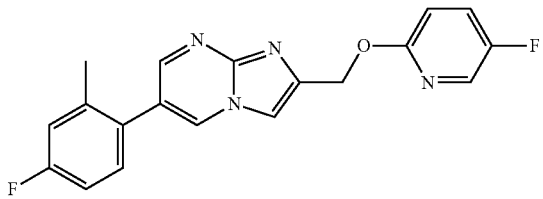

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and (4-fluoro-2-methyl-phenyl)boronic acid were used in the same manner as in Example 1-3 to obtain the title compound.

$^1$H-NMR (CDCl$_3$, 500 MHz) δ 8.51 (s, 1H), 8.35 (s, 1H), 8.03 (s, 1H), 7.67 (s, 1H), 7.38 (m, 1H), 7.22 (t, 1H), 7.04 (m, 2H), 6.83 (m, 1H), 5.61 (s, 2H), 2.31 (s, 3H)

Example 115: Synthesis of 6-(2-ethylphenyl)-2-(2-pyridyloxymethyl)imidazo[1,2-a]pyrimidine

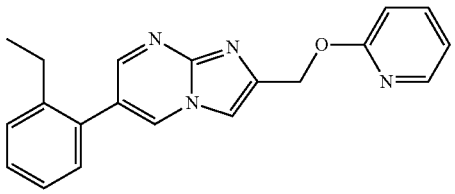 [SMILES: CCc1ccccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and (2-ethylphenyl)boronic acid were used in the same manner as in Example 1-3 to obtain the title compound.

$^1$H-NMR (CDCl$_3$, 500 MHz) δ 8.55 (s, 1H), 8.34 (s, 1H), 8.21 (d, 1H), 7.67 (s, 1H), 7.62 (m, 1H), 7.42 (m, 2H), 7.32 (m, 1H), 7.23 (d, 1H), 6.93 (t, 1H), 6.87 (d, 1H), 5.67 (s, 2H), 2.63 (q, 2H), 1.15 (t, 3H)

Example 116: Synthesis of 6-(4-fluoro-2-methylphenyl)-2-[(4-fluoro-2-pyridyl)oxymethyl)imidazo[1,2-a]pyrimidine

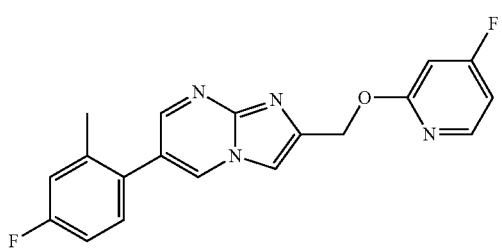 [SMILES: Cc1cc(F)ccc1-c1cnc2nc(COc3cc(F)ccn3)cn2c1]

4-Fluoropyridin-2-ol as a starting material and silver carbonate were used in the same manner as in Example 1-2 to obtain 6-bromo-2-[(4-fluoro-2-pyridyl)oxymethyl)imidazo[1,2-a]pyrimidine. The obtained 6-bromo-2-[(4-fluoro-2-pyridyl)oxymethyl)imidazo[1,2-a]pyrimidine and (4-fluoro-2-methyl-phenyl)boronic acid were used in the same manner as in Example 1-3 to obtain the title compound.

$^1$H-NMR (CDCl$_3$, 500 MHz) δ 8.64 (s, 1H), 8.08 (d, 1H), 8.05 (d, 1H), 7.48 (t, 2H), 7.40 (m, 2H), 6.91 (m, 1H), 6.59 (s, 1H), 5.47 (s, 2H), 2.47 (s, 3H)

Example 117: Synthesis of 6-(2-fluoro-4-methylphenyl)-2-(2-pyridyloxymethyl)imidazo[1,2-a]pyrimidine

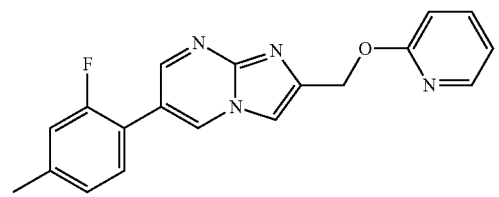 [SMILES: Cc1ccc(-c2cnc3nc(COc4ccccn4)cn3c2)c(F)c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and (2-fluoro-4-methylphenyl)boronic acid were used in the same manner as in Example 1-3 to obtain the title compound.

$^1$H-NMR (CDCl$_3$, 500 MHz) δ 8.64 (s, 1H), 8.08 (d, 1H), 8.05 (d, 1H), 7.48 (t, 2H), 7.40 (m, 2H), 6.91 (m, 1H), 6.59 (s, 1H), 5.47 (s, 2H), 2.47 (s, 3H)

Example 118: Synthesis of 6-(4-fluoro-2-methoxyphenyl)-2-[(4-fluoro-2-pyridyl)oxymethyl)imidazo[1,2-a]pyrimidine

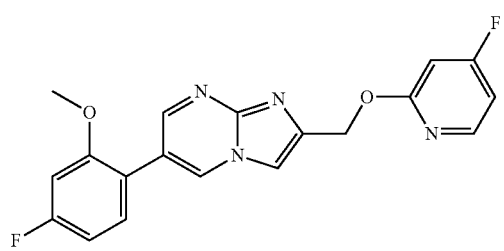 [SMILES: COc1cc(F)ccc1-c1cnc2nc(COc3cc(F)ccn3)cn2c1]

4-Fluoropyridin-2-ol as a starting material and silver carbonate were used in the same manner as in Example 1-2 to obtain 6-bromo-2-[(4-fluoro-2-pyridyl)oxymethyl)imidazo[1,2-a]pyrimidine. The obtained 6-bromo-2-[(4-fluoro-2-pyridyl)oxymethyl)imidazo[1,2-a]pyrimidine and (4-fluoro-2-methoxy-phenyl)boronic acid were used in the same manner as in Example 1-3 to obtain the title compound.

$^1$H-NMR (CDCl$_3$, 500 MHz) δ 8.67 (s, 1H), 8.49 (s, 1H), 8.16 (d, 1H), 7.61 (s, 1H), 7.31 (m, 1H), 6.78 (m, 2H), 6.69 (m, 1H), 6.55 (d, 1H), 5.65 (s, 2H), 3.85 (s, 3H)

Example 119: Synthesis of 2-[(5-fluoro-2-pyridyl)oxymethyl]-6-[4-fluoro-2-(trifluoromethyl)phenyl]imidazo[1,2-a]pyrimidine

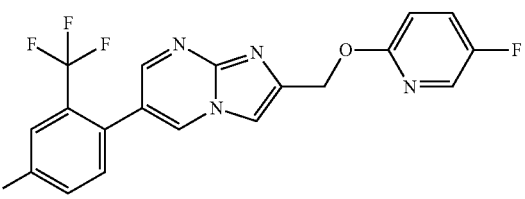

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and [4-fluoro-2-(trifluoromethyl)phenyl]boronic acid were used in the same manner as in Example 1-3 to obtain the title compound.

$^1$H-NMR (CDCl$_3$, 500 MHz) δ 8.48 (s, 1H), 8.35 (s, 1H), 8.02 (s, 1H), 7.63 (s, 1H), 7.55 (d, 1H), 7.39 (m, 3H), 6.83 (m, 1H), 5.60 (s, 2H)

Example 120: Synthesis of 6-(2,4-difluorophenyl)-2-[(4-fluoro-2-pyridyl)oxymethyl)imidazo[1,2-a]pyrimidine

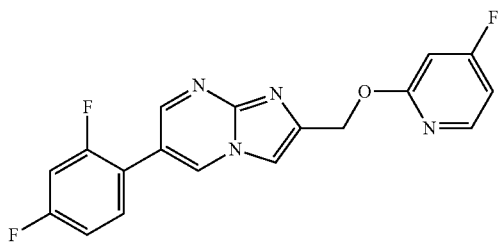 [SMILES: Fc1ccnc(OCc2cn3cc(-c4ccc(F)cc4F)cnc3n2)c1]

4-Fluoropyridin-2-ol as a starting material and silver carbonate were used in the same manner as in Example 1-2 to obtain 6-bromo-2-[(4-fluoro-2-pyridyl)oxymethyl)imidazo[1,2-a]pyrimidine. The obtained 6-bromo-2-[(4-fluoro-2-pyridyl)oxymethyl)imidazo[1,2-a]pyrimidine and (2,4-difluorophenyl)boronic acid were used in the same manner as in Example 1-3 to obtain the title compound.

$^1$H-NMR (CDCl$_3$, 500 MHz) δ 8.71 (s, 1H), 8.59 (s, 1H), 8.17 (d, 1H), 7.68 (s, 1H), 7.50 (m, 1H), 7.08 (m, 2H), 6.73 (m, 1H), 6.58 (m, 1H), 5.69 (s, 2H)

Example 121: Synthesis of 6-(3-fluoro-2-methoxyphenyl)-2-[(4-fluoro-2-pyridyl)oxymethyl)imidazo[1,2-a]pyrimidine

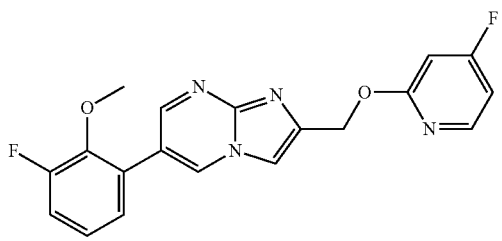 [SMILES: COc1c(F)cccc1-c1cnc2nc(COc3cc(F)ccn3)cn2c1]

4-Fluoropyridin-2-ol as a starting material and silver carbonate were used in the same manner as in Example 1-2 to obtain 6-bromo-2-[(4-fluoro-2-pyridyl)oxymethyl)imidazo[1,2-a]pyrimidine. The obtained 6-bromo-2-[(4-fluoro-2-pyridyl)oxymethyl)imidazo[1,2-a]pyrimidine and (3-fluoro-2-methoxy-phenyl)boronic acid were used in the same manner as in Example 1-3 to obtain the title compound.

$^1$H-NMR (CDCl$_3$, 500 MHz) δ 8.72 (s, 1H), 8.61 (s, 1H), 8.16 (s, 1H), 7.64 (s, 1H), 7.17 (m, 3H), 6.70 (m, 1H), 6.55 (m, 1H), 5.66 (s, 2H), 3.84 (s, 3H)

Example 122: Synthesis of 6-(2,3-difluorophenyl)-2-[(4-fluoro-2-pyridyl)oxymethyl)imidazo[1,2-a]pyrimidine

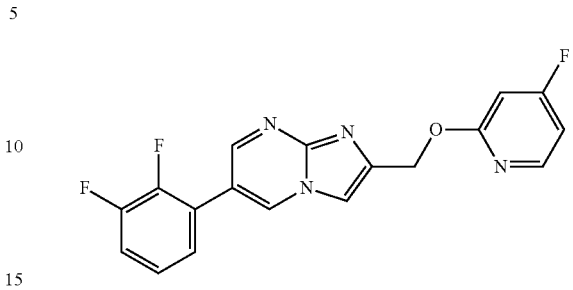

4-Fluoropyridin-2-ol as a starting material and silver carbonate were used in the same manner as in Example 1-2 to obtain 6-bromo-2-[(4-fluoro-2-pyridyl)oxymethyl)imidazo[1,2-a]pyrimidine. The obtained 6-bromo-2-[(4-fluoro-2-pyridyl)oxymethyl)imidazo[1,2-a]pyrimidine and (2,3-difluorophenyl)boronic acid were used in the same manner as in Example 1-3 to obtain the title compound.

$^1$H-NMR (CDCl$_3$, 500 MHz) δ 8.77 (s, 1H), 8.68 (s, 1H), 8.19 (s, 1H), 7.72 (s, 1H), 7.30 (m, 3H), 6.74 (m, 1H), 6.59 (m, 1H), 5.70 (s, 2H)

Example 123: Synthesis of 6-(4-fluorophenyl)-2-[(4-fluoro-2-pyridyl)oxymethyl)imidazo[1,2-a]pyrimidine

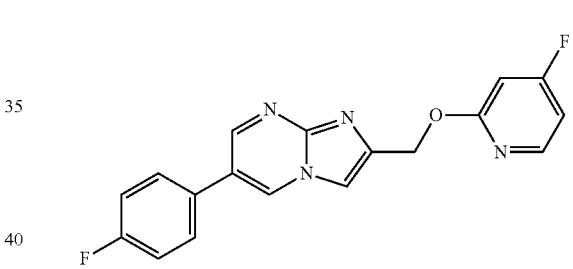

4-Fluoropyridin-2-ol as a starting material and silver carbonate were used in the same manner as in Example 1-2 to obtain 6-bromo-2-[(4-fluoro-2-pyridyl)oxymethyl)imidazo[1,2-a]pyrimidine. The obtained 6-bromo-2-[(4-fluoro-2-pyridyl)oxymethyl)imidazo[1,2-a]pyrimidine and (4-fluorophenyl)boronic acid were used in the same manner as in Example 1-3 to obtain the title compound.

$^1$H-NMR (CDCl$_3$, 500 MHz) δ 8.81 (s, 1H), 8.53 (s, 1H), 8.19 (s, 1H), 7.69 (m, 1H), 7.57 (m, 2H), 7.29 (m, 2H), 6.74 (m, 1H), 6.59 (m, 1H), 5.70 (s, 2H)

Example 124: Synthesis of 6-(3-fluoro-2-methylphenyl)-2-[(5-fluoro-2-pyridyl)oxymethyl)imidazo[1,2-a]pyrimidine

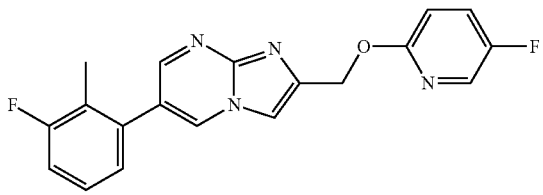

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and (3-fluoro-2-methyl-phenyl)boronic acid were used in the same manner as in Example 1-3 to obtain the title compound.

¹H-NMR (CDCl₃, 500 MHz) δ 8.50 (s, 1H), 8.41 (s, 1H), 8.00 (s, 1H), 7.68 (s, 1H), 7.37 (m, 1H), 7.29 (m, 1H), 7.16 (m, 1H), 7.04 (m, 1H), 6.81 (m, 1H), 5.58 (s, 2H), 2.21 (s, 3H)

Example 125: Synthesis of 2-[(4-fluoro-2-pyridyl)oxymethyl]-6-[4-fluoro-2-(trifluoromethyl)phenyl]imidazo[1,2-a]pyrimidine

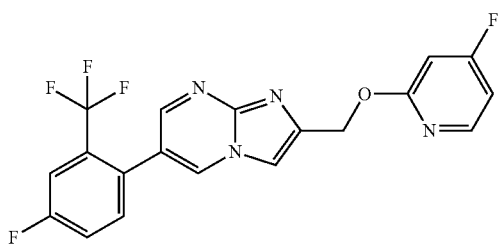 [SMILES: Fc1ccnc(OCc2cn3cc(-c4ccc(F)cc4C(F)(F)F)cnc3n2)c1]

4-Fluoropyridin-2-ol as a starting material and silver carbonate were used in the same manner as in Example 1-2 to obtain 6-bromo-2-[(4-fluoro-2-pyridyl)oxymethyl)imidazo[1,2-a]pyrimidine. The obtained 6-bromo-2-[(4-fluoro-2-pyridyl)oxymethyl)imidazo[1,2-a]pyrimidine and [4-fluoro-2-(trifluoromethyl)phenyl]boronic acid were used in the same manner as in Example 1-3 to obtain the title compound. ¹H-NMR (CDCl₃, 500 MHz) δ 8.48 (s, 1H), 8.36 (s, 1H), 8.17 (m, 1H), 7.65 (m, 1H), 7.57 (m, 1H), 7.41 (m, 2H), 6.72 (m, 1H), 6.56 (m, 1H), 5.67 (s, 2H)

Example 126: Synthesis of 2-[(5-fluoro-2-pyridyl)oxymethyl]-6-(o-tolyl)imidazo[1,2-a]pyrimidine

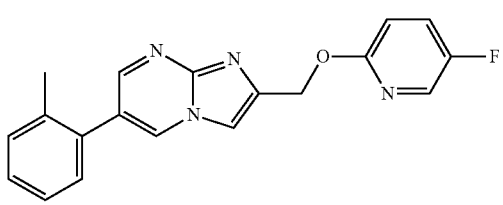 [SMILES: Cc1ccccc1-c1cnc2nc(COc3ccc(F)cn3)cn2c1]

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and o-tolylboronic acid were used in the same manner as in Example 1-3 to obtain the title compound.

¹H-NMR (CDCl₃, 500 MHz) δ 8.56 (s, 1H), 8.30 (s, 1H), 8.02 (s, 1H), 7.62 (m, 1H), 7.37 (m, 3H), 7.25 (m, 2H), 6.83 (m, 1H), 5.60 (s, 2H), 2.31 (s, 3H)

Example 127: Synthesis of 6-(4-chloro-2-methylphenyl)-2-[(5-fluoro-2-pyridyl)oxymethyl)imidazo[1,2-a]pyrimidine

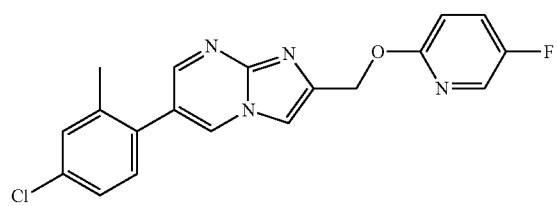

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and (4-chloro-2-methyl-phenyl)boronic acid were used in the same manner as in Example 1-3 to obtain the title compound.

¹H-NMR (CDCl₃, 500 MHz) δ 8.49 (s, 1H), 8.29 (s, 1H), 8.01 (s, 1H), 7.62 (s, 1H), 7.37 (m, 2H), 7.28 (m, 1H), 7.17 (m, 1H), 6.80 (m, 1H), 5.59 (s, 2H), 2.27 (s, 3H)

Example 128: Synthesis of 6-(2,4-dimethylphenyl)-2-[(5-fluoro-2-pyridyl)oxymethyl)imidazo[1,2-a]pyrimidine

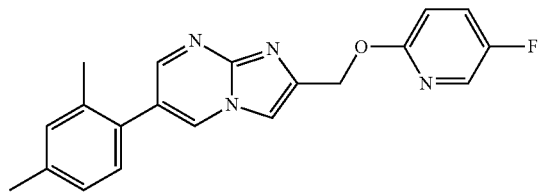 [SMILES: Cc1ccc(-c2cnc3nc(COc4ccc(F)cn4)cn3c2)c(C)c1]

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and (2,4-dimethylphenyl)boronic acid were used in the same manner as in Example 1-3 to obtain the title compound.

¹H-NMR (CDCl₃, 500 MHz) δ 8.54 (s, 1H), 8.29 (s, 1H), 8.03 (s, 1H), 7.62 (s, 1H), 7.38 (m, 1H), 7.16 (s, 1H), 7.13 (m, 2H), 6.82 (m, 1H), 5.60 (s, 2H), 2.39 (s, 3H), 2.28 (s, 3H)

Example 129: Synthesis of 6-(4-fluorophenyl)-2-[(5-fluoro-2-pyridyl)oxymethyl)imidazo[1,2-a]pyrimidine

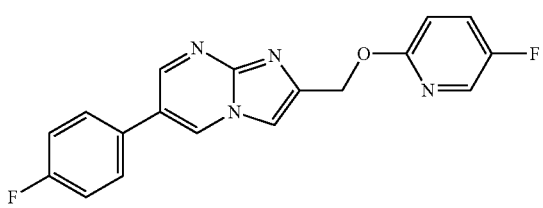

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and (4-fluorophenyl)boronic acid were used in the same manner as in Example 1-3 to obtain the title compound.

$^1$H-NMR (DMSO-d6, 500 MHz) δ 9.27 (s, 1H), 8.88 (d, 1H), 8.20 (d, 1H), 7.91 (s, 1H), 7.83 (m, 2H), 7.74 (m, 1H), 7.38 (m, 2H), 6.97 (m, 1H), 5.47 (s, 2H)

Example 130: Synthesis of 2-(2-pyridyloxymethyl)-6-[6-(trifluoromethyl)-3-pyridyl]imidazo[1,2-a]pyrimidine

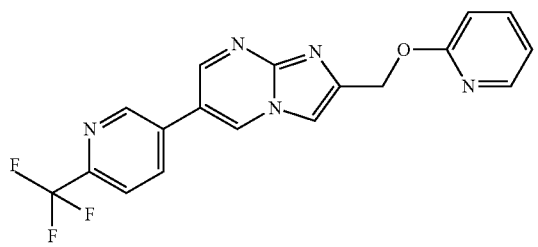

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and [6-(trifluoromethyl)-3-pyridyl]boronic acid were used in the same manner as in Example 1-3 to obtain the title compound.

$^1$H-NMR (CDCl$_3$, 500 MHz) δ 8.95 (s, 1H), 8.77 (s, 1H), 8.63 (s, 1H), 8.19 (s, 1H), 8.09 (d, 1H), 7.86 (s, 1H), 7.73 (s, 1H), 7.61 (s, 1H), 6.86 (m, 2H), 5.67 (s, 2H)

Example 131: Synthesis of 2-[(5-fluoro-2-pyridyl)oxymethyl]-6-[6-(trifluoromethyl)-3-pyridyl]imidazo[1,2-a]pyrimidine

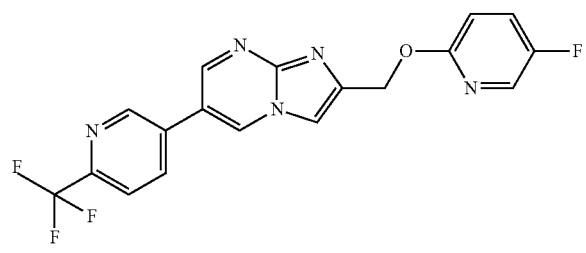

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and [6-(trifluoromethyl)-3-pyridyl]boronic acid were used in the same manner as in Example 1-3 to obtain the title compound.

$^1$H-NMR (CDCl$_3$, 500 MHz) δ 8.96 (s, 1H), 8.80 (s, 1H), 8.64 (s, 1H), 8.10 (m, 1H), 7.88 (m, 1H), 7.73 (s, 1H), 7.61 (m, 1H), 7.51 (m, 1H), 6.85 (m, 1H), 5.64 (s, 2H)

Example 132: Synthesis of 6-(5-fluoro-2-pyridyl)-2-(2-pyridyloxymethyl)imidazo[1,2-a]pyrimidine

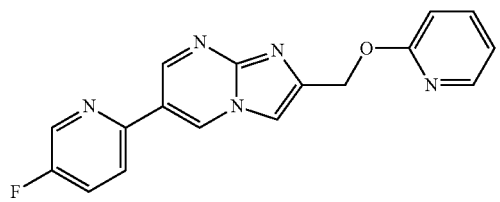 [SMILES: Fc1ccc(-c2cnc3nc(COc4ccccn4)cn3c2)nc1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and (5-fluoro-2-pyridyl)boronic acid were used in the same manner as in Example 1-3 to obtain the title compound.

$^1$H-NMR (DMSO-d6, 500 MHz) δ 9.58 (s, 1H), 9.17 (s, 1H), 8.69 (s, 1H), 8.20 (s, 1H), 8.12 (t, 1H), 7.98 (s, 1H), 7.92 (t, 1H), 7.71 (t, 1H), 6.99 (t, 1H), 6.87 (d, 1H), 5.47 (s, 2H)

Example 133: Synthesis of 2-fluoro-5-[2-[(5-fluoro-2-pyridyl)oxymethyl]imidazo[1,2-a]pyrimidin-6-yl]aniline

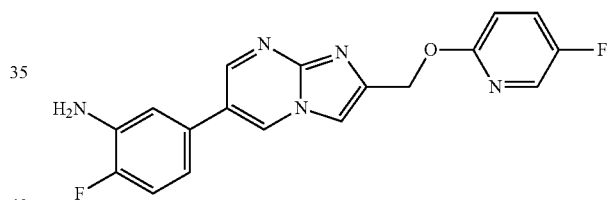

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and (3-amino-4-fluoro-phenyl)boronic acid were used in the same manner as in Example 1-3 to obtain the title compound.

$^1$H-NMR (CDCl$_3$, 500 MHz) δ 8.74 (s, 1H), 8.45 (s, 1H), 8.03 (s, 1H), 7.63 (s, 1H), 7.38 (t, 1H), 7.12 (m, 1H), 6.95 (m, 1H), 6.84 (m, 2H), 5.64 (s, 2H), 3.92 (s, 2H)

Example 134: Synthesis of 2-fluoro-5-[2-(2-pyridyloxymethyl)imidazo[1,2-a]pyrimidin-6-yl]aniline

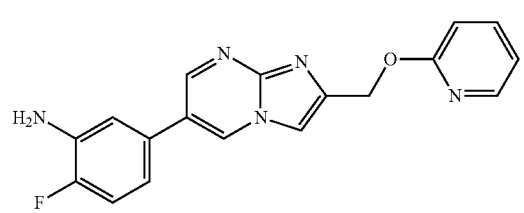 [SMILES: Nc1cc(-c2cnc3nc(COc4ccccn4)cn3c2)ccc1F]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and (3-amino-4-fluoro-phenyl)boronic acid were used in the same manner as in Example 1-3 to obtain the title compound.

$^1$H-NMR (CDCl$_3$, 500 MHz) δ 8.73 (s, 1H), 8.44 (s, 1H), 8.21 (s, 1H), 7.62 (m, 2H), 7.11 (m, 1H), 6.92 (m, 4H), 5.65 (s, 2H), 3.92 (s, 2H)

Example 135: Synthesis of [5-fluoro-2-[2-(2-pyridyloxymethyl)imidazo[1,2-a]pyrimidin-6-yl]phenyl]methanol

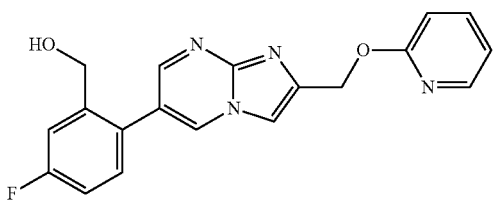

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and [4-fluoro-2-(hydroxymethyl)phenyl]boronic acid were used in the same manner as in Example 1-3 to obtain the title compound.

$^1$H-NMR (DMSO-d6, 500 MHz) δ 8.96 (s, 1H), 8.54 (s, 1H), 8.20 (d, 1H), 7.89 (s, 1H), 7.75 (t, 1H), 7.40 (m, 2H), 7.24 (m, 1H), 7.00 (m, 1H), 6.89 (d, 1H), 5.49 (s, 2H), 5.40 (m, 1H), 4.45 (d, 2H)

Example 136: Synthesis of 3-methoxy-4-[2-(2-pyridyloxymethyl)imidazo[1,2-a]pyrimidin-6-yl]benzonitrile

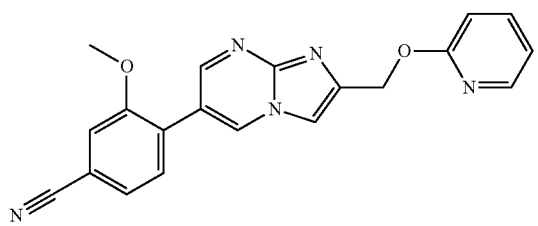 [SMILES: COc1cc(C#N)ccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and (4-cyano-2-methoxyphenyl)boronic acid were used in the same manner as in Example 1-3 to obtain the title compound.

$^1$H-NMR (CDCl$_3$, 500 MHz) δ 8.66 (s, 1H), 8.60 (s, 1H), 8.18 (d, 1H), 7.64 (s, 1H), 7.60 (m, 1H), 7.47 (d, 1H), 7.40 (d, 1H), 7.26 (d, 1H), 6.90 (m, 1H), 6.84 (m, 1H), 5.63 (s, 1H), 3.89 (s, 3H)

Example 137: Synthesis of 4-[2-[(5-fluoro-2-pyridyl)oxymethyl]imidazo[1,2-a]pyrimidin-6-yl]-3-methoxy-benzonitrile

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and (4-cyano-2-methoxy-phenyl)boronic acid were used in the same manner as in Example 1-3 to obtain the title compound.

$^1$H-NMR (DMSO-d6, 500 MHz) δ 9.16 (s, 1H), 8.69 (s, 1H), 8.17 (s, 1H), 7.93 (s, 1H), 7.72 (m, 3H), 7.58 (m, 1H), 6.95 (m, 1H), 5.45 (s, 2H), 3.88 (s, 3H)

Example 138: Synthesis of 6-(4-fluoro-2-methylsulfanyl-phenyl)-2-(2-pyridyloxymethyl)imidazo[1,2-a]pyrimidine

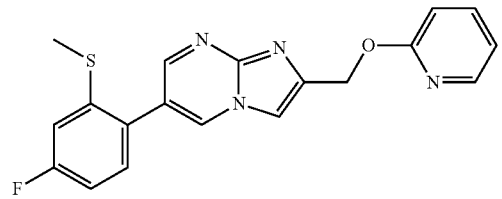

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and (4-fluoro-2-methylsulfanyl-phenyl)boronic acid were used in the same manner as in Example 1-3 to obtain the title compound.

$^1$H-NMR (DMSO-d6, 500 MHz) δ 8.99 (s, 1H), 8.51 (s, 1H), 8.22 (d, 1H), 7.94 (s, 1H), 7.76 (m, 1H), 7.41 (m, 1H), 7.28 (d, 1H), 7.15 (t, 1H), 7.01 (t, 1H), 6.90 (d, 1H), 5.51 (s, 2H), 2.48 (s, 3H)

Example 139: Synthesis of [5-fluoro-2-[2-[(5-fluoro-2-pyridyl)oxymethyl]imidazo[1,2-a]pyrimidin-6-yl]phenyl]methanol

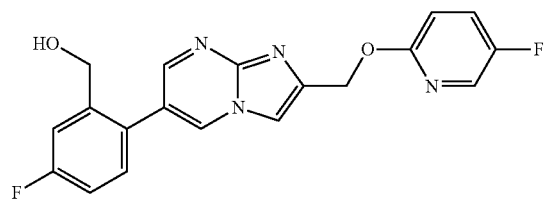

5-Fluoropyridin-2-ol as a starting material and silver carbonate were used in the same manner as in Example 1-2 to obtain 6-bromo-2-[(5-fluoro-2-pyridyl)oxymethyl)imidazo[1,2-a]pyrimidine. The obtained 6-bromo-2-[(5-fluoro-2-pyridyl)oxymethyl)imidazo[1,2-a]pyrimidine and [4-fluoro-2-(hydroxymethyl)phenyl]boronic acid were used in the same manner as in Example 1-3 to obtain the title compound.

¹H-NMR (DMSO-d6, 500 MHz) δ 8.99 (s, 1H), 8.54 (s, 1H), 8.21 (s, 1H), 7.89 (s, 1H), 7.71 (t, 1H), 7.43 (m, 2H), 7.22 (t, 1H), 6.97 (d, 1H), 5.46 (s, 2H), 5.41 (s, 1H), 4.45 (s, 2H)

Example 140: Synthesis of 4-[2-(2-pyridyloxymethyl)imidazo[1,2-a]pyrimidin-6-yl]benzonitrile

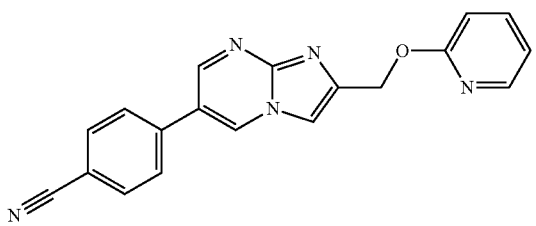 [SMILES: N#Cc1ccc(-c2cnc3nc(COc4ccccn4)cn3c2)cc1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and (4-cyanophenyl)boronic acid were used in the same manner as in Example 1-3 to obtain the title compound.

¹H-NMR (CDCl₃, 500 MHz) δ 8.81 (s, 1H), 8.60 (s, 1H), 8.22 (s, 1H), 7.85 (d, 2H), 7.71 (t, 3H), 7.63 (m, 1H), 6.95 (m, 1H), 6.89 (m, 1H), 5.69 (s, 2H)

Example 141: Synthesis of 6-[4-fluoro-2-(methoxymethyl)phenyl]-2-(2-pyridyloxymethyl)imidazo[1,2-a]pyrimidine

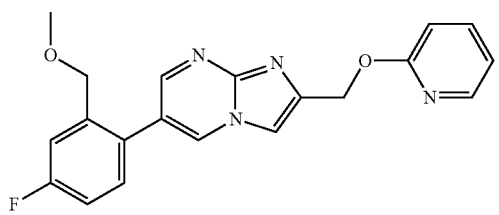 [SMILES: COCc1cc(F)ccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and [4-fluoro-2-(methoxymethyl)phenyl]boronic acid were used in the same manner as in Example 1-3 to obtain the title compound.

¹H-NMR (DMSO-d6, 500 MHz) δ 8.95 (s, 1H), 8.52 (s, 1H), 8.20 (t, 1H), 7.91 (s, 1H), 7.74 (m, 1H), 7.48 (m, 1H), 7.36 (m, 1H), 7.31 (m, 1H), 7.02 (m, 1H), 6.88 (d, 1H), 5.49 (s, 2H), 4.37 (s, 2H), 3.23 (s, 3H)

Example 142: Synthesis of [2-[2-(2-pyridyloxymethyl)imidazo[1,2-a]pyrimidin-6-yl]-5-(trifluoromethyl)phenyl]methanol

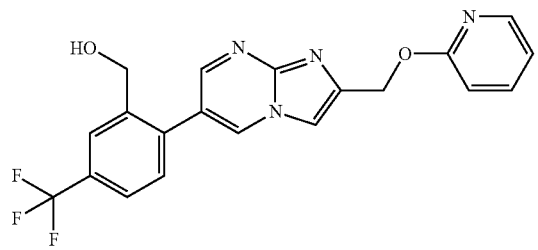 [SMILES: OCc1cc(C(F)(F)F)ccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and [2-(hydroxymethyl)-4-(trifluoromethyl)phenyl]boronic acid were used in the same manner as in Example 1-3 to obtain the title compound.

¹H-NMR (CDCl₃, 500 MHz) δ 8.63 (s, 1H), 8.55 (d, 1H), 8.20 (d, 1H), 7.89 (s, 1H), 7.72 (d, 1H), 7.63 (m, 2H), 7.49 (d, 1H), 6.93 (t, 1H), 6.85 (d, 1H), 5.63 (s, 2H), 4.72 (s, 2H)

Example 143: Synthesis of 6-(2-isopropylphenyl)-2-(2-pyridyloxymethyl)imidazo[1,2-a]pyrimidine

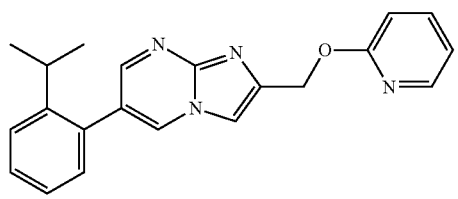 [SMILES: CC(C)c1ccccc1-c1cnc2nc(COc3ccccn3)cn2c1]

2-hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and (2-isopropylphenyl)boronic acid were used in the same manner as in Example 1-3 to obtain the title compound.

¹H-NMR (DMSO-d6, 500 MHz) δ 8.92 (s, 1H), 8.46 (s, 1H), 8.20 (s, 1H), 7.90 (s, 1H), 7.73 (t, 1H), 7.45 (m, 2H), 7.28 (t, 2H), 7.02 (t, 1H), 6.89 (d, 1H), 5.50 (s, 2H), 2.93 (m, 1H), 1.14 (d, 6H)

Example 144: Synthesis of 4-[2-(2-pyridyloxymethyl)imidazo[1,2-a]pyrimidin-6-yl]-3-(trifluoromethyl)benzaldehyde

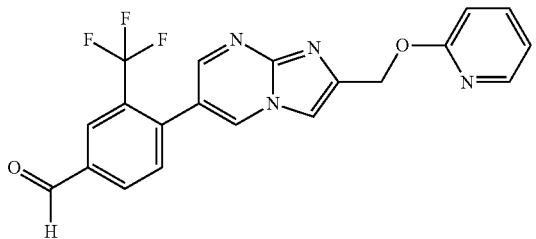 [SMILES: O=Cc1ccc(-c2cnc3nc(COc4ccccn4)cn3c2)c(C(F)(F)F)c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and [4-formyl-2-(trifluoromethyl)phenyl]boronic acid were used in the same manner as in Example 1-3 to obtain the title compound.

$^1$H-NMR (DMSO-d6, 500 MHz) δ 10.18 (s, 1H), 9.10 (s, 1H), 8.53 (s, 1H), 8.40 (s, 1H), 8.29 (d, 1H), 8.19 (d, 1H), 7.95 (s, 1H), 7.87 (d, 1H), 7.74 (t, 1H), 7.02 (t, 1H), 6.90 (d, 1H), 5.51 (s, 2H)

Example 145: Synthesis of 6-[4-chloro-2-(trifluoromethyl)phenyl]-2-(2-pyridyloxymethyl)imidazo[1,2-a]pyrimidine

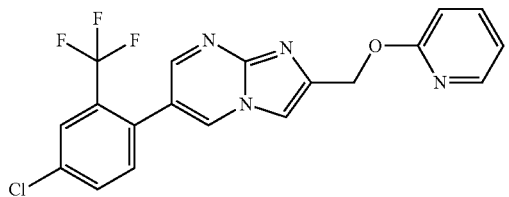 [SMILES: FC(F)(F)c1cc(Cl)ccc1-c1cnc2nc(COc3ccccn3)cn2c1]

2-Hydroxypyridine as a starting material and silver carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and [4-chloro-2-(trifluoromethyl)phenyl]boronic acid were used in the same manner as in Example 1-3 to obtain the title compound.

$^1$H-NMR (DMSO-d6, 500 MHz) δ 9.38 (s, 1H), 8.91 (s, 1H), 8.31 (s, 1H), 8.23 (d, 1H), 8.07 (s, 1H), 7.98 (d, 1H), 7.80 (t, 1H), 7.65 (d, 1H), 7.09 (t, 1H), 6.95 (d, 1H), 5.63 (s, 2H)

Example 146: Synthesis of 6-(4-fluorophenyl)-2-(pyridin-3-yloxymethyl)imidazo[1,2-a]pyrimidine

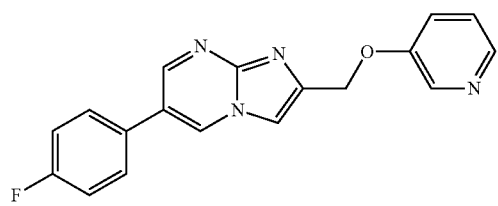 [SMILES: Fc1ccc(-c2cnc3nc(COc4cccnc4)cn3c2)cc1]

3-Hydroxypyridine as a starting material and cesium carbonate were used in the same manner as in Example 1-2 to obtain 6-bromo-2-(pyridin-3-yloxymethyl)imidazo[1,2-a]pyrimidine. The obtained 6-bromo-2-(pyridin-3-yloxymethyl)imidazo[1,2-a]pyrimidine and 4-fluorophenylboronic acid were used in the same manner as in Example 1-3 to obtain the title compound.

$^1$H-NMR (CDCl$_3$, 500 MHz) δ 8.79 (s, 1H), 8.53 (s, 1H), 8.46 (s, 1H), 8.25 (s, 1H), 7.68 (s, 1H), 7.55 (m, 2H), 7.39 (m, 1H), 7.25 (m, 3H), 5.43 (s, 2H)

Example 147: Synthesis of 6-(4-fluoro-2-methoxyphenyl)-2-(pyridin-3-yloxymethyl)imidazo[1,2-a]pyrimidine

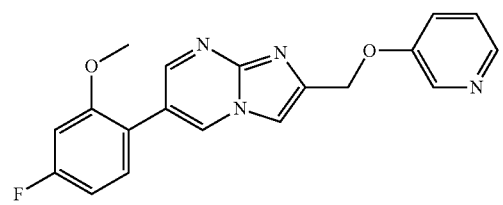 [SMILES: COc1cc(F)ccc1-c1cnc2nc(COc3cccnc3)cn2c1]

3-Hydroxypyridine as a starting material and cesium carbonate were used in the same manner as in Example 1-2 to obtain 6-bromo-2-(pyridin-3-yloxymethyl)imidazo[1,2-a]pyrimidine. The obtained 6-bromo-2-(pyridin-3-yloxymethyl)imidazo[1,2-a]pyrimidine and 4-fluoro-2-methoxyphenylboronic acid were used in the same manner as in Example 1-3 to obtain the title compound.

$^1$H-NMR (CDCl$_3$, 500 MHz) δ 8.70 (s, 1H), 8.52 (s, 1H), 8.46 (s, 1H), 8.27 (s, 1H), 7.63 (s, 1H), 7.35 (m, 2H), 7.24 (m, 1H), 6.84 (m, 2H), 5.43 (s, 2H), 3.87 (s, 3H)

Example 148: Synthesis of 6-(2,4-difluorophenyl)-2-(pyridin-3-yloxymethyl)imidazo[1,2-a]pyrimidine

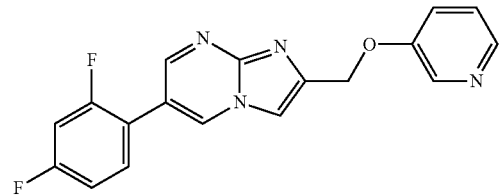 [SMILES: Fc1ccc(-c2cnc3nc(COc4cccnc4)cn3c2)c(F)c1]

3-Hydroxypyridine as a starting material and cesium carbonate were used in the same manner as in Example 1-2 to obtain 6-bromo-2-(pyridin-3-yloxymethyl)imidazo[1,2-a]pyrimidine. The obtained 6-bromo-2-(pyridin-3-yloxymethyl)imidazo[1,2-a]pyrimidine and 2,4-difluorophenylboronic acid were used in the same manner as in Example 1-3 to obtain the title compound.

$^1$H-NMR (CDCl$_3$, 500 MHz) δ 8.71 (s, 1H), 8.60 (s, 1H), 8.46 (s, 1H), 8.27 (s, 1H), 7.68 (s, 1H), 7.50 (m, 1H), 7.38 (m, 1H), 7.26 (m, 1H), 7.08 (m, 2H), 5.43 (s, 2H)

Example 149: Synthesis of 6-(4-fluoro-2-methylphenyl)-2-(pyridin-3-yloxymethyl)imidazo[1,2-a]pyrimidine

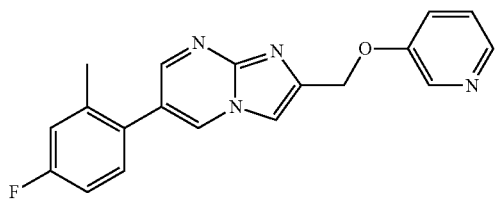 [SMILES: Cc1cc(F)ccc1-c1cnc2nc(COc3cccnc3)cn2c1]

3-Hydroxypyridine as a starting material and cesium carbonate were used in the same manner as in Example 1-2 to obtain 6-bromo-2-(pyridin-3-yloxymethyl)imidazo[1,2-a]pyrimidine. The obtained 6-bromo-2-(pyridin-3-yloxymethyl)imidazo[1,2-a]pyrimidine and 4-fluoro-2-methylphenylboronic acid were used in the same manner as in Example 1-3 to obtain the title compound.

$^1$H-NMR (CDCl$_3$, 500 MHz) δ 8.50 (s, 1H), 8.38 (d, 2H), 8.23 (s, 1H), 7.67 (s, 1H), 7.36 (m, 1H), 7.21 (m, 2H), 7.03 (m, 2H), 5.39 (s, 2H), 2.30 (s, 3H)

Example 150: Synthesis of 6-(4-fluoro-2-hydroxyphenyl)-2-(pyridin-3-yloxymethyl)imidazo[1,2-a]pyrimidine

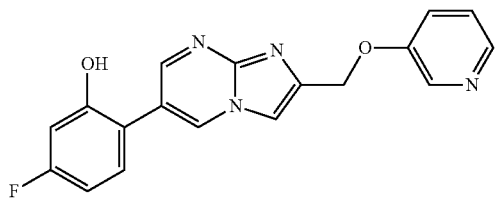 [SMILES: Oc1cc(F)ccc1-c1cnc2nc(COc3cccnc3)cn2c1]

3-Hydroxypyridine as a starting material and cesium carbonate were used in the same manner as in Example 1-2 to obtain 6-bromo-2-(pyridin-3-yloxymethyl)imidazo[1,2-a]pyrimidine. The obtained 6-bromo-2-(pyridin-3-yloxymethyl)imidazo[1,2-a]pyrimidine and 4-fluoro-2-hydroxyphenylboronic acid were used in the same manner as in Example 1-3 to obtain the title compound.

$^1$H-NMR (DMSO-d6, 500 MHz) δ 9.21 (s, 1H), 8.75 (s, 1H), 8.45 (s, 1H), 8.19 (s, 1H), 7.98 (s, 1H), 7.55 (m, 1H), 7.45 (m, 1H), 7.34 (m, 1H), 6.62 (s, 2H), 5.34 (s, 2H), 4.05 (m, 1H)

Example 151: Synthesis of 6-(4-fluoro-2-methoxyphenyl)-2-(pyridin-4-yloxymethyl)imidazo[1,2-a]pyrimidine

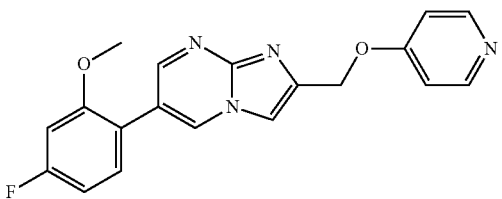 [SMILES: COc1cc(F)ccc1-c1cnc2nc(COc3ccncc3)cn2c1]

4-Hydroxypyridine as a starting material and cesium carbonate were used in the same manner as in Example 1-2 to obtain 6-bromo-2-(pyridin-4-yloxymethyl)imidazo[1,2-a]pyrimidine. The obtained 6-bromo-2-(pyridin-4-yloxymethyl)imidazo[1,2-a]pyrimidine and 4-fluoro-2-methoxyphenylboronic acid were used in the same manner as in Example 1-3 to obtain the title compound.

$^1$H-NMR (CDCl$_3$, 500 MHz) δ 8.68 (s, 1H), 8.54 (s, 1H), 8.43 (s, 2H), 7.61 (s, 1H), 7.29 (m, 1H), 6.95 (d, 2H), 6.79 (m, 2H), 5.39 (s, 2H), 3.84 (s, 3H)

Example 152: Synthesis of 6-(2,4-difluorophenyl)-2-(pyridin-4-yloxymethyl)imidazo[1,2-a]pyrimidine

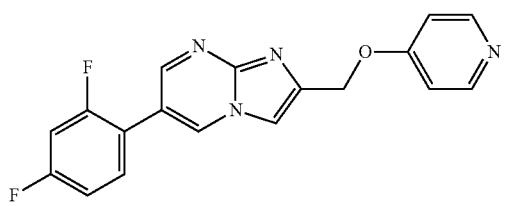 [SMILES: Fc1ccc(-c2cnc3nc(COc4ccncc4)cn3c2)c(F)c1]

4-Hydroxypyridine as a starting material and cesium carbonate were used in the same manner as in Example 1-2 to obtain 6-bromo-2-(pyridin-2-yloxymethyl)imidazo[1,2-a]pyrimidine. The obtained 6-bromo-2-(pyridin-2-yloxymethyl)imidazo[1,2-a]pyrimidine and 2,4-difluorophenylboronic acid were used in the same manner as in Example 1-3 to obtain the title compound.

$^1$H-NMR (CDCl$_3$, 500 MHz) δ 8.68 (s, 1H), 8.62 (s, 1H), 8.45 (m, 2H), 7.67 (s, 1H), 7.47 (m, 1H), 7.06 (m, 1H), 7.02 (m, 1H), 6.95 (m, 2H), 5.39 (s, 2H)

Example 153: Synthesis of 6-(2-methylphenyl)-2-(5-fluoro-pyridin-3-yloxymethyl)imidazo[1,2-a]pyrimidine

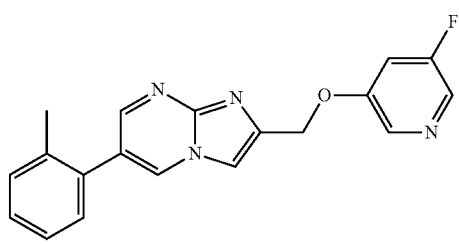 [SMILES: Cc1ccccc1-c1cnc2nc(COc3cncc(F)c3)cn2c1]

3-Fluoro-5-hydroxypyridine as a starting material and cesium carbonate were used in the same manner as in Example 1-2 to obtain 6-bromo-2-(5-fluoropyridin-3-yloxymethyl)imidazo[1,2-a]pyrimidine. The obtained 6-bromo-2-(5-fluoropyridin-3-yloxymethyl)imidazo[1,2-a]pyrimidine and 2-methylphenylboronic acid were used in the same manner as in Example 1-3 to obtain the title compound.

$^1$H-NMR (CDCl$_3$, 500 MHz) δ 8.62 (s, 1H), 8.36 (s, 1H), 8.31 (s, 1H), 8.16 (s, 1H), 7.66 (s, 1H), 7.38 (m, 4H), 7.19 (m, 1H), 5.44 (s, 2H), 2.35 (s, 3H)

Example 154: Synthesis of 6-(4-fluoro-2-methylphenyl)-2-(5-fluoro-pyridin-3-yloxymethyl)imidazo[1,2-a]pyrimidine

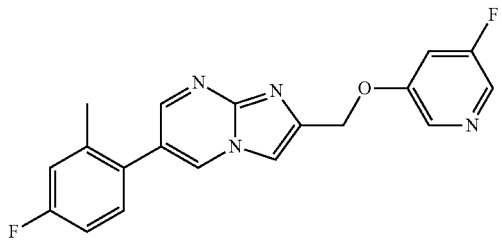 [SMILES: Cc1cc(F)ccc1-c1cnc2nc(COc3cncc(F)c3)cn2c1]

3-Fluoro-5-hydroxypyridine as a starting material and cesium carbonate were used in the same manner as in Example 1-2 to obtain 6-bromo-2-(5-fluoropyridin-3-yloxymethyl)imidazo[1,2-a]pyrimidine. The obtained 6-bromo-2-(5-fluoropyridin-3-yloxymethyl)imidazo[1,2-a]pyrimidine and 4-fluoro-2-methylphenylboronic acid were used in the same manner as in Example 1-3 to obtain the title compound.

$^1$H-NMR (CDCl$_3$, 500 MHz) δ 8.55 (s, 1H), 8.36 (s, 1H), 8.29 (s, 1H), 8.14 (s, 1H), 7.67 (s, 1H), 7.23 (m, 1H), 7.17 (m, 1H), 7.04 (m, 2H), 5.42 (s, 2H), 3.32 (s, 3H)

Example 155: Synthesis of 6-(4-fluoro-2-methoxyphenyl)-2-(5-fluoropyridin-3-yloxymethyl)imidazo[1,2-a]pyrimidine

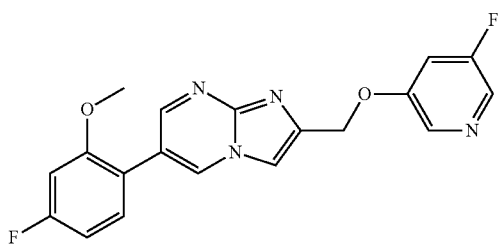 [SMILES: COc1cc(F)ccc1-c1cnc2nc(COc3cncc(F)c3)cn2c1]

3-Fluoro-5-hydroxypyridine as a starting material and cesium carbonate were used in the same manner as in Example 1-2 to obtain 6-bromo-2-(5-fluoropyridin-3-yloxymethyl)imidazo[1,2-a]pyrimidine. The obtained 6-bromo-2-(5-fluoropyridin-3-yloxymethyl)imidazo[1,2-a]pyrimidine and 4-fluoro-2-methoxyphenylboronic acid were used in the same manner as in Example 1-3 to obtain the title compound.

$^1$H-NMR (CDCl$_3$, 500 MHz) δ 8.71 (s, 1H), 8.52 (s, 1H), 8.29 (s, 1H), 8.14 (s, 1H), 7.62 (s, 1H), 7.33 (m, 1H), 7.16 (m, 1H), 6.82 (m, 2H), 5.41 (s, 2H), 3.87 (s, 3H)

Example 156: Synthesis of 6-(4-fluoro-2-hydroxyphenyl)-2-(5-fluoropyridin-3-yloxymethyl)imidazo[1,2-a]pyrimidine

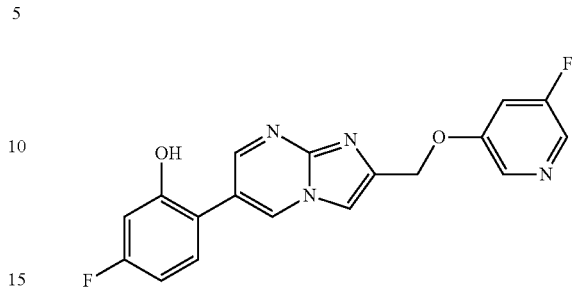

3-Fluoro-5-hydroxypyridine as a starting material and cesium carbonate were used in the same manner as in Example 1-2 to obtain 6-bromo-2-(5-fluoropyridin-3-yloxymethyl)imidazo[1,2-a]pyrimidine. The obtained 6-bromo-2-(5-fluoropyridin-3-yloxymethyl)imidazo[1,2-a]pyrimidine and 4-fluoro-2-hydroxyphenylboronic acid were used in the same manner as in Example 1-3 to obtain the title compound.

$^1$H-NMR (DMSO-d6, 500 MHz) δ 10.52 (s, 1H), 9.10 (s, 1H), 8.71 (s, 1H), 8.31 (s, 1H), 8.20 (s, 1H), 8.03 (s, 1H), 7.65 (m, 1H), 7.47 (m, 1H), 6.80 (m, 2H), 5.38 (s, 2H)

Example 157: Synthesis of 6-(2,4-difluorophenyl)-2-(6-fluoropyridin-3-yloxymethyl)imidazo[1,2-a]pyrimidine

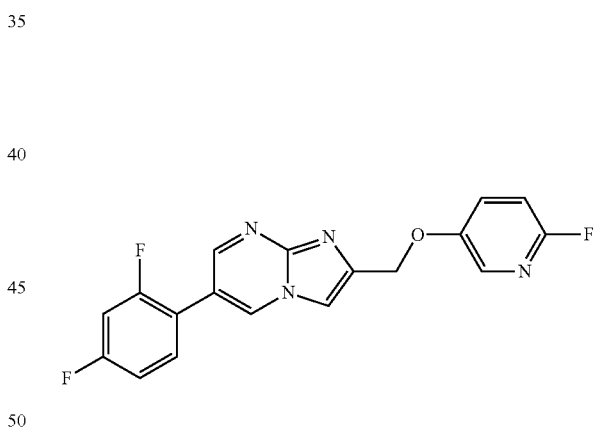

6-Fluoro-3-hydroxypyridine as a starting material and cesium carbonate were used in the same manner as in Example 1-2 to obtain 6-bromo-2-(6-fluoropyridin-3-yloxymethyl)imidazo[1,2-a]pyrimidine. The obtained 6-bromo-2-(6-fluoropyridin-3-yloxymethyl)imidazo[1,2-a]pyrimidine and 2,4-difluorophenylboronic acid were used in the same manner as in Example 1-3 to obtain the title compound.

$^1$H-NMR (CDCl$_3$, 500 MHz) δ 8.73 (s, 1H), 8.59 (s, 1H), 7.99 (s, 1H), 7.67 (s, 1H), 7.50 (m, 2H), 7.07 (m, 2H), 6.90 (m, 1H), 5.40 (s, 2H)

Example 158: Synthesis of 6-(4-fluoro-2-methylphenyl)-2-(6-fluoropyridin-3-yloxymethyl)imidazo[1,2-a]pyrimidine

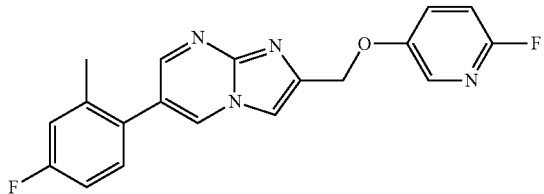 [SMILES: Cc1cc(F)ccc1-c1cnc2nc(COc3ccc(F)nc3)cn2c1]

2-Fluoro-5-hydroxypyridine as a starting material and cesium carbonate were used in the same manner as in Example 1-2 to obtain 6-bromo-2-(6-fluoropyridin-3-yloxymethyl)imidazo[1,2-a]pyrimidine. The obtained 6-bromo-2-(6-fluoropyridin-3-yloxymethyl)imidazo[1,2-a]pyrimidine and 4-fluoro-2-methylphenylboronic acid were used in the same manner as in Example 1-3 to obtain the title compound.

$^1$H-NMR (CDCl$_3$, 500 MHz) δ 8.56 (s, 1H), 8.34 (s, 1H), 7.99 (s, 1H), 7.65 (s, 1H), 7.53 (m, 1H), 7.25 (m, 1H), 7.11 (m, 1H), 7.07 (m, 1H), 6.89 (m, 1H), 5.41 (s, 2H), 2.33 (s, 3H)

Example 159: Synthesis of 6-(4-fluoro-2-methylphenyl)-2-(2-fluoropyridin-3-yloxymethyl)imidazo[1,2-a]pyrimidine

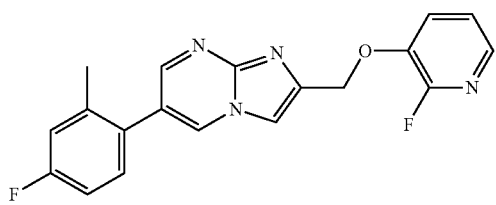 [SMILES: Cc1cc(F)ccc1-c1cnc2nc(COc3cccnc3F)cn2c1]

2-Fluoro-3-hydroxypyridine as a starting material and cesium carbonate were used in the same manner as in Example 1-2 to obtain 6-bromo-2-(2-fluoropyridin-3-yloxymethyl)imidazo[1,2-a]pyrimidine. The obtained 6-bromo-2-(2-fluoropyridin-3-yloxymethyl)imidazo[1,2-a]pyrimidine and 4-fluoro-2-methylphenylboronic acid were used in the same manner as in Example 1-3 to obtain the title compound.

$^1$H-NMR (DMSO-d6, 500 MHz) δ 9.17 (s, 1H), 8.79 (s, 1H), 8.17 (s, 1H), 7.94 (m, 1H), 7.80 (s, 1H), 7.44 (t, 1H), 7.38 (m, 1H), 7.30 (m, 1H), 7.21 (m, 1H), 5.50 (s, 2H), 2.34 (s, 3H)

Example 160: Synthesis of 6-(4-fluoro-2-methylphenyl)-2-(5-chloropyridin-3-yloxymethyl)imidazo[1,2-a]pyrimidine

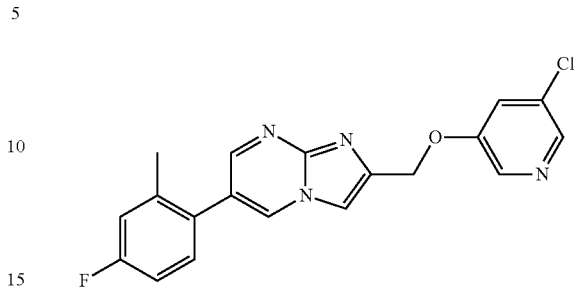

5-Chloro-3-hydroxypyridine as a starting material and cesium carbonate were used in the same manner as in Example 1-2 to obtain 6-bromo-2-(5-chloropyridin-3-yloxymethyl)imidazo[1,2-a]pyrimidine. The obtained 6-bromo-2-(5-chloropyridin-3-yloxymethyl)imidazo[1,2-a]pyrimidine and 4-fluoro-2-methylphenylboronic acid were used in the same manner as in Example 1-3 to obtain the title compound.

$^1$H-NMR (CDCl$_3$, 500 MHz) δ 8.56 (d, 1H), 8.35 (s, 2H), 8.24 (s, 1H), 7.66 (s, 1H), 7.40 (s, 1H), 7.25 (m, 1H), 7.05 (m, 2H), 5.42 (s, 2H), 2.33 (s, 3H)

Example 161: Synthesis of 6-(2,4-difluorophenyl)-2-(2-fluoropyridin-4-yloxymethyl)imidazo[1,2-a]pyrimidine

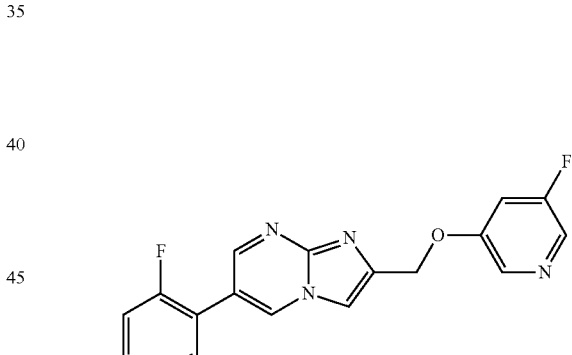

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 2,4-difluorophenylboronic acid were used in the same manner as in Example 1-3 to obtain the title compound.

$^1$H-NMR (DMSO-d6, 500 MHz) δ 9.20 (s, 1H), 8.73 (s, 1H), 8.04 (s, 1H), 7.99 (d, 1H), 7.68 (m, 1H), 7.41 (m, 1H), 7.22 (m, 1H), 6.97 (m, 1H), 6.86 (s, 1H), 5.35 (s, 2H)

Example 162: Synthesis of 6-(4-fluoro-2-methylphenyl)-2-(2-fluoropyridin-4-yloxymethyl)imidazo[1,2-a]pyrimidine

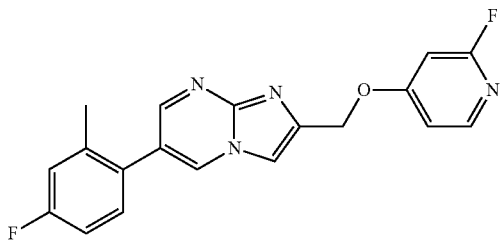

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 4-fluoro-2-methylphenylboronic acid were used in the same manner as in Example 1-3 to obtain the title compound.

$^1$H-NMR (CDCl$_3$, 500 MHz) δ 8.53 (s, 1H), 8.29 (s, 1H), 8.04 (d, 1H), 7.60 (s, 1H), 7.20 (t, 1H), 7.03 (d, 1H), 7.00 (t, 1H), 6.86 (m, 1H), 6.54 (s, 1H), 5.40 (s, 2H), 2.29 (s, 3H)

Example 163: Synthesis of 6-(4-fluoro-2-methoxyphenyl)-2-(2-fluoropyridin-4-yloxymethyl)imidazo[1,2-a]pyrimidine

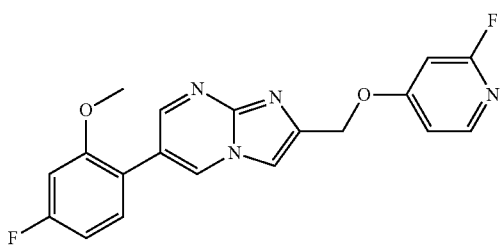 [SMILES: COc1cc(F)ccc1-c1cnc2nc(COc3ccnc(F)c3)cn2c1]

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 4-fluoro-2-methoxyphenylboronic acid were used in the same manner as in Example 1-3 to obtain the title compound.

$^1$H-NMR (CDCl$_3$, 500 MHz) δ 8.69 (s, 1H), 8.54 (s, 1H), 8.04 (s, 1H), 7.62 (s, 1H), 7.32 (m, 1H), 6.87 (d, 1H), 6.78 (m, 2H), 6.55 (s, 1H), 5.40 (s, 2H), 3.85 (s, 3H)

Example 164: Synthesis of 6-(4-fluorophenyl)-2-(2-fluoropyridin-4-yloxymethyl)imidazo[1,2-a]pyrimidine

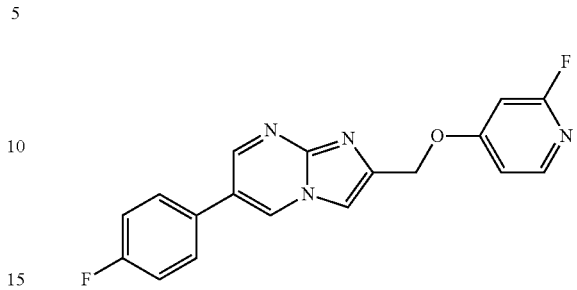

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 4-fluorophenylboronic acid were used in the same manner as in Example 1-3 to obtain the title compound.

$^1$H-NMR (CDCl$_3$, 500 MHz) δ 8.80 (s, 1H), 8.51 (s, 1H), 8.07 (d, 1H), 7.65 (s, 1H), 7.54 (m, 2H), 7.24 (m, 2H), 6.88 (s, 1H), 6.57 (s, 1H), 5.43 (s, 2H)

Example 165: Synthesis of 6-(2,3-difluorophenyl)-2-(2-fluoropyridin-4-yloxymethyl)imidazo[1,2-a]pyrimidine

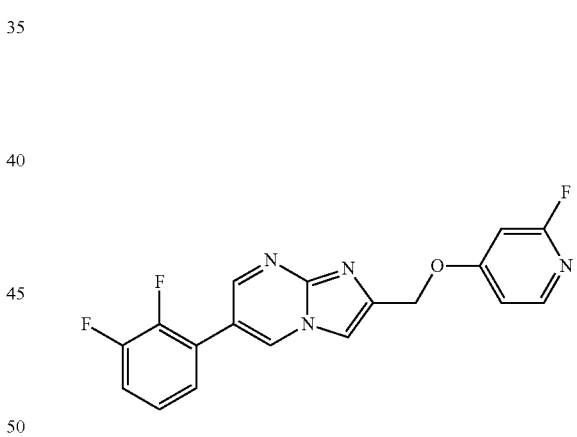

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 2,3-difluorophenylboronic acid were used in the same manner as in Example 1-3 to obtain the title compound.

$^1$H-NMR (CDCl$_3$, 500 MHz) δ 8.78 (s, 1H), 8.68 (s, 1H), 8.08 (s, 1H), 7.70 (s, 1H), 7.29 (s, 3H), 6.89 (s, 1H), 6.58 (s, 1H), 5.44 (s, 2H)

Example 166: Synthesis of 6-(2-fluorophenyl)-2-(2-fluoropyridin-4-yloxymethyl)imidazo[1,2-a]pyrimidine

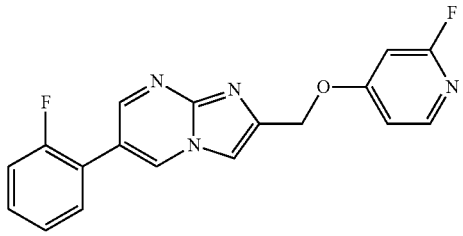 [SMILES: Fc1cc(OCc2cn3cc(-c4ccccc4F)cnc3n2)ccn1]

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 2-fluorophenylboronic acid were used in the same manner as in Example 1-3 to obtain the title compound.

$^1$H-NMR (CDCl$_3$, 500 MHz) δ 8.79 (s, 1H), 8.64 (s, 1H), 8.07 (s, 1H), 7.65 (s, 1H), 7.51 (m, 1H), 7.47 (m, 1H), 7.34 (m, 2H), 6.88 (s, 1H), 6.57 (s, 1H), 5.43 (s, 2H)

Example 167: Synthesis of 6-(4-fluoro-2-hydroxyphenyl)-2-(2-fluoropyridin-4-yloxymethyl)imidazo[1,2-a]pyrimidine

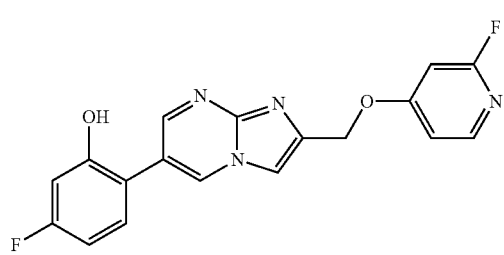 [SMILES: Oc1cc(F)ccc1-c1cnc2nc(COc3ccnc(F)c3)cn2c1]

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 4-fluoro-2-hydroxyphenylboronic acid were used in the same manner as in Example 1-3 to obtain the title compound.

$^1$H-NMR (DMSO-d6, 500 MHz) δ 9.53 (s, 1H), 9.19 (s, 1H), 8.42 (s, 1H), 8.13 (s, 1H), 7.55 (m, 2H), 7.10 (s, 1H), 7.01 (m, 2H), 6.86 (m, 1H), 5.59 (s, 2H)

Example 168: Synthesis of 6-(2-methylphenyl)-2-(2-fluoropyridin-4-yloxymethyl)imidazo[1,2-a]pyrimidine

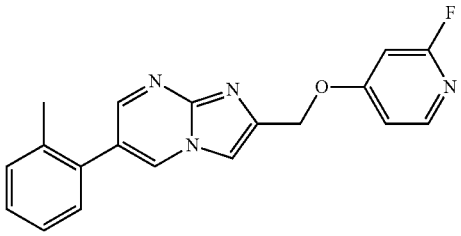 [SMILES: Cc1ccccc1-c1cnc2nc(COc3ccnc(F)c3)cn2c1]

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 2-methylphenylboronic acid were used in the same manner as in Example 1-3 to obtain the title compound.

$^1$H-NMR (CDCl$_3$, 500 MHz) δ 8.61 (s, 1H), 8.35 (s, 1H), 8.07 (s, 1H), 7.63 (s, 1H), 7.39 (m, 4H), 6.88 (s, 1H), 6.58 (s, 1H), 5.44 (s, 2H), 2.34 (s, 3H)

Example 169: Synthesis of 6-(2-hydroxyphenyl)-2-(2-fluoropyridin-4-yloxymethyl)imidazo[1,2-a]pyrimidine

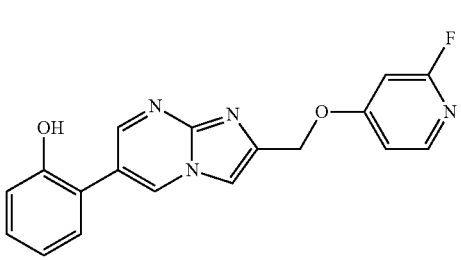 [SMILES: Oc1ccccc1-c1cnc2nc(COc3ccnc(F)c3)cn2c1]

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 2-hydroxyphenylboronic acid were used in the same manner as in Example 1-3 to obtain the title compound.

$^1$H-NMR (DMSO-d6, 500 MHz) δ 9.14 (s, 1H), 8.76 (s, 1H), 8.07 (m, 2H), 7.43 (m, 1H), 7.25 (m, 1H), 7.06 (m, 1H), 7.00 (m, 1H), 6.95 (m, 2H), 5.40 (s, 2H)

Example 170: Synthesis of 6-(4-fluoro-2-hydroxymethylphenyl)-2-(2-fluoropyridin-4-yloxymethyl)imidazo[1,2-a]pyrimidine

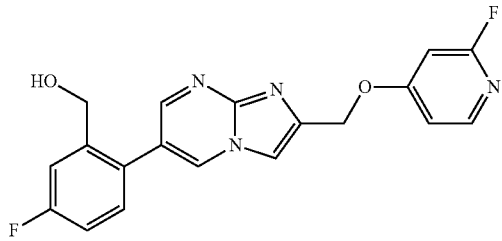 [SMILES: OCc1cc(F)ccc1-c1cnc2nc(COc3ccnc(F)c3)cn2c1]

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and 4-fluoro-2-hydroxymethylphenylboronic acid were used in the same manner as in Example 1-3 to obtain the title compound.

$^1$H-NMR (DMSO-d6, 500 MHz) δ 9.03 (s, 1H), 8.60 (s, 1H), 8.09 (s, 1H), 8.04 (s, 1H), 7.42 (m, 2H), 7.26 (m, 1H), 7.07 (d, 1H), 6.97 (s, 1H), 5.43 (s, 2H), 4.48 (m, 2H), 4.11 (m, 1H)

Example 171: Synthesis of 6-(4-fluorophenyl)-2-[(5-fluoro-3-pyridyl)oxymethyl)imidazo[1,2-a]pyrimidine

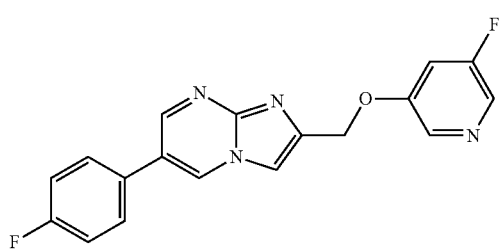

3-Fluoro-5-hydroxypyridine as a starting material and cesium carbonate were used in the same manner as in Example 1-2 to obtain 6-bromo-2-(5-fluoropyridin-3-yloxymethyl)imidazo[1,2-a]pyrimidine. The obtained 6-bromo-2-(5-fluoropyridin-3-yloxymethyl)imidazo[1,2-a]pyrimidine and (4-fluorophenyl)boronic acid were used in the same manner as in Example 1-3 to obtain the title compound.

$^1$H-NMR (DMSO-d6, 500 MHz) δ 9.30 (s, 1H), 8.91 (s, 1H), 8.32 (s, 1H), 8.20 (s, 1H), 8.02 (s, 1H), 7.82 (t, 2H), 7.66 (d, 1H), 7.39 (t, 2H), 5.39 (s, 2H)

Example 172: Synthesis of 2-[(2-chloro-4-pyridyl)oxymethyl]-6-(4-fluorophenyl)imidazo[1,2-a]pyrimidine

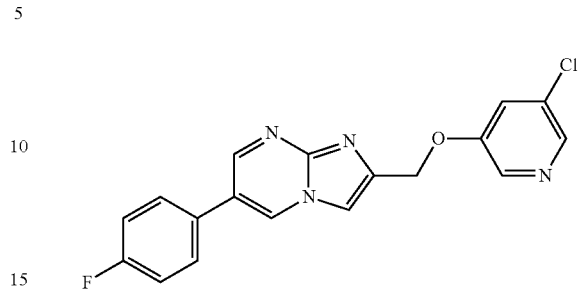

2-Chloro-4-hydroxypyridine as a starting material and cesium carbonate were used in the same manner as in Example 1-2 to obtain 6-bromo-2-(2-chloropyridin-4-yloxymethyl)imidazo[1,2-a]pyrimidine. The obtained 6-bromo-2-(2-chloropyridin-4-yloxymethyl)imidazo[1,2-a]pyrimidine and (4-fluorophenyl)boronic acid were used in the same manner as in Example 1-3 to obtain the title compound.

$^1$H-NMR (DMSO-d6, 500 MHz) δ 9.30 (s, 1H), 8.91 (s, 1H), 8.24 (d, 1H), 8.01 (s, 1H), 7.83 (m, 2H), 7.39 (t, 2H), 7.30 (s, 1H), 7.15 (m, 1H), 5.42 (s, 2H)

Example 173: Synthesis of 2-[(5-fluoro-3-pyridyl)oxymethyl]-6-[4-fluoro-2-(trifluoromethyl)phenyl]imidazo[1,2-a]pyrimidine

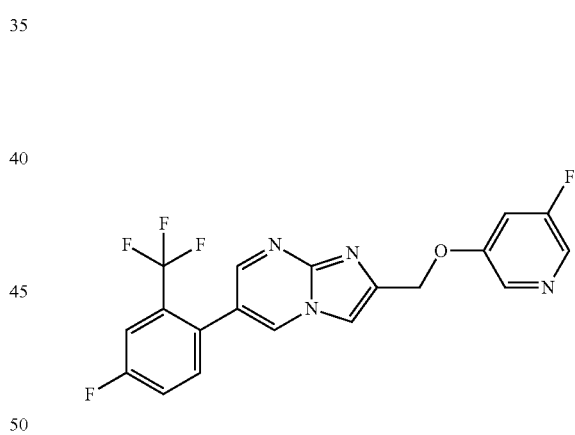

3-Fluoro-5-hydroxypyridine as a starting material and cesium carbonate were used in the same manner as in Example 1-2 to obtain 6-bromo-2-(5-fluoropyridin-3-yloxymethyl)imidazo[1,2-a]pyrimidine. The obtained 6-bromo-2-(5-fluoropyridin-3-yloxymethyl)imidazo[1,2-a]pyrimidine and [4-fluoro-2-(trifluoromethyl)phenyl]boronic acid were used in the same manner as in Example 1-3 to obtain the title compound.

$^1$H-NMR (DMSO-d6, 500 MHz) δ 9.08 (s, 1H), 8.51 (s, 1H), 8.32 (m, 1H), 8.21 (m, 1H), 7.98 (m, 1H), 7.88 (m, 1H), 7.70 (m, 2H), 7.65 (m, 1H), 5.40 (s, 2H)

Example 174: Synthesis of 2-[(2-fluoro-4-pyridyl)oxymethyl]-6-[4-fluoro-2-(trifluoromethyl)phenyl]imidazo[1,2-a]pyrimidine

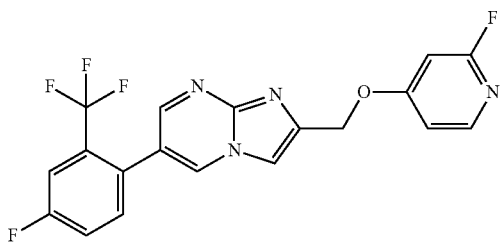 [SMILES: Fc1ccc(-c2cnc3nc(COc4ccnc(F)c4)cn3c2)c(C(F)(F)F)c1]

2-Fluoro-4-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and [4-fluoro-2-(trifluoromethyl)phenyl]boronic acid were used in the same manner as in Example 1-3 to obtain the title compound.

$^1$H-NMR (DMSO-d6, 500 MHz) δ 9.35 (s, 1H), 8.83 (s, 1H), 8.33 (s, 1H), 8.09 (d, 1H), 7.88 (m, 1H), 7.77 (m, 1H), 7.67 (m, 1H), 7.07 (d, 1H), 6.98 (s, 1H), 5.59 (s, 2H)

Example 175: Synthesis of 5-fluoro-2-[2-[(5-fluoro-3-pyridyl)oxymethyl]imidazo[1,2-a]pyrimidin-6-yl]aniline

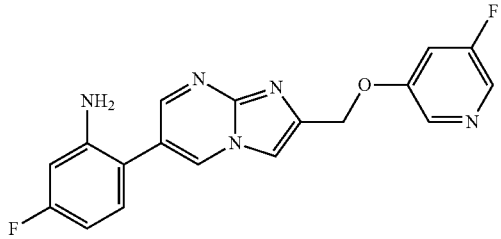 [SMILES: Nc1cc(F)ccc1-c1cnc2nc(COc3cncc(F)c3)cn2c1]

3-Fluoro-5-hydroxypyridine as a starting material and cesium carbonate were used in the same manner as in Example 1-2 to obtain 6-bromo-2-(5-fluoropyridin-3-yloxymethyl)imidazo[1,2-a]pyrimidine. The obtained 6-bromo-2-(5-fluoropyridin-3-yloxymethyl)imidazo[1,2-a]pyrimidine and (2-amino-4-fluoro-phenyl)boronic acid were used in the same manner as in Example 1-3 to obtain the title compound.

$^1$H-NMR (DMSO-d6, 500 MHz) δ 8.92 (s, 1H), 8.45 (s, 1H), 8.29 (s, 1H), 8.18 (s, 1H), 7.97 (s, 1H), 7.64 (d, 1H), 7.08 (t, 1H), 6.52 (d, 1H), 6.43 (m, 1H), 5.47 (s, 2H), 5.37 (s, 2H)

Example 176: Synthesis of 5-fluoro-2-[2-[(2-fluoro-4-pyridyl)oxymethyl]imidazo[1,2-a]pyrimidin-6-yl]aniline

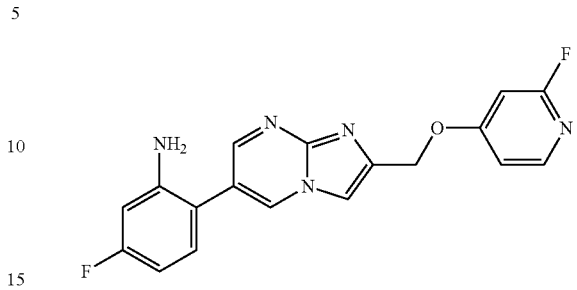

3-Fluoro-5-hydroxypyridine as a starting material and cesium carbonate were used in the same manner as in Example 1-2 to obtain 6-bromo-2-(2-fluoropyridin-4-yloxymethyl)imidazo[1,2-a]pyrimidine. The obtained 6-bromo-2-(2-fluoropyridin-4-yloxymethyl)imidazo[1,2-a]pyrimidine and (2-amino-4-fluoro-phenyl)boronic acid were used in the same manner as in Example 1-3 to obtain the title compound.

$^1$H-NMR (DMSO-d6, 500 MHz) δ 8.92 (s, 1H), 8.45 (s, 1H), 8.05 (d, 1H), 7.98 (s, 1H), 7.06 (m, 2H), 6.93 (s, 1H), 6.52 (d, 1H), 6.42 (t, 1H), 5.47 (m, 2H), 5.40 (s, 2H)

Example 177: Synthesis of [5-fluoro-2-[2-[(5-fluoro-3-pyridyl)oxymethyl]imidazo[1,2-a]pyrimidin-6-yl]phenyl]methanol

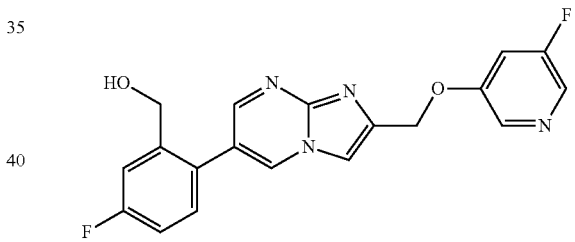

3-Fluoro-5-hydroxypyridine as a starting material and cesium carbonate were used in the same manner as in Example 1-2 to obtain 6-bromo-2-(5-fluoropyridin-3-yloxymethyl)imidazo[1,2-a]pyrimidine. The obtained 6-bromo-2-(5-fluoropyridin-3-yloxymethyl)imidazo[1,2-a]pyrimidine and [4-fluoro-2-(hydroxymethyl)phenyl]boronic acid were used in the same manner as in Example 1-3 to obtain the title compound.

$^1$H-NMR (DMSO-d6, 500 MHz) δ 9.01 (s, 1H), 8.56 (s, 1H), 8.30 (s, 1H), 8.21 (s, 1H), 8.02 (s, 1H), 7.64 (d, 1H), 7.40 (m, 2H), 7.22 (t, 1H), 5.41 (s, 2H), 5.40 (s, 2H), 4.46 (s, 2H)

Example 178: Synthesis of 2-(2,4-difluorophenyl)-6-(phenoxymethyl)imidazo[1,2-b][1,2,4]triazine

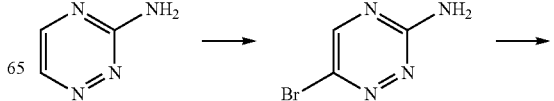

-continued

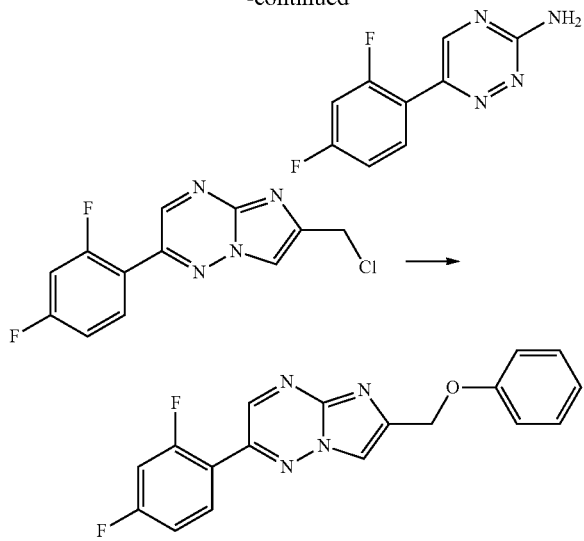

Example 178-1: Synthesis of 6-bromo-1,2,4-triazine-3-amine 1,2,4-Triazine-3-amine (2 g, 20.814 mmol) was dissolved in acetonitrile (20.8 ml) and water (31.5 ml). After the reaction temperature was cooled to 0° C., N-bromosuccinimide (3.89 g, 20.855 mmol) was added thereto. The resulting mixture was agitated for 10 minutes, and then heated to room temperature and agitated.

After the reaction termination, the resulting mixture was diluted with ethyl acetate and cooled to 0° C. Sodium carbonate was added thereto, agitated for 10 minutes, and washed with saturated sodium bicarbonate and brine. After drying with anhydrous magnesium sulfate and filtration, the solvent was concentrated under reduced pressure to obtain 6-bromo-1,2,4-triazine-3-amine (amount: 2.4 g, yield: 67%).

Example 178-2: Synthesis of 6-(2,4-difluorophenyl)-1,2,4-triazine-3-amine

6-Bromo-1,2,4-triazine-3-amine (0.5 g, 2.857 mmol), 2,4-difluorophenylboronic acid (0.68 g, 4.286 mmol), 2N sodium carbonate and [1,1'-bis(diphenylphosphine)ferrocene]dichloropalladium(II) complex with dichloromethane (0.28 g, 0.343 mmol) were added to 1,2-dimethoxyethane (28.6 ml) and agitated at 90° C. overnight. After the temperature of the reaction mixture was cooled to room temperature, the reaction mixture was filtrated with Cellite™ pad, and the solvent was concentrated under reduced pressure, and then washed with ethyl acetate and filtrated to obtain yellow solid, 6-(2,4-difluorophenyl)-1,2,4-triazine-3-amine (amount: 0.82 g, yield: 46%).

Example 178-3: Synthesis of 6-(chloromethyl)-2-(2,4-difluorophenyl)imidazo[1,2-b][1,2,4]triazine 6-(2,4-Difluorophenyl)-1,2,4-triazine-3-amine (0.2 g, 0.961 mmol) was dissolved in dimethylformamide (4.8 ml), and 1,3-dichloroacetone (0.24 g, 1.922 mmol) was added thereto and agitated at 110° C. for 2 hours. After the reaction termination, water and ethyl acetate were added thereto and extracted. After drying with anhydrous magnesium sulfate and filtration, the solvent was concentrated under reduced pressure. Flash column chromatography was carried out to obtain yellow solid, 6-(chloromethyl)-2-(2,4-difluorophenyl)imidazo[1,2-b][1,2,4]triazine (amount: 80 mg, yield: 30%).

Example 178-4: Synthesis of 2-(2,4-difluorophenyl)-6-phenoxymethylimidazo[1,2-b][1,2,4]triazine 6-(Chloromethyl)-2-(2,4-difluorophenyl)imidazo[1,2-b][1,2,4]triazine (20 mg, 0.071 mmol) was dissolved in dimethylformamide (1 ml), and phenol (14 mg, 0.143 mmol) and potassium carbonate (69 mg, 0.213 mmol) were added thereto and agitated at 60° C. for 2 hours. After the reaction termination, the resulting mixture was filtrated and the solvent was concentrated under reduced pressure. Flash column chromatography was carried out to obtain white solid, 2-(2,4-difluorophenyl)-6-phenoxymethylimidazo[1,2-b][1,2,4]triazine (amount: 12 mg, yield: 50%).

$^1$H-NMR (CDCl$_3$, 500 MHz) δ 8.86 (s, 1H), 8.06 (s, 1H), 7.90 (m, 1H), 7.33 (m, 2H), 7.12 (m, 1H), 7.05 (m, 3H), 7.00 (m, 1H), 5.43 (s, 2H)

Example 179: Synthesis of 2-(2,4-difluorophenyl)-6-((pyridin-4-yloxy)methyl)imidazo[1,2-b][1,2,4]triazine

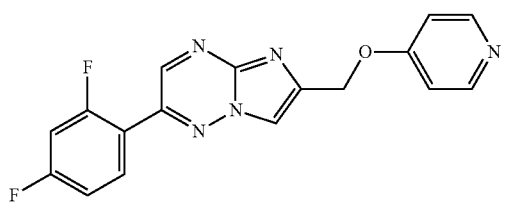 [SMILES: Fc1ccc(-c2cnc3nc(COc4ccncc4)cn3n2)c(F)c1]

6-(Chloromethyl)-2-(2,4-difluorophenyl)imidazo[1,2-b][1,2,4]triazine (66 mg, 0.235 mmol) obtained in Example 178-3 was dissolved in dimethylformamide (2.35 ml), and 4-hydroxypyridine (27 mg, 0.282 mmol) and cesium carbonate (0.23 g, 0.705 mmol) were added thereto and agitated at 40° C. for 2 hours. After the reaction termination, the resulting mixture was filtrated with Cellite™ pad, and the solvent was concentrated under reduced pressure. Column chromatography was carried out to obtain the title compound (amount: 10 mg, yield: 11%).

$^1$H-NMR (CDCl$_3$, 500 MHz) δ 8.88 (s, 1H), 8.50 (m, 2H), 8.05 (s, 1H), 7.89 (m, 1H), 7.09 (m, 2H), 6.99 (s, 2H), 5.49 (s, 2H)

Example 180: Synthesis of 2-(2,4-difluorophenyl)-6-((pyridin-2-yloxy)methyl)imidazo[1,2-b][1,2,4]triazine

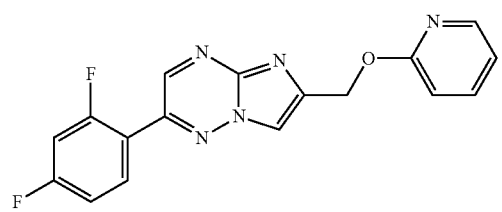 [SMILES: Fc1ccc(-c2cnc3nc(COc4ccccn4)cn3n2)c(F)c1]

6-(Chloromethyl)-2-(2,4-difluorophenyl)imidazo[1,2-b][1,2,4]triazine(90 mg, 0.321 mmol) obtained in Example 178-3 was dissolved in dimethylformamide (3.2 ml), and 2-hydroxypyridine (37 mg, 0.385 mmol) and silver carbonate were added thereto and agitated at 40° C. for 2 hours. After the reaction termination, the resulting mixture was filtrated with Cellite™ pad, and the solvent was concentrated under reduced pressure. Column chromatography was carried out to obtain the title compound (amount: 23 mg, yield: 19%).

$^1$H-NMR (CDCl$_3$, 500 MHz) δ 8.85 (s, 1H), 8.22 (s, 1H), 8.08 (s, 1H), 7.91 (m, 1H), 7.64 (m, 1H), 7.10 (m, 2H), 6.93 (m, 2H), 5.72 (s, 2H)

Example 181: Synthesis of 2-(4-fluorophenyl)-6-((pyridin-4-yloxy)methyl)imidazo[1,2-b][1,2,4]triazine

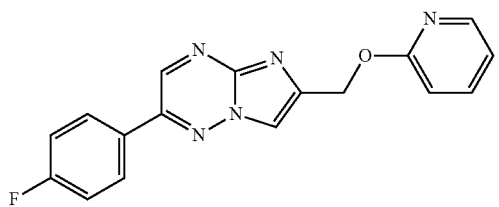 [SMILES: Fc1ccc(-c2cnc3nc(COc4ccccn4)cn3n2)cc1]

(4-Fluorophenyl)boronic acid as a starting material was used in the same manner as in Example 178-2 and Example 178-3 to obtain 6-(chloromethyl)-2-(4-fluorophenyl)imidazo[1,2-b][1,2,4]triazine. The obtained 6-(chloromethyl)-2-(4-fluorophenyl)imidazo[1,2-b][1,2,4]triazine was used in the same manner as in Example 180 to obtain the title compound.

$^1$H-NMR (CDCl$_3$, 500 MHz) δ 8.85 (s, 1H), 8.20 (s, 1H), 8.04 (S, 1H), 7.98 (m, 2H), 7.62 (t, 1H), 7.28 (m, 2H), 6.92 (m, 1H), 6.86 (m, 1H), 5.69 (s, 2H)

Example 182: Synthesis of 2-(2-methylphenyl)-6-((pyridin-4-yloxy)methyl)imidazo[1,2-b][1,2,4]triazine

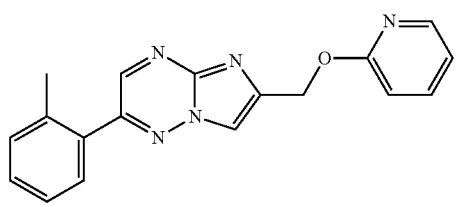 [SMILES: Cc1ccccc1-c1cnc2nc(COc3ccccn3)cn2n1]

(2-Methylphenyl)boronic acid as a starting material was used in the same manner as in Example 178-2 and Example 178-3 to obtain 6-(chloromethyl)-2-(2-methylphenyl)imidazo[1,2-b][1,2,4]triazine. The obtained 6-(chloromethyl)-2-(2-methylphenyl)imidazo[1,2-b][1,2,4]triazine was used in the same manner as in Example 180 to obtain the title compound.

$^1$H-NMR (CDCl$_3$, 500 MHz) δ 8.56 (s, 1H), 8.20 (s, 1H), 8.04 (s, 1H), 7.62 (m, 1H), 7.46 (m, 2H), 7.36 (m, 2H), 6.91 (m, 1H), 6.86 (m, 1H), 5.70 (s, 2H), 2.43 (s, 3H)

Example 183: Synthesis of 2-(2,4-difluorophenyl)-6-((2-fluoropyridin-4-yloxy)methyl)imidazo[1,2-b][1,2,4]triazine

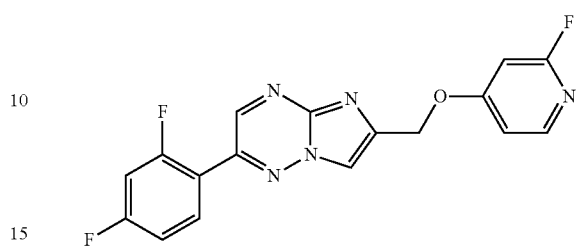

6-(Chloromethyl)-2-(2,4-difluorophenyl)imidazo[1,2-b][1,2,4]triazine obtained in Example 178-3 as a starting material and 2-fluoro-4-hydroxypyridine were used in the same manner as in Example 179 to obtain the title compound.

$^1$H-NMR (CDCl$_3$, 500 MHz) δ 8.89 (s, 1H), 8.07 (m, 2H), 7.91 (m, 1H), 7.12 (m, 1H), 7.06 (m, 1H), 6.89 (s, 1H), 6.57 (s, 1H), 5.46 (s, 2H)

Example 184: Synthesis of 2-(4-fluoro-2-methylphenyl)-6-((2-fluoropyridin-4-yloxy)methyl)imidazo[1,2-b][1,2,4]triazine

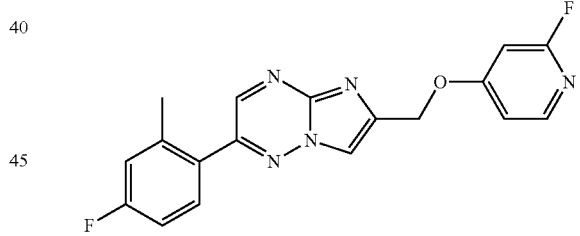

(4-Fluoro-2-methyl-phenyl)boronic acid as a starting material was used in the same manner as in Example 178-2 and Example 178-3 to obtain 6-(chloromethyl)-2-(4-fluoro-2-methyl-phenyl)imidazo[1,2-b][1,2,4]triazine. The obtained 6-(chloromethyl)-2-(4-fluoro-2-methyl-phenyl)imidazo[1,2-b][1,2,4]triazine and 2-fluoro-4-hydroxypyridine were used in the same manner as in Example 179 to obtain the title compound.

$^1$H-NMR (CDCl$_3$, 500 MHz) δ 8.59 (s, 1H), 8.09 (t, 1H), 8.02 (d, 1H), 7.45 (m, 1H), 7.10 (m, 2H), 6.89 (m, 1H), 6.58 (d, 1H), 5.44 (s, 2H), 2.47 (s, 3H)

Example 185: Synthesis of 2-(2-methylphenyl)-64 (2-fluoropyridin-4-yloxy)methyl)imidazo[1,2-b][1,2,4]triazine

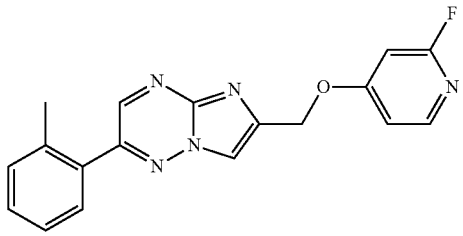

(2-Methylphenyl)boronic acid as a starting material was used in the same manner as in Example 178-2 and Example 178-3 to obtain 6-(chloromethyl)-2-(o-tolyl)imidazo[1,2-b][1,2,4]triazine. The obtained 6-(chloromethyl)-2-(o-tolyl)imidazo[1,2-b][1,2,4]triazine and 2-fluoro-4-hydroxypyridine were used in the same manner as in Example 179 to obtain the title compound.

¹H-NMR (CDCl₃, 500 MHz) δ 8.64 (s, 1H), 8.08 (d, 1H), 8.05 (d, 1H), 7.48 (t, 2H), 7.40 (m, 2H), 6.91 (m, 1H), 6.59 (s, 1H), 5.47 (s, 2H), 2.47 (s, 3H)

Example 186: Synthesis of 2-[4-fluoro-2-(trifluoromethyl)phenyl]-6-(2-pyridyloxymethyl)imidazo[1,2-b][1,2,4]triazine

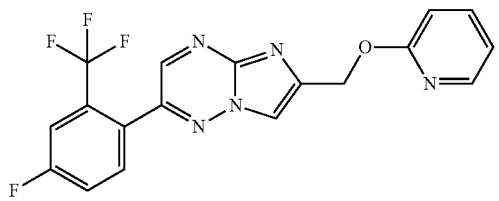 [SMILES: Fc1ccc(-c2cnc3nc(COc4ccccn4)cn3n2)c(C(F)(F)F)c1]

[4-Fluoro-2-(trifluoromethyl)phenyl]boronic acid as a starting material was used in the same manner as in Example 178-2 and Example 178-3 to obtain 6-(chloromethyl)-2-[4-fluoro-2-(trifluoromethyl)phenyl]imidazo[1,2-b][1,2,4]triazine. The obtained 6-(chloromethyl)-2-[4-fluoro-2-(trifluoromethyl)phenyl]imidazo[1,2-b][1,2,4]triazine and 2-hydroxypyridine were used in the same manner as in Example 180 to obtain the title compound.

¹H-NMR (CDCl₃, 500 MHz) δ 8.52 (s, 1H), 8.21 (d, 1H), 8.07 (s, 1H), 7.61 (m, 3H), 7.46 (m, 1H), 6.94 (m, 1H), 6.89 (d, 1H), 5.73 (s, 2H)

Example 187: Synthesis of 2-(3-fluoro-2-methylphenyl)-6-(2-pyridyloxymethyl)imidazo[1,2-b][1,2,4]triazine

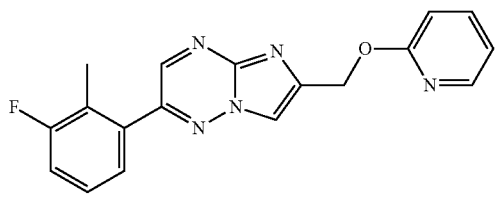 [SMILES: Cc1c(F)cccc1-c1cnc2nc(COc3ccccn3)cn2n1]

(3-Fluoro-2-methyl-phenyl)boronic acid as a starting material was used in the same manner as in Example 178-2 and Example 178-3 to obtain 6-(chloromethyl)-2-(3-fluoro-2-methyl-phenyl)imidazo[1,2-b][1,2,4]triazine. The obtained 6-(chloromethyl)-2-(3-fluoro-2-methyl-phenyl)imidazo[1,2-b][1,2,4]triazine and 2-hydroxypyridine were used in the same manner as in Example 180 to obtain the title compound.

¹H-NMR (DMSO-d6, 500 MHz) δ 8.78 (s, 1H), 8.41 (s, 1H), 8.22 (d, 1H), 7.76 (t, 1H), 7.44 (s, 2H), 7.40 (m, 1H), 7.03 (t, 1H), 6.91 (t, 1H), 5.55 (s, 2H), 2.30 (s, 3H)

Example 188: Synthesis of 2-(4-fluoro-2-methyl-phenyl)-6-(2-pyridyloxymethyl)imidazo[1,2-b][1,2,4]triazine

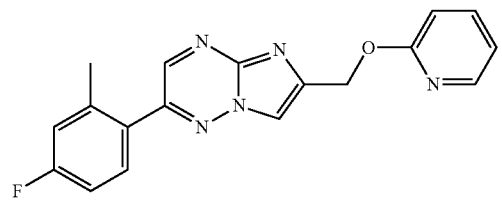 [SMILES: Cc1cc(F)ccc1-c1cnc2nc(COc3ccccn3)cn2n1]

(4-Fluoro-2-methyl-phenyl)boronic acid as a starting material was used in the same manner as in Example 178-2 and Example 178-3 to obtain 6-(chloromethyl)-2-(4-fluoro-2-methyl-phenyl)imidazo[1,2-b][1,2,4]triazine. The obtained 6-(chloromethyl)-2-(4-fluoro-2-methyl-phenyl)imidazo[1,2-b][1,2,4]triazine and 2-hydroxypyridine were used in the same manner as in Example 180 to obtain the title compound.

¹H-NMR (DMSO-d6, 500 MHz) δ 8.77 (s, 1H), 8.39 (s, 1H), 8.22 (d, 1H), 7.76 (m, 1H), 7.64 (m, 1H), 7.30 (m, 1H), 7.24 (t, 1H), 7.03 (t, 1H), 6.91 (d, 1H), 5.55 (s, 2H), 2.43 (s, 3H)

Example 189: Synthesis of 2-[4-chloro-2-(trifluoromethyl)phenyl]-6-(2-pyridyloxymethyl)imidazo[1,2-b][1,2,4]triazine

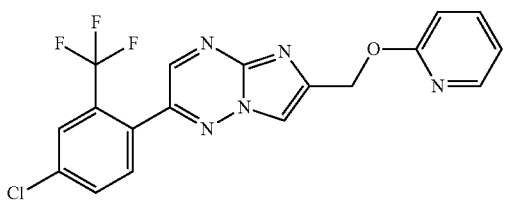

[4-Chloro-2-(trifluoromethyl)phenyl]boronic acid as a starting material was used in the same manner as in Example 178-2 and Example 178-3 to obtain 6-(chloromethyl)-2-[4-chloro-2-(trifluoromethyl)phenyl]imidazo[1,2-b][1,2,4]triazine. The obtained 6-(chloromethyl)-2-[4-chloro-2-(trifluoromethyl)phenyl]imidazo[1,2-b][1,2,4]triazine and 2-hydroxypyridine were used in the same manner as in Example 180 to obtain the title compound.

¹H-NMR (CDCl₃, 500 MHz) δ 8.51 (s, 1H), 8.21 (d, 1H), 8.06 (s, 1H), 7.87 (s, 1H), 7.73 (d, 1H), 7.63 (t, 1H), 7.53 (d, 1H), 6.94 (t, 1H), 6.88 (d, 1H), 5.72 (s, 2H)

Example 190: Synthesis of 2-(4-chloro-2-methyl-phenyl)-6-(2-pyridyloxymethyl)imidazo[1,2-b][1,2,4]triazine

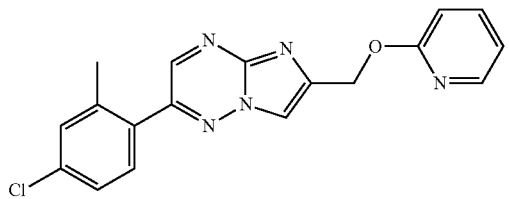 [SMILES: Cc1cc(Cl)ccc1-c1cnc2nc(COc3ccccn3)cn2n1]

(4-Chloro-2-methyl-phenyl)boronic acid as a starting material was used in the same manner as in Example 178-2 and Example 178-3 to obtain 6-(chloromethyl)-2-(4-chloro-2-methyl-phenyl)imidazo[1,2-b][1,2,4]triazine. The obtained 6-(chloromethyl)-2-(4-chloro-2-methyl-phenyl)imidazo[1,2-b][1,2,4]triazine and 2-hydroxypyridine were used in the same manner as in Example 180 to obtain the title compound.
$^1$H-NMR (CDCl$_3$, 500 MHz) δ 8.55 (s, 1H), 8.22 (d, 1H), 8.07 (s, 1H), 7.65 (m, 1H), 7.41 (m, 3H), 6.95 (m, 1H), 6.89 (m, 1H), 5.72 (s, 2H), 2.45 (s, 3H)

Example 191: Synthesis of 2-(4-fluoro-2-methyl-phenyl)-6-(2-pyridyloxymethyl)imidazo[1,2-b][1,2,4]triazine

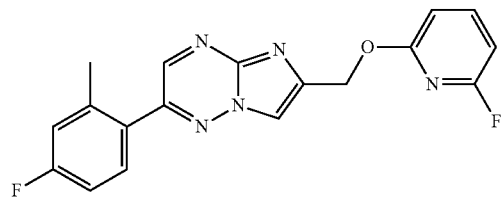 [SMILES: Cc1cc(F)ccc1-c1cnc2nc(COc3cccc(F)n3)cn2n1]

(4-Fluoro-2-methyl-phenyl)boronic acid as a starting material was used in the same manner as in Example 178-2 and Example 178-3 to obtain 6-(chloromethyl)-2-(4-fluoro-2-methyl-phenyl)imidazo[1,2-b][1,2,4]triazine. The obtained 6-(chloromethyl)-2-(4-fluoro-2-methyl-phenyl)imidazo[1,2-b][1,2,4]triazine and 6-fluoropyridin-2-ol were used in the same manner as in Example 180 to obtain the title compound.
$^1$H-NMR (DMSO-d6, 500 MHz) δ 8.78 (s, 1H), 8.42 (s, 1H), 7.93 (t, 1H), 7.65 (t, 1H), 7.30 (m, 1H), 7.24 (m, 1H), 6.87 (m, 1H), 6.77 (m, 1H), 5.50 (s, 2H), 2.42 (s, 3H)

Example 192: Synthesis of 2-(4-fluoro-2-methyl-phenyl)-6-[(5-fluoro-2-pyridyl)oxymethyl]imidazo[1,2-b][1,2,4]triazine

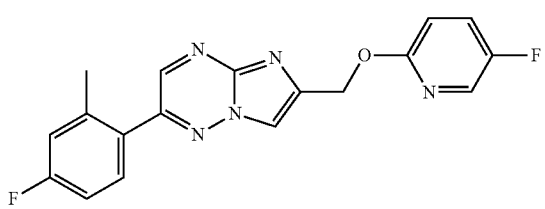 [SMILES: Cc1cc(F)ccc1-c1cnc2nc(COc3ccc(F)cn3)cn2n1]

(4-Fluoro-2-methyl-phenyl)boronic acid as a starting material was used in the same manner as in Example 178-2 and Example 178-3 to obtain 6-(chloromethyl)-2-(4-fluoro-2-methyl-phenyl)imidazo[1,2-b][1,2,4]triazine. The obtained 6-(chloromethyl)-2-(4-fluoro-2-methyl-phenyl)imidazo[1,2-b][1,2,4]triazine and 5-fluoropyridin-2-ol were used in the same manner as in Example 180 to obtain the title compound.
$^1$H-NMR (DMSO-d6, 500 MHz) δ 8.77 (s, 1H), 8.39 (s, 1H), 8.19 (s, 1H), 7.74 (m, 1H), 7.63 (m, 1H), 7.31 (m, 1H), 7.24 (m, 1H), 6.98 (m, 1H), 5.52 (s, 2H), 2.42 (s, 3H)

Example 193: Synthesis of [5-fluoro-2-[2-[(4-fluorophenoxy)methyl]imidazo[1,2-a]pyrimidin-6-yl]phenyl]methyl carbamate

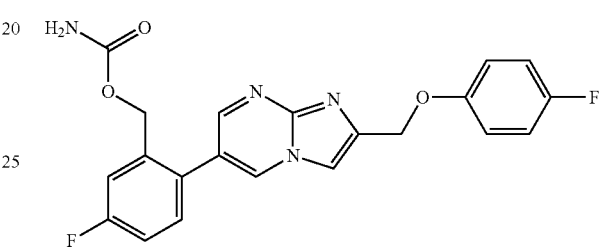

[5-Fluoro-2-[2-[(4-fluorophenoxy)methyl]imidazo[1,2-a]pyrimidin-6-yl]phenyl]methanol (100 mg, 0.27 mmol) obtained in Example 97 was dissolved in dimethylformamide (5 ml), and 1,1'-carbonyldiimidazole (88 mg, 0.54 mmol) was added thereto and agitated at room temperature for 30 minutes. Ammonia water (5 ml) was added to this solution and agitated at room temperature for 4 hours. Ethyl acetate was added to the reaction solution and extracted. After drying with anhydrous magnesium sulfate and filtration, the solvent was concentrated under reduced pressure. Flash column chromatography was carried out to obtain the title compound (amount: 88 mg, yield: 80%).
$^1$H-NMR (DMSO-d6, 500 MHz) δ 9.00 (s, 1H), 8.55 (s, 1H), 7.94 (s, 1H), 7.49 (t, 1H), 7.36 (m, 2H), 7.09 (m, 4H), 6.70 (m, 2H), 5.25 (s, 2H), 4.94 (s, 2H), 3.32 (s, 3H)

Example 194: Synthesis of [5-fluoro-2-[2-(phenoxymethyl)imidazo[1,2-a]pyrimidin-6-yl]phenyl]methyl carbamate

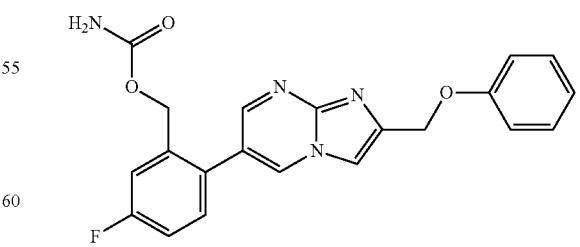

[5-Fluoro-2-[2-(phenoxymethyl)imidazo[1,2-a]pyrimidin-6-yl]phenyl]methanol obtained in Example 25 was used in the same manner as in Example 193 to obtain the title compound.

¹H-NMR (DMSO-d6, 500 MHz) δ 9.01 (s, 1H), 8.56 (s, 1H), 7.96 (s, 2H), 7.52 (m, 1H), 7.37 (m, 4H), 7.09 (m, 2H), 6.98 (m, 1H), 6.67 (m, 1H), 6.56 (m, 1H), 5.29 (s, 2H), 4.95 (s, 1H)

Example 195: Synthesis of [5-fluoro-2-[2-(2-pyridyloxymethyl)imidazo[1,2-a]pyrimidin-6-yl]phenyl]methyl carbamate

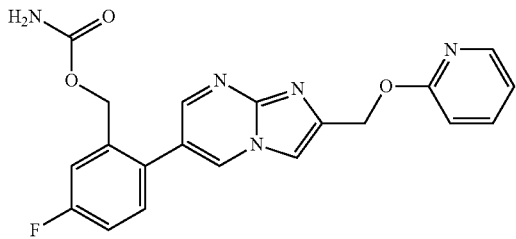 [SMILES: NC(=O)OCc1cc(F)ccc1-c1cnc2nc(COc3ccccn3)cn2c1]

[5-Fluoro-2-[2-(2-pyridyloxymethyl)imidazo[1,2-a]pyrimidin-6-yl]phenyl]methanol obtained in Example 135 was used in the same manner as in Example 193 to obtain the title compound.

¹H-NMR (DMSO-d6, 500 MHz) δ 8.99 (s, 1H), 8.55 (s, 1H), 8.22 (d, 1H), 7.91 (s, 1H), 7.77 (m, 1H), 7.50 (m, 1H), 7.37 (m, 2H), 7.04 (m, 1H), 6.92 (m, 1H), 6.68 (m, 1H), 6.57 (m, 1H), 5.52 (s, 2H), 4.95 (s, 2H)

Example 196: Synthesis of [5-fluoro-2-[2-(2-pyridyloxymethyl)imidazo[1,2-a]pyrimidin-6-yl]phenyl]methyl acetate

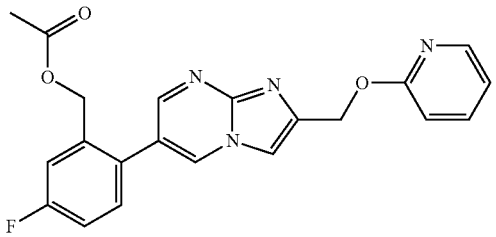 [SMILES: CC(=O)OCc1cc(F)ccc1-c1cnc2nc(COc3ccccn3)cn2c1]

[5-Fluoro-2-[2-(2-pyridyloxymethyl)imidazo[1,2-a]pyrimidin-6-yl]phenyl]methanol(100 mg, 0.29 mmol) obtained in Example 135 was dissolved in dimethylformamide (5 ml), and trimethylamine (58 mg, 0.57 mmol) and acetyl chloride (31 mg, 0.4 mmol) were added thereto at 0° C. and agitated at room temperature for 2 hours. After the reaction termination, water and ethyl acetate were added to the reaction solution and extracted. After drying ethyl acetate solution with anhydrous magnesium sulfate and filtration, the solvent was concentrated under reduced pressure. Flash column chromatography was carried out to obtain the title compound (amount: 57 mg, yield: 50%).

¹H-NMR (DMSO-d6, 500 MHz) δ 8.96 (s, 1H), 8.51 (s, 1H), 8.20 (t, 1H), 7.90 (s, 1H), 7.73 (t, 1H), 7.48 (t, 1H), 7.41 (m, 1H), 7.36 (m, 1H), 7.01 (t, 1H), 6.89 (d, 1H), 5.49 (s, 2H), 5.03 (s, 2H), 1.98 (s, 3H)

Example 197: Synthesis of 6-[2-(chloromethyl)-4-fluoro-phenyl]-2-[(4-fluorophenoxy)methyl)imidazo[1,2-a]pyrimidine

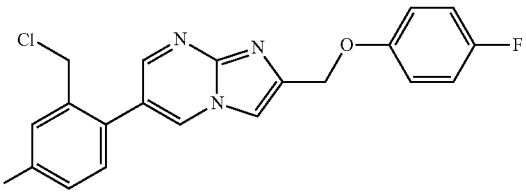

[5-Fluoro-2-[2-[(4-fluorophenoxy)methyl]imidazo[1,2-a]pyrimidin-6-yl]phenyl]methanol (100 mg, 0.27 mmol) obtained in Example 97 was dissolved in dimethylformamide (5 ml), and trimethylamine (58 mg, 0.57 mmol) and methanesulfonyl chloride (65 mg, 0.57 mmol) were added thereto at 0° C. and agitated at room temperature for 2 hours. Ethyl acetate and water were added to the reaction solution and extracted. The ethyl acetate solution was dried with anhydrous magnesium sulfate and filtrated, and the solvent was concentrated under reduced pressure. Flash column chromatography was carried out to obtain the title compound (amount: 73 mg, yield: 70%).

¹H-NMR (DMSO-d6, 500 MHz) δ 9.00 (s, 1H), 8.54 (s, 1H), 7.95 (s, 1H), 7.50 (m, 2H), 7.38 (m, 1H), 7.12 (m, 4H), 5.24 (s, 2H), 4.74 (s, 2H)

Example 198: Synthesis of 6-[4-fluoro-2-(fluoromethyl)phenyl]-2-(2-pyridyloxymethyl)imidazo[1,2-a]pyrimidine

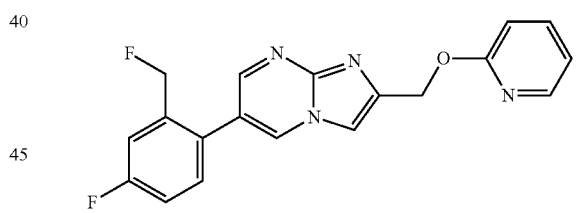

[5-Fluoro-2-[2-(2-pyridyloxymethyl)imidazo[1,2-a]pyrimidin-6-yl]phenyl]methanol(100 mg, 0.29 mmol) obtained in Example 135 was dissolved in methylene chloride (10 ml), and diethylaminosulfur trifluoride (70 mg, 0.44 mmol) was added thereto at 0° C. and agitated at room temperature for 30 minutes. Saturated ammonium chloride aqueous solution was added to the reaction solution and extracted by the use of methylene chloride and water. The methylene chloride extract solution was dried with anhydrous magnesium sulfate and filtrated, and the solvent was concentrated under reduced pressure. Flash column chromatography was carried out to obtain the title compound (amount: 92 mg, yield: 90%).

¹H-NMR (DMSO-d6, 500 MHz) δ 8.97 (s, 1H), 8.52 (s, 1H), 8.21 (m, 1H), 7.93 (s, 1H), 7.77 (m, 1H), 7.54 (m, 2H), 7.45 (m, 1H), 7.05 (m, 1H), 6.89 (m, 1H), 5.51 (s, 2H), 5.48 (s, 1H), 5.39 (s, 1H)

Example 199: Synthesis of 6-[4-fluoro-2-(fluoromethyl)phenyl]-2-[(4-fluorophenoxy)methyl]imidazo[1,2-a]pyrimidine

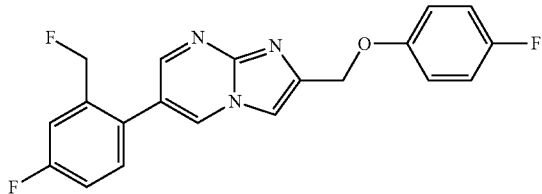 [SMILES: FCc1cc(F)ccc1-c1cnc2nc(COc3ccc(F)cc3)cn2c1]

[5-Fluoro-2-[2-[(4-fluorophenoxy)methyl]imidazo[1,2-a]pyrimidin-6-yl]phenyl]methanol obtained in Example 97 as a starting material was used in the same manner as in Example 198 to obtain the title compound.

$^1$H-NMR (DMSO-d6, 500 MHz) δ 8.98 (s, 1H), 8.54 (s, 1H), 7.97 (s, 1H), 7.57 (m, 2H), 7.44 (m, 1H), 7.12 (m, 4H), 5.49 (s, 1H), 5.39 (s, 1H), 5.26 (s, 2H)

Experimental Example: Pharmacological Activity Test

Efficacy as a positive allosteric modulator (PAM) of mGluR5 of the compounds of the Examples was tested as follows:

Calcium Influx Assay Based on Fluorescence $Ca^{2+}$ (calcium) influx assay is an experiment for measuring the activity of a positive allosteric modulator of mGluR5 receptor in which human mGluR5 receptor-overexpressed HEK293 cell line is used. The day before the experiment, cells were prepared in a cell culture medium (DMEM, 5% FBS) with the density of 80,000/well, and 100 μl of cells were dispensed into each well of a poly-D-lysine-coated 96-well plate. Cells were incubated in a 5% $CO_2$, 37° C. incubator. The next day, the cell culture medium was removed from the plate, and 100 μl of 1× Fluo-4 calcium indicator diluted with a buffer (1× Hank's balanced salt solution, 20 mM HEPES, 2.5 mM probenecid) were added to each well and incubated at 37° C. for 1 hour. The compound stock solutions were prepared in 100% DMSO, and the compounds were serially diluted with a 1/4 dilution to 6 or 7 concentrations (final concentration was 10 μM to 10 nM). The diluted compound solutions were added to the plate with 0.1 to 0.2% of final DMSO concentration. 1 hour after the addition of Fluo-4 calcium indicator, L-glutamate ($EC_{20}$ concentration) and the test compound solutions were added to the plate, and $Ca^{2+}$ reaction was then measured by FLIPR at room temperature. The activity of the compounds was standardized on the basis of the results of maximum value-minimum value of fluorescent reaction, and the activity value was calculated on the basis that no activity on glutamate $EC_{20}$ is 0% and the reaction to glutamate maximum value is 100%.

In the same manner as in the above assay, the efficacy of the test compounds as a human mGluR5 positive allosteric modulator was calculated to $EC_{50}$ and is represented in Table 1 (+: 500-1,000 nM, ++: 100-500 nM, +++: 100 nM or less).

TABLE 1

| Example | Human mGluR5 PAM $EC_{50}$ (nM) |
|---|---|
| 1 | ++ |
| 2 | ++ |
| 3 | +++ |
| 4 | ++ |
| 5 | +++ |
| 6 | +++ |
| 7 | ++ |
| 8 | ++ |
| 9 | + |
| 10 | ++ |
| 11 | ++ |
| 12 | + |
| 13 | + |
| 14 | ++ |
| 15 | ++ |
| 16 | + |
| 17 | + |
| 18 | ++ |
| 19 | + |
| 20 | ++ |
| 21 | + |
| 22 | + |
| 23 | ++ |
| 24 | ++ |
| 25 | +++ |
| 26 | ++ |
| 27 | ++ |
| 28 | + |
| 29 | ++ |
| 30 | + |
| 31 | ++ |
| 32 | ++ |
| 33 | ++ |
| 34 | ++ |
| 35 | ++ |
| 36 | ++ |
| 37 | + |
| 38 | ++ |
| 39 | ++ |
| 40 | ++ |
| 41 | ++ |
| 42 | + |
| 43 | ++ |
| 44 | ++ |
| 45 | ++ |
| 46 | ++ |
| 47 | ++ |
| 48 | ++ |
| 49 | + |
| 50 | + |
| 51 | ++ |
| 52 | ++ |
| 53 | ++ |
| 54 | ++ |
| 55 | ++ |
| 56 | ++ |
| 57 | ++ |
| 58 | ++ |
| 59 | ++ |
| 60 | ++ |
| 61 | + |
| 62 | + |
| 63 | ++ |
| 64 | + |
| 65 | ++ |
| 66 | ++ |
| 67 | +++ |
| 68 | ++ |
| 69 | ++ |
| 70 | ++ |
| 71 | ++ |
| 72 | ++ |
| 73 | + |
| 74 | ++ |
| 75 | ++ |
| 76 | ++ |
| 77 | ++ |
| 78 | ++ |
| 79 | ++ |
| 80 | +++ |

TABLE 1-continued

| Example | Human mGluR5 PAM EC$_{50}$ (nM) |
|---|---|
| 81 | ++ |
| 82 | ++ |
| 83 | ++ |
| 84 | + |
| 85 | ++ |
| 86 | ++ |
| 87 | + |
| 88 | ++ |
| 89 | + |
| 90 | ++ |
| 91 | +++ |
| 92 | ++ |
| 93 | ++ |
| 94 | ++ |
| 95 | ++ |
| 96 | ++ |
| 97 | ++ |
| 98 | ++ |
| 99 | + |
| 100 | + |
| 101 | ++ |
| 102 | ++ |
| 103 | ++ |
| 104 | ++ |
| 105 | ++ |
| 106 | ++ |
| 107 | + |
| 108 | + |
| 109 | ++ |
| 110 | ++ |
| 111 | ++ |
| 112 | ++ |
| 113 | ++ |
| 114 | ++ |
| 115 | ++ |
| 116 | +++ |
| 117 | ++ |
| 118 | ++ |
| 119 | ++ |
| 120 | ++ |
| 121 | ++ |
| 122 | + |
| 123 | ++ |
| 124 | ++ |
| 125 | ++ |
| 126 | ++ |
| 127 | ++ |
| 128 | + |
| 129 | + |
| 130 | ++ |
| 131 | ++ |
| 132 | +++ |
| 133 | + |
| 134 | ++ |
| 135 | ++ |
| 136 | + |
| 137 | ++ |
| 138 | ++ |
| 139 | + |
| 140 | ++ |
| 141 | ++ |
| 142 | ++ |
| 143 | + |
| 144 | + |
| 145 | ++ |
| 146 | + |
| 147 | + |
| 148 | + |
| 149 | ++ |
| 150 | + |
| 151 | ++ |
| 152 | ++ |
| 153 | ++ |
| 154 | ++ |
| 155 | ++ |
| 156 | ++ |
| 157 | + |

TABLE 1-continued

| Example | Human mGluR5 PAM EC$_{50}$ (nM) |
|---|---|
| 158 | ++ |
| 159 | + |
| 160 | + |
| 161 | ++ |
| 162 | +++ |
| 163 | ++ |
| 164 | ++ |
| 165 | ++ |
| 166 | ++ |
| 167 | ++ |
| 168 | +++ |
| 169 | ++ |
| 170 | ++ |
| 171 | ++ |
| 172 | ++ |
| 173 | + |
| 174 | ++ |
| 175 | + |
| 176 | ++ |
| 177 | + |
| 178 | ++ |
| 179 | ++ |
| 180 | ++ |
| 181 | + |
| 182 | ++ |
| 183 | ++ |
| 184 | ++ |
| 185 | ++ |
| 186 | ++ |
| 187 | ++ |
| 188 | +++ |
| 189 | + |
| 190 | ++ |
| 191 | + |
| 192 | ++ |
| 193 | ++ |
| 194 | ++ |
| 195 | ++ |
| 196 | ++ |
| 197 | ++ |
| 198 | +++ |
| 199 | ++ |

What is claimed is:

1. A method for preparing a compound of Formula (1) comprising:
carrying out a heterocycle synthesis reaction with a compound of Formula (2) as a starting material in dichloroacetone to obtain a compound of Formula (3);
carrying out a nucleophilic reaction with the compound of Formula (3) to obtain a compound of Formula (4); and
carrying out Suzuki coupling reaction with the compound of Formula (4) to obtain the compound of Formula (1),

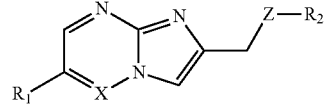

(1)

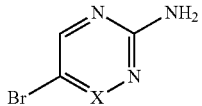

(2)

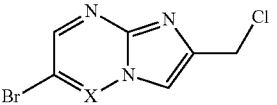

(3)

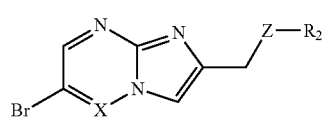
(4)

wherein
X is CH or N;
Z is O or S;
R₁ is aryl optionally substituted with one or more substituents selected from halo, hydroxy, alkyl, alkoxy, alkylthio, amino, dialkylamino, cyano, formyl, haloalkyl, hydroxyalkyl, alkoxyalkyl, carbamoyloxy alkyl, alkyl-C(O)O-alkyl, dialkylaminoalkyl and 5- or 6-membered heterocycloalkylalkyl; or 5- to 12-membered, unsaturated heterocyclyl optionally substituted with one or more substituents selected from halo, hydroxy, alkyl, alkoxy and haloalkyl; and
R₂ is aryl optionally substituted with one or more substituents selected from halo, deuterium, hydroxy and alkyl; or 5- to 12-membered, unsaturated heterocyclyl optionally substituted with one or more substituents selected from halo and alkyl.

2. The method according to claim 1, wherein R₁ is selected from the group consisting of:

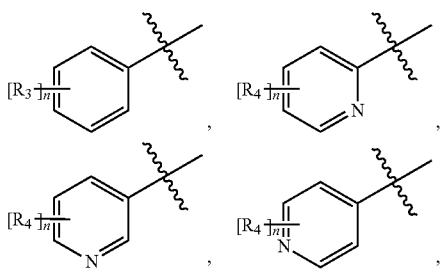

wherein n is 0, 1, 2, 3 or 4; each R₃ is selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl, $C_1$-$C_5$ alkyl-C(O)O—$C_1$-$C_5$ alkyl, di($C_1$-$C_5$ alkyl)amino-$C_1$-$C_5$ alkyl and 5- or 6-membered heterocycloalkyl-$C_1$-$C_5$ alkyl; and each R₄ is selected from halo, hydroxy, $C_1$-$C_5$ alkyl, $C_1$-$C_5$ alkoxy and halo-$C_1$-$C_5$ alkyl; and
R₂ is selected from the group consisting of:

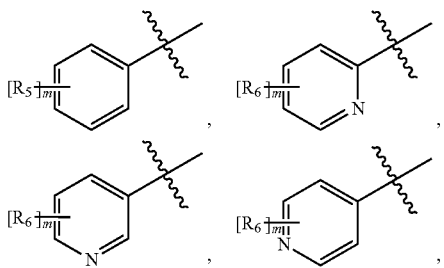

wherein m is 0, 1, 2, 3 or 4; R₅ is selected from halo, deuterium, hydroxy and $C_1$-$C_5$ alkyl; and R₆ is selected from halo and $C_1$-$C_5$ alkyl.

3. The method according to claim 1, wherein R₁ is phenyl optionally substituted with 1 to 3 substituents selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl and $C_1$-$C_5$ alkyl-C(O)O—$C_1$-$C_5$ alkyl; or 5- to 10-membered, unsaturated heterocyclyl having 1-3 heteroatoms selected from N, O and S, which is optionally substituted with 1 to 3 substituents selected from halo, hydroxy, $C_1$-$C_5$ alkyl, $C_1$-$C_5$ alkoxy and halo-$C_1$-$C_5$ alkyl.

4. The method according to claim 1, wherein R₂ is phenyl optionally substituted with 1 to 5 substituents selected from halo, deuterium, hydroxy and $C_1$-$C_5$ alkyl; or 5- or 6-membered heteroaryl having 1 to 3 heteroatoms selected from N, O and S, which is optionally substituted with 1 to 3 substituents selected from halo and $C_1$-$C_5$ alkyl.

5. The method according to according to claim 1,
wherein
X is CH;
Z is O;
R₁ is phenyl optionally substituted with 1 to 3 substituents selected from halo, hydroxy, $C_1$-$C_5$ alkyl, $C_1$-$C_5$ alkoxy, $C_1$-$C_5$ alkylthio, amino, halo-$C_1$-$C_5$ alkyl, hydroxy-$C_1$-$C_5$ alkyl and $C_1$-$C_5$ alkoxy-$C_1$-$C_5$ alkyl; and
R₂ is pyridyl optionally substituted with 1 or 2 substituents selected from halo and $C_1$-$C_5$ alkyl.

6. The method according to according to claim 1, wherein the compound of Formula (1) is selected from the group consisting of:
6-(2-fluorophenyl)-2-phenoxymethylimidazo[1,2-a]pyrimidine;
2-phenoxymethyl-6-phenylimidazo[1,2-a]pyrimidine;
6-(2,4-difluorophenyl)-2-phenoxymethylimidazo[1,2-a]pyrimidine;
6-(2-methoxyphenyl)-2-phenoxymethylimidazo[1,2-a]pyrimidine;
6-(2-methylphenyl)-2-phenoxymethylimidazo[1,2-a]pyrimidine;
6-(4-fluoro-2-methylphenyl)-2-phenoxymethylimidazo[1,2-a]pyrimidine;
6-(2,3-difluorophenyl)-2-phenoxymethylimidazo[1,2-a]pyrimidine;
6-(4-fluorophenyl)-2-phenoxymethylimidazo[1,2-a]pyrimidine;
6-(3-aminophenyl)-2-phenoxymethylimidazo[1,2-a]pyrimidine;
6-(2-aminophenyl)-2-phenoxymethylimidazo[1,2-a]pyrimidine;
6-(3-amino-6-methylphenyl)-2-phenoxymethylimidazo[1,2-a]pyrimidine;
6-(3-amino-4-fluorophenyl)-2-phenoxymethylimidazo[1,2-a]pyrimidine;
6-(3-chloro-4-fluorophenyl)-2-phenoxymethylimidazo[1,2-a]pyrimidine;
6-(2-dimethylaminophenyl)-2-phenoxymethylimidazo[1,2-a]pyrimidine;
6-(2-chloro-4-fluorophenyl)-2-phenoxymethylimidazo[1,2-a]pyrimidine;
6-(2-hydroxyphenyl)-2-phenoxymethylimidazo[1,2-a]pyrimidine;
6-(3-hydroxyphenyl)-2-phenoxymethylimidazo[1,2-a]pyrimidine;

6-(4-fluoro-2-trifluoromethylphenyl)-2-phenoxymethyl-imidazo[1,2-a]pyrimidine;
6-(3,4-difluorophenyl)-2-phenoxymethylimidazo[1,2-a]pyrimidine;
6-(2-methoxy-4-fluorophenyl)-2-phenoxymethylimidazo[1,2-a]pyrimidine;
6-(4-fluoro-3-methoxyphenyl)-2-phenoxymethylimidazo[1,2-a]pyrimidine;
6-(4-chloro-2-methoxyphenyl)-2-phenoxymethylimidazo[1,2-a]pyrimidine;
6-(4-cyano-2-methoxyphenyl)-2-phenoxymethylimidazo[1,2-a]pyrimidine;
6-(7-fluorobenzo[1,3]dioxol-4-yl)-2-phenoxymethylimidazo[1,2-a]pyrimidine;
6-(4-fluoro-2-hydroxymethylphenyl)-2-phenoxymethyl-imidazo[1,2-a]pyrimidine;
6-(4-fluoro-2-methylthiophenyl)-2-phenoxymethylimidazo[1,2-a]pyrimidine;
6-(2-amino-4-fluorophenyl)-2-phenoxymethylimidazo[1,2-a]pyrimidine;
6-(2,4-difluoro-5-methoxyphenyl)-2-phenoxymethylimidazo[1,2-a]pyrimidine;
6-(2-fluoropyridin-3-yl)-2-phenoxymethylimidazo[1,2-a]pyrimidine;
6-(6-methoxypyridin-3-yl)-2-phenoxymethylimidazo[1,2-a]pyrimidine;
6-(6-fluoropyridin-3-yl)-2-phenoxymethylimidazo[1,2-a]pyrimidine;
6-(4-methylpyridin-3-yl)-2-phenoxymethylimidazo[1,2-a]pyrimidine;
6-(2,6-difluoropyridin-3-yl)-2-phenoxymethylimidazo[1,2-a]pyrimidine;
6-(6-chloropyridin-3-yl)-2-phenoxymethylimidazo[1,2-a]pyrimidine;
6-(2-fluoropyridin-4-yl)-2-phenoxymethylimidazo[1,2-a]pyrimidine;
6-(3-chloropyridin-4-yl)-2-phenoxymethylimidazo[1,2-a]pyrimidine;
6-(4-chlorophenyl)-2-phenoxymethylimidazo[1,2-a]pyrimidine;
6-(6-fluoro-4-methyl-3-pyridyl)-2-phenoxymethylimidazo[1,2-a]pyrimidine;
6-(6-fluoro-5-methyl-3-pyridyl)-2-phenoxymethylimidazo[1,2-a]pyrimidine;
6-(5-fluoro-2-pyridyl)-2-phenoxymethylimidazo[1,2-a]pyrimidine;
6-(2,4-difluorophenyl)-2-(3-fluorophenoxymethyl)imidazo[1,2-a]pyrimidine;
6-(4-fluoro-2-methoxyphenyl)-2-(3-fluorophenoxymethyl)imidazo[1,2-a]pyrimidine;
6-(4-fluoro-3-hydroxyphenyl)-2-(3-fluorophenoxymethyl)-imidazo[1,2-a]pyrimidine;
6-(2-aminophenyl)-2-(3-fluorophenoxymethyl)imidazo[1,2-a]pyrimidine;
6-(3-chloropyridin-4-yl)-2-(3-fluorophenoxymethyl)imidazo[1,2-a]pyrimidine;
6-(4-methylpyridin-3-yl)-2-(3-fluorophenoxymethyl)imidazo[1,2-a]pyrimidine;
6-(2,4-difluorophenyl)-2-(4-fluorophenoxymethyl)imidazo[1,2-a]pyrimidine;
6-(4-fluoro-2-methylphenyl)-2-(4-fluorophenoxymethyl)imidazo[1,2-a]pyrimidine;
6-(3-chloropyridin-4-yl)-2-(4-fluorophenoxymethyl)imidazo[1,2-a]pyrimidine;
6-(2,6-dimethylphenyl)-2-(4-fluorophenoxymethyl)imidazo[1,2-a]pyrimidine;
2-[(4-fluorophenoxy)methyl]-6-(6-fluoro-3-pyridyl)imidazo[1,2-a]pyrimidine;
4-[[6-(4-fluorophenyl)imidazo[1,2-a]pyrimidin-2-yl]methoxy]phenol;
2-[(4-fluorophenoxy)methyl]-6-(4-fluorophenyl)imidazo[1,2-a]pyrimidine;
2-[(3-fluorophenoxy)methyl]-6-(4-fluorophenyl)imidazo[1,2-a]pyrimidine;
2-fluoro-5-[2-[(4-fluorophenoxy)methyl]imidazo[1,2-a]pyrimidin-6-yl]phenol;
2-[(4-fluorophenoxy)methyl]-6-phenyl-imidazo[1,2-a]pyrimidine;
5-fluoro-2-[2-[(3-fluorophenoxy)methyl]imidazo[1,2-a]pyrimidin-6-yl]phenol;
5-fluoro-2-[2-[(4-fluorophenoxy)methyl]imidazo[1,2-a]pyrimidin-6-yl]phenol;
6-(4-fluorophenyl)-2-[(2,3,4,5,6-pentadeuteriophenoxy)methyl]imidazo[1,2-a]pyrimidine;
2-[(4-fluorophenoxy)methyl]6-(o-tolyl)imidazo[1,2-a]pyrimidine;
6-(5-fluoro-2-methyl-phenyl)-2-[(4-fluorophenoxy)methyl]imidazo[1,2-a]pyrimidine;
2-[(4-fluorophenoxy)methyl]-6-(2-fluoro-4-pyridyl)imidazo[1,2-a]pyrimidine;
2-[2-[(4-fluorophenoxy)methyl]imidazo[1,2-a]pyrimidin-6-yl]phenol;
6-(2-fluoro-4-methyl-phenyl)-2-[(4-fluorophenoxy)methyl]imidazo[1,2-a]pyrimidine;
2-[(4-fluorophenoxy)methyl]-6-[6-(trifluoromethyl)-3-pyridyl]imidazo[1,2-a]pyrimidine;
2-[2-[(4-fluorophenoxy)methyl]imidazo[1,2-a]pyrimidin-6-yl]aniline;
6-(2-chloro-4-fluoro-phenyl)-2-[(4-fluorophenoxy)methyl]imidazo[1,2-a]pyrimidine;
4-[2-[(4-fluorophenoxy)methyl]imidazo[1,2-a]pyrimidin-6-yl]-3-methoxy-benzonitrile;
6-(4-chloro-2-methoxy-phenyl)-2-[(4-fluorophenoxy)methyl]imidazo[1,2-a]pyrimidine;
2-fluoro-5-[2-[(4-fluorophenoxy)methyl]imidazo[1,2-a]pyrimidin-6-yl]aniline;
6-(2,6-difluoro-3-pyridyl)-2-[(3-fluorophenoxy)methyl]imidazo[1,2-a]pyrimidine;
5-[2-[(4-fluorophenoxy)methyl]imidazo[1,2-a]pyrimidin-6-yl]-2-methyl-aniline;
4,5-difluoro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-5-methyl-aniline;
5-chloro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-4-methyl-aniline;
5-fluoro-2-[2-[(4-fluorophenoxy)methyl]imidazo[1,2-a]pyrimidin-6-yl]aniline;
2-[(4-fluorophenoxy)methyl]-6-(4-methyl-3-pyridyl)imidazo[1,2-a]pyrimidine;
2-[(3-fluorophenoxy)methyl]-6-(2-fluoro-4-pyridyl)imidazo[1,2-a]pyrimidine;
2-[(3-fluorophenoxy)methyl]-6-[6-(trifluoromethyl)-3-pyridyl]imidazo[1,2-a]pyrimidine;
2-[(3-fluorophenoxy)methyl]-6-(6-fluoro-3-pyridyl)imidazo[1,2-a]pyrimidine;
2-[(3-fluorophenoxy)methyl]-6-(2-fluoro-3-pyridyl)imidazo[1,2-a]pyrimidine;
6-(5,6-difluoro-3-pyridyl)-2-[(4-fluorophenoxy)methyl]imidazo[1,2-a]pyrimidine;

5-[2-[(4-fluorophenoxy)methyl]imidazo[1,2-a]pyrimidin-6-yl]-2-methoxy-aniline;
2-[(4-fluorophenoxy)methyl]-6-(5-fluoro-2-pyridyl)imidazo[1,2-a]pyrimidine;
2-[(4-fluorophenoxy)methyl]-6-(5-methoxy-2-pyridyl)imidazo[1,2-a]pyrimidine;
6-(4-chloro-3-pyridyl)-2-[(4-fluorophenoxy)methyl]imidazo[1,2-a]pyrimidine;
6-(5-chloro-3-pyridyl)-2-[(4-fluorophenoxy)methyl]imidazo[1,2-a]pyrimidine;
2-[(4-fluorophenoxy)methyl]-6-(5-methoxy-3-pyridyl)imidazo[1,2-a]pyrimidine;
5-[2-[(4-fluorophenoxy)methyl]imidazo[1,2-a]pyrimidin-6-yl]pyridin-2-ol;
6-(6-fluoro-5-methyl-3-pyridyl)-2-[(4-fluorophenoxy)methyl]imidazo[1,2-a]pyrimidine;
2-[(4-fluorophenoxy)methyl]-6-(6-methyl-3-pyridyl)imidazo[1,2-a]pyrimidine;
2-[(3-fluorophenoxy)methyl]-6-(5-fluoro-2-pyridyl)imidazo[1,2-a]pyrimidine;
2-[(3-fluorophenoxy)methyl]-6-[4-fluoro-2-(trifluoromethyl)phenyl]imidazo[1,2-a]pyrimidine;
4-[2-[(3-fluorophenoxy)methyl]imidazo[1,2-a]pyrimidin-6-yl]-3-methoxy-benzonitrile;
[5-fluoro-2-[2-[(3-fluorophenoxy)methyl]imidazo[1,2-a]pyrimidin-6-yl]phenyl]methanol;
[5-fluoro-2-[2-[(4-fluorophenoxy)methyl]imidazo[1,2-a]pyrimidin-6-yl]phenyl]methanol;
6-(4-fluoro-2-methylsulfanyl-phenyl)-2-[(4-fluorophenoxy)methyl]imidazo[1,2-a]pyrimidine;
2-[(4-fluorophenoxy)methyl]-6-(2-methoxy-4-pyridyl)imidazo[1,2-a]pyrimidine;
2-[2-[(3-fluorophenoxy)methyl]imidazo[1,2-a]pyrimidin-6-yl]-4-methyl-aniline;
5-fluoro-2-[2-[(3-fluorophenoxy)methyl]imidazo[1,2-a]pyrimidin-6-yl]aniline;
6-(4-fluorophenyl)-2-(pyridin-2-yloxymethyl)imidazo[1,2-a]pyrimidine;
6-(2-methylphenyl)-2-(pyridin-2-yloxymethyl)imidazo[1,2-a]pyrimidine;
6-(4-fluoro-2-methoxyphenyl)-2-(pyridin-2-yloxymethyl)imidazo[1,2-a]pyrimidine;
6-(2,4-difluorophenyl)-2-(pyridin-2-yloxymethyl)imidazo[1,2-a]pyrimidine;
6-(4-fluoro-2-methylphenyl)-2-(pyridin-2-yloxymethyl)imidazo[1,2-a]pyrimidine;
6-(2,3-difluorophenyl)-2-(pyridin-2-yloxymethyl)imidazo[1,2-a]pyrimidine;
6-(5-fluoro-2-methylphenyl)-2-(pyridin-2-yloxymethyl)imidazo[1,2-a]pyrimidine;
6-(3-fluoro-2-methylphenyl)-2-(pyridin-2-yloxymethyl)imidazo[1,2-a]pyrimidine;
6-(7-fluoro-2H-benzo[1,3]dioxol-4-yl)-2-(pyridin-2-yloxymethyl)imidazo[1,2-a]pyrimidine;
6-(4-chloro-2-methoxyphenyl)-2-(pyridin-2-yloxymethyl)imidazo[1,2-a]pyrimidine;
6-(3-fluoro-2-methoxy-phenyl)-2-(2-pyridyloxymethyl)imidazo[1,2-a]pyrimidine;
6-[4-fluoro-2-(trifluoromethyl)phenyl]-2-(2-pyridyloxymethyl)imidazo[1,2-a]pyrimidine;
6-(4-fluoro-2-methyl-phenyl)-2-[(5-fluoro-2-pyridyl)oxymethyl)imidazo[1,2-a]pyrimidine;
6-(2-ethylphenyl)-2-(2-pyridyloxymethyl)imidazo[1,2-a]pyrimidine;
6-(4-fluoro-2-methyl-phenyl)-2-[(4-fluoro-2-pyridyl)oxymethyl)imidazo[1,2-a]pyrimidine;
6-(2-fluoro-4-methyl-phenyl)-2-(2-pyridyloxymethyl)imidazo[1,2-a]pyrimidine;
6-(4-fluoro-2-methoxy-phenyl)-2-[(4-fluoro-2-pyridyl)oxymethyl)imidazo[1,2-a]pyrimidine;
2-[(5-fluoro-2-pyridyl)oxymethyl]-6-[4-fluoro-2-(trifluoromethyl)phenyl]imidazo[1,2-a]pyrimidine;
6-(2,4-difluorophenyl)-2-[(4-fluoro-2-pyridyl)oxymethyl]imidazo[1,2-a]pyrimidine;
6-(3-fluoro-2-methoxy-phenyl)-2-[(4-fluoro-2-pyridyl)oxymethyl)imidazo[1,2-a]pyrimidine;
6-(2,3-difluorophenyl)-2-[(4-fluoro-2-pyridyl)oxymethyl]imidazo[1,2-a]pyrimidine;
6-(4-fluorophenyl)-2-[(4-fluoro-2-pyridyl)oxymethyl)imidazo[1,2-a]pyrimidine;
6-(3-fluoro-2-methyl-phenyl)-2-[(5-fluoro-2-pyridyl)oxymethyl)imidazo[1,2-a]pyrimidine;
2-[(4-fluoro-2-pyridyl)oxymethyl]-6-[4-fluoro-2-(trifluoromethyl)phenyl]imidazo[1,2-a]pyrimidine;
2-[(5-fluoro-2-pyridyl)oxymethyl]-6-(o-tolyl)imidazo[1,2-a]pyrimidine;
6-(4-chloro-2-methyl-phenyl)-2-[(5-fluoro-2-pyridyl)oxymethyl)imidazo[1,2-a]pyrimidine;
6-(2,4-dimethylphenyl)-2-[(5-fluoro-2-pyridyl)oxymethyl]imidazo[1,2-a]pyrimidine;
6-(4-fluorophenyl)-2-[(5-fluoro-2-pyridyl)oxymethyl)imidazo[1,2-a]pyrimidine;
2-(2-pyridyloxymethyl)-6-[6-(trifluoromethyl)-3-pyridyl]imidazo[1,2-a]pyrimidine;
2-[(5-fluoro-2-pyridyl)oxymethyl]-6-[6-(trifluoromethyl)-3-pyridyl]imidazo[1,2-a]pyrimidine;
6-(5-fluoro-2-pyridyl)-2-(2-pyridyloxymethyl)imidazo[1,2-a]pyrimidine;
2-fluoro-5-[2-[(5-fluoro-2-pyridyl)oxymethyl]imidazo[1,2-a]pyrimidin-6-yl]aniline;
2-fluoro-5-[2-(2-pyridyloxymethyl)imidazo[1,2-a]pyrimidin-6-yl]aniline;
[5-fluoro-2-[2-(2-pyridyloxymethyl)imidazo[1,2-a]pyrimidin-6-yl]phenyl]methanol;
3-methoxy-4-[2-(2-pyridyloxymethyl)imidazo[1,2-a]pyrimidin-6-yl]benzonitrile;
4-[2-[(5-fluoro-2-pyridyl)oxymethyl]imidazo[1,2-a]pyrimidin-6-yl]-3-methoxy-benzonitrile;
6-(4-fluoro-2-methylsulfanyl-phenyl)-2-(2-pyridyloxymethyl)imidazo[1,2-a]pyrimidine;
[5-fluoro-2-[2-[(5-fluoro-2-pyridyl)oxymethyl]imidazo[1,2-a]pyrimidin-6-yl]phenyl]methanol;
4-[2-(2-pyridyloxymethyl)imidazo[1,2-a]pyrimidin-6-yl]benzonitrile;
6-[4-fluoro-2-(methoxymethyl)phenyl]-2-(2-pyridyloxymethyl)imidazo[1,2-a]pyrimidine;
[2-[2-(2-pyridyloxymethyl)imidazo[1,2-a]pyrimidin-6-yl]-5-(trifluoromethyl)phenyl]methanol;
6-(2-isopropylphenyl)-2-(2-pyridyloxymethyl)imidazo[1,2-a]pyrimidine;
4-[2-(2-pyridyloxymethyl)imidazo[1,2-a]pyrimidin-6-yl]-3-(trifluoromethyl)benzaldehyde;
6-[4-chloro-2-(trifluoromethyl)phenyl]-2-(2-pyridyloxymethyl)imidazo[1,2-a]pyrimidine;
6-(4-fluorophenyl)-2-(pyridin-3-yloxymethyl)imidazo[1,2-a]pyrimidine;
6-(4-fluoro-2-methoxyphenyl)-2-(pyridin-3-yloxymethyl)imidazo[1,2-a]pyrimidine;
6-(2,4-difluorophenyl)-2-(pyridin-3-yloxymethyl)imidazo[1,2-a]pyrimidine;
6-(4-fluoro-2-methylphenyl)-2-(pyridin-3-yloxymethyl)imidazo[1,2-a]pyrimidine;

6-(4-fluoro-2-hydroxyphenyl)-2-(pyridin-3-yloxymethyl)imidazo[1,2-a]pyrimidine;
6-(4-fluoro-2-methoxyphenyl)-2-(pyridin-4-yloxymethyl)imidazo[1,2-a]pyrimidine;
6-(2,4-difluorophenyl)-2-(pyridin-4-yloxymethyl)imidazo[1,2-a]pyrimidine;
6-(2-methylphenyl)-2-(5-fluoro-pyridin-3-yloxymethyl)imidazo[1,2-a]pyrimidine;
6-(4-fluoro-2-methylphenyl)-2-(5-fluoro-pyridin-3-yloxymethyl)imidazo[1,2-a]pyrimidine;
6-(4-fluoro-2-methoxyphenyl)-2-(5-fluoropyridin-3-yloxymethyl)imidazo[1,2-a]pyrimidine;
6-(4-fluoro-2-hydroxyphenyl)-2-(5-fluoropyridin-3-yloxymethyl)imidazo[1,2-a]pyrimidine;
6-(2,4-difluorophenyl)-2-(6-fluoropyridin-3-yloxymethyl)imidazo[1,2-a]pyrimidine;
6-(4-fluoro-2-methylphenyl)-2-(6-fluoropyridin-3-yloxymethyl)imidazo[1,2-a]pyrimidine;
6-(4-fluoro-2-methylphenyl)-2-(2-fluoropyridin-3-yloxymethyl)imidazo[1,2-a]pyrimidine;
6-(4-fluoro-2-methylphenyl)-2-(5-chloropyridin-3-yloxymethyl)imidazo[1,2-a]pyrimidine;
6-(2,4-difluorophenyl)-2-(2-fluoropyridin-4-yloxymethyl)imidazo[1,2-a]pyrimidine;
6-(4-fluoro-2-methylphenyl)-2-(2-fluoropyridin-4-yloxymethyl)imidazo[1,2-a]pyrimidine;
6-(4-fluoro-2-methoxyphenyl)-2-(2-fluoropyridin-4-yloxymethyl)imidazo[1,2-a]pyrimidine;
6-(4-fluorophenyl)-2-(2-fluoropyridin-4-yloxymethyl)imidazo[1,2-a]pyrimidine;
6-(2,3-difluorophenyl)-2-(2-fluoropyridin-4-yloxymethyl)imidazo[1,2-a]pyrimidine;
6-(2-fluorophenyl)-2-(2-fluoropyridin-4-yloxymethyl)imidazo[1,2-a]pyrimidine;
6-(4-fluoro-2-hydroxyphenyl)-2-(2-fluoropyridin-4-yloxymethyl)imidazo[1,2-a]pyrimidine;
6-(2-methylphenyl)-2-(2-fluoropyridin-4-yloxymethyl)imidazo[1,2-a]pyrimidine;
6-(2-hydroxyphenyl)-2-(2-fluoropyridin-4-yloxymethyl)imidazo[1,2-a]pyrimidine;
6-(4-fluoro-2-hydroxymethylphenyl)-2-(2-fluoropyridin-4-yloxymethyl)imidazo[1,2-a]pyrimidine;
6-(4-fluorophenyl)-2-[(5-fluoro-3-pyridyl)oxymethyl]imidazo[1,2-a]pyrimidine;
2-[(2-chloro-4-pyridyl)oxymethyl]-6-(4-fluorophenyl)imidazo[1,2-a]pyrimidine;
2-[(5-fluoro-3-pyridyl)oxymethyl]-6-[4-fluoro-2-(trifluoromethyl)phenyl]imidazo[1,2-a]pyrimidine;
2-[(2-fluoro-4-pyridyl)oxymethyl]-6-[4-fluoro-2-(trifluoromethyl)phenyl]imidazo[1,2-a]pyrimidine;
5-fluoro-2-[2-[(5-fluoro-3-pyridyl)oxymethyl]imidazo[1,2-a]pyrimidin-6-yl]aniline;
5-fluoro-2-[2-[(2-fluoro-4-pyridyl)oxymethyl]imidazo[1,2-a]pyrimidin-6-yl]aniline;
[5-fluoro-2-[2-[(5-fluoro-3-pyridyl)oxymethyl]imidazo[1,2-a]pyrimidin-6-yl]phenyl]methanol;
2-(2,4-difluorophenyl)-6-(phenoxymethyl)imidazo[1,2-b][1,2,4]triazine;
2-(2,4-difluorophenyl)-6-((pyridin-4-yloxy)methyl)imidazo[1,2-b][1,2,4]triazine;
2-(2,4-difluorophenyl)-6-((pyridin-2-yloxy)methyl)imidazo[1,2-b][1,2,4]triazine;
2-(4-fluorophenyl)-6-((pyridin-4-yloxy)methyl)imidazo[1,2-b][1,2,4]triazine;
2-(2-methylphenyl)-6-((pyridin-4-yloxy)methyl)imidazo[1,2-b][1,2,4]triazine;
2-(2,4-difluorophenyl)-6-((2-fluoropyridin-4-yloxy)methyl)imidazo[1,2-b][1,2,4]triazine;
2-(4-fluoro-2-methylphenyl)-6-((2-fluoropyridin-4-yloxy)methyl)imidazo[1,2-b][1,2,4]triazine;
2-(2-methylphenyl)-6-((2-fluoropyridin-4-yloxy)methyl)imidazo[1,2-b][1,2,4]triazine;
2-[4-fluoro-2-(trifluoromethyl)phenyl]-6-(2-pyridyloxymethyl)imidazo[1,2-b][1,2,4]triazine;
2-(3-fluoro-2-methyl-phenyl)-6-(2-pyridyloxymethyl)imidazo[1,2-b][1,2,4]triazine;
2-(4-fluoro-2-methyl-phenyl)-6-(2-pyridyloxymethyl)imidazo[1,2-b][1,2,4]triazine;
2-[4-chloro-2-(trifluoromethyl)phenyl]-6-(2-pyridyloxymethyl)imidazo[1,2-b][1,2,4]triazine;
2-(4-chloro-2-methyl-phenyl)-6-(2-pyridyloxymethyl)imidazo[1,2-b][1,2,4]triazine;
2-(4-fluoro-2-methyl-phenyl)-6-[(6-fluoro-2-pyridyl)oxymethyl]imidazo[1,2-b][1,2,4]triazine;
2-(4-fluoro-2-methyl-phenyl)-6-[(5-fluoro-2-pyridyl)oxymethyl]imidazo[1,2-b][1,2,4]triazine;
[5-fluoro-2-[2-[(4-fluorophenoxy)methyl]imidazo[1,2-a]pyrimidin-6-yl]phenyl]methyl carbamate;
[5-fluoro-2-[2-(phenoxymethyl)imidazo[1,2-a]pyrimidin-6-yl]phenyl]methyl carbamate;
[5-fluoro-2-[2-(2-pyridyloxymethyl)imidazo[1,2-a]pyrimidin-6-yl]phenyl]methyl carbamate;
[5-fluoro-2-[2-(2-pyridyloxymethyl)imidazo[1,2-a]pyrimidin-6-yl]phenyl]methyl acetate;
6-[2-(chloromethyl)-4-fluoro-phenyl]-2-[(4-fluorophenoxy)methyl]imidazo[1,2-a]pyrimidine;
6-[4-fluoro-2-(fluoromethyl)phenyl]-2-(2-pyridyloxymethyl)imidazo[1,2-a]pyrimidine;
and
6-[4-fluoro-2-(fluoromethyl)phenyl]-2-[(4-fluorophenoxy)methyl]imidazo[1,2-a]pyrimidine.

7. A method for preparing a compound of Formula (1) comprising:
carrying out Suzuki coupling reaction with a compound of Formula (2) as a starting material to obtain a compound of Formula (5);
carrying out a heterocycle synthesis reaction with the compound of Formula (5) and dichloroacetone to obtain a compound of Formula (6); and
carrying out a nucleophilic reaction with the compound of Formula (6) to obtain the compound of Formula (1),

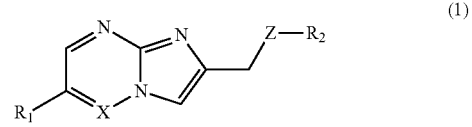

(1)

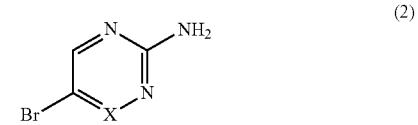

(2)

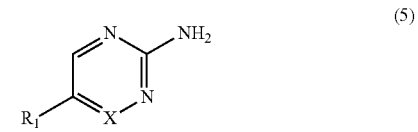

(5)

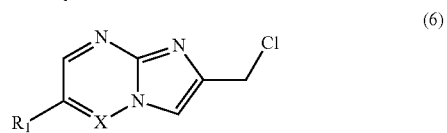

(6)

wherein
X is CH or N;
Z is O or S;
$R_1$ is aryl optionally substituted with one or more substituents selected from halo, hydroxy, alkyl, alkoxy, alkylthio, amino, dialkylamino, cyano, formyl, haloalkyl, hydroxyalkyl, alkoxyalkyl, carbamoyloxy alkyl, alkyl-C(O)O-alkyl, dialkylaminoalkyl and 5- or 6-membered heterocycloalkylalkyl; or 5- to 12-membered, unsaturated heterocyclyl optionally substituted with one or more substituents selected from halo, hydroxy, alkyl, alkoxy and haloalkyl; and
$R_2$ is aryl optionally substituted with one or more substituents selected from halo, deuterium, hydroxy and alkyl; or 5- to 12-membered, unsaturated heterocyclyl optionally substituted with one or more substituents selected from halo and alkyl.

8. The method according to claim 7, wherein $R_1$ is selected from the group consisting of:

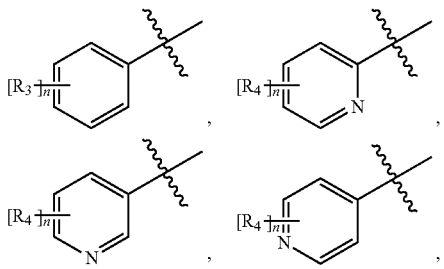

wherein n is 0, 1, 2, 3 or 4; each $R_3$ is selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl, $C_1$-$C_5$ alkyl-C(O)O—$C_1$-$C_5$ alkyl, di($C_1$-$C_5$ alkyl)amino-$C_1$-$C_5$ alkyl and 5- or 6-membered heterocycloalkyl-$C_1$-$C_5$ alkyl; and each $R_4$ is selected from halo, hydroxy, $C_1$-$C_5$ alkyl, $C_1$-$C_5$ alkoxy and halo-$C_1$-$C_5$ alkyl; and
$R_2$ is selected from the group consisting of:

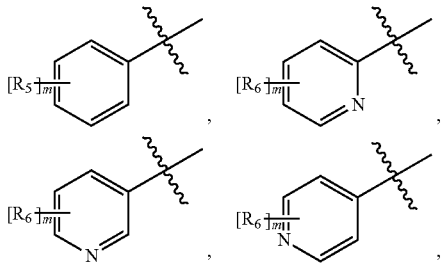

wherein m is 0, 1, 2, 3 or 4; $R_5$ is selected from halo, deuterium, hydroxy and $C_1$-$C_5$ alkyl; and $R_6$ is selected from halo and $C_1$-$C_5$ alkyl.

9. The method according to claim 7, wherein $R_1$ is phenyl optionally substituted with 1 to 3 substituents selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl and $C_1$-$C_5$ alkyl-C(O)O—$C_1$-$C_5$ alkyl; or 5- to 10-membered, unsaturated heterocyclyl having 1-3 heteroatoms selected from N, O and S, which is optionally substituted with 1 to 3 substituents selected from halo, hydroxy, $C_1$-$C_5$ alkyl, $C_1$-$C_5$ alkoxy and halo-$C_1$-$C_5$ alkyl.

10. The method according to claim 7, $R_2$ is phenyl optionally substituted with 1 to 5 substituents selected from halo, deuterium, hydroxy and $C_1$-$C_5$ alkyl; or 5- or 6-membered heteroaryl having 1 to 3 heteroatoms selected from N, O and S, which is optionally substituted with 1 to 3 substituents selected from halo and $C_1$-$C_5$ alkyl.

11. The method according to according to claim 7, wherein
X is CH;
Z is O;
$R_1$ is phenyl optionally substituted with 1 to 3 substituents selected from halo, hydroxy, $C_1$-$C_5$ alkyl, $C_1$-$C_5$ alkoxy, $C_1$-$C_5$ alkylthio, amino, halo-$C_1$-$C_5$ alkyl, hydroxy-$C_1$-$C_5$ alkyl and $C_1$-$C_5$ alkoxy-$C_1$-$C_5$ alkyl; and
$R_2$ is pyridyl optionally substituted with 1 or 2 substituents selected from halo and $C_1$-$C_5$ alkyl.

12. The method according to according to claim 7, wherein the compound of Formula (1) is selected from the group consisting of:
6-(2-fluorophenyl)-2-phenoxymethylimidazo[1,2-a]pyrimidine;
2-phenoxymethyl-6-phenylimidazo[1,2-a]pyrimidine;
6-(2,4-difluorophenyl)-2-phenoxymethylimidazo[1,2-a]pyrimidine;
6-(2-methoxyphenyl)-2-phenoxymethylimidazo[1,2-a]pyrimidine;
6-(2-methylphenyl)-2-phenoxymethylimidazo[1,2-a]pyrimidine;
6-(4-fluoro-2-methylphenyl)-2-phenoxymethylimidazo[1,2-a]pyrimidine;
6-(2,3-difluorophenyl)-2-phenoxymethylimidazo[1,2-a]pyrimidine;
6-(4-fluorophenyl)-2-phenoxymethylimidazo[1,2-a]pyrimidine;
6-(3-aminophenyl)-2-phenoxymethylimidazo[1,2-a]pyrimidine;
6-(2-aminophenyl)-2-phenoxymethylimidazo[1,2-a]pyrimidine;
6-(3-amino-6-methylphenyl)-2-phenoxymethylimidazo[1,2-a]pyrimidine;
6-(3-amino-4-fluorophenyl)-2-phenoxymethylimidazo[1,2-a]pyrimidine;
6-(3-chloro-4-fluorophenyl)-2-phenoxymethylimidazo[1,2-a]pyrimidine;
6-(2-dimethylaminophenyl)-2-phenoxymethylimidazo[1,2-a]pyrimidine;
6-(2-chloro-4-fluorophenyl)-2-phenoxymethylimidazo[1,2-a]pyrimidine;
6-(2-hydroxyphenyl)-2-phenoxymethylimidazo[1,2-a]pyrimidine;
6-(3-hydroxyphenyl)-2-phenoxymethylimidazo[1,2-a]pyrimidine;
6-(4-fluoro-2-trifluoromethylphenyl)-2-phenoxymethylimidazo[1,2-a]pyrimidine;
6-(3,4-difluorophenyl)-2-phenoxymethylimidazo[1,2-a]pyrimidine;
6-(2-methoxy-4-fluorophenyl)-2-phenoxymethylimidazo[1,2-a]pyrimidine;
6-(4-fluoro-3-methoxyphenyl)-2-phenoxymethylimidazo[1,2-a]pyrimidine;
6-(4-chloro-2-methoxyphenyl)-2-phenoxymethylimidazo[1,2-a]pyrimidine;

6-(4-cyano-2-methoxyphenyl)-2-phenoxymethylimidazo[1,2-a]pyrimidine;
6-(7-fluorobenzo[1,3]dioxol-4-yl)-2-phenoxymethylimidazo[1,2-a]pyrimidine;
6-(4-fluoro-2-hydroxymethylphenyl)-2-phenoxymethylimidazo[1,2-a]pyrimidine;
6-(4-fluoro-2-methylthiophenyl)-2-phenoxymethylimidazo[1,2-a]pyrimidine;
6-(2-amino-4-fluorophenyl)-2-phenoxymethylimidazo[1,2-a]pyrimidine;
6-(2,4-difluoro-5-methoxyphenyl)-2-phenoxymethylimidazo[1,2-a]pyrimidine;
6-(2-fluoropyridin-3-yl)-2-phenoxymethylimidazo[1,2-a]pyrimidine;
6-(6-methoxypyridin-3-yl)-2-phenoxymethylimidazo[1,2-a]pyrimidine;
6-(6-fluoropyridin-3-yl)-2-phenoxymethylimidazo[1,2-a]pyrimidine;
6-(4-methylpyridin-3-yl)-2-phenoxymethylimidazo[1,2-a]pyrimidine;
6-(2,6-difluoropyridin-3-yl)-2-phenoxymethylimidazo[1,2-a]pyrimidine;
6-(6-chloropyridin-3-yl)-2-phenoxymethylimidazo[1,2-a]pyrimidine;
6-(2-fluoropyridin-4-yl)-2-phenoxymethylimidazo[1,2-a]pyrimidine;
6-(3-chloropyridin-4-yl)-2-phenoxymethylimidazo[1,2-a]pyrimidine;
6-(4-chlorophenyl)-2-phenoxymethylimidazo[1,2-a]pyrimidine;
6-(6-fluoro-4-methyl-3-pyridyl)-2-phenoxymethylimidazo[1,2-a]pyrimidine;
6-(6-fluoro-5-methyl-3-pyridyl)-2-phenoxymethylimidazo[1,2-a]pyrimidine;
6-(5-fluoro-2-pyridyl)-2-phenoxymethylimidazo[1,2-a]pyrimidine;
6-(2,4-difluorophenyl)-2-(3-fluorophenoxymethyl)imidazo[1,2-a]pyrimidine;
6-(4-fluoro-2-methoxyphenyl)-2-(3-fluorophenoxymethyl)imidazo[1,2-a]pyrimidine;
6-(4-fluoro-3-hydroxyphenyl)-2-(3-fluorophenoxymethyl)-imidazo[1,2-a]pyrimidine;
6-(2-aminophenyl)-2-(3-fluorophenoxymethyl)imidazo[1,2-a]pyrimidine;
6-(3-chloropyridin-4-yl)-2-(3-fluorophenoxymethyl)imidazo[1,2-a]pyrimidine;
6-(4-methylpyridin-3-yl)-2-(3-fluorophenoxymethyl)imidazo[1,2-a]pyrimidine;
6-(2,4-difluorophenyl)-2-(4-fluorophenoxymethyl)imidazo[1,2-a]pyrimidine;
6-(4-fluoro-2-methylphenyl)-2-(4-fluorophenoxymethyl)imidazo[1,2-a]pyrimidine;
6-(3-chloropyridin-4-yl)-2-(4-fluorophenoxymethyl)imidazo[1,2-a]pyrimidine;
6-(2,6-dimethylphenyl)-2-(4-fluorophenoxymethyl)imidazo[1,2-a]pyrimidine;
2-[(4-fluorophenoxy)methyl]-6-(6-fluoro-3-pyridyl)imidazo[1,2-a]pyrimidine;
4-[[6-(4-fluorophenyl)imidazo[1,2-a]pyrimidin-2-yl]methoxy]phenol;
2-[(4-fluorophenoxy)methyl]-6-(4-fluorophenyl)imidazo[1,2-a]pyrimidine;
2-[(3-fluorophenoxy)methyl]-6-(4-fluorophenyl)imidazo[1,2-a]pyrimidine;
2-fluoro-5-[2-[(4-fluorophenoxy)methyl]imidazo[1,2-a]pyrimidin-6-yl]phenol;
2-[(4-fluorophenoxy)methyl]-6-phenyl-imidazo[1,2-a]pyrimidine;
5-fluoro-2-[2-[(3-fluorophenoxy)methyl]imidazo[1,2-a]pyrimidin-6-yl]phenol;
5-fluoro-2-[2-[(4-fluorophenoxy)methyl]imidazo[1,2-a]pyrimidin-6-yl]phenol;
6-(4-fluorophenyl)-2-[(2,3,4,5,6-pentadeuteriophenoxy)methyl]imidazo[1,2-a]pyrimidine;
2-[(4-fluorophenoxy)methyl]6-(o-tolyl)imidazo[1,2-a]pyrimidine;
6-(5-fluoro-2-methyl-phenyl)-2-[(4-fluorophenoxy)methyl]imidazo[1,2-a]pyrimidine;
2-[(4-fluorophenoxy)methyl]-6-(2-fluoro-4-pyridyl)imidazo[1,2-a]pyrimidine;
2-[2-[(4-fluorophenoxy)methyl]imidazo[1,2-a]pyrimidin-6-yl]phenol;
6-(2-fluoro-4-methyl-phenyl)-2-[(4-fluorophenoxy)methyl]imidazo[1,2-a]pyrimidine;
2-[(4-fluorophenoxy)methyl]-6-[6-(trifluoromethyl)-3-pyridyl]imidazo[1,2-a]pyrimidine;
2-[2-[(4-fluorophenoxy)methyl]imidazo[1,2-a]pyrimidin-6-yl]aniline;
6-(2-chloro-4-fluoro-phenyl)-2-[(4-fluorophenoxy)methyl]imidazo[1,2-a]pyrimidine;
4-[2-[(4-fluorophenoxy)methyl]imidazo[1,2-a]pyrimidin-6-yl]-3-methoxy-benzonitrile;
6-(4-chloro-2-methoxy-phenyl)-2-[(4-fluorophenoxy)methyl]imidazo[1,2-a]pyrimidine;
2-fluoro-5-[2-[(4-fluorophenoxy)methyl]imidazo[1,2-a]pyrimidin-6-yl]aniline;
6-(2,6-difluoro-3-pyridyl)-2-[(3-fluorophenoxy)methyl]imidazo[1,2-a]pyrimidine;
5-[2-[(4-fluorophenoxy)methyl]imidazo[1,2-a]pyrimidin-6-yl]-2-methyl-aniline;
4,5-difluoro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-5-methyl-aniline;
5-chloro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-4-methyl-aniline;
5-fluoro-2-[2-[(4-fluorophenoxy)methyl]imidazo[1,2-a]pyrimidin-6-yl]aniline;
2-[(4-fluorophenoxy)methyl]-6-(4-methyl-3-pyridyl)imidazo[1,2-a]pyrimidine;
2-[(3-fluorophenoxy)methyl]-6-(2-fluoro-4-pyridyl)imidazo[1,2-a]pyrimidine;
2-[(3-fluorophenoxy)methyl]-6-[6-(trifluoromethyl)-3-pyridyl]imidazo[1,2-a]pyrimidine;
2-[(3-fluorophenoxy)methyl]-6-(6-fluoro-3-pyridyl)imidazo[1,2-a]pyrimidine;
2-[(3-fluorophenoxy)methyl]-6-(2-fluoro-3-pyridyl)imidazo[1,2-a]pyrimidine;
6-(5,6-difluoro-3-pyridyl)-2-[(4-fluorophenoxy)methyl]imidazo[1,2-a]pyrimidine;
5-[2-[(4-fluorophenoxy)methyl]imidazo[1,2-a]pyrimidin-6-yl]-2-methoxy-aniline;
2-[(4-fluorophenoxy)methyl]-6-(5-fluoro-2-pyridyl)imidazo[1,2-a]pyrimidine;
2-[(4-fluorophenoxy)methyl]-6-(5-methoxy-2-pyridyl)imidazo[1,2-a]pyrimidine;
6-(4-chloro-3-pyridyl)-2-[(4-fluorophenoxy)methyl]imidazo[1,2-a]pyrimidine;
6-(5-chloro-3-pyridyl)-2-[(4-fluorophenoxy)methyl]imidazo[1,2-a]pyrimidine;

2-[(4-fluorophenoxy)methyl]-6-(5-methoxy-3-pyridyl)imidazo[1,2-a]pyrimidine;
5-[2-[(4-fluorophenoxy)methyl]imidazo[1,2-a]pyrimidin-6-yl]pyridin-2-ol;
6-(6-fluoro-5-methyl-3-pyridyl)-2-[(4-fluorophenoxy)methyl]imidazo[1,2-a]pyrimidine;
2-[(4-fluorophenoxy)methyl]-6-(6-methyl-3-pyridyl)imidazo[1,2-a]pyrimidine;
2-[(3-fluorophenoxy)methyl]-6-(5-fluoro-2-pyridyl)imidazo[1,2-a]pyrimidine;
2-[(3-fluorophenoxy)methyl]-6-[4-fluoro-2-(trifluoromethyl)phenyl]imidazo[1,2-a]pyrimidine;
4-[2-[(3-fluorophenoxy)methyl]imidazo[1,2-a]pyrimidin-6-yl]-3-methoxy-benzonitrile;
[5-fluoro-2-[2-[(3-fluorophenoxy)methyl]imidazo[1,2-a]pyrimidin-6-yl]phenyl]methanol;
[5-fluoro-2-[2-[(4-fluorophenoxy)methyl]imidazo[1,2-a]pyrimidin-6-yl]phenyl]methanol;
6-(4-fluoro-2-methylsulfanyl-phenyl)-2-[(4-fluorophenoxy)methyl]imidazo[1,2-a]pyrimidine;
2-[(4-fluorophenoxy)methyl]-6-(2-methoxy-4-pyridyl)imidazo[1,2-a]pyrimidine;
2-[2-[(3-fluorophenoxy)methyl]imidazo[1,2-a]pyrimidin-6-yl]-4-methyl-aniline;
5-fluoro-2-[2-[(3-fluorophenoxy)methyl]imidazo[1,2-a]pyrimidin-6-yl]aniline;
6-(4-fluorophenyl)-2-(pyridin-2-yloxymethyl)imidazo[1,2-a]pyrimidine;
6-(2-methylphenyl)-2-(pyridin-2-yloxymethyl)imidazo[1,2-a]pyrimidine;
6-(4-fluoro-2-methoxyphenyl)-2-(pyridin-2-yloxymethyl)imidazo[1,2-a]pyrimidine;
6-(2,4-difluorophenyl)-2-(pyridin-2-yloxymethyl)imidazo[1,2-a]pyrimidine;
6-(4-fluoro-2-methylphenyl)-2-(pyridin-2-yloxymethyl)imidazo[1,2-a]pyrimidine;
6-(2,3-difluorophenyl)-2-(pyridin-2-yloxymethyl)imidazo[1,2-a]pyrimidine;
6-(5-fluoro-2-methylphenyl)-2-(pyridin-2-yloxymethyl)imidazo[1,2-a]pyrimidine;
6-(3-fluoro-2-methylphenyl)-2-(pyridin-2-yloxymethyl)imidazo[1,2-a]pyrimidine;
6-(7-fluoro-2H-benzo[1,3]dioxol-4-yl)-2-(pyridin-2-yloxymethyl)imidazo[1,2-a]pyrimidine;
6-(4-chloro-2-methoxyphenyl)-2-(pyridin-2-yloxymethyl)imidazo[1,2-a]pyrimidine;
6-(3-fluoro-2-methoxy-phenyl)-2-(2-pyridyloxymethyl)imidazo[1,2-a]pyrimidine;
6-[4-fluoro-2-(trifluoromethyl)phenyl]-2-(2-pyridyloxymethyl)imidazo[1,2-a]pyrimidine;
6-(4-fluoro-2-methyl-phenyl)-2-[(5-fluoro-2-pyridyl)oxymethyl]imidazo[1,2-a]pyrimidine;
6-(2-ethylphenyl)-2-(2-pyridyloxymethyl)imidazo[1,2-a]pyrimidine;
6-(4-fluoro-2-methyl-phenyl)-2-[(4-fluoro-2-pyridyl)oxymethyl]imidazo[1,2-a]pyrimidine;
6-(2-fluoro-4-methyl-phenyl)-2-(2-pyridyloxymethyl)imidazo[1,2-a]pyrimidine;
6-(4-fluoro-2-methoxy-phenyl)-2-[(4-fluoro-2-pyridyl)oxymethyl]imidazo[1,2-a]pyrimidine;
2-[(5-fluoro-2-pyridyl)oxymethyl]-6-[4-fluoro-2-(trifluoromethyl)phenyl]imidazo[1,2-a]pyrimidine;
6-(2,4-difluorophenyl)-2-[(4-fluoro-2-pyridyl)oxymethyl]imidazo[1,2-a]pyrimidine;
6-(3-fluoro-2-methoxy-phenyl)-2-[(4-fluoro-2-pyridyl)oxymethyl]imidazo[1,2-a]pyrimidine;
6-(2,3-difluorophenyl)-2-[(4-fluoro-2-pyridyl)oxymethyl]imidazo[1,2-a]pyrimidine;
6-(4-fluorophenyl)-2-[(4-fluoro-2-pyridyl)oxymethyl]imidazo[1,2-a]pyrimidine;
6-(3-fluoro-2-methyl-phenyl)-2-[(5-fluoro-2-pyridyl)oxymethyl]imidazo[1,2-a]pyrimidine;
2-[(4-fluoro-2-pyridyl)oxymethyl]-6-[4-fluoro-2-(trifluoromethyl)phenyl]imidazo[1,2-a]pyrimidine;
2-[(5-fluoro-2-pyridyl)oxymethyl]-6-(o-tolyl)imidazo[1,2-a]pyrimidine;
6-(4-chloro-2-methyl-phenyl)-2-[(5-fluoro-2-pyridyl)oxymethyl]imidazo[1,2-a]pyrimidine;
6-(2,4-dimethylphenyl)-2-[(5-fluoro-2-pyridyl)oxymethyl]imidazo[1,2-a]pyrimidine;
6-(4-fluorophenyl)-2-[(5-fluoro-2-pyridyl)oxymethyl]imidazo[1,2-a]pyrimidine;
2-(2-pyridyloxymethyl)-6-[6-(trifluoromethyl)-3-pyridyl]imidazo[1,2-a]pyrimidine;
2-[(5-fluoro-2-pyridyl)oxymethyl]-6-[6-(trifluoromethyl)-3-pyridyl]imidazo[1,2-a]pyrimidine;
6-(5-fluoro-2-pyridyl)-2-(2-pyridyloxymethyl)imidazo[1,2-a]pyrimidine;
2-fluoro-5-[2-[(5-fluoro-2-pyridyl)oxymethyl]imidazo[1,2-a]pyrimidin-6-yl]aniline;
2-fluoro-5-[2-(2-pyridyloxymethyl)imidazo[1,2-a]pyrimidin-6-yl]aniline;
[5-fluoro-2-[2-(2-pyridyloxymethyl)imidazo[1,2-a]pyrimidin-6-yl]phenyl]methanol;
3-methoxy-4-[2-(2-pyridyloxymethyl)imidazo[1,2-a]pyrimidin-6-yl]benzonitrile;
4-[2-[(5-fluoro-2-pyridyl)oxymethyl]imidazo[1,2-a]pyrimidin-6-yl]-3-methoxy-benzonitrile;
6-(4-fluoro-2-methylsulfanyl-phenyl)-2-(2-pyridyloxymethyl)imidazo[1,2-a]pyrimidine;
[5-fluoro-2-[2-[(5-fluoro-2-pyridyl)oxymethyl]imidazo[1,2-a]pyrimidin-6-yl]phenyl]methanol;
4-[2-(2-pyridyloxymethyl)imidazo[1,2-a]pyrimidin-6-yl]benzonitrile;
6-[4-fluoro-2-(methoxymethyl)phenyl]-2-(2-pyridyloxymethyl)imidazo[1,2-a]pyrimidine;
[2-[2-(2-pyridyloxymethyl)imidazo[1,2-a]pyrimidin-6-yl]-5-(trifluoromethyl)phenyl]methanol;
6-(2-isopropylphenyl)-2-(2-pyridyloxymethyl)imidazo[1,2-a]pyrimidine;
4-[2-(2-pyridyloxymethyl)imidazo[1,2-a]pyrimidin-6-yl]-3-(trifluoromethyl)benzaldehyde;
6-[4-chloro-2-(trifluoromethyl)phenyl]-2-(2-pyridyloxymethyl)imidazo[1,2-a]pyrimidine;
6-(4-fluorophenyl)-2-(pyridin-3-yloxymethyl)imidazo[1,2-a]pyrimidine;
6-(4-fluoro-2-methoxyphenyl)-2-(pyridin-3-yloxymethyl)imidazo[1,2-a]pyrimidine;
6-(2,4-difluorophenyl)-2-(pyridin-3-yloxymethyl)imidazo[1,2-a]pyrimidine;
6-(4-fluoro-2-methylphenyl)-2-(pyridin-3-yloxymethyl)imidazo[1,2-a]pyrimidine;
6-(4-fluoro-2-hydroxyphenyl)-2-(pyridin-3-yloxymethyl)imidazo[1,2-a]pyrimidine;
6-(4-fluoro-2-methoxyphenyl)-2-(pyridin-4-yloxymethyl)imidazo[1,2-a]pyrimidine;
6-(2,4-difluorophenyl)-2-(pyridin-4-yloxymethyl)imidazo[1,2-a]pyrimidine;
6-(2-methylphenyl)-2-(5-fluoro-pyridin-3-yloxymethyl)imidazo[1,2-a]pyrimidine;
6-(4-fluoro-2-methylphenyl)-2-(5-fluoro-pyridin-3-yloxymethyl)imidazo[1,2-a]pyrimidine;

6-(4-fluoro-2-methoxyphenyl)-2-(5-fluoropyridin-3-yloxymethyl)imidazo[1,2-a]pyrimidine;
6-(4-fluoro-2-hydroxyphenyl)-2-(5-fluoropyridin-3-yloxymethyl)imidazo[1,2-a]pyrimidine;
6-(2,4-difluorophenyl)-2-(6-fluoropyridin-3-yloxymethyl)imidazo[1,2-a]pyrimidine;
6-(4-fluoro-2-methylphenyl)-2-(6-fluoropyridin-3-yloxymethyl)imidazo[1,2-a]pyrimidine;
6-(4-fluoro-2-methylphenyl)-2-(2-fluoropyridin-3-yloxymethyl)imidazo[1,2-a]pyrimidine;
6-(4-fluoro-2-methylphenyl)-2-(5-chloropyridin-3-yloxymethyl)imidazo[1,2-a]pyrimidine;
6-(2,4-difluorophenyl)-2-(2-fluoropyridin-4-yloxymethyl)imidazo[1,2-a]pyrimidine;
6-(4-fluoro-2-methylphenyl)-2-(2-fluoropyridin-4-yloxymethyl)imidazo[1,2-a]pyrimidine;
6-(4-fluoro-2-methoxyphenyl)-2-(2-fluoropyridin-4-yloxymethyl)imidazo[1,2-a]pyrimidine;
6-(4-fluorophenyl)-2-(2-fluoropyridin-4-yloxymethyl)imidazo[1,2-a]pyrimidine;
6-(2,3-difluorophenyl)-2-(2-fluoropyridin-4-yloxymethyl)imidazo[1,2-a]pyrimidine;
6-(2-fluorophenyl)-2-(2-fluoropyridin-4-yloxymethyl)imidazo[1,2-a]pyrimidine;
6-(4-fluoro-2-hydroxyphenyl)-2-(2-fluoropyridin-4-yloxymethyl)imidazo[1,2-a]pyrimidine;
6-(2-methylphenyl)-2-(2-fluoropyridin-4-yloxymethyl)imidazo[1,2-a]pyrimidine;
6-(2-hydroxyphenyl)-2-(2-fluoropyridin-4-yloxymethyl)imidazo[1,2-a]pyrimidine;
6-(4-fluoro-2-hydroxymethylphenyl)-2-(2-fluoropyridin-4-yloxymethyl)imidazo[1,2-a]pyrimidine;
6-(4-fluorophenyl)-2-[(5-fluoro-3-pyridyl)oxymethyl)imidazo[1,2-a]pyrimidine;
2-[(2-chloro-4-pyridyl)oxymethyl]-6-(4-fluorophenyl)imidazo[1,2-a]pyrimidine;
2-[(5-fluoro-3-pyridyl)oxymethyl]-6-[4-fluoro-2-(trifluoromethyl)phenyl]imidazo[1,2-a]pyrimidine;
2-[(2-fluoro-4-pyridyl)oxymethyl]-6-[4-fluoro-2-(trifluoromethyl)phenyl]imidazo[1,2-a]pyrimidine;
5-fluoro-2-[2-[(5-fluoro-3-pyridyl)oxymethyl]imidazo[1,2-a]pyrimidin-6-yl]aniline;
5-fluoro-2-[2-[(2-fluoro-4-pyridyl)oxymethyl]imidazo[1,2-a]pyrimidin-6-yl]aniline;
[5-fluoro-2-[2-[(5-fluoro-3-pyridyl)oxymethyl]imidazo[1,2-a]pyrimidin-6-yl]phenyl]methanol;
2-(2,4-difluorophenyl)-6-(phenoxymethyl)imidazo[1,2-b][1,2,4]triazine;
2-(2,4-difluorophenyl)-6-((pyridin-4-yloxy)methyl)imidazo[1,2-b][1,2,4]triazine;
2-(2,4-difluorophenyl)-6-((pyridin-2-yloxy)methyl)imidazo[1,2-b][1,2,4]triazine;
2-(4-fluorophenyl)-6-((pyridin-4-yloxy)methyl)imidazo[1,2-b][1,2,4]triazine;
2-(2-methylphenyl)-6-((pyridin-4-yloxy)methyl)imidazo[1,2-b][1,2,4]triazine;
2-(2,4-difluorophenyl)-6-((2-fluoropyridin-4-yloxy)methyl)imidazo[1,2-b][1,2,4]triazine;
2-(4-fluoro-2-methylphenyl)-6-((2-fluoropyridin-4-yloxy)methyl)imidazo[1,2-b][1,2,4]triazine;
2-(2-methylphenyl)-6-((2-fluoropyridin-4-yloxy)methyl)imidazo[1,2-b][1,2,4]triazine;
2-[4-fluoro-2-(trifluoromethyl)phenyl]-6-(2-pyridyloxymethyl)imidazo[1,2-b][1,2,4]triazine;
2-(3-fluoro-2-methyl-phenyl)-6-(2-pyridyloxymethyl)imidazo[1,2-b][1,2,4]triazine;
2-(4-fluoro-2-methyl-phenyl)-6-(2-pyridyloxymethyl)imidazo[1,2-b][1,2,4]triazine;
2-[4-chloro-2-(trifluoromethyl)phenyl]-6-(2-pyridyloxymethyl)imidazo[1,2-b][1,2,4]triazine;
2-(4-chloro-2-methyl-phenyl)-6-(2-pyridyloxymethyl)imidazo[1,2-b][1,2,4]triazine;
2-(4-fluoro-2-methyl-phenyl)-6-[(6-fluoro-2-pyridyl)oxymethyl]imidazo[1,2-b][1,2,4]triazine;
2-(4-fluoro-2-methyl-phenyl)-6-[(5-fluoro-2-pyridyl)oxymethyl]imidazo[1,2-b][1,2,4]triazine;
[5-fluoro-2-[2-[(4-fluorophenoxy)methyl]imidazo[1,2-a]pyrimidin-6-yl]phenyl]methyl carbamate;
[5-fluoro-2-[2-(phenoxymethyl)imidazo[1,2-a]pyrimidin-6-yl]phenyl]methyl carbamate;
[5-fluoro-2-[2-(2-pyridyloxymethyl)imidazo[1,2-a]pyrimidin-6-yl]phenyl]methyl carbamate;
[5-fluoro-2-[2-(2-pyridyloxymethyl)imidazo[1,2-a]pyrimidin-6-yl]phenyl]methyl acetate;
6-[2-(chloromethyl)-4-fluoro-phenyl]-2-[(4-fluorophenoxy)methyl]imidazo[1,2-a]pyrimidine;
6-[4-fluoro-2-(fluoromethyl)phenyl]-2-(2-pyridyloxymethyl)imidazo[1,2-a]pyrimidine;
and
6-[4-fluoro-2-(fluoromethyl)phenyl]-2-[(4-fluorophenoxy)methyl]imidazo[1,2-a]pyrimidine.

13. A method for preparing a compound of Formula (9) comprising:
carrying out a heterocycle synthesis reaction with a compound of Formula (5) and 1-acetoxy-3-chloroacetone to obtain a compound of Formula (7);
hydrolyzing the compound of Formula (7) to obtain a compound of Formula (8); and
carrying out an aromatic nucleophilic reaction with the compound of Formula (8) to obtain the compound of Formula (9),

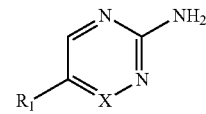
(5)

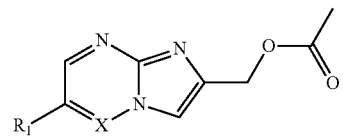
(7)

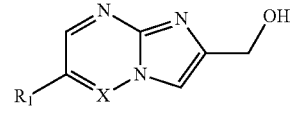
(8)

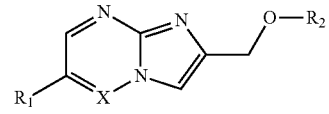
(9)

wherein
X is CH or N;
$R_1$ is aryl optionally substituted with one or more substituents selected from halo, hydroxy, alkyl, alkoxy, alkylthio, amino, dialkylamino, cyano, formyl, haloalkyl, hydroxyalkyl, alkoxyalkyl, carbamoyloxy alkyl, alkyl-C(O)O-alkyl, dialkylaminoalkyl and 5- or 6-membered heterocycloalkylalkyl; or 5- to 12-membered, unsaturated heterocyclyl optionally substituted with one or more substituents selected from halo, hydroxy, alkyl, alkoxy and haloalkyl; and $R_2$ is aryl optionally substituted with one or more substituents selected from halo, deuterium, hydroxy and alkyl; or 5- to 12-membered, unsaturated heterocyclyl optionally substituted with one or more substituents selected from halo and alkyl.

14. The method according to claim 13, wherein $R_1$ is selected from the group consisting of:

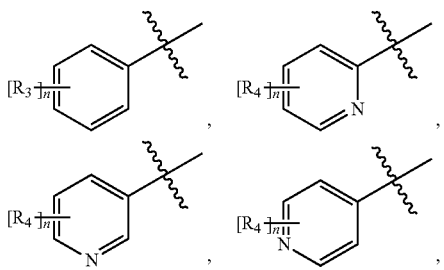

wherein n is 0, 1, 2, 3 or 4; each $R_3$ is selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl, $C_1$-$C_5$ alkyl-C(O)O—$C_1$-$C_5$ alkyl, di($C_1$-$C_5$ alkyl)amino-$C_1$-$C_5$ alkyl and 5- or 6-membered heterocycloalkyl-$C_1$-$C_5$ alkyl; and each $R_4$ is selected from halo, hydroxy, $C_1$-$C_5$ alkyl, $C_1$-$C_5$ alkoxy and halo-$C_1$-$C_5$ alkyl; and $R_2$ is selected from the group consisting of:

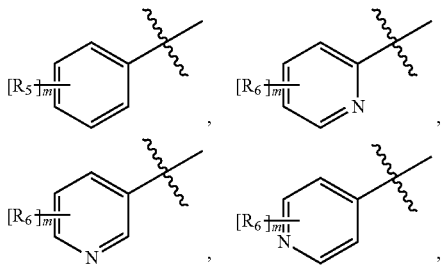

wherein m is 0, 1, 2, 3 or 4; $R_5$ is selected from halo, deuterium, hydroxy and $C_1$-$C_5$ alkyl; and $R_6$ is selected from halo and $C_1$-$C_5$ alkyl.

15. The method according to claim 13, wherein $R_1$ is phenyl optionally substituted with 1 to 3 substituents selected from halo, hydroxy, $C_1$-$C_5$ alkyl, $C_1$-$C_5$ alkoxy, $C_1$-$C_5$ alkylthio, amino, di($C_1$-$C_5$ alkyl)amino, cyano, formyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl and $C_1$-$C_5$ alkyl-C(O)O—$C_1$-$C_5$ alkyl; or 5- to 10-membered, unsaturated heterocyclyl having 1-3 heteroatoms selected from N, O and S, which is optionally substituted with 1 to 3 substituents selected from halo, hydroxy, $C_1$-$C_5$ alkyl, $C_1$-$C_5$ alkoxy and halo-$C_1$-$C_5$ alkyl.

16. The method according to claim 13, wherein $R_2$ is phenyl optionally substituted with 1 to 5 substituents selected from halo, deuterium, hydroxy and $C_1$-$C_5$ alkyl; or 5- or 6-membered heteroaryl having 1 to 3 heteroatoms selected from N, O and S, which is optionally substituted with 1 to 3 substituents selected from halo and $C_1$-$C_5$ alkyl.

17. The method according to according to claim 13, wherein
X is CH;
$R_1$ is phenyl optionally substituted with 1 to 3 substituents selected from halo, hydroxy, $C_1$-$C_5$ alkyl, $C_1$-$C_5$ alkoxy, $C_1$-$C_5$ alkylthio, amino, halo-$C_1$-$C_5$ alkyl, hydroxy-$C_1$-$C_5$ alkyl and $C_1$-$C_5$ alkoxy-$C_1$-$C_5$ alkyl; and
$R_2$ is pyridyl optionally substituted with 1 or 2 substituents selected from halo and $C_1$-$C_5$ alkyl.

18. The method according to according to claim 13, wherein the compound of Formula (9) is selected from the group consisting of:
6-(2-fluorophenyl)-2-phenoxymethylimidazo[1,2-a]pyrimidine;
2-phenoxymethyl-6-phenylimidazo[1,2-a]pyrimidine;
6-(2,4-difluorophenyl)-2-phenoxymethylimidazo[1,2-a]pyrimidine;
6-(2-methoxyphenyl)-2-phenoxymethylimidazo[1,2-a]pyrimidine;
6-(2-methylphenyl)-2-phenoxymethylimidazo[1,2-a]pyrimidine;
6-(4-fluoro-2-methylphenyl)-2-phenoxymethylimidazo[1,2-a]pyrimidine;
6-(2,3-difluorophenyl)-2-phenoxymethylimidazo[1,2-a]pyrimidine;
6-(4-fluorophenyl)-2-phenoxymethylimidazo[1,2-a]pyrimidine;
6-(3-aminophenyl)-2-phenoxymethylimidazo[1,2-a]pyrimidine;
6-(2-aminophenyl)-2-phenoxymethylimidazo[1,2-a]pyrimidine;
6-(3-amino-6-methylphenyl)-2-phenoxymethylimidazo[1,2-a]pyrimidine;
6-(3-amino-4-fluorophenyl)-2-phenoxymethylimidazo[1,2-a]pyrimidine;
6-(3-chloro-4-fluorophenyl)-2-phenoxymethylimidazo[1,2-a]pyrimidine;
6-(2-dimethylaminophenyl)-2-phenoxymethylimidazo[1,2-a]pyrimidine;
6-(2-chloro-4-fluorophenyl)-2-phenoxymethylimidazo[1,2-a]pyrimidine;
6-(2-hydroxyphenyl)-2-phenoxymethylimidazo[1,2-a]pyrimidine;
6-(3-hydroxyphenyl)-2-phenoxymethylimidazo[1,2-a]pyrimidine;
6-(4-fluoro-2-trifluoromethylphenyl)-2-phenoxymethylimidazo[1,2-a]pyrimidine;
6-(3,4-difluorophenyl)-2-phenoxymethylimidazo[1,2-a]pyrimidine;
6-(2-methoxy-4-fluorophenyl)-2-phenoxymethylimidazo[1,2-a]pyrimidine;
6-(4-fluoro-3-methoxyphenyl)-2-phenoxymethylimidazo[1,2-a]pyrimidine;
6-(4-chloro-2-methoxyphenyl)-2-phenoxymethylimidazo[1,2-a]pyrimidine;
6-(4-cyano-2-methoxyphenyl)-2-phenoxymethylimidazo[1,2-a]pyrimidine;
6-(7-fluorobenzo[1,3]dioxol-4-yl)-2-phenoxymethylimidazo[1,2-a]pyrimidine;
6-(4-fluoro-2-hydroxymethylphenyl)-2-phenoxymethylimidazo[1,2-a]pyrimidine;
6-(4-fluoro-2-methylthiophenyl)-2-phenoxymethylimidazo[1,2-a]pyrimidine;

6-(2-amino-4-fluorophenyl)-2-phenoxymethylimidazo[1,2-a]pyrimidine;
6-(2,4-difluoro-5-methoxyphenyl)-2-phenoxymethylimidazo[1,2-a]pyrimidine;
6-(2-fluoropyridin-3-yl)-2-phenoxymethylimidazo[1,2-a]pyrimidine;
6-(6-methoxypyridin-3-yl)-2-phenoxymethylimidazo[1,2-a]pyrimidine;
6-(6-fluoropyridin-3-yl)-2-phenoxymethylimidazo[1,2-a]pyrimidine;
6-(4-methylpyridin-3-yl)-2-phenoxymethylimidazo[1,2-a]pyrimidine;
6-(2,6-difluoropyridin-3-yl)-2-phenoxymethylimidazo[1,2-a]pyrimidine;
6-(6-chloropyridin-3-yl)-2-phenoxymethylimidazo[1,2-a]pyrimidine;
6-(2-fluoropyridin-4-yl)-2-phenoxymethylimidazo[1,2-a]pyrimidine;
6-(3-chloropyridin-4-yl)-2-phenoxymethylimidazo[1,2-a]pyrimidine;
6-(4-chlorophenyl)-2-phenoxymethylimidazo[1,2-a]pyrimidine;
6-(6-fluoro-4-methyl-3-pyridyl)-2-phenoxymethylimidazo[1,2-a]pyrimidine;
6-(6-fluoro-5-methyl-3-pyridyl)-2-phenoxymethylimidazo[1,2-a]pyrimidine;
6-(5-fluoro-2-pyridyl)-2-phenoxymethylimidazo[1,2-a]pyrimidine;
6-(2,4-difluorophenyl)-2-(3-fluorophenoxymethyl)imidazo[1,2-a]pyrimidine;
6-(4-fluoro-2-methoxyphenyl)-2-(3-fluorophenoxymethyl)imidazo[1,2-a]pyrimidine;
6-(4-fluoro-3-hydroxyphenyl)-2-(3-fluorophenoxymethyl)-imidazo[1,2-a]pyrimidine;
6-(2-aminophenyl)-2-(3-fluorophenoxymethyl)imidazo[1,2-a]pyrimidine;
6-(3-chloropyridin-4-yl)-2-(3-fluorophenoxymethyl)imidazo[1,2-a]pyrimidine;
6-(4-methylpyridin-3-yl)-2-(3-fluorophenoxymethyl)imidazo[1,2-a]pyrimidine;
6-(2,4-difluorophenyl)-2-(4-fluorophenoxymethyl)imidazo[1,2-a]pyrimidine;
6-(4-fluoro-2-methylphenyl)-2-(4-fluorophenoxymethyl)imidazo[1,2-a]pyrimidine;
6-(3-chloropyridin-4-yl)-2-(4-fluorophenoxymethyl)imidazo[1,2-a]pyrimidine;
6-(2,6-dimethylphenyl)-2-(4-fluorophenoxymethyl)imidazo[1,2-a]pyrimidine;
2-[(4-fluorophenoxy)methyl]-6-(6-fluoro-3-pyridyl)imidazo[1,2-a]pyrimidine;
4-[[6-(4-fluorophenyl)imidazo[1,2-a]pyrimidin-2-yl]methoxy]phenol;
2-[(4-fluorophenoxy)methyl]-6-(4-fluorophenyl)imidazo[1,2-a]pyrimidine;
2-[(3-fluorophenoxy)methyl]-6-(4-fluorophenyl)imidazo[1,2-a]pyrimidine;
2-fluoro-5-[2-[(4-fluorophenoxy)methyl]imidazo[1,2-a]pyrimidin-6-yl]phenol;
2-[(4-fluorophenoxy)methyl]-6-phenyl-imidazo[1,2-a]pyrimidine;
5-fluoro-2-[2-[(3-fluorophenoxy)methyl]imidazo[1,2-a]pyrimidin-6-yl]phenol;
5-fluoro-2-[2-[(4-fluorophenoxy)methyl]imidazo[1,2-a]pyrimidin-6-yl]phenol;
6-(4-fluorophenyl)-2-[(2,3,4,5,6-pentadeuteriophenoxy)methyl]imidazo[1,2-a]pyrimidine;
2-[(4-fluorophenoxy)methyl]6-(o-tolyl)imidazo[1,2-a]pyrimidine;
6-(5-fluoro-2-methyl-phenyl)-2-[(4-fluorophenoxy)methyl]imidazo[1,2-a]pyrimidine;
2-[(4-fluorophenoxy)methyl]-6-(2-fluoro-4-pyridyl)imidazo[1,2-a]pyrimidine;
2-[2-[(4-fluorophenoxy)methyl]imidazo[1,2-a]pyrimidin-6-yl]phenol;
6-(2-fluoro-4-methyl-phenyl)-2-[(4-fluorophenoxy)methyl]imidazo[1,2-a]pyrimidine;
2-[(4-fluorophenoxy)methyl]-6-[6-(trifluoromethyl)-3-pyridyl]imidazo[1,2-a]pyrimidine;
2-[2-[(4-fluorophenoxy)methyl]imidazo[1,2-a]pyrimidin-6-yl]aniline;
6-(2-chloro-4-fluoro-phenyl)-2-[(4-fluorophenoxy)methyl]imidazo[1,2-a]pyrimidine;
4-[2-[(4-fluorophenoxy)methyl]imidazo[1,2-a]pyrimidin-6-yl]-3-methoxy-benzonitrile;
6-(4-chloro-2-methoxy-phenyl)-2-[(4-fluorophenoxy)methyl]imidazo[1,2-a]pyrimidine;
2-fluoro-5-[2-[(4-fluorophenoxy)methyl]imidazo[1,2-a]pyrimidin-6-yl]aniline;
6-(2,6-difluoro-3-pyridyl)-2-[(3-fluorophenoxy)methyl]imidazo[1,2-a]pyrimidine;
5-[2-[(4-fluorophenoxy)methyl]imidazo[1,2-a]pyrimidin-6-yl]-2-methyl-aniline;
4,5-difluoro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-5-methyl-aniline;
5-chloro-2-[2-[(4-fluorophenoxy)methyl]imidazo[1,2-a]pyrimidin-6-yl]aniline;
2-[2-[(4-fluorophenoxy)methyl]imidazo[1,2-a]pyrimidin-6-yl]-4-methyl-aniline;
5-fluoro-2-[2-[(4-fluorophenoxy)methyl]imidazo[1,2-a]pyrimidin-6-yl]aniline;
2-[(4-fluorophenoxy)methyl]-6-(4-methyl-3-pyridyl)imidazo[1,2-a]pyrimidine;
2-[(3-fluorophenoxy)methyl]-6-(2-fluoro-4-pyridyl)imidazo[1,2-a]pyrimidine;
2-[(3-fluorophenoxy)methyl]-6-[6-(trifluoromethyl)-3-pyridyl]imidazo[1,2-a]pyrimidine;
2-[(3-fluorophenoxy)methyl]-6-(6-fluoro-3-pyridyl)imidazo[1,2-a]pyrimidine;
2-[(3-fluorophenoxy)methyl]-6-(2-fluoro-3-pyridyl)imidazo[1,2-a]pyrimidine;
6-(5,6-difluoro-3-pyridyl)-2-[(4-fluorophenoxy)methyl]imidazo[1,2-a]pyrimidine;
5-[2-[(4-fluorophenoxy)methyl]imidazo[1,2-a]pyrimidin-6-yl]-2-methoxy-aniline;
2-[(4-fluorophenoxy)methyl]-6-(5-fluoro-2-pyridyl)imidazo[1,2-a]pyrimidine;
2-[(4-fluorophenoxy)methyl]-6-(5-methoxy-2-pyridyl)imidazo[1,2-a]pyrimidine;
6-(4-chloro-3-pyridyl)-2-[(4-fluorophenoxy)methyl]imidazo[1,2-a]pyrimidine;
6-(5-chloro-3-pyridyl)-2-[(4-fluorophenoxy)methyl]imidazo[1,2-a]pyrimidine;
2-[(4-fluorophenoxy)methyl]-6-(5-methoxy-3-pyridyl)imidazo[1,2-a]pyrimidine;
5-[2-[(4-fluorophenoxy)methyl]imidazo[1,2-a]pyrimidin-6-yl]pyridin-2-ol;
6-(6-fluoro-5-methyl-3-pyridyl)-2-[(4-fluorophenoxy)methyl]imidazo[1,2-a]pyrimidine;
2-[(4-fluorophenoxy)methyl]-6-(6-methyl-3-pyridyl)imidazo[1,2-a]pyrimidine;

2-[(3-fluorophenoxy)methyl]-6-(5-fluoro-2-pyridyl)imidazo[1,2-a]pyrimidine;
2-[(3-fluorophenoxy)methyl]-6-[4-fluoro-2-(trifluoromethyl)phenyl]imidazo[1,2-a]pyrimidine;
4-[2-[(3-fluorophenoxy)methyl]imidazo[1,2-a]pyrimidin-6-yl]-3-methoxy-benzonitrile;
[5-fluoro-2-[2-[(3-fluorophenoxy)methyl]imidazo[1,2-a]pyrimidin-6-yl]phenyl]methanol;
[5-fluoro-2-[2-[(4-fluorophenoxy)methyl]imidazo[1,2-a]pyrimidin-6-yl]phenyl]methanol;
6-(4-fluoro-2-methylsulfanyl-phenyl)-2-[(4-fluorophenoxy)methyl]imidazo[1,2-a]pyrimidine;
2-[(4-fluorophenoxy)methyl]-6-(2-methoxy-4-pyridyl)imidazo[1,2-a]pyrimidine;
2-[2-[(3-fluorophenoxy)methyl]imidazo[1,2-a]pyrimidin-6-yl]-4-methyl-aniline;
5-fluoro-2-[2-[(3-fluorophenoxy)methyl]imidazo[1,2-a]pyrimidin-6-yl]aniline;
6-(4-fluorophenyl)-2-(pyridin-2-yloxymethyl)imidazo[1,2-a]pyrimidine;
6-(2-methylphenyl)-2-(pyridin-2-yloxymethyl)imidazo[1,2-a]pyrimidine;
6-(4-fluoro-2-methoxyphenyl)-2-(pyridin-2-yloxymethyl)imidazo[1,2-a]pyrimidine;
6-(2,4-difluorophenyl)-2-(pyridin-2-yloxymethyl)imidazo[1,2-a]pyrimidine;
6-(4-fluoro-2-methylphenyl)-2-(pyridin-2-yloxymethyl)imidazo[1,2-a]pyrimidine;
6-(2,3-difluorophenyl)-2-(pyridin-2-yloxymethyl)imidazo[1,2-a]pyrimidine;
6-(5-fluoro-2-methylphenyl)-2-(pyridin-2-yloxymethyl)imidazo[1,2-a]pyrimidine;
6-(3-fluoro-2-methylphenyl)-2-(pyridin-2-yloxymethyl)imidazo[1,2-a]pyrimidine;
6-(7-fluoro-2H-benzo[1,3]dioxol-4-yl)-2-(pyridin-2-yloxymethyl)imidazo[1,2-a]pyrimidine;
6-(4-chloro-2-methoxyphenyl)-2-(pyridin-2-yloxymethyl)imidazo[1,2-a]pyrimidine;
6-(3-fluoro-2-methoxy-phenyl)-2-(2-pyridyloxymethyl)imidazo[1,2-a]pyrimidine;
6-[4-fluoro-2-(trifluoromethyl)phenyl]-2-(2-pyridyloxymethyl)imidazo[1,2-a]pyrimidine;
6-(4-fluoro-2-methyl-phenyl)-2-[(5-fluoro-2-pyridyl)oxymethyl]imidazo[1,2-a]pyrimidine;
6-(2-ethylphenyl)-2-(2-pyridyloxymethyl)imidazo[1,2-a]pyrimidine;
6-(4-fluoro-2-methyl-phenyl)-2-[(4-fluoro-2-pyridyl)oxymethyl]imidazo[1,2-a]pyrimidine;
6-(2-fluoro-4-methyl-phenyl)-2-(2-pyridyloxymethyl)imidazo[1,2-a]pyrimidine;
6-(4-fluoro-2-methoxy-phenyl)-2-[(4-fluoro-2-pyridyl)oxymethyl]imidazo[1,2-a]pyrimidine;
2-[(5-fluoro-2-pyridyl)oxymethyl]-6-[4-fluoro-2-(trifluoromethyl)phenyl]imidazo[1,2-a]pyrimidine;
6-(2,4-difluorophenyl)-2-[(4-fluoro-2-pyridyl)oxymethyl]imidazo[1,2-a]pyrimidine;
6-(3-fluoro-2-methoxy-phenyl)-2-[(4-fluoro-2-pyridyl)oxymethyl]imidazo[1,2-a]pyrimidine;
6-(2,3-difluorophenyl)-2-[(4-fluoro-2-pyridyl)oxymethyl]imidazo[1,2-a]pyrimidine;
6-(4-fluorophenyl)-2-[(4-fluoro-2-pyridyl)oxymethyl]imidazo[1,2-a]pyrimidine;
6-(3-fluoro-2-methyl-phenyl)-2-[(5-fluoro-2-pyridyl)oxymethyl]imidazo[1,2-a]pyrimidine;
2-[(4-fluoro-2-pyridyl)oxymethyl]-6-[4-fluoro-2-(trifluoromethyl)phenyl]imidazo[1,2-a]pyrimidine;
2-[(5-fluoro-2-pyridyl)oxymethyl]-6-(o-tolyl)imidazo[1,2-a]pyrimidine;
6-(4-chloro-2-methyl-phenyl)-2-[(5-fluoro-2-pyridyl)oxymethyl]imidazo[1,2-a]pyrimidine;
6-(2,4-dimethylphenyl)-2-[(5-fluoro-2-pyridyl)oxymethyl]imidazo[1,2-a]pyrimidine;
6-(4-fluorophenyl)-2-[(5-fluoro-2-pyridyl)oxymethyl]imidazo[1,2-a]pyrimidine;
2-(2-pyridyloxymethyl)-6-[6-(trifluoromethyl)-3-pyridyl]imidazo[1,2-a]pyrimidine;
2-[(5-fluoro-2-pyridyl)oxymethyl]-6-[6-(trifluoromethyl)-3-pyridyl]imidazo[1,2-a]pyrimidine;
6-(5-fluoro-2-pyridyl)-2-(2-pyridyloxymethyl)imidazo[1,2-a]pyrimidine;
2-fluoro-5-[2-[(5-fluoro-2-pyridyl)oxymethyl]imidazo[1,2-a]pyrimidin-6-yl]aniline;
2-fluoro-5-[2-(2-pyridyloxymethyl)imidazo[1,2-a]pyrimidin-6-yl]aniline;
[5-fluoro-2-[2-(2-pyridyloxymethyl)imidazo[1,2-a]pyrimidin-6-yl]phenyl]methanol;
3-methoxy-4-[2-(2-pyridyloxymethyl)imidazo[1,2-a]pyrimidin-6-yl]benzonitrile;
4-[2-[(5-fluoro-2-pyridyl)oxymethyl]imidazo[1,2-a]pyrimidin-6-yl]-3-methoxy-benzonitrile;
6-(4-fluoro-2-methylsulfanyl-phenyl)-2-(2-pyridyloxymethyl)imidazo[1,2-a]pyrimidine;
[5-fluoro-2-[2-[(5-fluoro-2-pyridyl)oxymethyl]imidazo[1,2-a]pyrimidin-6-yl]phenyl]methanol;
4-[2-(2-pyridyloxymethyl)imidazo[1,2-a]pyrimidin-6-yl]benzonitrile;
6-[4-fluoro-2-(methoxymethyl)phenyl]-2-(2-pyridyloxymethyl)imidazo[1,2-a]pyrimidine;
[2-[2-(2-pyridyloxymethyl)imidazo[1,2-a]pyrimidin-6-yl]-5-(trifluoromethyl)phenyl]methanol;
6-(2-isopropylphenyl)-2-(2-pyridyloxymethyl)imidazo[1,2-a]pyrimidine;
4-[2-(2-pyridyloxymethyl)imidazo[1,2-a]pyrimidin-6-yl]-3-(trifluoromethyl)benzaldehyde;
6-[4-chloro-2-(trifluoromethyl)phenyl]-2-(2-pyridyloxymethyl)imidazo[1,2-a]pyrimidine;
6-(4-fluorophenyl)-2-(pyridin-3-yloxymethyl)imidazo[1,2-a]pyrimidine;
6-(4-fluoro-2-methoxyphenyl)-2-(pyridin-3-yloxymethyl)imidazo[1,2-a]pyrimidine;
6-(2,4-difluorophenyl)-2-(pyridin-3-yloxymethyl)imidazo[1,2-a]pyrimidine;
6-(4-fluoro-2-methylphenyl)-2-(pyridin-3-yloxymethyl)imidazo[1,2-a]pyrimidine;
6-(4-fluoro-2-hydroxyphenyl)-2-(pyridin-3-yloxymethyl)imidazo[1,2-a]pyrimidine;
6-(4-fluoro-2-methoxyphenyl)-2-(pyridin-4-yloxymethyl)imidazo[1,2-a]pyrimidine;
6-(2,4-difluorophenyl)-2-(pyridin-4-yloxymethyl)imidazo[1,2-a]pyrimidine;
6-(2-methylphenyl)-2-(5-fluoro-pyridin-3-yloxymethyl)imidazo[1,2-a]pyrimidine;
6-(4-fluoro-2-methylphenyl)-2-(5-fluoro-pyridin-3-yloxymethyl)imidazo[1,2-a]pyrimidine;
6-(4-fluoro-2-methoxyphenyl)-2-(5-fluoropyridin-3-yloxymethyl)imidazo[1,2-a]pyrimidine;
6-(4-fluoro-2-hydroxyphenyl)-2-(5-fluoropyridin-3-yloxymethyl)imidazo[1,2-a]pyrimidine;
6-(2,4-difluorophenyl)-2-(6-fluoropyridin-3-yloxymethyl)imidazo[1,2-a]pyrimidine;
6-(4-fluoro-2-methylphenyl)-2-(6-fluoropyridin-3-yloxymethyl)imidazo[1,2-a]pyrimidine;

6-(4-fluoro-2-methylphenyl)-2-(2-fluoropyridin-3-yloxymethyl)imidazo[1,2-a]pyrimidine;
6-(4-fluoro-2-methylphenyl)-2-(5-chloropyridin-3-yloxymethyl)imidazo[1,2-a]pyrimidine;
6-(2,4-difluorophenyl)-2-(2-fluoropyridin-4-yloxymethyl)imidazo[1,2-a]pyrimidine;
6-(4-fluoro-2-methylphenyl)-2-(2-fluoropyridin-4-yloxymethyl)imidazo[1,2-a]pyrimidine;
6-(4-fluoro-2-methoxyphenyl)-2-(2-fluoropyridin-4-yloxymethyl)imidazo[1,2-a]pyrimidine;
6-(4-fluorophenyl)-2-(2-fluoropyridin-4-yloxymethyl)imidazo[1,2-a]pyrimidine;
6-(2,3-difluorophenyl)-2-(2-fluoropyridin-4-yloxymethyl)imidazo[1,2-a]pyrimidine;
6-(2-fluorophenyl)-2-(2-fluoropyridin-4-yloxymethyl)imidazo[1,2-a]pyrimidine;
6-(4-fluoro-2-hydroxyphenyl)-2-(2-fluoropyridin-4-yloxymethyl)imidazo[1,2-a]pyrimidine;
6-(2-methylphenyl)-2-(2-fluoropyridin-4-yloxymethyl)imidazo[1,2-a]pyrimidine;
6-(2-hydroxyphenyl)-2-(2-fluoropyridin-4-yloxymethyl)imidazo[1,2-a]pyrimidine;
6-(4-fluoro-2-hydroxymethylphenyl)-2-(2-fluoropyridin-4-yloxymethyl)imidazo[1,2-a]pyrimidine;
6-(4-fluorophenyl)-2-[(5-fluoro-3-pyridyl)oxymethyl)imidazo[1,2-a]pyrimidine;
2-[(2-chloro-4-pyridyl)oxymethyl]-6-(4-fluorophenyl)imidazo[1,2-a]pyrimidine;
2-[(5-fluoro-3-pyridyl)oxymethyl]-6-[4-fluoro-2-(trifluoromethyl)phenyl]imidazo[1,2-a]pyrimidine;
2-[(2-fluoro-4-pyridyl)oxymethyl]-6-[4-fluoro-2-(trifluoromethyl)phenyl]imidazo[1,2-a]pyrimidine;
5-fluoro-2-[2-[(5-fluoro-3-pyridyl)oxymethyl]imidazo[1,2-a]pyrimidin-6-yl]aniline;
5-fluoro-2-[2-[(2-fluoro-4-pyridyl)oxymethyl]imidazo[1,2-a]pyrimidin-6-yl]aniline;
[5-fluoro-2-[2-[(5-fluoro-3-pyridyl)oxymethyl]imidazo[1,2-a]pyrimidin-6-yl]phenyl]methanol;
2-(2,4-difluorophenyl)-6-(phenoxymethyl)imidazo[1,2-b][1,2,4]triazine;
2-(2,4-difluorophenyl)-6-((pyridin-4-yloxy)methyl)imidazo[1,2-b][1,2,4]triazine;
2-(2,4-difluorophenyl)-6-((pyridin-2-yloxy)methyl)imidazo[1,2-b][1,2,4]triazine;
2-(4-fluorophenyl)-6-((pyridin-4-yloxy)methyl)imidazo[1,2-b][1,2,4]triazine;
2-(2-methylphenyl)-6-((pyridin-4-yloxy)methyl)imidazo[1,2-b][1,2,4]triazine;
2-(2,4-difluorophenyl)-64(2-fluoropyridin-4-yloxy)methyl)imidazo[1,2-b][1,2,4]triazine;
2-(4-fluoro-2-methylphenyl)-6-((2-fluoropyridin-4-yloxy)methyl)imidazo[1,2-b][1,2,4]triazine;
2-(2-methylphenyl)-64(2-fluoropyridin-4-yloxy)methyl)imidazo[1,2-b][1,2,4]triazine;
2-[4-fluoro-2-(trifluoromethyl)phenyl]-6-(2-pyridyloxymethyl)imidazo[1,2-b][1,2,4]triazine;
2-(3-fluoro-2-methyl-phenyl)-6-(2-pyridyloxymethyl)imidazo[1,2-b][1,2,4]triazine;
2-(4-fluoro-2-methyl-phenyl)-6-(2-pyridyloxymethyl)imidazo[1,2-b][1,2,4]triazine;
2-[4-chloro-2-(trifluoromethyl)phenyl]-6-(2-pyridyloxymethyl)imidazo[1,2-b][1,2,4]triazine;
2-(4-chloro-2-methyl-phenyl)-6-(2-pyridyloxymethyl)imidazo[1,2-b][1,2,4]triazine;
2-(4-fluoro-2-methyl-phenyl)-6-[(6-fluoro-2-pyridyl)oxymethyl]imidazo[1,2-b][1,2,4]triazine;
2-(4-fluoro-2-methyl-phenyl)-6-[(5-fluoro-2-pyridyl)oxymethyl]imidazo[1,2-b][1,2,4]triazine;
[5-fluoro-2-[2-[(4-fluorophenoxy)methyl]imidazo[1,2-a]pyrimidin-6-yl]phenyl]methyl carbamate;
[5-fluoro-2-[2-(phenoxymethyl)imidazo[1,2-a]pyrimidin-6-yl]phenyl]methyl carbamate;
[5-fluoro-2-[2-(2-pyridyloxymethyl)imidazo[1,2-a]pyrimidin-6-yl]phenyl]methyl carbamate;
[5-fluoro-2-[2-(2-pyridyloxymethyl)imidazo[1,2-a]pyrimidin-6-yl]phenyl]methyl acetate;
6-[2-(chloromethyl)-4-fluoro-phenyl]-2-[(4-fluorophenoxy)methyl)imidazo[1,2-a]pyrimidine;
6-[4-fluoro-2-(fluoromethyl)phenyl]-2-(2-pyridyloxymethyl)imidazo[1,2-a]pyrimidine;
and
6-[4-fluoro-2-(fluoromethyl)phenyl]-2-[(4-fluorophenoxy)methyl]imidazo[1,2-a]pyrimidine.

\* \* \* \* \*